(12) United States Patent
Aukerman et al.

(10) Patent No.: US 8,338,181 B2
(45) Date of Patent: Dec. 25, 2012

(54) PLANTS HAVING ALTERED AGRONOMIC CHARACTERISTICS UNDER NITROGEN LIMITING CONDITIONS AND RELATED CONSTRUCTS AND METHODS INVOLVING GENES ENCODING LNT2 POLYPEPTIDES AND HOMOLOGS THEREOF

(75) Inventors: Milo Aukerman, Newark, DE (US); Dale Loussaert, Clive, IA (US); Stanley Luck, Wilmington, DE (US); Hajime Sakai, Newark, DE (US); Scott V. Tingey, Wilmington, DE (US)

(73) Assignees: E. I. du Pont de Nemours and Company, Wilmington, DE (US); Pioneer Hi-Bred International, Johnston, IA (US)

( * ) Notice: Subject to any disclaimer, the term of this patent is extended or adjusted under 35 U.S.C. 154(b) by 0 days.

(21) Appl. No.: 12/848,277

(22) Filed: Aug. 2, 2010

(65) Prior Publication Data

US 2011/0039263 A1 Feb. 17, 2011

Related U.S. Application Data

(63) Continuation of application No. 12/264,990, filed on Nov. 5, 2008, now abandoned.

(60) Provisional application No. 60/986,088, filed on Nov. 7, 2007.

(51) Int. Cl.
*A01H 1/00* (2006.01)
*C07H 21/04* (2006.01)
*C07K 14/415* (2006.01)
*C12N 15/00* (2006.01)

(52) U.S. Cl. ...... 435/468; 435/6.1; 435/320.1; 435/419; 530/370; 536/23.1; 536/23.6; 800/278; 800/295

(58) Field of Classification Search .................. 435/6.1, 435/69.1, 468, 419, 320.1; 530/370; 536/23.6; 800/278, 295

See application file for complete search history.

(56) References Cited

U.S. PATENT DOCUMENTS

2004/0172684 A1  9/2004  Kovalic et al.

FOREIGN PATENT DOCUMENTS

| EP | 1033405 | * | 9/2000 |
| EP | 1586654 A | | 10/2005 |
| WO | 2007/022195 | | 2/2007 |

OTHER PUBLICATIONS

DATABASE EMBL Accession #CX548557, Jan. 13, 2005, XP002511664.
DATABASE EMBL Accession #CD401485, Jun. 10, 2003, XP002511665.

\* cited by examiner

*Primary Examiner* — Phuong T Bui

(57) ABSTRACT

Isolated polynucleotides and polypeptides and recombinant DNA constructs particularly useful for altering agronomic characteristics of plants under nitrogen limiting conditions, compositions (such as plants or seeds) comprising these recombinant DNA constructs, and methods utilizing these recombinant DNA constructs. The recombinant DNA construct comprises a polynucleotide operably linked to a promoter functional in a plant, wherein said polynucleotide encodes an LNT2 polypeptide.

2 Claims, 33 Drawing Sheets

FIG. 11

| | | | | | | | |
|---|---|---|---|---|---|---|---|
| O 1 | O C1 | O 3 | O 5 | O 1 | O 2 | O 4 | O 3 |
| O 2 | O 1 | O C1 | O 3 | O 5 | O 1 | O 2 | O 4 |
| O 5 | O 2 | O 1 | O C1 | O 3 | O 5 | O 1 | O 2 |
| O 4 | O 5 | O 2 | O 1 | O C1 | O 3 | O 5 | O 1 |
| O 3 | O 4 | O 5 | O 2 | O 1 | O C1 | O 3 | O 5 |
| O 1 | O 3 | O 4 | O 5 | O 2 | O 1 | O C1 | O 3 |
| O C1 | O 1 | O 2 | O 4 | O 3 | O 5 | O 4 | O C1 |
| O 2 | O C1 | O 5 | O 2 | O 4 | O 3 | O 2 | O 4 |

Typical grid pattern for 5 lines (labeled 1 through 5), plus wild-type control C1, used in screens.

FIG. 13

**Modified Hoagland's solutions -
16X concentrations for semi-hydroponics maize growth.**

| Nutrient | 1 mM KNO$_3$ | 6.5 mM KNO$_3$ |
|---|---|---|
| KNO$_3$ | 16 mM | 104 mM |
| KCl | 48 mM | ---- |
| KH$_2$PO$_4$ | 11 mM | 11 mM |
| MgSO$_4$ | 16 mM | 16 mM |
| CaCl$_2$·2H$_2$O | 16 mM | 16 mM |
| Sprint 330 | 1.6 g/L | 1.6 g/L |
| H$_3$BO$_3$ | 24 µM | 24 µM |
| 5 mM MnCl$_2$·4H$_2$O | 8 µM | 8 µM |
| 5 mM ZnSO$_4$·7 H$_2$O | 8 µM | 8 µM |
| 0.5 mM CuSO$_4$·5 H$_2$O | 800 nM | 800 nM |
| 0.5 mM H$_2$MoO$_4$·H$_2$O | 800 nM | 800 nM |

Dilute 16X with tap water and determine the pH of the final mixture.
Add 3-12 mL H$_2$SO$_4$ if the pH is above 6.5.
Optimum pH is 5.0 - 5.5

FIG. 14A

```
                        10            20            30            40            50            60       Majority
          MX-------------------------------------------------------------------

1    MDPD---------------------------------------------------LDLD-----LDMD---    SEQ ID NO:18 (maize).pro
     1    MDAE---------------------------------------------------MDL--------------    SEQ ID NO:20 (rice).pro
     1    MESV---------------------------------------------------------------------    SEQ ID NO:24 (soybean).pro
     1    MENA---------------------------------------------------------------------    SEQ ID NO:26 (soybean).pro
     1    MFNI SYAKRNAKYLFKLLAWCMMI EEAGPNI GNKQKVVLQLSKMLI MYI I LHI NAAFWTW    SEQ ID NO:28 (Arabidopsis).pro
     1    M------------------------------MI EEAGPNI GNKQK--------------------------    SEQ ID NO:30 (Arabidopsis).pro
     1    M------------------------------------------------------------------------    SEQ ID NO:32 (Arabidopsis).pro
     1    MDAE---------------------------------------------------MDL--------------    SEQ ID NO:33 (rice).pro
     1    M------------------------------------------------------------------------    SEQ ID NO:34 (grape).pro 70            80            90           100           110           120       Majority
          -------------------------------------------EAI SELEVDQI EEAXXX-----

13    ------------METLAGDSGGEAERN-----------------EAAEAEAEVERYEAAEAE           SEQ ID NO:18 (maize).pro
     8    ----------------LADDDGGEAER-----------------------LEAAEAQ                SEQ ID NO:20 (rice).pro
     5    ---------------------------------------------DANSEVENDAEMK---            SEQ ID NO:24 (soybean).pro
     5    ---------------------------------------------DANSEVENDAEMK---            SEQ ID NO:26 (soybean).pro
    61    RGYLKRCVLHFVFPRI FLPLLSDSPTI TQAKKPSYCFAMDVGGEDI SDLQVDQI VEEYSM          SEQ ID NO:28 (Arabidopsis).pro
    16    --------------------AKKPSYCFAMDVGGEDI SDLQVDQI VEEYSM                    SEQ ID NO:30 (Arabidopsis).pro
     2    -------------------------DVGGEDI SDLQVDQI VEEYSM                         SEQ ID NO:32 (Arabidopsis).pro
     8    ----------------LADDDGGEAER-----------------------LEAAEAQ                SEQ ID NO:33 (rice).pro
     2    ------------------------------EEARSELEREEDEEA---                         SEQ ID NO:34 (grape).pro 130           140           150           160           170           180       Majority
          XDLLRDRFRLSAI AEAEAKKNGMEVSXPVVACI ADLAFKYAEQLAKDLELFAQHAGRK 46    ADI LRDRFRLSAI SI ATAEGKKAGMTVADPVVSCI ADLAFKSAEQLAKDAELFAQHAGRK           SEQ ID NO:18 (maize).pro
    26    ADLLRDRLRLAVI SI ATSEGKKAGMEVSDPVVACI ADLAYKTVEQLAKDVELFAQHAGRK           SEQ ID NO:20 (rice).pro
    18    --LLRDKFRLSAI SI I ESQAKQNGMEVSKVVVTCVADLAFKYTERLARDLHLFAQHANRK           SEQ ID NO:24 (soybean).pro
    18    --LLRDKFRLSAI SI I ESQAKQNGMEVAKI VVTCI ADLAFKYTECVARDLHLFAQHANRK          SEQ ID NO:26 (soybean).pro
   121    DDLI RDRFRLSAI SI AEAEAKKNGMEI GGPVVACVADLAFKYAENVAKDLELFAHHAGRK          SEQ ID NO:28 (Arabidopsis).pro
    47    DDLI RDRFRLSAI SI AEAEAKKNGMEI GGPVVACVADLAFKYAENVAKDLELFAHHAGRK          SEQ ID NO:30 (Arabidopsis).pro
    23    DDLI RDRFRLSAI SI AEAEAKKNGMEI GGPVVACVADLAFKYAENVAKDLELFAHHAGRK          SEQ ID NO:32 (Arabidopsis).pro
    26    ADLLRDRLRLAVI SI ATSEGKKAGMEVSDPVVACI ADLAYKTVEQLAKDVELFAQHAGRK           SEQ ID NO:33 (rice).pro
    17    TELLRDRFRLSTI SI VEAQAKKSDMEI SEPI VACI SDLAFKYTEQLAKDLELFSQHAGRK         SEQ ID NO:34 (grape).pro
```

FIG. 14B

```
     SVNMEDVILSAHRNEHLAGSLRSFSNELKAKEPQSERKRKKXSXKKEDKASXS- XVXI XT   Majority
                190             200             210             220             230            240
106  SVRMDDVILTAHRNEHLMGLLRTFSQELKGKEPASERKRKKSSKKDET------VI          SEQ ID NO:18 (maize).pro
 86  SIKMEDVILTAHRNEHLMGLLRTFSQELKGKEPSSERKRKKSSKKDDN------VM          SEQ ID NO:20 (rice).pro
 76  SVNMEDVILCGHRNEHVSGMLRSFSNDLKAKDPQSERKRKKEP- KKNDKGTA             SEQ ID NO:24 (soybean).pro
 76  SVNMEDVILCGHRNEHVSGMLRSFSNVLKANDPQSERKRKKET- KKNDKGTA             SEQ ID NO:26 (soybean).pro
181  VVNMDDVVLSAHRNDNLAASLRSLCNELKAKEPQSERKRKKGSAKKEDKASSSNAVRI TT     SEQ ID NO:28 (Arabidopsis).pro
107  VVNMDDVVLSAHRNDNLAASLRSLCNELKAKEPQSERKRKKGSAKKEDKASSSNAVRI TT     SEQ ID NO:30 (Arabidopsis).pro
 83  VVVNMDDVVLSAHRNDNLAASLRSLCNELKAKEPQSERKRKKGSAKKEDKASSSNAVRI TT    SEQ ID NO:32 (Arabidopsis).pro
 86  SIKMEDVILTAHRNEHLMGLLRTFSQELKGKEPSSERKRKKSSKKDDN------VM          SEQ ID NO:33 (rice).pro
 77  TVNMEDVILSAHRNKHLASSLRSFCNDLKAKEI PSERKRKKAS- RKEDKASTS- VVHI P-  SEQ ID NO:34 (grape).pro DL                                                                Majority
     __
     EV
     QI
156  DL                                                                SEQ ID NO:18 (maize).pro
136  DL                                                                SEQ ID NO:20 (rice).pro
126  DL                                                                SEQ ID NO:24 (soybean).pro
126  DL                                                                SEQ ID NO:26 (soybean).pro
241  DL                                                                SEQ ID NO:28 (Arabidopsis).pro
167  DL                                                                SEQ ID NO:30 (Arabidopsis).pro
143  DL                                                                SEQ ID NO:32 (Arabidopsis).pro
136  QI                                                                SEQ ID NO:33 (rice).pro
134  DL                                                                SEQ ID NO:34 (grape).pro
```

FIG. 15

Percent Identity

|   | 1 | 2 | 3 | 4 | 5 | 6 | 7 | 8 | 9 |   |
|---|---|---|---|---|---|---|---|---|---|---|
| 1 |   | 77.4 | 54.0 | 54.8 | 47.8 | 46.5 | 50.0 | 77.4 | 52.6 | 1 | SEQ ID NO:18 (maize).pro
| 2 | 21.9 |   | 54.8 | 53.2 | 49.6 | 49.6 | 48.9 | 100.0 | 52.6 | 2 | SEQ ID NO:20 (rice).pro
| 3 | 67.6 | 58.8 |   | 92.1 | 54.8 | 54.8 | 54.8 | 54.8 | 58.7 | 3 | SEQ ID NO:24 (soybean).pro
| 4 | 67.6 | 62.6 | 8.4 |   | 54.0 | 54.0 | 54.0 | 53.2 | 57.1 | 4 | SEQ ID NO:26 (soybean).pro
| 5 | 84.2 | 77.0 | 60.9 | 60.9 |   | 98.2 | 100.0 | 49.6 | 58.5 | 5 | SEQ ID NO:28 (Arabidopsis).pro
| 6 | 70.4 | 67.6 | 57.9 | 59.6 | 0.0 |   | 100.0 | 49.6 | 58.5 | 6 | SEQ ID NO:30 (Arabidopsis).pro
| 7 | 67.5 | 65.5 | 57.9 | 59.6 | 0.0 | 0.0 |   | 48.9 | 58.5 | 7 | SEQ ID NO:32 (Arabidopsis).pro
| 8 | 21.9 | 0.0 | 58.8 | 62.6 | 77.0 | 67.6 | 65.5 |   | 52.6 | 8 | SEQ ID NO:33 (rice).pro
| 9 | 59.2 | 56.6 | 53.0 | 57.9 | 43.9 | 43.9 | 43.9 | 56.6 |   | 9 | SEQ ID NO:34 (grape).pro
|   | 1 | 2 | 3 | 4 | 5 | 6 | 7 | 8 | 9 |   |

FIG. 16A
PHP29689 Event Data

| Event name | Treatment | Variable | Event p-value over null |
|---|---|---|---|
| EA2391.314.1.5 | 1.0 mMol KNO3 | % green_end exponential | 13.490 |
| EA2391.314.1.6 | 1.0 mMol KNO3 | % green_end exponential | 1.000 |
| EA2391.314.1.8 | 1.0 mMol KNO3 | % green_end exponential | 1.000 |
| EA2391.314.1.9 | 1.0 mMol KNO3 | % green_end exponential | 1.000 |
| EA2391.314.1.5 | 6.5 mMol KNO3 | % green_end exponential | 33.113 |
| EA2391.314.1.6 | 6.5 mMol KNO3 | % green_end exponential | 1.000 |
| EA2391.314.1.8 | 6.5 mMol KNO3 | % green_end exponential | 1.000 |
| EA2391.314.1.9 | 6.5 mMol KNO3 | % green_end exponential | 1.000 |
| EA2391.314.1.5 | 1.0 mMol KNO3 | % green_harvest | 42.658 |
| EA2391.314.1.6 | 1.0 mMol KNO3 | % green_harvest | 1.000 |
| EA2391.314.1.8 | 1.0 mMol KNO3 | % green_harvest | 1.000 |
| EA2391.314.1.9 | 1.0 mMol KNO3 | % green_harvest | 1.000 |
| EA2391.314.1.5 | 6.5 mMol KNO3 | % green_harvest | 1.000 |
| EA2391.314.1.6 | 6.5 mMol KNO3 | % green_harvest | 1.000 |
| EA2391.314.1.8 | 6.5 mMol KNO3 | % green_harvest | 1071.519 |
| EA2391.314.1.9 | 6.5 mMol KNO3 | % green_harvest | 1.000 |

FIG. 16B (cont.)

| Event name | Treatment | Variable | Event p-value over null |
|---|---|---|---|
| EA2391.314.1.5 | 1.0 mMol KNO3 | % lightgreen_end exponential | 0.043 * |
| EA2391.314.1.6 | 1.0 mMol KNO3 | % lightgreen_end exponential | 1.000 |
| EA2391.314.1.8 | 1.0 mMol KNO3 | % lightgreen_end exponential | 1.000 |
| EA2391.314.1.9 | 1.0 mMol KNO3 | % lightgreen_end exponential | 1.000 |
| EA2391.314.1.5 | 6.5 mMol KNO3 | % lightgreen_end exponential | 0.007 * |
| EA2391.314.1.6 | 6.5 mMol KNO3 | % lightgreen_end exponential | 0.029 * |
| EA2391.314.1.8 | 6.5 mMol KNO3 | % lightgreen_end exponential | 0.062 * |
| EA2391.314.1.9 | 6.5 mMol KNO3 | % lightgreen_end exponential | 0.047 * |
| EA2391.314.1.5 | 1.0 mMol KNO3 | % lightgreen_harvest | 0.018 * |
| EA2391.314.1.6 | 1.0 mMol KNO3 | % lightgreen_harvest | 1.000 |
| EA2391.314.1.8 | 1.0 mMol KNO3 | % lightgreen_harvest | 1.000 |
| EA2391.314.1.9 | 1.0 mMol KNO3 | % lightgreen_harvest | 1.000 |
| EA2391.314.1.5 | 6.5 mMol KNO3 | % lightgreen_harvest | 1.000 |
| EA2391.314.1.6 | 6.5 mMol KNO3 | % lightgreen_harvest | 0.019 * |
| EA2391.314.1.8 | 6.5 mMol KNO3 | % lightgreen_harvest | 0.005 * |
| EA2391.314.1.9 | 6.5 mMol KNO3 | % lightgreen_harvest | 0.027 * |

FIG. 16C (cont.)

| Event name | Treatment | Variable | Event p-value over null |
|---|---|---|---|
| EA2391.314.1.5 | 1.0 mMol KNO3 | area_end exponential | 1.000 |
| EA2391.314.1.6 | 1.0 mMol KNO3 | area_end exponential | 0.003* |
| EA2391.314.1.8 | 1.0 mMol KNO3 | area_end exponential | 1.000 |
| EA2391.314.1.9 | 1.0 mMol KNO3 | area_end exponential | 18.621 |
| EA2391.314.1.5 | 6.5 mMol KNO3 | area_end exponential | 1.000 |
| EA2391.314.1.6 | 6.5 mMol KNO3 | area_end exponential | 7.413E-04* |
| EA2391.314.1.8 | 6.5 mMol KNO3 | area_end exponential | 1.000 |
| EA2391.314.1.9 | 6.5 mMol KNO3 | area_end exponential | 1.000 |
| EA2391.314.1.5 | 1.0 mMol KNO3 | area_harvest | 0.006* |
| EA2391.314.1.6 | 1.0 mMol KNO3 | area_harvest | 0.024* |
| EA2391.314.1.8 | 1.0 mMol KNO3 | area_harvest | 1.000 |
| EA2391.314.1.9 | 1.0 mMol KNO3 | area_harvest | 30.903 |
| EA2391.314.1.5 | 6.5 mMol KNO3 | area_harvest | 1.000 |
| EA2391.314.1.6 | 6.5 mMol KNO3 | area_harvest | 2.138E-05* |
| EA2391.314.1.8 | 6.5 mMol KNO3 | area_harvest | 1.000 |
| EA2391.314.1.9 | 6.5 mMol KNO3 | area_harvest | 0.089* |

FIG. 16D (cont.)

| Event name | Treatment | Variable | Event p-value over null |
|---|---|---|---|
| EA2391.314.1.5 | 1.0 mMol KNO3 | days to emergence | 1.000 |
| EA2391.314.1.6 | 1.0 mMol KNO3 | days to emergence | 1.000 |
| EA2391.314.1.8 | 1.0 mMol KNO3 | days to emergence | 1.000 |
| EA2391.314.1.9 | 1.0 mMol KNO3 | days to emergence | 1.000 |
| EA2391.314.1.5 | 6.5 mMol KNO3 | days to emergence | 1.000 |
| EA2391.314.1.6 | 6.5 mMol KNO3 | days to emergence | 1.000 |
| EA2391.314.1.8 | 6.5 mMol KNO3 | days to emergence | 1.000 |
| EA2391.314.1.9 | 6.5 mMol KNO3 | days to emergence | 1.000 |
| EA2391.314.1.5 | 1.0 mMol KNO3 | days to shed | 8.511E-04* |
| EA2391.314.1.6 | 1.0 mMol KNO3 | days to shed | 1.000 |
| EA2391.314.1.8 | 1.0 mMol KNO3 | days to shed | 0.026* |
| EA2391.314.1.9 | 1.0 mMol KNO3 | days to shed | 1.000 |
| EA2391.314.1.5 | 6.5 mMol KNO3 | days to shed | n/a |
| EA2391.314.1.6 | 6.5 mMol KNO3 | days to shed | 1.000 |
| EA2391.314.1.8 | 6.5 mMol KNO3 | days to shed | 7.079E-06* |
| EA2391.314.1.9 | 6.5 mMol KNO3 | days to shed | 1.000 |

FIG. 16E (cont.)

| Event name | Treatment | Variable | Event p-value over null |
|---|---|---|---|
| EA2391.314.1.5 | 1.0 mMol KNO3 | ear diameter | 77.625 |
| EA2391.314.1.6 | 1.0 mMol KNO3 | ear diameter | 1.000 |
| EA2391.314.1.8 | 1.0 mMol KNO3 | ear diameter | 1.000 |
| EA2391.314.1.9 | 1.0 mMol KNO3 | ear diameter | 1.000 |
| EA2391.314.1.5 | 6.5 mMol KNO3 | ear diameter | 0.048 * |
| EA2391.314.1.6 | 6.5 mMol KNO3 | ear diameter | 1.000 |
| EA2391.314.1.8 | 6.5 mMol KNO3 | ear diameter | 12.303 |
| EA2391.314.1.9 | 6.5 mMol KNO3 | ear diameter | 1.000 |
| EA2391.314.1.5 | 1.0 mMol KNO3 | ear dry weight | 275.423 |
| EA2391.314.1.6 | 1.0 mMol KNO3 | ear dry weight | 1.000 |
| EA2391.314.1.8 | 1.0 mMol KNO3 | ear dry weight | 1.000 |
| EA2391.314.1.9 | 1.0 mMol KNO3 | ear dry weight | 13.804 |
| EA2391.314.1.5 | 6.5 mMol KNO3 | ear dry weight | 0.012 * |
| EA2391.314.1.6 | 6.5 mMol KNO3 | ear dry weight | 1.000 |
| EA2391.314.1.8 | 6.5 mMol KNO3 | ear dry weight | 1.000 |
| EA2391.314.1.9 | 6.5 mMol KNO3 | ear dry weight | 1.000 |

FIG. 16F (cont.)

| Event name | Treatment | Variable | Event p-value over null |
|---|---|---|---|
| EA2391.314.1.5 | 1.0 mMol KNO3 | ear fresh weight | 70.795 |
| EA2391.314.1.6 | 1.0 mMol KNO3 | ear fresh weight | 1.000 |
| EA2391.314.1.8 | 1.0 mMol KNO3 | ear fresh weight | 60.256 |
| EA2391.314.1.9 | 1.0 mMol KNO3 | ear fresh weight | 1.000 |
| EA2391.314.1.5 | 6.5 mMol KNO3 | ear fresh weight | 0.014* |
| EA2391.314.1.6 | 6.5 mMol KNO3 | ear fresh weight | 1.000 |
| EA2391.314.1.8 | 6.5 mMol KNO3 | ear fresh weight | 1.000 |
| EA2391.314.1.9 | 6.5 mMol KNO3 | ear fresh weight | 1.000 |
| EA2391.314.1.5 | 1.0 mMol KNO3 | maximum area | 0.017* |
| EA2391.314.1.6 | 1.0 mMol KNO3 | maximum area | 0.007* |
| EA2391.314.1.8 | 1.0 mMol KNO3 | maximum area | 1.000 |
| EA2391.314.1.9 | 1.0 mMol KNO3 | maximum area | 30.903 |
| EA2391.314.1.5 | 6.5 mMol KNO3 | maximum area | 1.000 |
| EA2391.314.1.6 | 6.5 mMol KNO3 | maximum area | 4.074E-07* |
| EA2391.314.1.8 | 6.5 mMol KNO3 | maximum area | 1.000 |
| EA2391.314.1.9 | 6.5 mMol KNO3 | maximum area | 0.091* |

FIG. 16G (cont.)

| Event name | Treatment | Variable | Event p-value over null |
|---|---|---|---|
| EA2391.314.1.5 | 1.0 mMol KNO3 | sgr - r2 > 0.9 | 0.009* |
| EA2391.314.1.6 | 1.0 mMol KNO3 | sgr - r2 > 0.9 | 1.000 |
| EA2391.314.1.8 | 1.0 mMol KNO3 | sgr - r2 > 0.9 | 0.024* |
| EA2391.314.1.9 | 1.0 mMol KNO3 | sgr - r2 > 0.9 | 1.000 |
| EA2391.314.1.5 | 6.5 mMol KNO3 | sgr - r2 > 0.9 | 1.000 |
| EA2391.314.1.6 | 6.5 mMol KNO3 | sgr - r2 > 0.9 | 0.069* |
| EA2391.314.1.8 | 6.5 mMol KNO3 | sgr - r2 > 0.9 | 0.013* |
| EA2391.314.1.9 | 6.5 mMol KNO3 | sgr - r2 > 0.9 | 0.007* |
| EA2391.314.1.5 | 1.0 mMol KNO3 | shoot dry weight | 1.000 |
| EA2391.314.1.6 | 1.0 mMol KNO3 | shoot dry weight | 5.623E-04* |
| EA2391.314.1.8 | 1.0 mMol KNO3 | shoot dry weight | 1.000 |
| EA2391.314.1.9 | 1.0 mMol KNO3 | shoot dry weight | 1.000 |
| EA2391.314.1.5 | 6.5 mMol KNO3 | shoot dry weight | 1.000 |
| EA2391.314.1.6 | 6.5 mMol KNO3 | shoot dry weight | 2.884E-04* |
| EA2391.314.1.8 | 6.5 mMol KNO3 | shoot dry weight | 1.000 |
| EA2391.314.1.9 | 6.5 mMol KNO3 | shoot dry weight | 1.000 |

FIG. 16H (cont.)

| Event name | Treatment | Variable | Event p-value over null |
|---|---|---|---|
| EA2391.314.1.5 | 1.0 mMol KNO3 | shoot fresh weight | 0.021* |
| EA2391.314.1.6 | 1.0 mMol KNO3 | shoot fresh weight | 5.888E-04* |
| EA2391.314.1.8 | 1.0 mMol KNO3 | shoot fresh weight | 0.030* |
| EA2391.314.1.9 | 1.0 mMol KNO3 | shoot fresh weight | 31.623 |
| EA2391.314.1.5 | 6.5 mMol KNO3 | shoot fresh weight | 1.000 |
| EA2391.314.1.6 | 6.5 mMol KNO3 | shoot fresh weight | 8.913E-05* |
| EA2391.314.1.8 | 6.5 mMol KNO3 | shoot fresh weight | 1.000 |
| EA2391.314.1.9 | 6.5 mMol KNO3 | shoot fresh weight | 1.000 |
| EA2391.314.1.5 | 1.0 mMol KNO3 | shoot+ear dry weight | 1.000 |
| EA2391.314.1.6 | 1.0 mMol KNO3 | shoot+ear dry weight | 0.008* |
| EA2391.314.1.8 | 1.0 mMol KNO3 | shoot+ear dry weight | 1.000 |
| EA2391.314.1.9 | 1.0 mMol KNO3 | shoot+ear dry weight | 1.000 |
| EA2391.314.1.5 | 6.5 mMol KNO3 | shoot+ear dry weight | 1.000 |
| EA2391.314.1.6 | 6.5 mMol KNO3 | shoot+ear dry weight | 7.586E-04* |
| EA2391.314.1.8 | 6.5 mMol KNO3 | shoot+ear dry weight | 1.000 |
| EA2391.314.1.9 | 6.5 mMol KNO3 | shoot+ear dry weight | 1.000 |

FIG. 16l (cont.)

| Event name | Treatment | Variable | Event p-value over null |
|---|---|---|---|
| EA2391.314.1.5 | 1.0 mMol KNO3 | shoot+ear fresh weight | 1.000 |
| EA2391.314.1.6 | 1.0 mMol KNO3 | shoot+ear fresh weight | 0.078* |
| EA2391.314.1.8 | 1.0 mMol KNO3 | shoot+ear fresh weight | 0.093* |
| EA2391.314.1.9 | 1.0 mMol KNO3 | shoot+ear fresh weight | 30.903 |
| EA2391.314.1.5 | 6.5 mMol KNO3 | shoot+ear fresh weight | 1.000 |
| EA2391.314.1.6 | 6.5 mMol KNO3 | shoot+ear fresh weight | 1.585E-04* |
| EA2391.314.1.8 | 6.5 mMol KNO3 | shoot+ear fresh weight | 1.000 |
| EA2391.314.1.9 | 6.5 mMol KNO3 | shoot+ear fresh weight | 1.000 |
| EA2391.314.1.5 | 1.0 mMol KNO3 | stalk+ear diameter | 107.152 |
| EA2391.314.1.6 | 1.0 mMol KNO3 | stalk+ear diameter | 0.041* |
| EA2391.314.1.8 | 1.0 mMol KNO3 | stalk+ear diameter | 1.000 |
| EA2391.314.1.9 | 1.0 mMol KNO3 | stalk+ear diameter | 1.000 |
| EA2391.314.1.5 | 6.5 mMol KNO3 | stalk+ear diameter | 1.000 |
| EA2391.314.1.6 | 6.5 mMol KNO3 | stalk+ear diameter | 1.000 |
| EA2391.314.1.8 | 6.5 mMol KNO3 | stalk+ear diameter | 1.000 |
| EA2391.314.1.9 | 6.5 mMol KNO3 | stalk+ear diameter | 1.000 |

FIG. 17A
PHP29689 Construct Data

| Treatment | Variable | Construct p-value over null |
|---|---|---|
| 1.0 mMol KNO3 | % green_end exponential | 1 |
| 6.5 mMol KNO3 | % green_end exponential | 128.825 |
| 1.0 mMol KNO3 | % green_harvest | 10.715 |
| 6.5 mMol KNO3 | % green_harvest | 112.202 |
| 1.0 mMol KNO3 | % lightgreen_end exponential | 1 |
| 6.5 mMol KNO3 | % lightgreen_end exponential | 0.001 * |
| 1.0 mMol KNO3 | % lightgreen_harvest | 0.066 * |
| 6.5 mMol KNO3 | % lightgreen_harvest | 0.001 * |
| 1.0 mMol KNO3 | area_end exponential | 1 |
| 6.5 mMol KNO3 | area_end exponential | 0.011 * |
| 1.0 mMol KNO3 | area_harvest | 0.078 * |
| 6.5 mMol KNO3 | area_harvest | 0.005 * |

FIG. 17B

| Treatment | Variable | Construct p-value over null |
|---|---|---|
| 1.0 mMol KNO3 | days to emergence | 1 |
| 6.5 mMol KNO3 | days to emergence | 1 |
| 1.0 mMol KNO3 | days to shed | 0.008* |
| 6.5 mMol KNO3 | days to shed | 0.046* |
| 1.0 mMol KNO3 | ear diameter | 1 |
| 6.5 mMol KNO3 | ear diameter | 1 |
| 1.0 mMol KNO3 | ear dry weight | 602.56 |
| 6.5 mMol KNO3 | ear dry weight | 1 |
| 1.0 mMol KNO3 | ear fresh weight | 316.228 |
| 6.5 mMol KNO3 | ear fresh weight | 1 |
| 1.0 mMol KNO3 | maximum area | 0.091* |
| 6.5 mMol KNO3 | maximum area | 0.005* |

FIG. 17C

| Treatment | Variable | Construct p-value over null |
|---|---|---|
| 1.0 mMol KNO3 | sgr - r2 > 0.9 | 0.018* |
| 6.5 mMol KNO3 | sgr - r2 > 0.9 | 0* |
| 1.0 mMol KNO3 | shoot dry weight | 1 |
| 6.5 mMol KNO3 | shoot dry weight | 0.001* |
| 1.0 mMol KNO3 | shoot fresh weight | 0.024* |
| 6.5 mMol KNO3 | shoot fresh weight | 0.009* |
| 1.0 mMol KNO3 | shoot+ear dry weight | 1 |
| 6.5 mMol KNO3 | shoot+ear dry weight | 0.074* |
| 1.0 mMol KNO3 | shoot+ear fresh weight | 1 |
| 6.5 mMol KNO3 | shoot+ear fresh weight | 0.023* |
| 1.0 mMol KNO3 | stalk+ear diameter | 1 |
| 6.5 mMol KNO3 | stalk+ear diameter | 1 |

FIG. 18: Yield trial results for PHP28840-containing plants under low nitrogen conditions

| Year | Location | Treatment | PHP | Construct | Event | YIELD |
|---|---|---|---|---|---|---|
| 2007 | Woodland | LN | PHP28840 | UBI:AT-Int2-3 | E6919.105.1.11 | 162 |
| 2007 | Woodland | LN | PHP28840 | UBI:AT-Int2-3 | E6919.105.1.2 | 120 |
| 2007 | Woodland | LN | PHP28840 | UBI:AT-Int2-3 | E6919.105.1.21 | 149 |
| 2007 | Woodland | LN | PHP28840 | UBI:AT-Int2-3 | E6919.105.1.24 | n/a |
| 2007 | Woodland | LN | PHP28840 | UBI:AT-Int2-3 | E6919.105.1.5 | 131 |
| 2007 | Woodland | LN | PHP28840 | UBI:AT-Int2-3 | E6919.105.1.8 | 118 |
| 2007 | Woodland | LN |  |  | CN | 127 |

| Year | Location | Treatment | PHP | Construct | Event | YIELD |
|---|---|---|---|---|---|---|
| 2007 | Johnston | LN | PHP28840 | UBI:AT-Int2-3 | E6919.105.1.11 | 137 |
| 2007 | Johnston | LN | PHP28840 | UBI:AT-Int2-3 | E6919.105.1.2 | n/a |
| 2007 | Johnston | LN | PHP28840 | UBI:AT-Int2-3 | E6919.105.1.21 | 151 |
| 2007 | Johnston | LN | PHP28840 | UBI:AT-Int2-3 | E6919.105.1.24 | 141 |
| 2007 | Johnston | LN | PHP28840 | UBI:AT-Int2-3 | E6919.105.1.5 | 133 |
| 2007 | Johnston | LN | PHP28840 | UBI:AT-Int2-3 | E6919.105.1.8 | 140 |
| 2007 | Johnston | LN |  |  | CN | 147 |

| Year | Location | Treatment | PHP | Construct | Event | YIELD |
|---|---|---|---|---|---|---|
| 2008 | Woodland | LN | PHP28840 | UBI:AT-Int2-3 | E6919.105.1.11 | 173.8 |
| 2008 | Woodland | LN | PHP28840 | UBI:AT-Int2-3 | E6919.105.1.2 | 179 |
| 2008 | Woodland | LN | PHP28840 | UBI:AT-Int2-3 | E6919.105.1.21 | 176.8 |
| 2008 | Woodland | LN | PHP28840 | UBI:AT-Int2-3 | E6919.105.1.24 | 165.6 |
| 2008 | Woodland | LN | PHP28840 | UBI:AT-Int2-3 | E6919.105.1.33 | 170.6 |
| 2008 | Woodland | LN |  |  | CN | 168.3 |

| Year | Location | Treatment | PHP | Construct | Event | YIELD |
|---|---|---|---|---|---|---|
| 2008 | Johnston | LN | PHP28840 | UBI:AT-Int2-3 | E6919.105.1.11 | 164.5 |
| 2008 | Johnston | LN | PHP28840 | UBI:AT-Int2-3 | E6919.105.1.2 | 170.2 |
| 2008 | Johnston | LN | PHP28840 | UBI:AT-Int2-3 | E6919.105.1.21 | 186.8 |
| 2008 | Johnston | LN | PHP28840 | UBI:AT-Int2-3 | E6919.105.1.24 | 176.4 |
| 2008 | Johnston | LN | PHP28840 | UBI:AT-Int2-3 | E6919.105.1.33 | 175.3 |
| 2008 | Johnston | LN |  |  | CN | 166.9 |

Significant positive
Significant negative

FIG. 19: Yield trial results for PHP28841-containing plants under low nitrogen conditions

| Year | Location | Treatment | PHP | Construct | Event | YIELD |
|------|----------|-----------|----------|-------------|---------------|-------|
| 2007 | Woodland | LN | PHP28841 | UBI:AT-Int2-2 | E6919.106.1.11 | 137 |
| 2007 | Woodland | LN | PHP28841 | UBI:AT-Int2-2 | E6919.106.1.14 | 136 |
| 2007 | Woodland | LN | PHP28841 | UBI:AT-Int2-2 | E6919.106.1.17 | 148 |
| 2007 | Woodland | LN | PHP28841 | UBI:AT-Int2-2 | E6919.106.1.22 | 138 |
| 2007 | Woodland | LN | PHP28841 | UBI:AT-Int2-2 | E6919.106.1.3 | 147 |
| 2007 | Woodland | LN | PHP28841 | UBI:AT-Int2-2 | E6919.106.1.8 | 140 |
| 2007 | Woodland | LN | | | CN | 131 |

| Year | Location | Treatment | PHP | Construct | Event | YIELD |
|------|----------|-----------|----------|-------------|---------------|-------|
| 2007 | Johnston | LN | PHP28841 | UBI:AT-Int2-2 | E6919.106.1.11 | 142 |
| 2007 | Johnston | LN | PHP28841 | UBI:AT-Int2-2 | E6919.106.1.14 | n/a |
| 2007 | Johnston | LN | PHP28841 | UBI:AT-Int2-2 | E6919.106.1.17 | n/a |
| 2007 | Johnston | LN | PHP28841 | UBI:AT-Int2-2 | E6919.106.1.22 | 148 |
| 2007 | Johnston | LN | PHP28841 | UBI:AT-Int2-2 | E6919.106.1.3 | 133 |
| 2007 | Johnston | LN | PHP28841 | UBI:AT-Int2-2 | E6919.106.1.8 | 150 |
| 2007 | Johnston | LN | | | CN | 145 |

Significant positive
Significant negative

FIG. 20: Yield trial results for PHP28840-containing plants under normal nitrogen conditions

| Year | Location | Treatment | PHP | Construct | Event | YIELD |
|---|---|---|---|---|---|---|
| 2007 | Woodland | NN | PHP28840 | UBI:AT-Int2-3 | E6919.105.1.11 | 197 |
| 2007 | Woodland | NN | PHP28840 | UBI:AT-Int2-3 | E6919.105.1.2 | 208 |
| 2007 | Woodland | NN | PHP28840 | UBI:AT-Int2-3 | E6919.105.1.21 | 199 |
| 2007 | Woodland | NN | PHP28840 | UBI:AT-Int2-3 | E6919.105.1.24 | 202 |
| 2007 | Woodland | NN | PHP28840 | UBI:AT-Int2-3 | E6919.105.1.5 | 200 |
| 2007 | Woodland | NN | PHP28840 | UBI:AT-Int2-3 | E6919.105.1.8 | 198 |
| 2007 | Woodland | NN | | | CN | 197 |

| Year | Location | Treatment | PHP | Construct | Event | YIELD |
|---|---|---|---|---|---|---|
| 2007 | Johnston | NN | PHP28840 | UBI:AT-Int2-3 | E6919.105.1.11 | 188 |
| 2007 | Johnston | NN | PHP28840 | UBI:AT-Int2-3 | E6919.105.1.2 | n/a |
| 2007 | Johnston | NN | PHP28840 | UBI:AT-Int2-3 | E6919.105.1.21 | 181 |
| 2007 | Johnston | NN | PHP28840 | UBI:AT-Int2-3 | E6919.105.1.24 | 179 |
| 2007 | Johnston | NN | PHP28840 | UBI:AT-Int2-3 | E6919.105.1.5 | 188 |
| 2007 | Johnston | NN | PHP28840 | UBI:AT-Int2-3 | E6919.105.1.8 | 189 |
| 2007 | Johnston | NN | | | CN | 194 |

| Year | Location | Treatment | PHP | Construct | Event | YIELD |
|---|---|---|---|---|---|---|
| 2008 | Woodland | NN | PHP28840 | UBI:AT-Int2-3 | E6919.105.1.11 | 193.8 |
| 2008 | Woodland | NN | PHP28840 | UBI:AT-Int2-3 | E6919.105.1.2 | 210.7 |
| 2008 | Woodland | NN | PHP28840 | UBI:AT-Int2-3 | E6919.105.1.21 | 207.3 |
| 2008 | Woodland | NN | PHP28840 | UBI:AT-Int2-3 | E6919.105.1.24 | 207.4 |
| 2008 | Woodland | NN | PHP28840 | UBI:AT-Int2-3 | E6919.105.1.33 | 209.2 |
| 2008 | Woodland | NN | | | CN | 202.4 |

| Year | Location | Treatment | PHP | Construct | Event | YIELD |
|---|---|---|---|---|---|---|
| 2008 | Johnston | NN | PHP28840 | UBI:AT-Int2-3 | E6919.105.1.11 | 183.8 |
| 2008 | Johnston | NN | PHP28840 | UBI:AT-Int2-3 | E6919.105.1.2 | 196.6 |
| 2008 | Johnston | NN | PHP28840 | UBI:AT-Int2-3 | E6919.105.1.21 | 184.2 |
| 2008 | Johnston | NN | PHP28840 | UBI:AT-Int2-3 | E6919.105.1.24 | 165.9 |
| 2008 | Johnston | NN | PHP28840 | UBI:AT-Int2-3 | E6919.105.1.33 | 193.3 |
| 2008 | Johnston | NN | | | CN | 193.3 |

Significant positive
Significant negative

FIG. 21: Yield trial results for PHP28841-containing plants under normal nitrogen conditions

| Year | Location | Treatment | PHP | Construct | Event | YIELD |
|---|---|---|---|---|---|---|
| 2007 | Woodland | NN | PHP28841 | UBI:AT-Int2-2 | E6919.106.1.11 | 200 |
| 2007 | Woodland | NN | PHP28841 | UBI:AT-Int2-2 | E6919.106.1.14 | 201 |
| 2007 | Woodland | NN | PHP28841 | UBI:AT-Int2-2 | E6919.106.1.17 | 207 |
| 2007 | Woodland | NN | PHP28841 | UBI:AT-Int2-2 | E6919.106.1.22 | 195 |
| 2007 | Woodland | NN | PHP28841 | UBI:AT-Int2-2 | E6919.106.1.3 | 213 |
| 2007 | Woodland | NN | PHP28841 | UBI:AT-Int2-2 | E6919.106.1.8 | 197 |
| 2007 | Woodland | NN | | | CN | 203 |

| Year | Location | Treatment | PHP | Construct | Event | YIELD |
|---|---|---|---|---|---|---|
| 2007 | Johnston | NN | PHP28841 | UBI:AT-Int2-2 | E6919.106.1.11 | 193 |
| 2007 | Johnston | NN | PHP28841 | UBI:AT-Int2-2 | E6919.106.1.14 | 182 |
| 2007 | Johnston | NN | PHP28841 | UBI:AT-Int2-2 | E6919.106.1.17 | 193 |
| 2007 | Johnston | NN | PHP28841 | UBI:AT-Int2-2 | E6919.106.1.22 | 187 |
| 2007 | Johnston | NN | PHP28841 | UBI:AT-Int2-2 | E6919.106.1.3 | 195 |
| 2007 | Johnston | NN | PHP28841 | UBI:AT-Int2-2 | E6919.106.1.8 | 192 |
| 2007 | Johnston | NN | | | CN | 190 |

Significant positive
Significant negative

FIG. 22 NUE seedling assay results

Transgene positive means compared to respective null means          * indicates statistically significant POSITIVE result

| SID | PHP | Event | SPAD | Stem Diameter | Root Dwt | Shoot Dwt | Total Dwt | [N] | Total N |
|---|---|---|---|---|---|---|---|---|---|
| 16038010 | PHP28840 | E6919.105.1.8 | NS | NS | NS | NS | NS | 0.078* | NS |
| 16038002 | PHP28840 | E6919.105.1.2 | NS | NS | 0.034 | 0.024 | 0.053 | NS | NS |
| 16038013 | PHP28840 | E6919.105.1.11 | NS | NS | NS | 0.075 | NS | 0.076 | 0.049 |
| 16038017 | PHP28840 | E6919.105.1.21 | NS | NS | NS | 0.097* | NS | 0.061* | 0.051* |
| 16038023 | PHP28840 | E6919.105.1.24 | NS | NS | NS | 0.04 | NS | NS | NS |
| 16038027 | PHP28841 | E6919.106.1.3 | NS | NS | NS | NS | 0.097 | 0.075* | NS |
| 16038031 | PHP28841 | E6919.106.1.8 | NS | NS | NS | 0.043 | 0.082 | 0.068* | NS |
| 16038034 | PHP28841 | E6919.106.1.11 | NS | NS | NS | NS | NS | <0.001* | 0.006* |
| 16038038 | PHP28841 | E6919.106.1.14 | NS | NS | NS | NS | NS | NS | 0.066 |
| 16038040 | PHP28841 | E6919.106.1.17 | NS | NS | NS | NS | NS | 0.009* | 0.052* |
| 16038043 | PHP28841 | E6919.106.1.22 | NS | NS | NS | 0.062 | 0.094 | NS | NS |

PLANTS HAVING ALTERED AGRONOMIC CHARACTERISTICS UNDER NITROGEN LIMITING CONDITIONS AND RELATED CONSTRUCTS AND METHODS INVOLVING GENES ENCODING LNT2 POLYPEPTIDES AND HOMOLOGS THEREOF

CROSS-REFERENCE TO RELATED APPLICATION

This application is a continuation of U.S. Application Ser. No. 12/264,990, filed Nov. 5, 2008 and currently pending, which claims the benefit of U.S. Provisional Application No. 60/986,088, filed Nov. 7, 2007, the entire contents of which are hereby incorporated by reference.

FIELD OF THE INVENTION

The field of invention relates to plant breeding and genetics and, in particular, relates to recombinant DNA constructs useful in plants for conferring nitrogen use efficiency and/or tolerance to nitrogen limiting conditions.

BACKGROUND OF THE INVENTION

Abiotic stressors significantly limit crop production worldwide. Cumulatively, these factors are estimated to be responsible for an average 70% reduction in agricultural production. Plants are sessile and have to adjust to the prevailing environmental conditions of their surroundings. This has led to their development of a great plasticity in gene regulation, morphogenesis, and metabolism. Adaptation and defense strategies involve the activation of genes encoding proteins important in the acclimation or defense towards the different stressors.

The absorption of nitrogen by plants plays an important role in their growth (Gallais et al., *J. Exp. Bot.* 55(396):295-306 (2004)). Plants synthesize amino acids from inorganic nitrogen in the environment. Consequently, nitrogen fertilization has been a powerful tool for increasing the yield of cultivated plants, such as maize and soybean. Today farmers desire to reduce the use of nitrogen fertilizer, in order to avoid pollution by nitrates and to maintain a sufficient profit margin. If the nitrogen assimilation capacity of a plant can be increased, then increases in plant growth and yield increase are also expected. In summary, plant varieties that have a better nitrogen use efficiency (NUE) are desirable.

Activation tagging can be utilized to identify genes with the ability to affect a trait. This approach has been used in the model plant species *Arabidopsis thaliana* (Weigel et al., *Plant Physiol.* 122:1003-1013 (2000)). Insertions of transcriptional enhancer elements can dominantly activate and/or elevate the expression of nearby endogenous genes. This method can be used to identify genes of interest for a particular trait (e.g. nitrogen use efficiency in a plant), genes that when placed in an organism as a transgene can alter that trait.

SUMMARY OF THE INVENTION

The present invention includes:

In one embodiment, a plant comprising in its genome a recombinant DNA construct comprising a polynucleotide operably linked to at least one regulatory element, wherein said polynucleotide encodes a polypeptide having an amino acid sequence of at least 50% sequence identity, based on the Clustal V method of alignment, when compared to SEQ ID NO:18, 20, 24, 26, 28, 30, or 32, and wherein said plant exhibits increased nitrogen stress tolerance when compared to a control plant not comprising said recombinant DNA construct.

In another embodiment, a plant comprising in its genome a recombinant DNA construct comprising:
(a) a polynucleotide operably linked to at least one regulatory element, wherein said polynucleotide encodes a polypeptide having an amino acid sequence of at least 50% sequence identity, based on the Clustal V method of alignment, when compared to SEQ ID NO:18, 20, 24, 26, 28, 30, or 32; or
(b) a suppression DNA construct comprising at least one regulatory element operably linked to: (i) all or part of: (A) a nucleic acid sequence encoding a polypeptide having an amino acid sequence of at least 50% sequence identity, based on the Clustal V method of alignment, when compared to SEQ ID NO:18, 20, 24, 26, 28, 30, or 32, or (B) a full complement of the nucleic acid sequence of (b)(i)(A); or (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes an LNT2 or LNT2-like polypeptide, and wherein said plant exhibits an alteration of at least one agronomic characteristic when compared to a control plant not comprising said recombinant DNA construct.

In another embodiment, a method of increasing nitrogen stress tolerance in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO:18, 20, 24, 26, 28, 30, or 32; (b) regenerating a transgenic plant from the regenerable plant cell after step (a), wherein the transgenic plant comprises in its genome the recombinant DNA construct and exhibits increased nitrogen stress tolerance when compared to a control plant not comprising the recombinant DNA construct; and optionally, (c) obtaining a progeny plant derived from the transgenic plant, wherein said progeny plant comprises in its genome the recombinant DNA construct and exhibits increased nitrogen stress tolerance when compared to a control plant not comprising the recombinant DNA construct.

In another embodiment, a method of evaluating nitrogen stress tolerance in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO:18, 20, 24, 26, 28, 30, or 32; (b) regenerating a transgenic plant from the regenerable plant cell after step (a), wherein the transgenic plant comprises in its genome the recombinant DNA construct; and (c) evaluating the transgenic plant for nitrogen stress tolerance compared to a control plant not comprising the recombinant DNA construct; and optionally, (d) obtaining a progeny plant derived from the transgenic plant, wherein the progeny plant comprises in its genome the recombinant DNA construct; and optionally, (e) evaluating the progeny plant for nitrogen stress tolerance compared to a control plant not comprising the recombinant DNA construct.

In another embodiment, a method of evaluating nitrogen stress tolerance in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO:18, 20, 24, 26, 28, 30, or 32; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) evaluating the progeny plant for nitrogen stress tolerance compared to a control plant not comprising the recombinant DNA construct.

In another embodiment, a method of determining an alteration of an agronomic characteristic in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO:18, 20, 24, 26, 28, 30, or 32; (b) regenerating a transgenic plant from the regenerable plant cell after step (a), wherein the transgenic plant comprises in its genome the recombinant DNA construct; and (c) determining whether the transgenic plant exhibits an alteration of at least one agronomic characteristic when compared to a control plant not comprising the recombinant DNA construct; and optionally, (d) obtaining a progeny plant derived from the transgenic plant, wherein the progeny plant comprises in its genome the recombinant DNA construct; and optionally, (e) determining whether the progeny plant exhibits an alteration of at least one agronomic characteristic when compared, optionally under nitrogen limiting conditions, to a control plant not comprising the recombinant DNA construct.

In another embodiment, a method of determining an alteration of an agronomic characteristic in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO:18, 20, 24, 26, 28, 30, or 32; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) determining whether the progeny plant exhibits an alteration of at least one agronomic characteristic when compared optionally under nitrogen limiting conditions, to a control plant not comprising the recombinant DNA construct.

In another embodiment, a method of determining an alteration of an agronomic characteristic in a plant, comprising:
(a) introducing into a regenerable plant cell a suppression DNA construct comprising at least one regulatory element operably linked to:
  (i) all or part of: (A) a nucleic acid sequence encoding a polypeptide having an amino acid sequence of at least 50% sequence identity, based on the Clustal V method of alignment, when compared to SEQ ID NO:18, 20, 24, 26, 28, 30, or 32, or (B) a full complement of the nucleic acid sequence of (b)(i)(A); or
  (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes an LNT2 or LNT2-like polypeptide;
(b) regenerating a transgenic plant from the regenerable plant cell after step (a), wherein the transgenic plant comprises in its genome the suppression DNA construct; and
(c) determining whether the transgenic plant exhibits an alteration of at least one agronomic characteristic when compared to a control plant not comprising the suppression DNA construct;
and optionally, (d) obtaining a progeny plant derived from the transgenic plant, wherein the progeny plant comprises in its genome the suppression DNA construct;
and optionally, (e) determining whether the progeny plant exhibits an alteration of at least one agronomic characteristic when compared optionally under nitrogen limiting conditions, to a control plant not comprising the suppression DNA construct.

In another embodiment, a method of determining an alteration of an agronomic characteristic in a plant, comprising:
(a) introducing into a regenerable plant cell a suppression DNA construct comprising at least one regulatory element operably linked to:
  (i) all or part of: (A) a nucleic acid sequence encoding a polypeptide having an amino acid sequence of at least 50% sequence identity, based on the Clustal V method of alignment, when compared to SEQ ID NO:18, 20, 24, 26, 28, 30, or 32, or (B) a full complement of the nucleic acid sequence of (b)(i)(A); or
  (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes an LNT2 or LNT2-like polypeptide;
(b) regenerating a transgenic plant from the regenerable plant cell after step (a), wherein the transgenic plant comprises in its genome the suppression DNA construct and exhibits an alteration of at least one agronomic trait when compared to a control plant not comprising the suppression DNA construct;
(c) obtaining a progeny plant derived from the transgenic plant, wherein the progeny plant comprises in its genome the suppression DNA construct; and
(d) determining whether the progeny plant exhibits an alteration of at least one agronomic characteristic when compared to a control plant not comprising the suppression DNA construct;
and optionally, (e) determining whether the transgenic plant exhibits an alteration of at least one agronomic characteristic when compared, optionally, under nitrogen limiting conditions, to a control plant not comprising the recombinant DNA construct.

In another embodiment, the present invention concerns an isolated polynucleotide comprising: (a) a nucleotide sequence encoding a polypeptide, wherein the amino acid sequence of the polypeptide and the amino acid sequence of SEQ ID NO:18, 24, or 26 have at least 85%, 86%, 87%, 88%, 89%, 90%, 91%, 92%, 93%, 94%, 95%, 96%, 97%, 98%, 99%, or 100% sequence identity based on the Clustal V alignment method, or (b) the complement of the nucleotide sequence, wherein the complement and the nucleotide sequence contain the same number of nucleotides and are 100% complementary. The polypeptide In an embodiment comprises the amino acid sequence of SEQ ID NO:18, 24, or 26, and the nucleotide sequence comprises the nucleotide sequence of SEQ ID NO:17, 23, or 25.

BRIEF DESCRIPTION OF THE FIGURES AND SEQUENCE LISTINGS

The invention can be more fully understood from the following detailed description and the accompanying drawings and Sequence Listing which form a part of this application.

FIG. 11 shows a typical grid pattern for five lines (labeled 1 through 5—eleven individuals for each line), plus wild-type control C1 (nine individuals), used in screens.

FIG. 13 shows the growth medium used for semi-hydroponics maize growth in Example 18.

FIGS. 14A and 14B show the multiple alignment of the full length amino acid sequences of the *Arabidopsis thaliana* LNT2 polypeptide (SEQ ID NO:28) and the LNT2 homologs (SEQ ID NOs: 18, 20, 24, 26, 30, 32, 33, and 34).

FIG. 15 shows a chart of the percent sequence identity and the divergence values for each pair of amino acids sequences displayed in FIGS. 14A and 14B.

Figure 1:
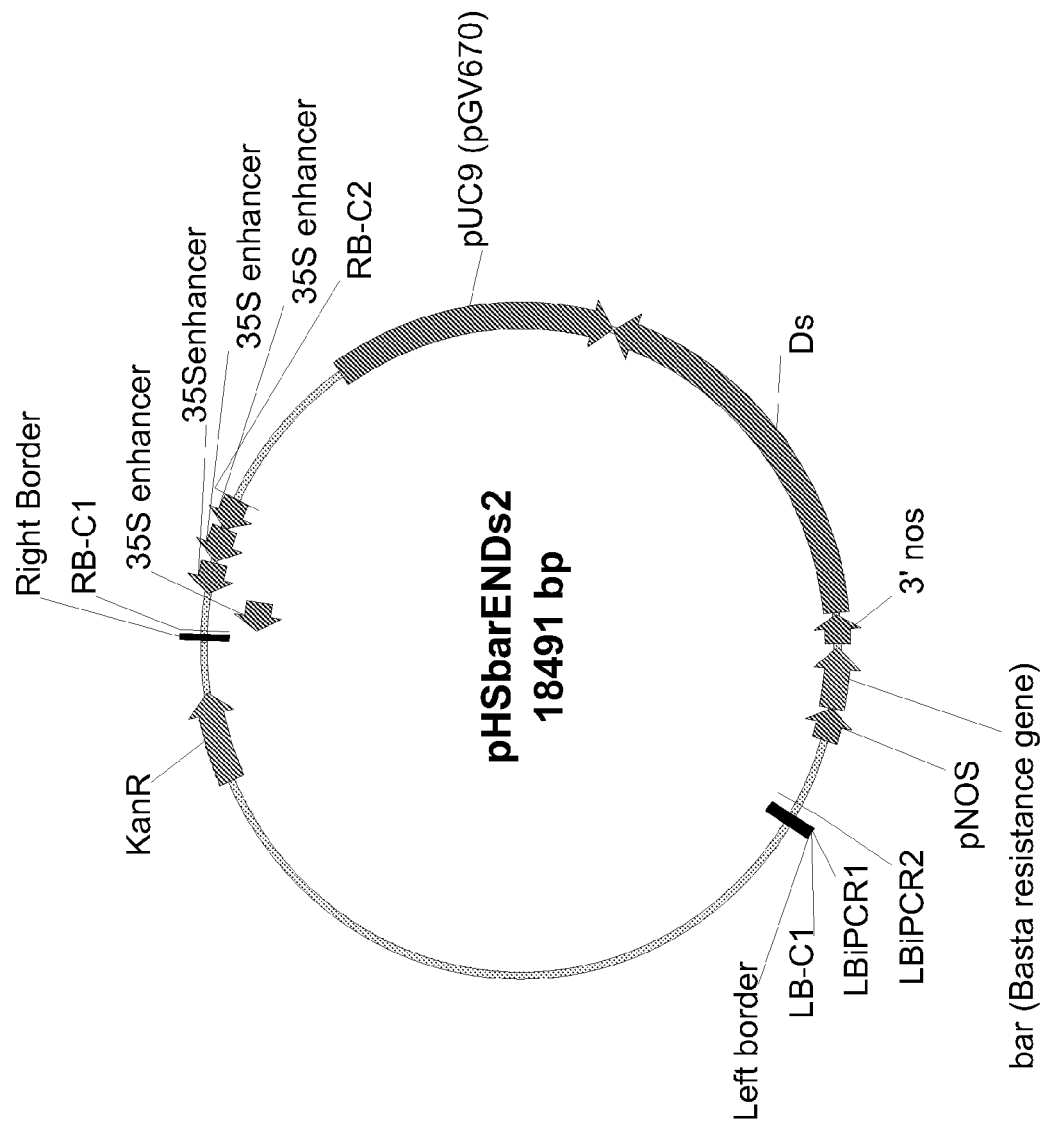
FIG. 1 shows a schematic of the pHSbarENDs2 activation tagging construct used to make the *Arabidopsis* populations (SEQ ID NO:1).

FIG. 16 shows the results from screening of Gaspe Flint derived maize lines under reduced nitrogen (1 mM $KNO_3$) and optimal nitrogen (6.5 mM $KNO_3$) conditions. Four events containing PHP29689 were evaluated for a number of traits. Event means were compared to that of the segregant nulls. A p-value $\leq 0.1$ was used as the cut off.

FIG. 17 shows the results from screening of Gaspe Flint derived maize lines under reduced nitrogen (1 mM $KNO_3$) and optimal nitrogen (6.5 mM $KNO_3$) conditions. All events containing PHP29689 were considered in the analysis. For each variable, the construct mean was compared to that of the construct null. A p-value $\leq 0.1$ was used as the cut off.

FIG. 18 shows the yield trial results for PHP28840-containing plants under low nitrogen conditions. The yield values in gray represent significant increases, and the yield values in black represent significant decreases. The remaining values represent non-significant differences.

FIG. 19 shows the yield trial results for PHP28841-containing plants under low nitrogen conditions. The yield values in gray represent significant increases, and the yield values in black represent significant decreases. The remaining values represent non-significant differences.

FIG. 20 shows the yield trial results for PHP28840-containing plants under normal nitrogen conditions. The yield values in gray represent significant increases, and the yield values in black represent significant decreases. The remaining values represent non-significant differences.

FIG. 21 shows the yield trial results for PHP28841-containing plants under normal nitrogen conditions. The yield values in gray represent significant increases, and the yield values in black represent significant decreases. The remaining values represent non-significant differences.

FIG. 22 shows the results of the NUE seedling assay for plants containing either PHP28840 (expression cassette=Int2-3) or PHP28841 (expression cassette=Int2-2).

The sequence descriptions and Sequence Listing attached hereto comply with the rules governing nucleotide and/or amino acid sequence disclosures in patent applications as set forth in 37 C.F.R. §1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. §1.822.

Table 1 lists certain polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing.

TABLE 1

Low Nitrogen tolerant proteins (LNT)

| | | SEQ ID NO: | |
|---|---|---|---|
| | Clone Designation | Nucleotide | Amino Acid |
| LNT2-like | cpg1c.pk013.o6:fis | 17 | 18 |
| LNT2-like | rca1n.pk001.f6:fis | 19 | 20 |
| LNT2-like | sfl1n1.pk002.j1 | 21 | |
| LNT2-like | sds1f.pk001.k5 | 22 | |

SEQ ID NO:1 is the nucleotide sequence of the pHSbarENDs2 activation tagging vector (FIG. 1).

Figure 2:
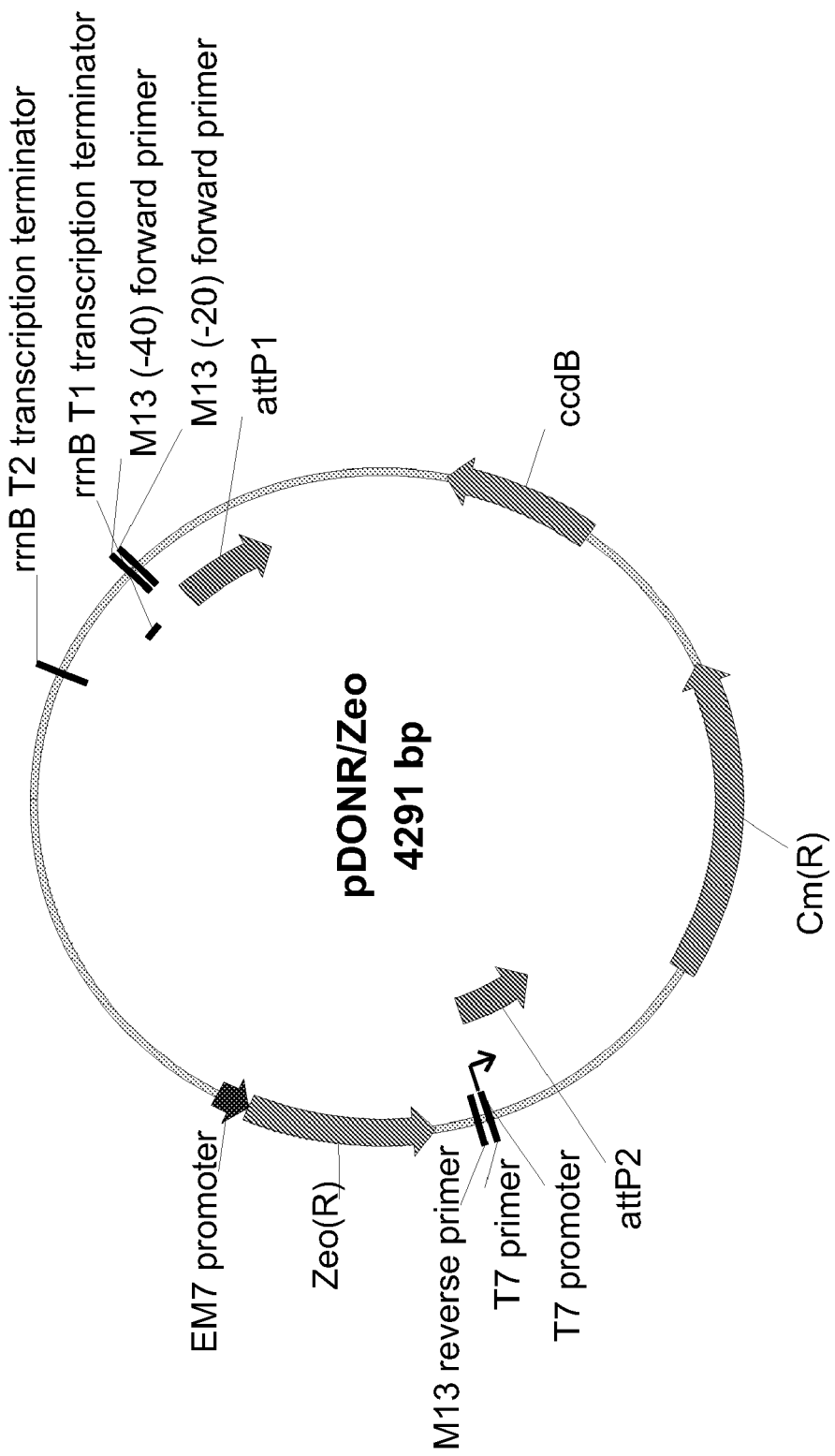
FIG. 2 shows a schematic of the vector pDONR™ Zeo (SEQ ID NO:2), GATEWAY® donor vector. The attP1 site is at nucleotides 570-801; the attP2 site is at nucleotides 2754-2985 (complementary strand).

SEQ ID NO:2 is the nucleotide sequence of the pDONR™ Zeo construct (FIG. 2).

Figure 3:
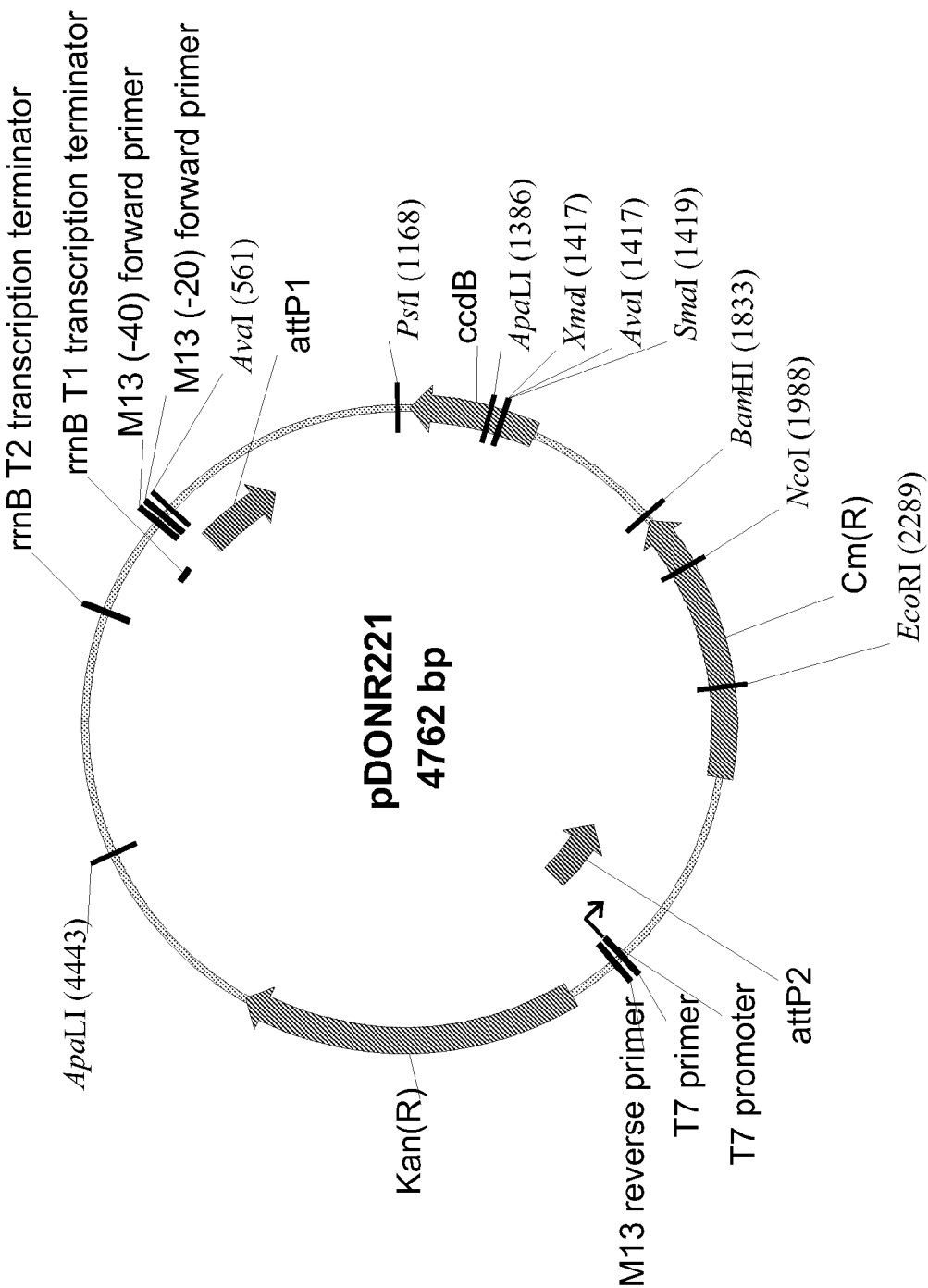
FIG. 3 shows a schematic of the vector pDONR™ 221 (SEQ ID NO:3), GATEWAY® donor vector. The attP1 site is at nucleotides 570-801; the attP2 site is at nucleotides 2754-2985 (complementary strand).

SEQ ID NO:3 is the nucleotide sequence of the pDONR™ 221 construct (FIG. 3).

Figure 4:
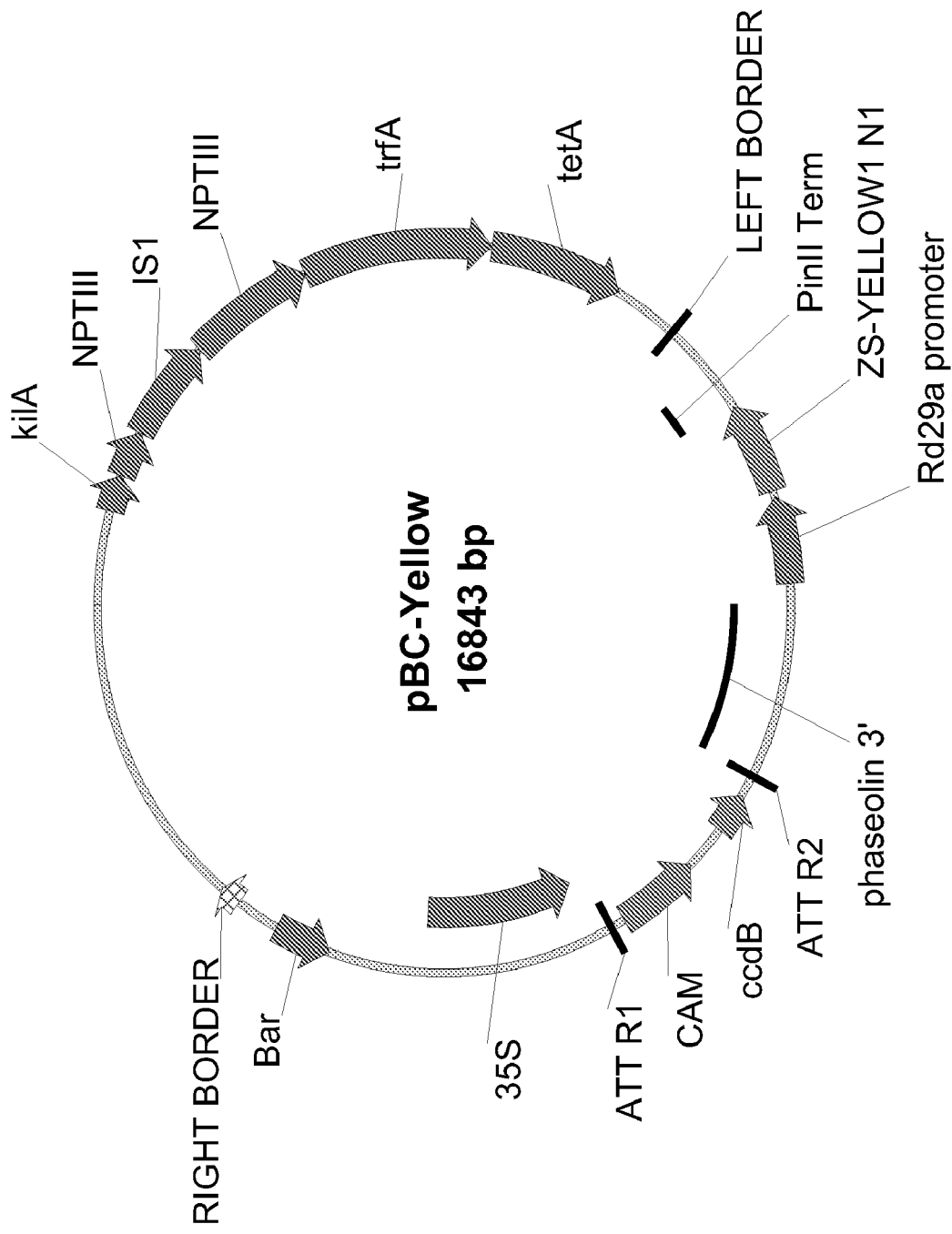
FIG. 4 shows a schematic of the vector pBC-yellow (SEQ ID NO:4), a destination vector for use in construction of expression vectors for *Arabidopsis*. The attR1 site is at nucleotides 11276-11399 (complementary strand); the attR2 site is at nucleotides 9695-9819 (complementary strand).

SEQ ID NO:4 is the nucleotide sequence of the pBC-yellow vector (FIG. 4).

Figure 5:
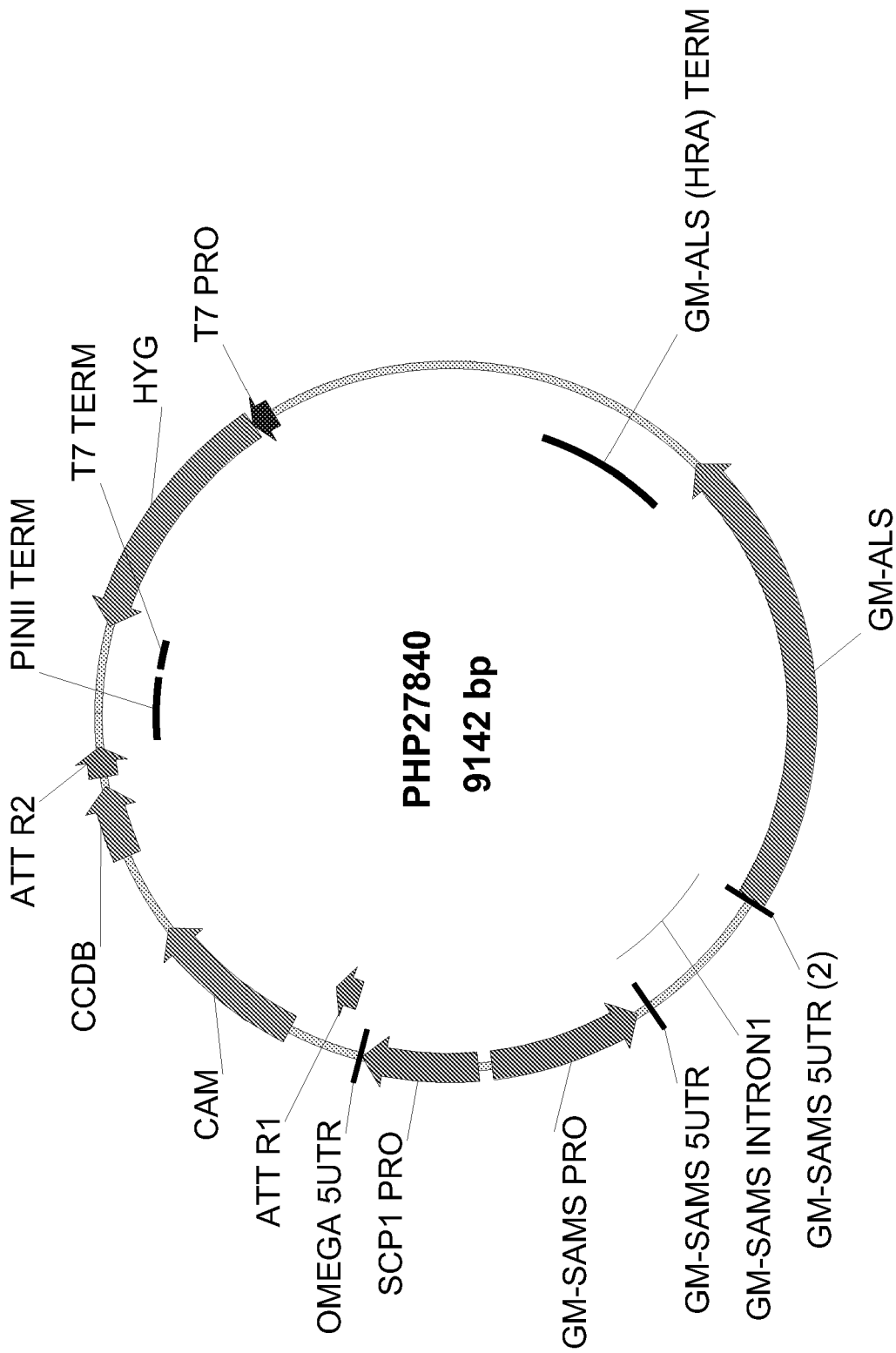
FIG. 5 shows a schematic of the vector PHP27840 (SEQ ID NO:5), a destination vector for use in construction of expression vectors for soybean. The attR1 site is at nucleotides 7310-7434; the attR2 site is at nucleotides 8890-9014.

SEQ ID NO:5 is the nucleotide sequence of the PHP27840 vector (FIG. 5).

Figure 6:
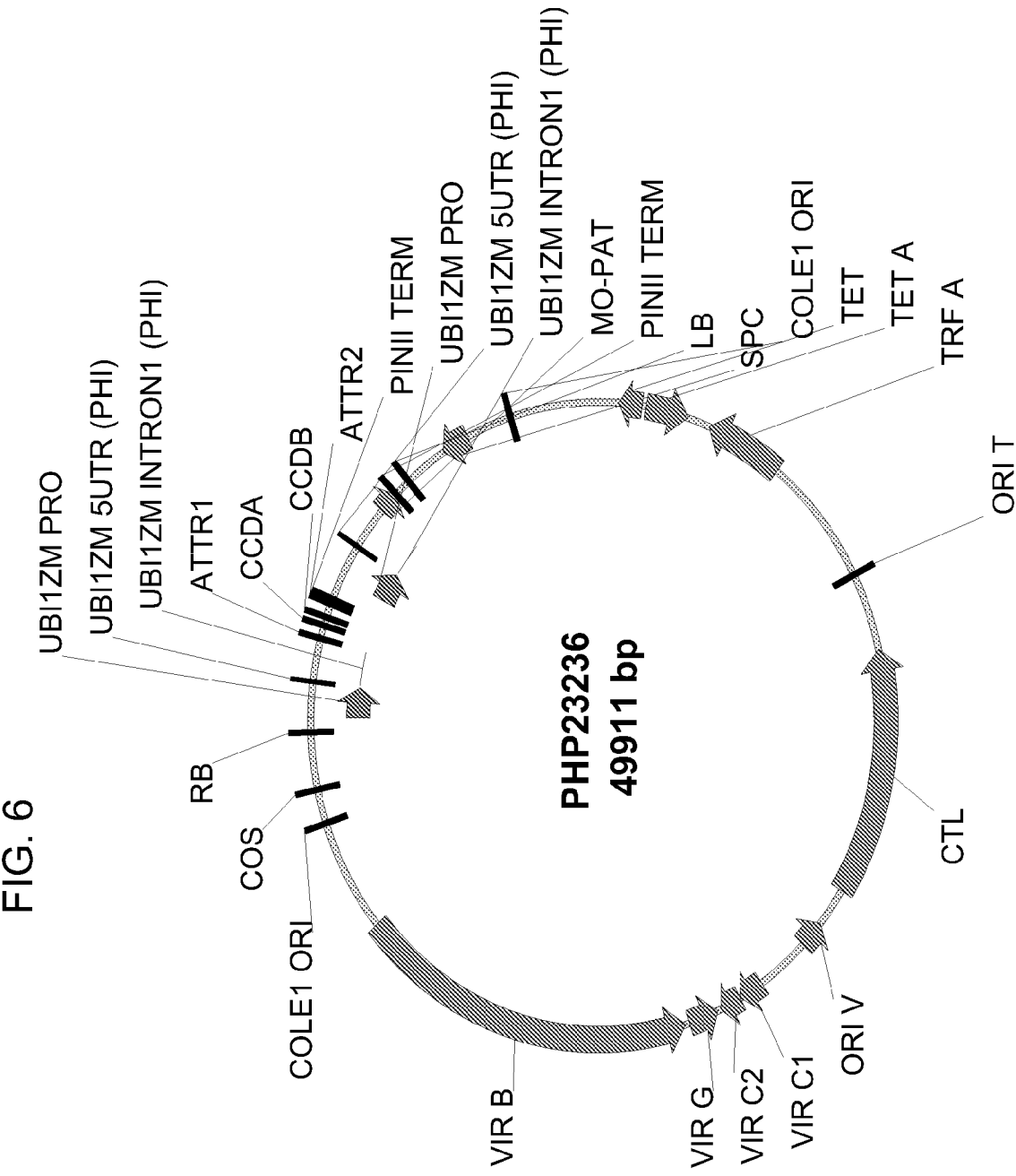
FIG. 6 shows a schematic of the vector PHP23236 (SEQ ID NO:6), a destination vector for use in construction of expression vectors for Gaspe Flint derived maize lines. The attR1 site is at nucleotides 2006-2130; the attR2 site is at nucleotides 2899-3023.

SEQ ID NO:6 is the nucleotide sequence of the destination vector PHP23236 (FIG. 6).

Figure 7:
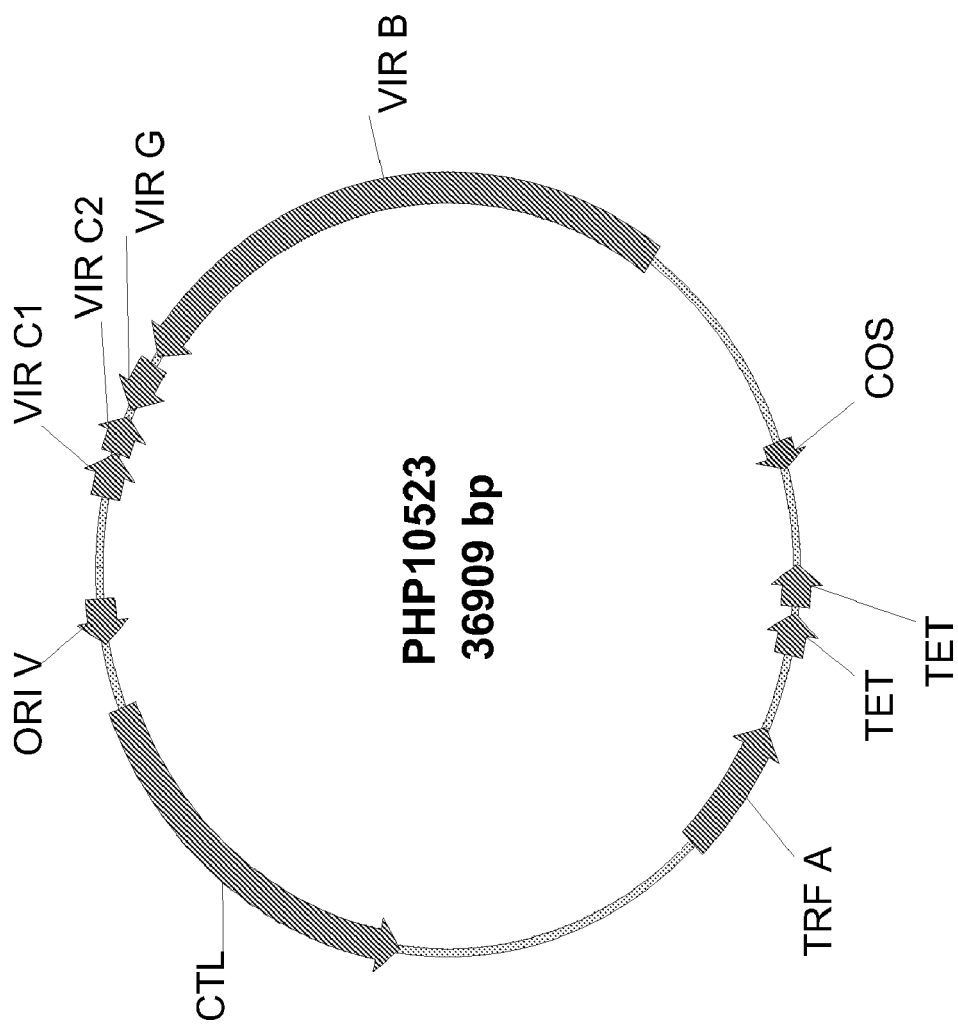
FIG. 7 shows a schematic of the vector PHP10523 (SEQ ID NO:7), a plasmid DNA present in *Agrobacterium* strain LBA4404 (Komari et al., *Plant J.* 10:165-174 (1996); NCBI General Identifier No. 59797027).

SEQ ID NO:7 is the nucleotide sequence of the PHP10523 vector (FIG. 7).

Figure 8:
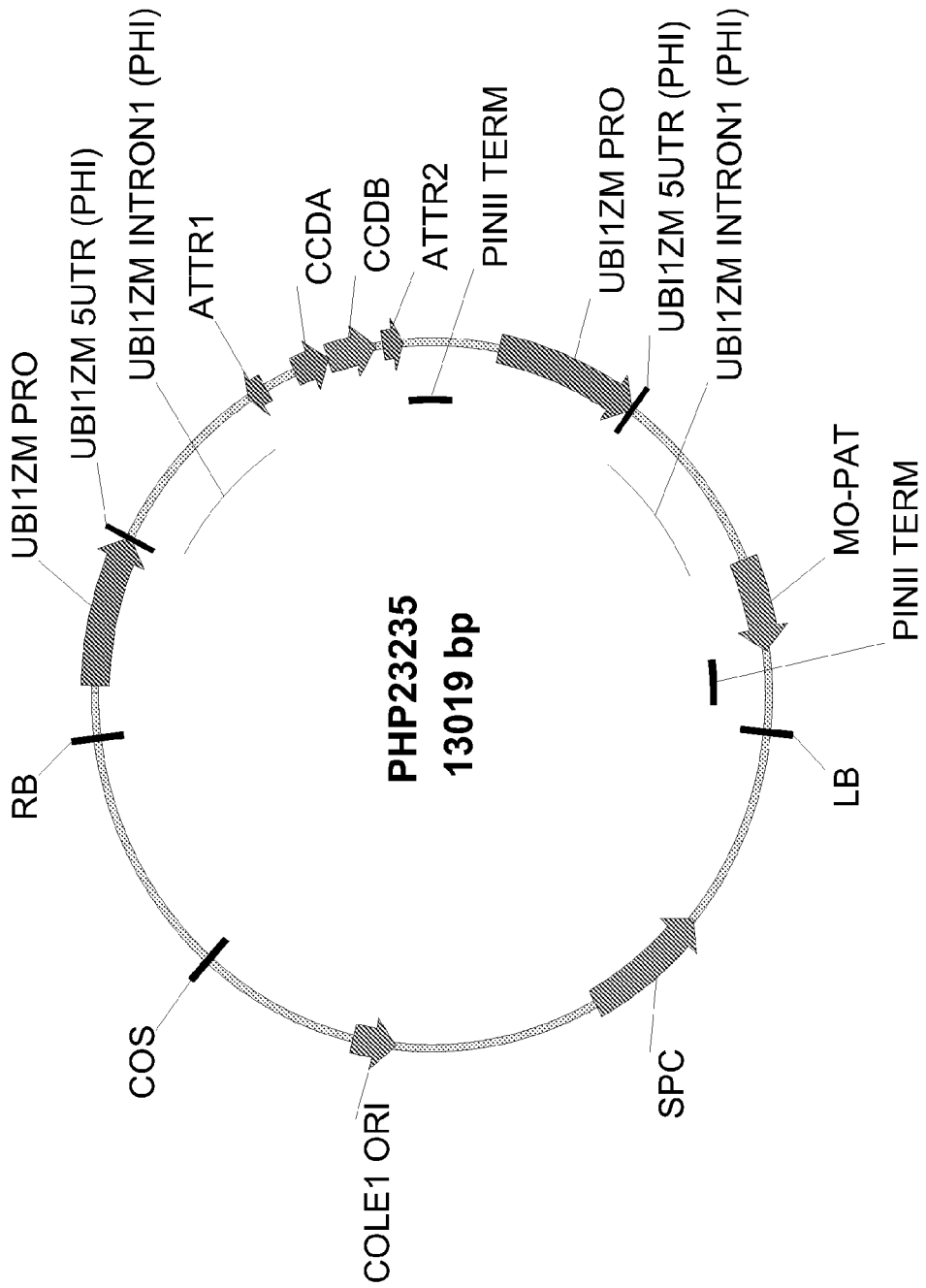
FIG. 8 shows a schematic of the vector PHP23235 (SEQ ID NO:8), a vector used to construct the destination vector PHP23236.

SEQ ID NO:8 is the nucleotide sequence of the PHP23235 vector (FIG. 8).

Figure 9:
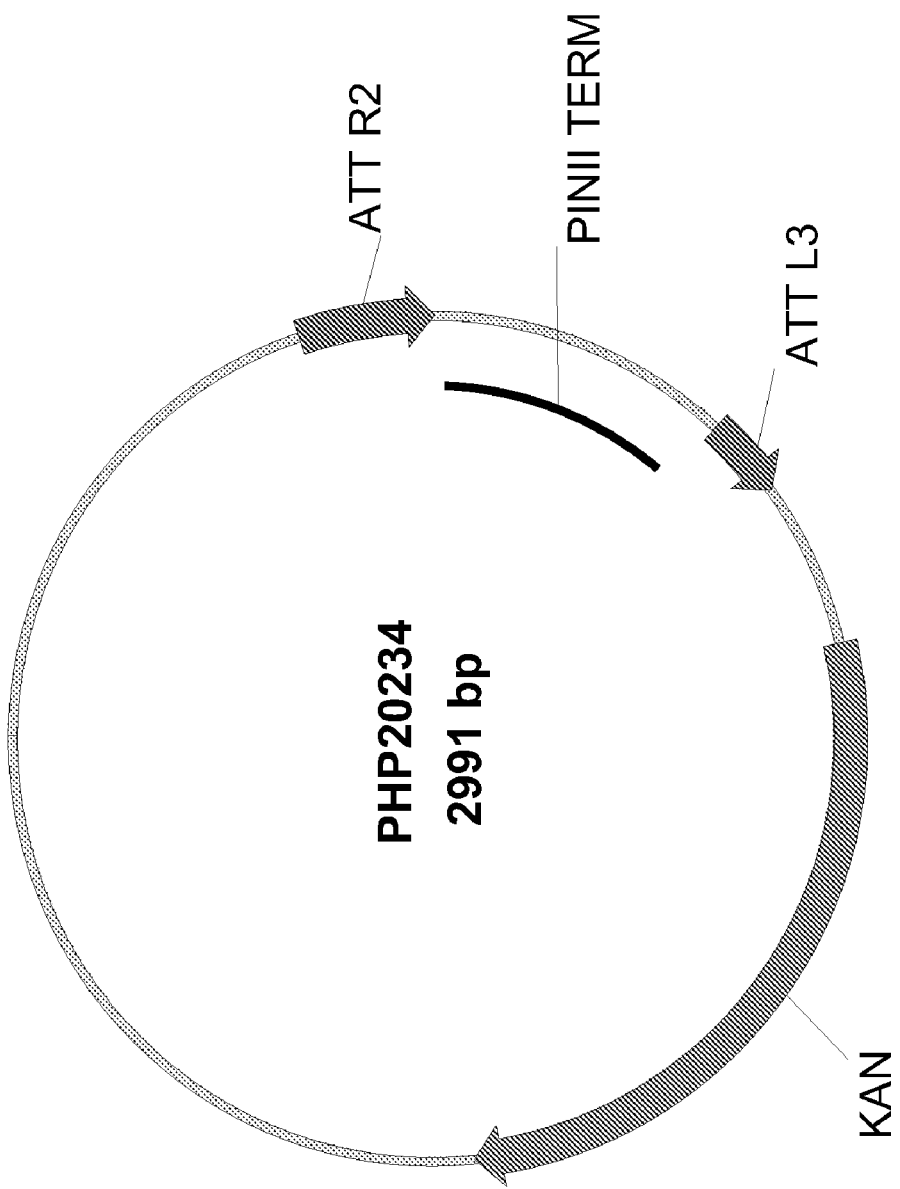
FIG. 9 shows a schematic of the vector PHP20234 (SEQ ID NO:9).

SEQ ID NO:9 is the nucleotide sequence of the PHP20234 vector (FIG. 9).

Figure 10:
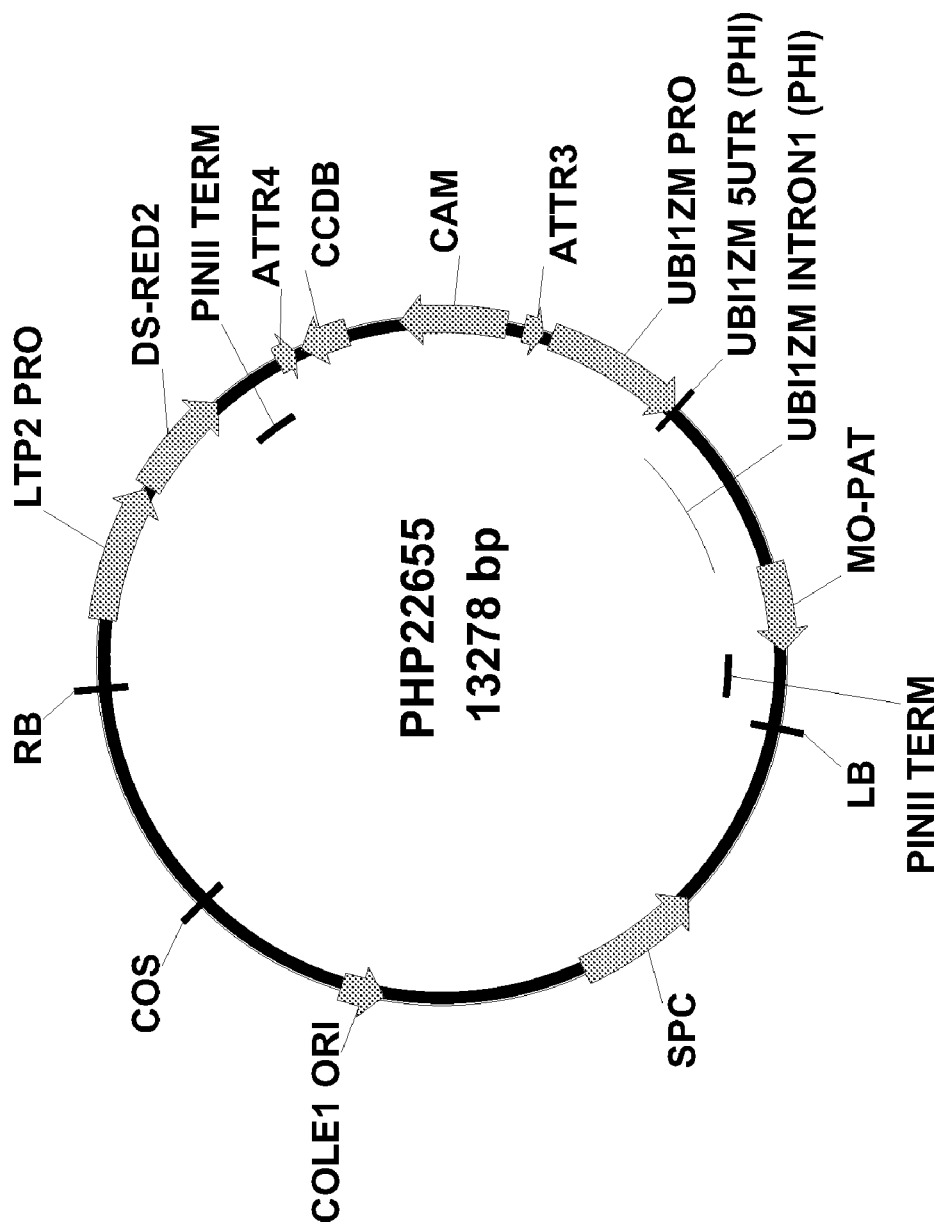
FIG. 10 shows a schematic of the destination vector PHP22655 (SEQ ID NO:10).

SEQ ID NO:10 is the nucleotide sequence of the destination vector PHP22655 (FIG. 10).

SEQ ID NO:11 is the nucleotide sequence of the polylinker used to substitute the PacI restriction site at position 5775 of pHSbarENDs2.

SEQ ID NO:12 is the nucleotide sequence of the attB1 sequence.

SEQ ID NO:13 is the nucleotide sequence of the attB2 sequence.

SEQ ID NO:14 is the nucleotide sequence of the entry clone PHP23112.

SEQ ID NO:15 is the forward primer VC062 in Example 5.

SEQ ID NO:16 is the reverse primer VC063 in Example 5.

SEQ ID NOs:17-22 (see Table 1).

SEQ ID NO:23 is the consensus nucleotide sequence of a contig, referred to herein as PSO415619, containing BI316280 (NCBI General Identifier No. 14990607), CD401-485 (NCBI General Identifier No. 31459457) and sfl1n1.pk002.j1 (SEQ ID NO:21).

SEQ ID NO:24 is the amino acid sequence of the polypeptide encoded by PSO415619 (SEQ ID NO:23).

SEQ ID NO:25 is the consensus nucleotide sequence of a contig, referred to herein as PSO415620, containing CX548557 (NCBI General Identifier No. 57575582) and sds1f.pk001.k5 (SEQ ID NO:22).

SEQ ID NO:26 is the amino acid sequence of the polypeptide encoded by PSO415620 (SEQ ID NO:25).

SEQ ID NO:27 is the nucleotide sequence of the gene that encodes the *Arabidopsis thaliana* "unknown protein" (LNT2) (At5g50930; NCBI General Identifier No. 145359102).

SEQ ID NO:28 is the amino acid sequence of the *Arabidopsis thaliana* "unknown protein" (LNT2) (At5g50930; NCBI General Identifier No. 15241317).

SEQ ID NO:29 is the nucleotide sequence of an alternative splice variant (referred to herein as "Int2-2") of At5g50930.

SEQ ID NO:30 is the amino acid sequence of the polypeptide encoded by Int2-2 (SEQ ID NO:29) and is referred to herein as "LNT2-2".

SEQ ID NO:31 is the nucleotide sequence of a second alternative splice variant (referred to herein as "Int2-3") of At5g50930.

SEQ ID NO:32 is the amino acid sequence of the polypeptide encoded by Int2-3 (SEQ ID NO:29) and is referred to herein as "LNT2-3". SEQ ID NO:32 is 100% identical to SEQ ID NO:52198 in EP1033405 based on the Clustal V method of alignment, using default parameters.

SEQ ID NO:33 is the amino acid sequence of the *Oryza sativa* "unknown protein" (NCBI General Identifier No. 38347162).

SEQ ID NO:34 is the amino acid sequence of the *Vitis vinifera* "hypothetical protein" (NCBI General Identifier No. 147791927).

SEQ ID NO:35 is the nucleotide sequence of the At5g50930-5' attB forward primer.

SEQ ID NO:36 is the nucleotide sequence of the At5g50930-3' attB reverse primer.

DETAILED DESCRIPTION OF OTHER EMBODIMENTS

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

"Nitrogen limiting conditions" refers to conditions where the amount of total available nitrogen (e.g., from nitrates, ammonia, or other known sources of nitrogen) is not sufficient to sustain optimal plant growth and development. One skilled in the art would recognize conditions where total available nitrogen is sufficient to sustain optimal plant growth and development. One skilled in the art would recognize what constitutes sufficient amounts of total available nitrogen, and what constitutes soils, media and fertilizer inputs for providing nitrogen to plants. Nitrogen limiting conditions will vary depending upon a number of factors, including but not limited to, the particular plant and environmental conditions.

"Agronomic characteristic" is a measurable parameter including but not limited to, greenness, yield, growth rate, biomass, fresh weight at maturation, dry weight at maturation, fruit yield, seed yield, total plant nitrogen content, fruit nitrogen content, seed nitrogen content, nitrogen content in vegetative tissue, whole plant amino acid content, vegetative tissue free amino acid content, fruit free amino acid content, seed free amino acid content, total plant protein content, fruit protein content, seed protein content, protein content in a vegetative tissue, drought tolerance, nitrogen uptake, resistance to root lodging, harvest index, stalk lodging, plant height, ear height, and ear length.

"Harvest index" refers to the grain weight divided by the total plant weight.

"Int2" refers to the *Arabidopsis thaliana* gene locus, At5g50930 (SEQ ID NO: 27). "LNT2" refers to the protein (SEQ ID NO:28) encoded by SEQ ID NO:27.

"Int2-2" (SEQ ID NO:29) and "Int2-3" (SEQ ID NO:31) are naturally occurring alternative splice variants of the At5g50930 gene. "LNT2-2" (SEQ ID NO:30) and "LNT2-3" (SEQ ID NO:32) refer to the proteins encoded by "Int2-2" and "Int2-3", respectively.

"Int2-like" refers to nucleotide homologs from different species, such as corn and soybean, of the *Arabidopsis thaliana* "Int2" locus At5g50930 (SEQ ID NO: 28) and includes without limitation any of the nucleotide sequences of SEQ ID NOs: 17, 19, 23, and 25.

"LNT2-like" refers to protein homologs from different species, such as corn and soybean, of the *Arabidopsis thaliana* "LNT2" (SEQ ID NO: 28) and includes without limitation any of the amino acid sequences of SEQ ID NOs: 18, 20, 24, and 26.

"Alternative splice variants" used herein refers to alternative forms of RNA transcribed from a gene. Splice variation naturally occurs as a result of alternative sites being spliced within a single transcribed RNA molecule or between separately transcribed RNA molecules, and may result in several different forms of mRNA transcribed from the same gene. Thus, splice variants may encode polypeptides having different amino acid sequences, which may or may not have similar functions in the organism.

"Nitrogen stress tolerance" is a trait of a plant and refers to the ability of the plant to survive under nitrogen limiting conditions.

"Increased nitrogen stress tolerance" of a plant is measured relative to a reference or control plant, and means that the nitrogen stress tolerance of the plant is increased by any amount or measure when compared to the nitrogen stress tolerance of the reference or control plant.

A "nitrogen stress tolerant plant" is a plant that exhibits nitrogen stress tolerance. A nitrogen stress tolerant plant is In an embodiment a plant that exhibits an increase in at least one agronomic characteristic relative to a control plant under nitrogen limiting conditions.

"Environmental conditions" refer to conditions under which the plant is grown, such as the availability of water, availability of nutrients (for example nitrogen), or the presence of insects or disease.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. In an embodiment, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" and "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, *CABIOS.* 5:151-153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Turning now to several embodiments:

Other embodiments include isolated polynucleotides and polypeptides, recombinant DNA constructs, compositions (such as plants or seeds) comprising these recombinant DNA constructs, and methods utilizing these recombinant DNA constructs.

Other Isolated Polynucleotides and Polypeptides

The present invention includes the following other isolated polynucleotides and polypeptides:

An isolated polynucleotide comprising: (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 24, 26, 28, 30, or 32; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs (including suppression DNA constructs) of the present invention. The polypeptide can be an LNT2 or LNT2-like protein.

An isolated polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 24, 26, 28, 30, or 32. The polypeptide is can be an LNT2 or LNT2-like protein.

An isolated polynucleotide comprising (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:17, 19, 23, 25, 27, 29, or 31; or (ii) a full complement of the nucleic acid sequence of (i). Any of the foregoing isolated polynucleotides may be utilized in any recombinant DNA constructs (including suppression DNA constructs) of the present invention. The isolated polynucleotide can be encodes an LNT2 or LNT2-like protein.

Other Recombinant DNA Constructs and Suppression DNA Constructs

In one aspect, the present invention includes recombinant DNA constructs (including suppression DNA constructs).

In one other embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 24, 26, 28, 30, or 32; or (ii) a full complement of the nucleic acid sequence of (i).

In another other embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:17, 19, 23, 25, 27, 29, or 31; or (ii) a full complement of the nucleic acid sequence of (i).

FIGS. 14A and 14B show the multiple alignment of the amino acid sequences of SEQ ID NOs: 18, 20, 24, 26, 28, 30, 32, 33, and 34 The multiple alignment of the sequences was performed using the MEGALIGN® program of the LASERGENE® bioinformatics computing suite (DNASTAR® Inc., Madison, Wis.); in particular, using the Clustal V method of alignment (Higgins and Sharp, CABIOS. 5:151-153 (1989)) with the multiple alignment default parameters of GAP PENALTY=10 and GAP LENGTH PENALTY=10, and the pairwise alignment default parameters of KTUPLE=1, GAP PENALTY=3, WINDOW=5 and DIAGONALS SAVED=5.

FIG. 15 is a chart of the percent sequence identity and the divergence values for each pair of amino acids sequences displayed in FIGS. 14A and 14B.

In another other embodiment, a recombinant DNA construct comprises a polynucleotide operably linked to at least one regulatory sequence (e.g., a promoter functional in a plant), wherein said polynucleotide encodes an LNT2 or LNT2-like protein.

In another aspect, the present invention includes suppression DNA constructs.

A suppression DNA construct can comprise at least one regulatory sequence (in an embodiment a promoter functional in a plant) operably linked to (a) all or part of: (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 24, 26, 28, 30, or 32; or (ii) a full complement of the nucleic acid sequence of (a)(i); or (b) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT2 or LNT2-like protein; or (c) all or part of: (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:17, 19, 23, 25, 27, 29, or 31; or (ii) a full complement of the nucleic acid sequence of (c)(i). The suppression DNA construct in an embodiment, comprises a cosuppression construct, antisense construct, viral-suppression construct, hairpin suppression construct, stem-loop suppression construct, double-stranded RNA-producing construct, RNAi construct, or small RNA construct (e.g., an siRNA construct or an miRNA construct).

It is understood, as those skilled in the art will appreciate, that the invention encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, includes lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al., Plant J. 16:651-659 (1998); and Gura, Nature 404:804-808 (2000)).

Another variation describes the use of plant viral sequences to direct the suppression of proximal mRNA encoding sequences (PCT Publication No. WO 98/36083 published on Aug. 20, 1998).

Previously described is the use of "hairpin" structures that incorporate all, or part, of an mRNA encoding sequence in a complementary orientation that results in a potential "stem-loop" structure for the expressed RNA (PCT Publication No. WO 99/53050 published on Oct. 21, 1999). In this case the stem is formed by polynucleotides corresponding to the gene of interest inserted in either sense or anti-sense orientation with respect to the promoter and the loop is formed by some polynucleotides of the gene of interest, which do not have a complement in the construct. This increases the frequency of cosuppression or silencing in the recovered transgenic plants.

For a review of hairpin suppression see Wesley, S. V. et al. (2003) Methods in Molecular Biology, Plant Functional Genomics: Methods and Protocols 236:273-286.

A construct where the stem is formed by at least 30 nucleotides from a gene to be suppressed and the loop is formed by a random nucleotide sequence has also effectively been used for suppression (PCT Publication No. WO 99/61632 published on Dec. 2, 1999).

The use of poly-T and poly-A sequences to generate the stem in the stem-loop structure has also been described (PCT Publication No. WO 02/00894 published Jan. 3, 2002).

Yet another variation includes using synthetic repeats to promote formation of a stem in the stem-loop structure. Transgenic organisms prepared with such recombinant DNA fragments have been shown to have reduced levels of the protein encoded by the nucleotide fragment forming the loop as described in PCT Publication No. WO 02/00904, published Jan. 3, 2002.

RNA interference refers to the process of sequence-specific post-transcriptional gene silencing in animals mediated by short interfering RNAs (siRNAs) (Fire et al., Nature 391: 806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., Trends Genet. 15:358 (1999)). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Berstein et al., Nature 409:363 (2001)). Short interfering RNAs derived from dicer activity are typically about 21 to about 23 nucleotides in length and comprise about 19 base pair duplexes (Elbashir et al., Genes Dev. 15:188 (2001)). Dicer has also been implicated in the excision of 21- and 22-nucleotide small temporal RNAs (stRNAs) from precursor RNA of conserved structure that are implicated in translational control (Hutvagner et al., Science 293:834 (2001)). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex. In addition, RNA interference can also involve small RNA (e.g., miRNA) mediated gene silencing, presumably through cellular mechanisms that regulate chromatin structure and thereby prevent transcription of target gene sequences (see, e.g., Allshire, Science 297:1818-1819 (2002); Volpe et al., Science 297:1833-1837 (2002); Jenuwein, Science 297:2215-2218 (2002); and Hall et al., Science 297:2232-2237 (2002)). As such, miRNA molecules of the invention can be used to mediate gene silencing via interaction with RNA transcripts or alternately by interaction with particular gene sequences, wherein such interaction results in gene silencing either at the transcriptional or post-transcriptional level.

RNAi has been studied in a variety of systems. Fire et al. (*Nature* 391:806 (1998)) were the first to observe RNAi in *Caenorhabditis elegans*. Wianny and Goetz (*Nature Cell Biol.* 2:70 (1999)) describe RNAi mediated by dsRNA in mouse embryos. Hammond et al. (*Nature* 404:293 (2000)) describe RNAi in *Drosophila* cells transfected with dsRNA. Elbashir et al., (*Nature* 411:494 (2001)) describe RNAi induced by introduction of duplexes of synthetic 21-nucleotide RNAs in cultured mammalian cells including human embryonic kidney and HeLa cells.

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

It is thought that sequence complementarity between small RNAs and their RNA targets helps to determine which mechanism, RNA cleavage or translational inhibition, is employed. It is believed that siRNAs which are perfectly complementary with their targets, work by RNA cleavage. Some miRNAs have perfect or near-perfect complementarity with their targets, and RNA cleavage has been demonstrated for at least a few of these miRNAs. Other miRNAs have several mismatches with their targets, and apparently inhibit their targets at the translational level. Again, without being held to a particular theory on the mechanism of action, a general rule is emerging that perfect or near-perfect complementarity causes RNA cleavage, whereas translational inhibition is favored when the miRNA/target duplex contains many mismatches. The apparent exception to this is microRNA 172 (miR172) in plants. One of the targets of miR172 is APETALA2 (AP2), and although miR172 shares near-perfect complementarity with AP2 it appears to cause translational inhibition of AP2 rather than RNA cleavage.

MicroRNAs (miRNAs) are noncoding RNAs of about 19 to about 24 nucleotides (nt) in length that have been identified in both animals and plants (Lagos-Quintana et al., *Science* 294:853-858 (2001), Lagos-Quintana et al., *Curr. Biol.* 12:735-739 (2002); Lau et al., *Science* 294:858-862 (2001); Lee and Ambros, *Science* 294:862-864 (2001); Llave et al., *Plant Cell* 14:1605-1619 (2002); Mourelatos et al., *Genes. Dev.* 16:720-728 (2002); Park et al., *Curr. Biol.* 12:1484-1495 (2002); Reinhart et al., *Genes. Dev.* 16:1616-1626 (2002)). They are processed from longer precursor transcripts that range in size from approximately 70 to 200 nt, and these precursor transcripts have the ability to form stable hairpin structures. In animals, the enzyme involved in processing miRNA precursors is called dicer, an RNAse III-like protein (Grishok et al., *Cell* 106:23-34 (2001); Hutvagner et al., *Science* 293:834-838 (2001); Ketting et al., *Genes. Dev.* 15:2654-2659 (2001)). Plants also have a dicer-like enzyme, DCL1 (previously named CARPEL FACTORY/SHORT INTEGUMENTS1/SUSPENSOR1), and recent evidence indicates that it, like dicer, is involved in processing the hairpin precursors to generate mature miRNAs (Park et al., *Curr. Biol.* 12:1484-1495 (2002); Reinhart et al., *Genes Dev.* 16:1616-1626 (2002)). Furthermore, it is becoming clear from recent work that at least some miRNA hairpin precursors originate as longer polyadenylated transcripts, and several different miRNAs and associated hairpins can be present in a single transcript (Lagos-Quintana et al., *Science* 294:853-858 (2001); Lee et al., *EMBO J.* 21:4663-4670 (2002)). Recent work has also examined the selection of the miRNA strand from the dsRNA product arising from processing of the hairpin by DICER (Schwartz et al., *Cell* 115:199-208 (2003)). It appears that the stability (i.e., G:C versus A:U content, and/or mismatches) of the two ends of the processed dsRNA affects the strand selection, with the low stability end being easier to unwind by a helicase activity. The 5' end strand at the low stability end is incorporated into the RISC complex, while the other strand is degraded.

MicroRNAs (miRNAs) appear to regulate target genes by binding to complementary sequences located in the transcripts produced by these genes. In the case of lin-4 and let-7, the target sites are located in the 3' UTRs of the target mRNAs (Lee et al., *Cell* 75:843-854 (1993); Wightman et al., *Cell* 75:855-862 (1993); Reinhart et al., *Nature* 403:901-906 (2000); Slack et al., *Mol. Cell.* 5:659-669 (2000)), and there are several mismatches between the lin-4 and let-7 miRNAs and their target sites. Binding of the lin-4 or let-7 miRNA appears to cause downregulation of steady-state levels of the protein encoded by the target mRNA without affecting the transcript itself (Olsen and Ambros, *Dev. Biol.* 216:671-680 (1999)). On the other hand, recent evidence suggests that miRNAs can in some cases cause specific RNA cleavage of the target transcript within the target site, and this cleavage step appears to require 100% complementarity between the miRNA and the target transcript (Hutvagner and Zamore, *Science* 297:2056-2060 (2002); Llave et al., *Plant Cell* 14:1605-1619 (2002)). It seems likely that miRNAs can enter at least two pathways of target gene regulation: (1) protein downregulation when target complementarity is <100%; and (2) RNA cleavage when target complementarity is 100%. MicroRNAs entering the RNA cleavage pathway are analogous to the 21-25 nt short interfering RNAs (siRNAs) generated during RNA interference (RNAi) in animals and post-transcriptional gene silencing (PTGS) in plants, and likely are incorporated into an RNA-induced silencing complex (RISC) that is similar or identical to that seen for RNAi.

Identifying the targets of miRNAs with bioinformatics has not been successful in animals, and this is probably due to the fact that animal miRNAs have a low degree of complementarity with their targets. On the other hand, bioinformatic approaches have been successfully used to predict targets for plant miRNAs (Llave et al., *Plant Cell* 14:1605-1619 (2002); Park et al., *Curr. Biol.* 12:1484-1495 (2002); Rhoades et al., *Cell* 110:513-520 (2002)), and thus it appears that plant miRNAs have higher overall complementarity with their putative targets than do animal miRNAs. Most of these predicted target transcripts of plant miRNAs encode members of transcription factor families implicated in plant developmental patterning or cell differentiation.

Regulatory Sequences:

A recombinant DNA construct (including a suppression DNA construct) of the present invention can comprise at least one regulatory sequence.

A regulatory sequence is a promoter.

A number of promoters can be used in recombinant DNA constructs (and suppression DNA constructs) of the present invention. The promoters can be selected based on the desired outcome, and may include constitutive, tissue-specific, inducible, or other promoters for expression in the host organism.

High level, constitutive expression of the candidate gene under control of the 35S or UBI promoter may (or may not) have pleiotropic effects, although candidate gene efficacy may be estimated when driven by a constitutive promoter. Use of tissue-specific and/or stress-specific promoters may eliminate undesirable effects, but retain the ability to enhance nitrogen tolerance. This type of effect has been observed in *Arabidopsis* for drought and cold tolerance (Kasuga et al., *Nature Biotechnol.* 17:287-91 (1999)).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., *Nature* 313:810-812 (1985)); rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the invention, it may be desirable to use a tissue-specific or developmentally regulated promoter.

Another tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present invention which causes the desired temporal and spatial expression.

Promoters which are seed or embryo-specific and may be useful in the invention include soybean Kunitz trypsin inhibitor (Kti3, Jofuku and Goldberg, *Plant Cell* 1:1079-1093 (1989)), patatin (potato tubers) (Rocha-Sosa, M., et al., *EMBO J.* 8:23-29 (1989)), convicilin, vicilin, and legumin (pea cotyledons) (Rerie, W. G., et al., *Mol. Gen. Genet.* 259: 149-157 (1991); Newbigin, E. J., et al., *Planta* 180:461-470 (1990); Higgins, T. J. V., et al., *Plant. Mol. Biol.* 11:683-695 (1988)), zein (maize endosperm) (Schemthaner, J. P., et al., *EMBO J.* 7:1249-1255 (1988)), phaseolin (bean cotyledon) (Segupta-Gopalan, C., et al., *Proc. Natl. Acad. Sci. U.S.A.* 82:3320-3324 (1995)), phytohemagglutinin (bean cotyledon) (Voelker, T. et al., *EMBO J.* 6:3571-3577 (1987)), B-conglycinin and glycinin (soybean cotyledon) (Chen, Z-L, et al., *EMBO J.* 7:297-302 (1988)), glutelin (rice endosperm), hordein (barley endosperm) (Marris, C., et al., *Plant Mol. Biol.* 10:359-366 (1988)), glutenin and gliadin (wheat endosperm) (Colot, V., et al., *EMBO J.* 6:3559-3564 (1987)), and sporamin (sweet potato tuberous root) (Hattori, T., et al., *Plant Mol. Biol.* 14:595-604 (1990)). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al., *Bio/Technology* 7:L929-932 (1989)), bean lectin and bean beta-phaseolin promoters to express luciferase (Riggs et al., *Plant Sci.* 63:47-57 (1989)), and wheat glutenin promoters to express chloramphenicol acetyl transferase (Colot et al., *EMBO J.* 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Other promoters include the following: 1) the stress-inducible RD29A promoter (Kasuga et al., *Nature Biotechnol.* 17:287-91 (1999)); 2) the barley promoter, B22E; expression of B22E is specific to the pedicel in developing maize kernels ("Primary Structure of a Novel Barley Gene Differentially Expressed in Immature Aleurone Layers", Klemsdal et al., *Mol. Gen. Genet.* 228(1/2):9-16 (1991)); and 3) maize promoter, Zag2 ("Identification and molecular characterization of ZAG1, the maize homolog of the *Arabidopsis* floral homeotic gene AGAMOUS", Schmidt et al., *Plant Cell* 5(7): 729-737 (1993); "Structural characterization, chromosomal localization and phylogenetic evaluation of two pairs of AGAMOUS-like MADS-box genes from maize", Theissen et al., *Gene* 156(2):155-166 (1995); NCBI GenBank Accession No. X80206)). Zag2 transcripts can be detected five days prior to pollination to seven to eight days after pollination ("DAP"), and directs expression in the carpel of developing female inflorescences and Ciml which is specific to the nucleus of developing maize kernels. Ciml transcript is detected four to five days before pollination to six to eight DAP. Other useful promoters include any promoter which can be derived from a gene whose expression is maternally associated with developing female florets.

Additional other promoters for regulating the expression of the nucleotide sequences of the present invention in plants are stalk-specific promoters. Such stalk-specific promoters include the alfalfa S2A promoter (GenBank Accession No. EF030816; Abrahams et al., *Plant Mol. Biol.* 27:513-528 (1995)) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B., *Biochem. Plants* 15:1-82 (1989).

Other promoters may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue other promoters S2A (Genbank accession number EF030816) and S2B (GenBank Accession No. EF030817), and the constitutive promoter GOS2 from *Zea mays*. Other promoters include root promoters, such as the maize NAS2 promoter, the maize Cyclo promoter (US Publication No. 2006/0156439, published Jul. 13, 2006), the maize ROOTMET2 promoter (WO 2005/063998, published Jul. 14, 2005), the CR1BIO promoter (WO 2006/055487, published May 26, 2006), the CRWAQ81 (WO 2005/035770, published Apr. 21, 2005) and the maize ZRP2.47 promoter (NCBI Accession No. U38790; NCBI GI No. 1063664).

Recombinant DNA constructs (and suppression DNA constructs) of the present invention may also include other regulatory sequences including, but not limited to, translation leader sequences, introns, and polyadenylation recognition sequences. In another other embodiment of the present invention, a recombinant DNA construct of the present invention further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, *Mol. Cell. Biol.* 8:4395-4405 (1988); Callis et al., *Genes Dev.* 1:1183-1200 (1987)). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, New York (1994).

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3'-end sequence to be added can be derived from, for example, the nopaline synthase or octopine synthase genes, or alternatively from another plant gene, or less in an embodiment from any other eukaryotic gene.

A translation leader sequence is a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Mol. Biotech.* 3:225 (1995)).

Any plant can be selected for the identification of regulatory sequences and genes to be used in recombinant DNA constructs of the present invention. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, maize, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini. Particularly other plants for the identification of regulatory sequences are *Arabidopsis*, maize, wheat, soybean, and cotton.

Other Compositions

A other composition of the present invention is a plant comprising in its genome any of the recombinant DNA constructs (including any of the suppression DNA constructs) of the present invention (such as any of the other constructs discussed above). Other compositions also include any progeny of the plant, and any seed obtained from the plant or its progeny, wherein the progeny or seed comprises within its genome the recombinant DNA construct (or suppression DNA construct). Progeny includes subsequent generations obtained by self-pollination or out-crossing of a plant. Progeny also includes hybrids and inbreds.

In an embodiment, in hybrid seed propagated crops, mature transgenic plants can be self-pollinated to produce a homozygous inbred plant. The inbred plant produces seed containing the newly introduced recombinant DNA construct (or suppression DNA construct). These seeds can be grown to produce plants that would exhibit an altered agronomic characteristic (e.g., an increased agronomic characteristic, e.g. under nitrogen limiting conditions), or used in a breeding program to produce hybrid seed, which can be grown to produce plants that would exhibit such an altered agronomic characteristic. In an embodiment, the seeds are maize.

In an embodiment, the plant is a monocotyledonous or dicotyledonous plant, a maize or soybean plant, a maize plant, such as a maize hybrid plant or a maize inbred plant. The plant may also be sunflower, sorghum, canola, wheat, alfalfa, cotton, rice, barley or millet.

In an embodiment, the recombinant DNA construct is stably integrated into the genome of the plant.

Particularly other embodiments include but are not limited to the following other embodiments 1-8:

1. A plant (in an embodiment a maize or soybean plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 24, 26, 28, 30, or 32, and wherein said plant exhibits increased nitrogen stress tolerance when compared to a control plant not comprising said recombinant DNA construct. In an embodiment, the plant further exhibits an alteration of at least one agronomic characteristic when compared to the control plant.

2. A plant (in an embodiment a maize or soybean plant) comprising in its genome a recombinant DNA construct comprising:

(a) a polynucleotide operably linked to at least one regulatory element, wherein said polynucleotide encodes a polypeptide having an amino acid sequence of at least 50% sequence identity, based on the Clustal V method of alignment, when compared to SEQ ID NO:18, 20, 24, 26, 28, 30, or 32; or (b) a suppression DNA construct comprising at least one regulatory element operably linked to:

(i) all or part of: (A) a nucleic acid sequence encoding a polypeptide having an amino acid sequence of at least 50% sequence identity, based on the Clustal V method of alignment, when compared to SEQ ID NO:18, 20, 24, 26, 28, 30, or 32, or (B) a full complement of the nucleic acid sequence of (b)(i)(A); or (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes an LNT2 or LNT2-like polypeptide, and wherein said plant exhibits an alteration of at least one agronomic characteristic when compared to a control plant not comprising said recombinant DNA construct.

3. A plant (in an embodiment a maize or soybean plant) comprising in its genome a recombinant DNA construct comprising a polynucleotide operably linked to at least one regulatory sequence, wherein said polynucleotide encodes an LNT2 or LNT2-like polypeptide, and wherein said plant exhibits increased nitrogen stress tolerance when compared to a control plant not comprising said recombinant DNA construct. In an embodiment, the plant further exhibits an alteration of at least one agronomic characteristic when compared to the control plant. In an embodiment, the LNT2 polypeptide is from *Arabidopsis thaliana, Zea mays, Glycine max, Glycine tabacina, Glycine soja* or *Glycine tomentella*.

4. A plant (in an embodiment a maize or soybean plant) comprising in its genome a recombinant DNA construct comprising a polynucleotide operably linked to at least one regulatory sequence, wherein said polynucleotide encodes an LNT2 or LNT2-like polypeptide, and wherein said plant exhibits an alteration of at least one agronomic characteristic under nitrogen limiting conditions when compared to a control plant not comprising said recombinant DNA construct. In an embodiment, the LNT2 polypeptide is from *Arabidopsis thaliana, Zea mays, Glycine max, Glycine tabacina, Glycine soja* or *Glycine tomentella*.

5. A plant (in an embodiment a maize or soybean plant) comprising in its genome a recombinant DNA construct comprising a polynucleotide operably linked to at least one regulatory element, wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 24, 26, 28, 30, or 32, and wherein said plant exhibits an alteration of at least one agronomic characteristic under nitrogen limiting conditions when compared to a control plant not comprising said recombinant DNA construct.

6. A plant (in an embodiment a maize or soybean plant) comprising in its genome a suppression DNA construct comprising at least one regulatory element operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT2 or LNT2-like polypeptide, and wherein said plant exhibits an alteration of at least one agronomic characteristic under nitrogen limiting conditions when compared to a control plant not comprising said suppression DNA construct.

7. A plant (in an embodiment a maize or soybean plant) comprising in its genome a suppression DNA construct comprising at least one regulatory element operably linked to all or part of: (a) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 24, 26, 28, 30, or 32; or (b) a full complement of the nucleic acid sequence of (a), and wherein said plant exhibits an alteration of at least one agronomic characteristic under nitrogen limiting conditions when compared to a control plant not comprising said suppression DNA construct.

8. Any progeny of the above plants in other embodiments 1-7, any seeds of the above plants in other embodiments 1-7, any seeds of progeny of the above plants in other embodiments 1-7, and cells from any of the above plants in other embodiments 1-7 and progeny thereof.

In any of the foregoing other embodiments 1-8 or any other embodiments of the present invention, the recombinant DNA construct (or suppression DNA construct) In an embodiment comprises at least a promoter functional in a plant as a other regulatory sequence.

In any of the foregoing other embodiments 1-8 or any other embodiments of the present invention, the alteration of at least one agronomic characteristic is either an increase or decrease, In an embodiment an increase.

In any of the foregoing other embodiments 1-8 or any other embodiments of the present invention, the at least one agronomic characteristic selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, whole plant amino acid content, vegetative tissue free amino acid content, fruit free amino acid content, seed free amino acid content, total plant protein content, fruit protein content, seed protein content, protein content in a vegetative tissue, drought tolerance, nitrogen uptake, resistance to root lodging, harvest index, stalk lodging, plant height, ear height, and ear length. Yield, greenness and biomass are particularly other agronomic characteristics for alteration (In an embodiment an increase).

In any of the foregoing other embodiments 1-8 or any other embodiments of the present invention, the plant In an embodiment exhibits the alteration of at least one agronomic characteristic when compared, under nitrogen stress conditions, to a control plant not comprising said recombinant DNA construct (or suppression DNA construct).

One of ordinary skill in the art is familiar with protocols for simulating nitrogen conditions, whether limiting or non-limiting, and for evaluating plants that have been subjected to simulated or naturally-occurring nitrogen conditions, whether limiting or non-limiting. For example, one can simulate nitrogen conditions by giving plants less nitrogen than normally required or no nitrogen over a period of time, and one can evaluate such plants by looking for differences in agronomic characteristics, e.g., changes in physiological and/ or physical condition, including (but not limited to) vigor, growth, size, or root length, or in particular, leaf color or leaf area size. Other techniques for evaluating such plants include measuring chlorophyll fluorescence, photosynthetic rates, root growth or gas exchange rates.

The Examples below describe some representative protocols and techniques for simulating nitrogen limiting conditions and/or evaluating plants under such conditions.

One can also evaluate nitrogen stress tolerance by the ability of a plant to maintain sufficient yield (In an embodiment at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring low or high nitrogen conditions (e.g., by measuring for substantially equivalent yield under low or high nitrogen conditions compared to normal nitrogen conditions, or by measuring for less yield loss under low or high nitrogen conditions compared to a control or reference plant).

One of ordinary skill in the art would readily recognize a suitable control or reference plant to be utilized when assessing or measuring an agronomic characteristic or phenotype of a transgenic plant in any embodiment of the present invention in which a control or preference plant is utilized (e.g., compositions or methods as described herein). For example, by way of non-limiting illustrations:

1. Progeny of a transformed plant which is hemizygous with respect to a recombinant DNA construct (or suppression DNA construct), such that the progeny are segregating into plants either comprising or not comprising the recombinant DNA construct (or suppression DNA construct): the progeny comprising the recombinant DNA construct (or suppression DNA construct) would be typically measured relative to the progeny not comprising the recombinant DNA construct (or suppression DNA construct) (i.e., the progeny not comprising the recombinant DNA construct (or the suppression DNA construct) is the control or reference plant).

2. Introgression of a recombinant DNA construct (or suppression DNA construct) into an inbred line, such as in maize, or into a variety, such as in soybean: the introgressed line would typically be measured relative to the parent inbred or variety line (i.e., the parent inbred or variety line is the control or reference plant).

3. Two hybrid lines, where the first hybrid line is produced from two parent inbred lines, and the second hybrid line is produced from the same two parent inbred lines except that one of the parent inbred lines contains a recombinant DNA construct (or suppression DNA construct): the second hybrid line would typically be measured relative to the first hybrid line (i.e., the first hybrid line is the control or reference plant).

4. A plant comprising a recombinant DNA construct (or suppression DNA construct): the plant may be assessed or measured relative to a control plant not comprising the recombinant DNA construct (or suppression DNA construct) but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct (or suppression DNA construct)). There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

Furthermore, one of ordinary skill in the art would readily recognize that a suitable control or reference plant to be utilized when assessing or measuring an agronomic characteristic or phenotype of a transgenic plant would not include a plant that had been previously selected, via mutagenesis or transformation, for the desired agronomic characteristic or phenotype.

Other Methods

Other methods include but are not limited to methods for increasing nitrogen stress tolerance in a plant, methods for evaluating nitrogen stress tolerance in a plant, methods for altering an agronomic characteristic in a plant, methods for determining an alteration of an agronomic characteristic in a plant, and methods for producing seed. In an embodiment, the plant is a monocotyledonous or dicotyledonous plant, a maize or soybean plant, even more In an embodiment a maize plant. The plant may also be sunflower, sorghum, canola, wheat, alfalfa, cotton, rice, barley, or millet. The seed is can be a maize or soybean seed a maize seed, and even more In an embodiment, a maize hybrid seed or maize inbred seed.

Particularly other methods include but are not limited to the following:

A method of increasing nitrogen stress tolerance in a plant, comprising: (a) introducing into a regenerable plant cell a recombinant DNA construct comprising a polynucleotide operably linked to at least one regulatory sequence (in an embodiment a promoter functional in a plant), wherein the polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 24, 26, 28, 30, or 32; and (b) regenerating a transgenic plant from the regenerable plant cell after step (a), wherein the transgenic plant comprises in its genome the recombinant DNA construct and exhibits increased nitrogen stress tolerance when compared to a control plant not comprising the recombinant DNA construct. The method may further comprise (c) obtaining a progeny plant derived from the transgenic plant, wherein said progeny plant comprises in its genome the suppression DNA construct and exhibits increased nitrogen tolerance when compared to a control plant not comprising the recombinant DNA construct.

A method of increasing nitrogen stress tolerance in a plant, comprising: (a) introducing into a regenerable plant cell a suppression DNA construct comprising at least one regulatory sequence (in an embodiment a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 24, 26, 28, 30, or 32, or (ii) a full complement of the nucleic acid sequence of (a)(i); and (b) regenerating a transgenic plant from the regenerable plant cell after step (a), wherein the transgenic plant comprises in its genome the suppression DNA construct and exhibits increased nitrogen stress tolerance when compared to a control plant not comprising the suppression DNA construct. The method may further comprise (c) obtaining a progeny plant derived from the transgenic plant, wherein said progeny plant comprises in its genome the suppression DNA construct and exhibits increased nitrogen tolerance when compared to a control plant not comprising the suppression DNA construct.

A method of increasing nitrogen stress tolerance in a plant, comprising: (a) introducing into a regenerable plant cell a suppression DNA construct comprising at least one regulatory sequence (in an embodiment a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT2 or LNT2-like polypeptide; and (b) regenerating a transgenic plant from the regenerable plant cell after step (a), wherein the transgenic plant comprises in its genome the suppression DNA construct and exhibits increased nitrogen stress tolerance when compared to a control plant not comprising the suppression DNA construct. The method may further comprise (c) obtaining a progeny plant derived from the transgenic plant, wherein said progeny plant comprises in its genome the suppression DNA construct and exhibits increased nitrogen tolerance when compared to a control plant not comprising the suppression DNA construct.

A method of evaluating nitrogen stress tolerance in a plant, comprising (a) introducing into a regenerable plant cell a recombinant DNA construct comprising a polynucleotide operably linked to at least one regulatory sequence (in an embodiment a promoter functional in a plant), wherein the polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 24, 26, 28, 30, or 32; (b) regenerating a transgenic plant from the regenerable plant cell after step (a), wherein the transgenic plant comprises in its genome the recombinant DNA construct; and (c) evaluating the transgenic plant for nitrogen stress tolerance compared to a control plant not comprising the recombinant DNA construct. The method may further comprise (d) obtaining a progeny plant derived from the transgenic plant, wherein the progeny plant comprises in its genome the recombinant DNA construct; and (e) evaluating the progeny plant for nitrogen stress tolerance compared to a control plant not comprising the recombinant DNA construct.

A method of evaluating nitrogen stress tolerance in a plant, comprising (a) introducing into a regenerable plant cell a suppression DNA construct comprising at least one regulatory sequence (in an embodiment a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 24, 26, 28, 30, or 32; or (ii) a full complement of the nucleic acid sequence of (a)(i); (b) regenerating a transgenic plant from the regenerable plant cell after step (a), wherein the transgenic plant comprises in its genome the suppression DNA construct; and (c) evaluating the transgenic plant for nitrogen stress tolerance compared to a control plant not comprising the suppression DNA construct. The method may further comprise (d) obtaining a progeny plant derived from the transgenic plant, wherein the progeny plant comprises in its genome the suppression DNA construct; and (e) evaluating the progeny plant for nitrogen stress tolerance compared to a control plant not comprising the suppression DNA construct.

A method of evaluating nitrogen stress tolerance in a plant, comprising (a) introducing into a regenerable plant cell a suppression DNA construct comprising at least one regulatory sequence (in an embodiment a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT2 or LNT2-like polypeptide; (b) regenerating a transgenic plant from the regenerable plant cell after step (a), wherein the transgenic plant comprises in its genome the suppression DNA construct; and (c) evaluating the transgenic plant for nitrogen stress tolerance compared to a control plant not comprising the suppression DNA construct. The method may further comprise (d) obtaining a progeny plant derived from the transgenic plant, wherein the progeny plant comprises in its genome the suppression DNA construct; and (e) evaluating the progeny plant for nitrogen stress tolerance compared to a control plant not comprising the suppression DNA construct.

A method of evaluating nitrogen stress tolerance in a plant, comprising (a) introducing into a regenerable plant cell a recombinant DNA construct comprising a polynucleotide operably linked to at least one regulatory sequence (in an embodiment a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 24, 26, 28, 30, or 32; (b) regenerating a transgenic plant from the regenerable plant cell after step (a), wherein the transgenic plant comprises in its genome the recombinant DNA construct; (c) obtaining a progeny plant derived from said transgenic plant, wherein the progeny plant comprises in its genome the recombinant DNA construct; and (d) evaluating the progeny plant for nitrogen stress tolerance compared to a control plant not comprising the recombinant DNA construct.

A method of evaluating nitrogen stress tolerance in a plant, comprising (a) introducing into a regenerable plant cell a suppression DNA construct comprising at least one regulatory sequence (in an embodiment a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 24, 26, 28, 30, or 32; or (ii) a full complement of the nucleic acid sequence of (a)(i); (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) evaluating the progeny plant for nitrogen stress tolerance compared to a control plant not comprising the recombinant DNA construct.

A method of evaluating nitrogen stress tolerance in a plant, comprising (a) introducing into a regenerable plant cell a suppression DNA construct comprising at least one regulatory sequence (in an embodiment a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT2 or LNT2-like polypeptide; (b) regenerating a transgenic plant from the regenerable plant cell after step (a), wherein the transgenic plant comprises in its genome the suppression DNA construct; (c) obtaining a progeny plant derived from the transgenic plant, wherein the progeny plant comprises in its genome the suppression DNA construct; and (d) evaluating the progeny plant for nitrogen stress tolerance compared to a control plant not comprising the recombinant DNA construct.

A method of determining an alteration of an agronomic characteristic in a plant, comprising (a) introducing into a regenerable plant cell a recombinant DNA construct comprising a polynucleotide operably linked to at least on regulatory sequence (in an embodiment a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 24, 26, 28, 30, or 32; (b) regenerating a transgenic plant from the regenerable plant cell after step (a), wherein the transgenic plant comprises in its genome said recombinant DNA construct; and (c) determining whether the transgenic plant exhibits an alteration of at least one agronomic characteristic when compared, in an embodiment under nitrogen limiting conditions, to a control plant not comprising the recombinant DNA construct. The method may further comprise (d) obtaining a progeny plant derived from the transgenic plant, wherein the progeny plant comprises in its genome the recombinant DNA construct; and (e) determining whether the progeny plant exhibits an alteration of at least one agronomic characteristic when compared, in an embodiment under nitrogen limiting conditions, to a control plant not comprising the recombinant DNA construct.

A method of determining an alteration of an agronomic characteristic in a plant, comprising (a) introducing into a regenerable plant cell a suppression DNA construct comprising at least one regulatory sequence (in an embodiment a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 24, 26, 28, 30, or 32; or (ii) a full complement of the nucleic acid sequence of (i); (b) regenerating a transgenic plant from the regenerable plant cell after step (a), wherein the transgenic plant comprises in its genome the suppression DNA construct; and (c) determining whether the transgenic plant exhibits an alteration of at least one agronomic characteristic when compared, in an embodiment under nitrogen limiting conditions, to a control plant not comprising the suppression DNA construct. The method may further comprise (d) obtaining a progeny plant derived from the transgenic plant, wherein the progeny plant comprises in its genome the suppression DNA construct; and (e) determining whether the progeny plant exhibits an alteration of at least one agronomic characteristic when compared, in an embodiment under nitrogen limiting conditions, to a control plant not comprising the suppression DNA construct.

A method of determining an alteration of an agronomic characteristic in a plant, comprising (a) introducing into a regenerable plant cell a suppression DNA construct comprising at least one regulatory sequence (in an embodiment a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT2 or LNT2-like polypeptide; (b) regenerating a transgenic plant from the regenerable plant cell after step (a), wherein the transgenic plant comprises in its genome the suppression DNA construct; and (c) determining whether the transgenic plant exhibits an alteration of at least one agronomic characteristic when compared, in an embodiment under nitrogen limiting conditions, to a control plant not comprising the suppression DNA construct. The method may further comprise (d) obtaining a progeny plant derived from the transgenic plant, wherein the progeny plant comprises in its genome the suppression DNA construct; and (e) determining whether the progeny plant exhibits an alteration of at least one agronomic characteristic when compared, in an embodiment under nitrogen limiting conditions, to a control plant not comprising the suppression DNA construct.

A method of determining an alteration of an agronomic characteristic in a plant, comprising (a) introducing into a regenerable plant cell a recombinant DNA construct comprising a polynucleotide operably linked to at least one regulatory sequence (in an embodiment a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 24, 26, 28, 30, or 32; (b) regenerating a transgenic plant from the regenerable plant cell after step (a), wherein the transgenic plant comprises in its genome said recombinant DNA construct; (c) obtaining a progeny plant derived from said transgenic plant, wherein the progeny plant comprises in its genome the recombinant DNA construct; and (d) determining whether the progeny plant exhibits an alteration of at least one agronomic characteristic when compared, in an embodiment under nitrogen limiting conditions, to a control plant not comprising the recombinant DNA construct.

A method of determining an alteration of an agronomic characteristic in a plant, comprising (a) introducing into a regenerable plant cell a suppression DNA construct comprising at least one regulatory sequence (in an embodiment a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 24, 26, 28, 30, or 32; or (ii) a full complement of the nucleic acid sequence of (i); (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) determining whether the progeny plant exhibits an alteration of at least one agronomic characteristic when compared, in an embodiment under nitrogen limiting conditions, to a control plant not comprising the recombinant DNA construct.

A method of determining an alteration of an agronomic characteristic in a plant, comprising (a) introducing into a regenerable plant cell a suppression DNA construct comprising at least one regulatory sequence (in an embodiment a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an LNT2 or LNT2-like polypeptide; (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) determining whether the progeny plant exhibits an alteration of at least one agronomic characteristic when compared, in an embodiment under nitrogen limiting conditions, to a control plant not comprising the suppression DNA construct.

A method of producing seed (in an embodiment seed that can be sold as a nitrogen stress tolerant product offering) comprising any of the preceding other methods, and further comprising obtaining seeds from said progeny plant, wherein said seeds comprise in their genome said recombinant DNA construct (or suppression DNA construct).

In any of the foregoing other methods or any other embodiments of methods of the present invention, the step of determining an alteration of an agronomic characteristic in a transgenic plant, if applicable, may in an embodiment comprise determining whether the transgenic plant exhibits an alteration of at least one agronomic characteristic when compared, under varying environmental conditions, to a control plant not comprising the recombinant DNA construct.

In any of the foregoing other methods or any other embodiments of methods of the present invention, the step of determining an alteration of an agronomic characteristic in a progeny plant, if applicable, may comprise determining whether the progeny plant exhibits an alteration of at least one agronomic characteristic when compared, under varying environmental conditions, to a control plant not comprising the recombinant DNA construct.

In any of the preceding other methods or any other embodiments of methods of the present invention, in said introducing step said regenerable plant cell may comprises a callus cell (in an embodiment embryogenic), a gametic cell, a meristematic cell, or a cell of an immature embryo. The regenerable plant cells are in an embodiment from an inbred maize plant.

In any of the preceding other methods or any other embodiments of methods of the present invention, said regenerating step in an embodiment comprises: (i) culturing said transformed plant cells in a media comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding other methods or any other embodiments of methods of the present invention, the at least one agronomic characteristic is selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, whole plant amino acid content, vegetative tissue free amino acid content, fruit free amino acid content, seed free amino acid content, total plant protein content, fruit protein content, seed protein content, protein content in a vegetative tissue, drought tolerance, nitrogen uptake, resistance to root lodging, harvest index, stalk lodging, plant height, ear height, and ear length. Yield, greenness and biomass are particularly other agronomic characteristics for alteration (in an embodiment an increase).

In any of the preceding other methods or any other embodiments of methods of the present invention, the plant in an embodiment exhibits the alteration of at least one agronomic characteristic when compared, under nitrogen stress conditions, to a control plant not comprising said recombinant DNA construct (or suppression DNA construct).

In any of the preceding other methods or any other embodiments of methods of the present invention, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, in an embodiment as part of a transposable element), and then screen for an event in which the regulatory sequence is operably linked to an endogenous gene encoding a polypeptide of the instant invention.

The introduction of recombinant DNA constructs of the present invention into plants may be carried out by any suitable technique, including but not limited to direct DNA uptake, chemical treatment, electroporation, microinjection, cell fusion, infection, vector mediated DNA transfer, bombardment, or *Agrobacterium* mediated transformation.

Other techniques are set forth below in the Examples below for transformation of maize plant cells and soybean plant cells.

Other methods for transforming dicots, primarily by use of *Agrobacterium tumefaciens*, and obtaining transgenic plants include those published for cotton (U.S. Pat. Nos. 5,004,863, 5,159,135, 5,518,908); soybean (U.S. Pat. Nos. 5,569,834, 5,416,011, McCabe et. al., *Bio/Technology* 6:923 (1988), Christou et al., *Plant Physiol.* 87:671 674 (1988)); *Brassica* (U.S. Pat. No. 5,463,174); peanut (Cheng et al., *Plant Cell Rep.* 15:653 657 (1996), McKently et al., *Plant Cell Rep.* 14:699 703 (1995)); papaya; and pea (Grant et al., *Plant Cell Rep.* 15:254-258 (1995)).

Transformation of monocotyledons using electroporation, particle bombardment, and *Agrobacterium* have also been reported and are included as other methods, for example, transformation and plant regeneration as achieved in asparagus (Bytebier et al., *Proc. Natl. Acad. Sci. U.S.A.* 84:5354, (1987)); barley (Wan and Lemaux, *Plant Physiol.* 104:37 (1994)); corn (Rhodes et al., *Science* 240:204 (1988), Gordon-Kamm et al., *Plant Cell* 2:603 618 (1990), Fromm et al., *Bio/Technology* 8:833 (1990), Koziel et al., *Bio/Technology* 11:194 (1993), Armstrong et al., *Crop Science* 35:550-557 (1995)); oat (Somers et al., *Bio/Technology* 10:1589 (1992)); orchard grass (Horn et al., *Plant Cell Rep.* 7:469 (1988)); rice (Toriyama et al., *Theor. Appl. Genet.* 205:34 (1986); Part et al., *Plant Mol. Biol.* 32:1135 1148, (1996); Abedinia et al., *Aust. J. Plant Physiol.* 24:133 141 (1997); Zhang and Wu, *Theor. Appl. Genet.* 76:835 (1988); Zhang et al., *Plant Cell Rep.* 7:379, (1988); Battraw and Hall, *Plant Sci.* 86:191 202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al., *Bio/Technology* 10:691 (1992)); and wheat (Vasil et al., *Bio/Technology* 10:667 (1992); U.S. Pat. No. 5,631,152).

There are a variety of methods for the regeneration of plants from plant tissue. The particular method of regeneration will depend on the starting plant tissue and the particular plant species to be regenerated.

The regeneration, development, and cultivation of plants from single plant protoplast transformants or from various transformed explants is well known in the art (Weissbach and Weissbach, In: Methods for Plant Molecular Biology, (Eds.), Academic Press, Inc. San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous isolated nucleic acid fragment that encodes a protein of interest is well known in the art. In an embodiment, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

EXAMPLES

The present invention is further illustrated in the following Examples, in which parts and percentages are by weight and degrees are Celsius, unless otherwise stated. It should be understood that these Examples, while indicating other embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Furthermore, various modifications of the invention in addition to those shown and described herein will be apparent to those skilled in the art from the foregoing description. Such modifications are also intended to fall within the scope of the appended claims.

Example 1

Creation of an *Arabidopsis* Population with Activation-Tagged Genes

An 18.49-kb T-DNA based binary construct was created, pHSbarENDs2 (SEQ ID NO:1; FIG. 1), that contains four multimerized enhancer elements derived from the Cauliflower Mosaic Virus 35S promoter (corresponding to sequences −341 to −64, as defined by Odell et al., *Nature* 313:810-812 (1985)). The construct also contains vector sequences (pUC9) and a poly-linker (SEQ ID NO:11) to allow plasmid rescue, transposon sequences (Ds) to remobilize the T-DNA, and the bar gene to allow for glufosinate selection of transgenic plants. In principle, only the 10.8-kb segment from the right border (RB) to left border (LB) inclusive will be transferred into the host plant genome. Since the enhancer elements are located near the RB, they can induce cis-activation of genomic loci following T-DNA integration.

*Arabidopsis* activation-tagged populations were created by whole plant *Agrobacterium* transformation. The pHSbarENDs2 construct was transformed into *Agrobacterium tumefaciens* strain C58, grown in lysogeny broth medium at 25° C. to OD600~1.0. Cells were then pelleted by centrifugation and resuspended in an equal volume of 5% sucrose/0.05% Silwet L-77 (OSI Specialties, Inc). At early bolting, soil grown *Arabidopsis thaliana* ecotype Col-0 were top watered with the *Agrobacterium* suspension. A week later, the same plants were top watered again with the same *Agrobacterium* strain in sucrose/Silwet. The plants were then allowed to set seed as normal. The resulting T1 seed were sown on soil, and transgenic seedlings were selected by spraying with glufosinate (FINALE®; AgrEvo; Bayer Environmental Science). A total of 100,000 glufosinate resistant T1 seedlings were selected. T2 seed from each line was kept separate.

Example 2

Screens to Identify Lines with Tolerance to Low Nitrogen

From each of 100,000 separate T1 activation-tagged lines, eleven T2 plants are sown on square plates (15 mm×15 mm) containing 0.5×N-Free Hoagland's, 0.4 mM potassium nitrate, 0.1% sucrose, 1 mM MES and 0.25% Phytagel™ (Low N medium). Five lines are plated per plate, and the inclusion of 9 wild-type individuals on each plate makes for a total of 64 individuals in an 8×8 grid pattern (see FIG. 11). Plates are kept for three days in the dark at 4° C. to stratify seeds, and then placed horizontally for nine days at 22° C. light and 20° C. dark. Photoperiod is sixteen hours light and eight hours dark, with an average light intensity of ~200 mmol/m$^2$/s. Plates are rotated and shuffled daily within each shelf. At day twelve (nine days of growth), seedling status is evaluated by imaging the entire plate.

Figure 12:
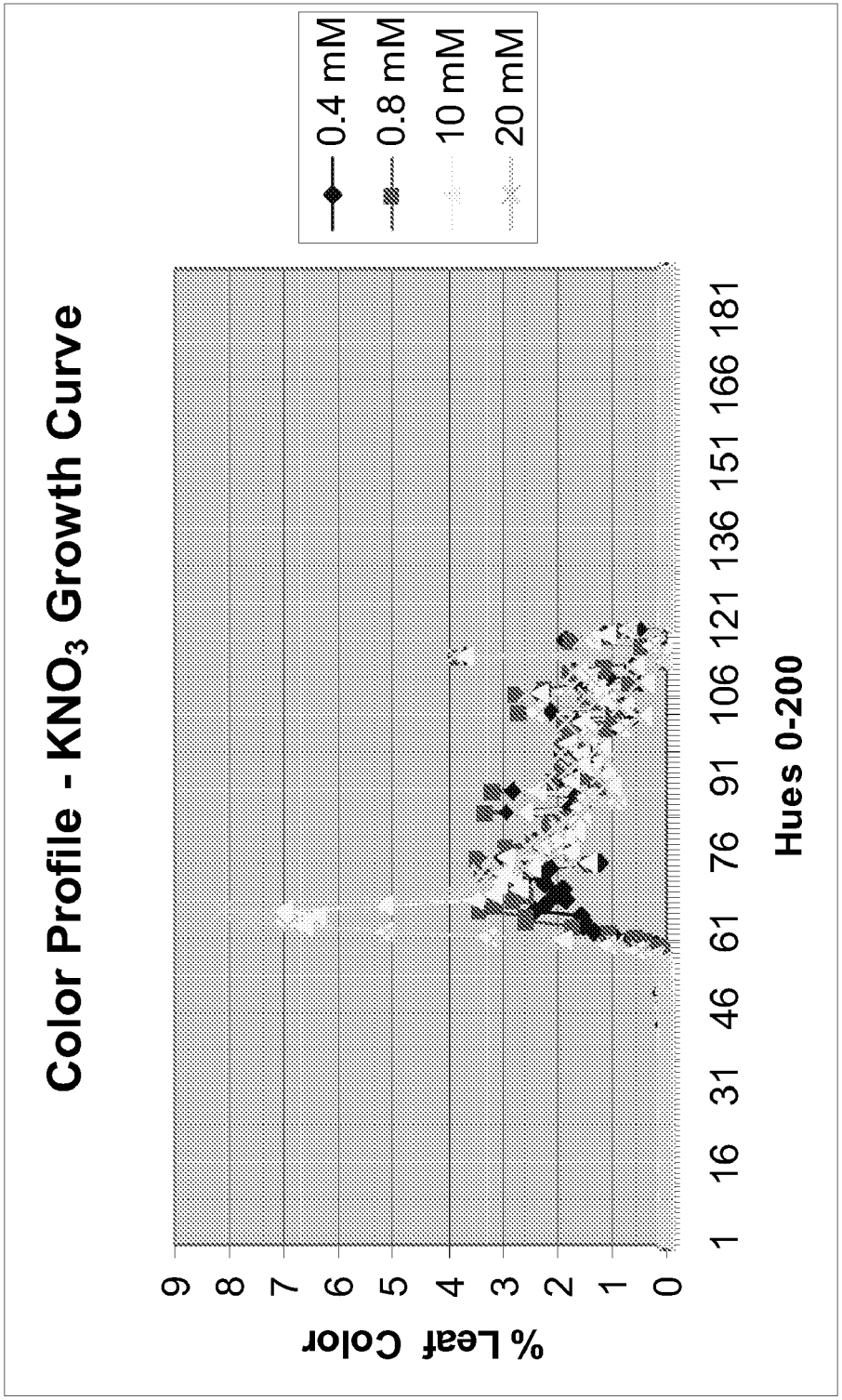
FIG. 12 shows a graph showing the effect of several different potassium nitrate concentrations on plant color as determined by image analysis. The response of the green color bin (hues 50 to 66) to nitrate dosage demonstrates that this bin can be used as an indicator of nitrogen assimilation.

After masking the plate image to remove background color, two different measurements are collected for each individual: total rosette area, and the percentage of color that falls into a green color bin. Using hue, saturation and intensity data (HSI), the green color bin consists of hues 50 to 66. Total rosette area is used as a measure of plant biomass, whereas the green color bin was shown by dose-response studies to be an indicator of nitrogen assimilation (see FIG. 12).

Lines with a significant increase in total rosette area and/or green color bin, when compared to the wild-type controls, are designated as Phase 1 hits. Phase 1 hits are re-screened in duplicate under the same assay conditions (Phase 2 screen). A Phase 3 screen is also employed to further validate mutants that passed through Phases 1 and 2. In Phase 3, each line is plated separately on Low N medium, such that 32 T2 individuals are grown next to 32 wild-type individuals on one plate, providing greater statistical rigor to the analysis. If a line shows a significant difference from the controls in Phase 3, the line is then considered a validated nitrogen-deficiency tolerant line.

Example 3

Identification of Activation-Tagged Genes

Genes flanking the T-DNA insert in nitrogen tolerant lines are identified using one, or both, of the following two standard procedures: (1) thermal asymmetric interlaced (TAIL) PCR (Liu et al., Plant J. 8:457-63 (1995)); and (2) SAIFF PCR (Siebert et al., *Nucleic Acids Res.* 23:1087-1088 (1995)). In lines with complex multimerized T-DNA inserts, TAIL PCR and SAIFF PCR may both prove insufficient to identify candidate genes. In these cases, other procedures, including inverse PCR, plasmid rescue and/or genomic library construction, can be employed.

A successful result is one where a single TAIL or SAIFF PCR fragment contains a T-DNA border sequence and *Arabidopsis* genomic sequence. Once a tag of genomic sequence flanking a T-DNA insert is obtained, candidate genes are identified by alignment to publicly available *Arabidopsis* genome sequence. Specifically, the annotated gene nearest the 35S enhancer elements/T-DNA RB are candidates for genes that are activated.

To verify that an identified gene is truly near a T-DNA and to rule out the possibility that the TAIL/SAIFF fragment is a chimeric cloning artifact, a diagnostic PCR on genomic DNA is done with one oligo in the T-DNA and one oligo specific for the candidate gene. Genomic DNA samples that give a PCR product are interpreted as representing a T-DNA insertion. This analysis also verifies a situation in which more than one insertion event occurs in the same line, e.g., if multiple differing genomic fragments are identified in TAIL and/or SAIFF PCR analyses.

Example 4

Identification of Activation-Tagged LNT2 Gene

An activation tagged-line (line 111786) showing nitrogen-deficiency tolerance was further analyzed. DNA from the line was extracted, and genes flanking the T-DNA insert in the mutant line were identified using ligation-mediated PCR (Siebert et al., Nucleic Acids Res. 23:1087-1088 (1995)). A single amplified fragment was identified that contained a T-DNA border sequence and *Arabidopsis* genomic sequence. Once a tag of genomic sequence flanking a T-DNA insert was obtained, a candidate gene was identified by alignment to the completed *Arabidopsis* genome. Specifically, the annotated gene nearest the 35S enhancer elements/T-DNA RB was the candidate for the gene activated in the line. In the case of line 111786 the gene nearest the 35S enhancers was At5g50930 (SEQ ID NO:27) encoding the *Arabidopsis thaliana* "unknown protein" referred to herein as LNT2 (SEQ ID NO:28; NCBI GI 15241317).

Example 5

Validation of Candidate *Arabidopsis* Gene (At5g50930) via Transformation into *Arabidopsis*

Candidate genes can be transformed into *Arabidopsis* and overexpressed under the 35S promoter. If the same or similar phenotype is observed in the transgenic line as in the parent activation-tagged line, then the candidate gene is considered to be a validated "lead gene" in *Arabidopsis*.

The *Arabidopsis* At5g50930 gene (SEQ ID NO:27) was tested for its ability to confer nitrogen-deficiency tolerance in the following manner.

The At5g50930 cDNA was amplified by RT-PCR with the following primers:

1. At5g50930-5' attB forward primer (SEQ ID NO:35) The forward primer contains the attB1 sequence (ACAAGTTTGTACAAAAAAGCAGGCT; SEQ ID NO:12) and a consensus Kozak sequence (CAACA) upstream of the first 21 nucleotides of the protein-coding region, beginning with the ATG start codon, of said cDNA.

2. At5g50930-3' attB reverse primer (SEQ ID NO:36) The reverse primer contains the attB2 sequence (AC-CACTTTGTACAAGAAAGCTGGGT; SEQ ID NO:13) adjacent to the reverse complement of the last 21 nucleotides of the protein-coding region, beginning with the reverse complement of the stop codon, of said cDNA.

The RT-PCR reaction yielded two products, referred to herein as Int2-2 and Int2-3 (SEQ ID NOs:29 and 31, respectively). The products were identified as splice variants of the At5g50930 gene.

Using the INVITROGEN™ GATEWAY® CLONASE™ technology, a BP Recombination Reaction was performed for each RT-PCR product with pDONR™ Zeo (SEQ ID NO:2; FIG. 2). This process removes the bacteria lethal ccdB gene, as well as the chloramphenicol resistance gene (CAM), from pDONR™ Zeo and directionally clones the PCR product with flanking attB1 and attB2 sites, creating an entry clone. One positively identified entry clone for each splice variant sequence was used for a subsequent LR Recombination Reaction with a destination vector, as follows.

A 16.8-kb T-DNA based binary vector (destination vector), called pBC-yellow (SEQ ID NO:4; FIG. 4), was constructed with a 1.3-kb 35S promoter immediately upstream of the INVITROGEN™ GATEWAY C1 conversion insert, which contains the bacterial lethal ccdB gene as well as the chloramphenicol resistance gene (CAM) flanked by attR1 and attR2 sequences. The vector also contains the RD29a promoter driving expression of the gene for ZS-Yellow (INVITROGEN™), which confers yellow fluorescence to transformed seed. Using the INVITROGEN™ GATEWAY® technology, an LR Recombination Reaction was performed with the entry clone containing Int2-2 and the pBC-yellow vector. This amplification allowed for rapid and directional cloning of Int2-2 (SEQ ID NO: 29) behind the 35S promoter in pBC-yellow. An LR Recombination Reaction was also performed with the entry clone containing Int2-3 and the pBC-yellow vector.

Applicants then introduced the 35S promoter:At5g50930 expression constructs into wild-type *Arabidopsis* ecotype Col-0, using the same *Agrobacterium*-mediated transformation procedure described in Example 1. Transgenic T1 seeds were selected by yellow fluorescence, and 32 of these T1 seeds were plated next to 32 wild-type *Arabidopsis* ecotype Col-0 seeds on low nitrogen medium. All subsequent growth and imaging conditions were performed as described in Example 1. It was found that the original phenotype from activation tagging, tolerance to nitrogen limiting conditions, could be recapitulated in wild-type *Arabidopsis* plants that were transformed with a construct where an At5g50930 gene was directly expressed by the 35S promoter.

Example 6

Composition of cDNA Libraries, Isolation and Sequencing of cDNA Clones cDNA libraries may be prepared by any one of many methods available. For example, the cDNAs may be introduced into plasmid vectors by first preparing the cDNA libraries in UNI-ZAP™ XR vectors according to the manufacturer's protocol (Stratagene Cloning Systems, La Jolla, Calif.). The UNI-ZAP™ XR libraries are converted into plasmid libraries according to the protocol provided by Stratagene. Upon conversion, cDNA inserts will be contained in the plasmid vector pBLUESCRIPT®. In addition, the cDNAs may be introduced directly into precut BLUESCRIPT® II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBLUESCRIPT® plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., *Science* 252:1651-1656 (1991)). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke, *Nucleic Acids Res.* 22:3765-3772 (1994)). The in vitro transposition system places unique binding sites randomly throughout a population of large DNA molecules. The transposed DNA is then used to transform DH10B electro-competent cells (GIBCO BRL/Life Technologies, Rockville, Md.) via electroporation. The transposable element contains an additional selectable marker (named DHFR; Fling and Richards, *Nucleic Acids Res.* 11:5147-5158 (1983)), allowing for dual selection on agar plates of only those subclones containing the integrated transposon. Multiple subclones are randomly selected from each transposition reaction, plasmid DNAs are prepared via alkaline lysis, and templates are sequenced (ABI PRISM dye-terminator ReadyReaction mix) outward from the transposition event site, utilizing unique primers specific to the binding sites within the transposon.

Sequence data is collected (ABI PRISM® Collections) and assembled using Phred and Phrap (Ewing et al., *Genome Res.* 8:175-185 (1998); Ewing et al., *Genome Res.* 8:186-194 (1998)). Phred is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (Gordon et al., *Genome Res.* 8:195-202 (1998)).

In some of the clones the cDNA fragment corresponds to a portion of the 3'-terminus of the gene and does not cover the entire open reading frame. In order to obtain the upstream information one of two different protocols is used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries sometimes are chosen based on previous knowledge that the specific gene should be found in a certain tissue and sometimes are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBLUE-SCRIPT® vector using a commercial kit and following the manufacturer's protocol. This kit is selected from many available from several vendors including INVITROGEN™ (Carlsbad, Calif.), Promega Biotech (Madison, Wis.), and GIBCO-BRL (Gaithersburg, Md.). The plasmid DNA is isolated by alkaline lysis method and submitted for sequencing and assembly using Phred/Phrap, as above.

Example 7

Identification of cDNA Clones cDNA clones encoding LNT2-like polypeptides are identified by conducting BLAST (Basic Local Alignment Search Tool; Altschul et al., *J. Mol. Biol.* 215:403-410 (1993); see also the explanation of the BLAST algorithm on the world wide web site for the National Center for Biotechnology Information at the National Library of Medicine of the National Institutes of Health) searches for similarity to amino acid sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The DNA sequences from clones can be translated in all reading frames and compared for similarity to all publicly available protein sequences contained in the "nr" database using the BLASTX algorithm (Gish and States, *Nat. Genet.* 3:266-272 (1993)) provided by the NCBI. The polypeptides encoded by the cDNA sequences can be analyzed for similarity to all publicly available amino acid sequences contained in the "nr" database using the BLASTP algorithm provided by the National Center for Biotechnology Information (NCBI). For convenience, the P-value (probability) or the E-value (expectation) of observing a match of a cDNA-encoded sequence to a sequence contained in the searched databases merely by chance as calculated by BLAST are reported herein as "pLog" values, which represent the negative of the logarithm of the reported P-value or E-value. Accordingly, the greater the pLog value, the greater the likelihood that the cDNA-encoded sequence and the BLAST "hit" represent homologous proteins.

EST sequences can be compared to the GenBank database as described above. ESTs that contain sequences more 5- or 3-prime can be found by using the BLASTN algorithm (Altschul et al., *Nucleic Acids Res.* 25:3389-3402 (1997)) against the Dupont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing.

Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 8

Characterization of cDNA Clones Encoding LNT2-like Polypeptides cDNA libraries representing mRNAs from various tissues of *Zea mays* (maize), *Oryza sativa* (rice), and *Glycine max* (soybean) were prepared. The characteristics of the libraries are described below.

TABLE 2 cDNA Libraries from Maize, Rice, and Soybean

| Library | Description (tissue) | Clone |
| --- | --- | --- |
| cpg1c | Corn (*Zea mays L.*) pooled BMS treated with chemicals related to RNA, DNA synthesis | cpg1c.pk013.o6:fis |
| rca1n | Rice (*Oryza sativa L.*, Nipponbare) callus normalized | rca1n.pk001.f6:fis |
| sfl1n1 | Soybean (*Glycine max L.*, Wye) immature flower normalized. | sfl1n1.pk002.j1 |
| sds1f | Soybean (*Glycine max*, Wye) 11 day old seedling full length library using trehalose | sds1f.pk001.k5 |

As shown in Table 3, FIGS. 14A-14B, and FIG. 15, cDNAs identified in Table 2 encode polypeptides similar to the LNT2 polypeptide from *Arabidopsis thaliana* (At5g50930; NCBI General Identifier No. 15241317; SEQ ID NO:28) and to the LNT2-like polypeptides from *Oryza sativa* (GI No. 38347162 corresponding to SEQ ID NO: 33) and from *Vitis vinifera* (GI No. 147791927 corresponding to SEQ ID NO: 34).

Shown in Table 3 (non-patent literature) and Table 4 (patent literature) are the BLASTP results for individual ESTs ("EST"), the sequences of the entire cDNA inserts comprising the indicated cDNA clones ("FIS"), the sequences of contigs assembled from two or more EST, FIS or PCR sequences ("Contig"), or sequences encoding an entire or functional protein derived from an FIS or a contig ("CGS"). Also shown in Tables 3 and 4 are the percent sequence identity values for each pair of amino acid sequences using the Clustal V method of alignment with default parameters (described below).

TABLE 3

BLASTP Results for Polypeptides Homologous to LNT2 Polypeptides

| Sequence (SEQ ID NO: #) | Status | NCBI GI No. | % identity | BLAST pLog Score |
| --- | --- | --- | --- | --- |
| cpg1c.pk013.o6:fis (SEQ ID NO: 18) | CGS | 38347162 (SEQ ID: 33) | 77.4 | 17.8 |
| rca1n.pk001.f6:fis (SEQ ID NO: 20) | CGS | 38347162 (SEQ ID: 33) | 100.0 | 15.8 |
| PSO415619 (SEQ ID NO: 24) | contig | 147791927 (SEQ ID: 34) | 58.7 | 13.0 |
| PSO415620 (SEQ ID NO: 26) | contig | 147791927 (SEQ ID: 34) | 57.1 | 11.8 |

TABLE 4

BLASTP Results for Polypeptides Homologous to LNT2 Polypeptides

| Sequence (SEQ ID NO: #) | Status | Reference | % Identity | BLAST pLog score |
| --- | --- | --- | --- | --- |
| cpg1c.pk013.o6:fis (SEQ ID NO: 18) | CGS | SEQ ID NO: 224380 In US2004214272-A1 | 92.3 | 21.0 |
| rca1n.pk001.f6:fis (SEQ ID NO: 20) | CGS | SEQ ID NO: 188525 In US2004123343-A1 | 100.0 | 15.7 |
| PSO415619 (SEQ ID NO: 24) | contig | SEQ ID NO: 183694 In US2004031072-A1 | 92.1 | 21.4 |
| PSO415620 (SEQ ID NO: 26) | contig | SEQ ID NO: 183694 In US2004031072-A1 | 84.9 | 19.8 |

FIGS. 14A and 14B present an alignment of the amino acid sequences set forth in SEQ ID NOs:18, 20, 24, 26, and the amino acid sequences of the LNT2 (At5g50930; NCBI General Identifier No. 15241317), LNT2-2, and LNT2-3 polypeptides from *Arabidopsis thaliana* (SEQ ID NOs: 28, 30, and 32, respectively). Also included in the alignment are the LNT2-like polypeptides from *Oryza sativa* (GI No. 38347162 corresponding to SEQ ID NO: 33) and from *Vitis vinifera* (GI No. 147791927 corresponding to SEQ ID NO: 34). FIG. 15 is a chart of the percent sequence identity and the divergence values for each pair of amino acids sequences presented in FIGS. 14A and 14B.

Sequence alignments and percent identity calculations were performed using the MEGALIGN® program of the LASERGENE® bioinformatics computing suite (DNASTAR® Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Example 9

Preparation of a Plant Expression Vector Containing a Homolog to the *Arabidopsis* Lead Gene Sequences homologous to the lead LNT2 genes can be identified using sequence comparison algorithms such as BLAST (Basic Local Alignment Search Tool; Altschul et al., *J. Mol. Biol.* 215:403-410 (1993); see also the explanation of the BLAST algorithm on the world wide web site for the National Center for Biotechnology Information at the National Library of Medicine of the National Institutes of Health). Homologous LNT2-like sequences, such as the ones described in Example 8, can be PCR-amplified by either of the following methods.

Method 1 (RNA-based): If the 5' and 3' sequence information for the protein-coding region of an LNT2 homolog is available, gene-specific primers can be designed as outlined in Example 5. RT-PCR can be used with plant RNA to obtain a nucleic acid fragment containing the protein-coding region flanked by attB1 (SEQ ID NO:12) and attB2 (SEQ ID NO:13) sequences. The primer may contain a consensus Kozak sequence (CAACA) upstream of the start codon.

Method 2 (DNA-based): Alternatively, if a cDNA clone is available for the LNT2 homolog, the entire cDNA insert (containing 5' and 3' non-coding regions) can be PCR amplified. Forward and reverse primers can be designed that contain either the attB1 sequence and vector-specific sequence that precedes the cDNA insert or the attB2 sequence and vector-specific sequence that follows the cDNA insert, respectively. For a cDNA insert cloned into the vector pBLUESCRIPT SK+, the forward primer VC062 (SEQ ID NO:15) and the reverse primer VC063 (SEQ ID NO:16) can be used.

Methods 1 and 2 can be modified according to procedures known by one skilled in the art. For example, the primers of Method 1 may contain restriction sites instead of attB1 and attB2 sites, for subsequent cloning of the PCR product into a vector containing attB1 and attB2 sites. Additionally, Method 2 can involve amplification from a cDNA clone, a lambda clone, a BAC clone or genomic DNA.

A PCR product obtained by either method above can be combined with the GATEWAY® donor vector, such as pDONR™ Zeo (SEQ ID NO:2; FIG. 2) or pDONR™ 221 (SEQ ID NO:3; FIG. 3), using a BP Recombination Reaction. This process removes the bacteria lethal ccdB gene, as well as the chloramphenicol resistance gene (CAM) from pDONR™ Zeo or pDONR™ 221 and directionally clones the PCR product with flanking attB1 and attB2 sites to create an entry clone. Using the INVITROGEN™ GATEWAY® CLONASE™ technology, the sequence encoding the homologous LNT2 polypeptide from the entry clone can then be transferred to a suitable destination vector, such as pBC-Yellow (SEQ ID NO:4; FIG. 4), PHP27840 (SEQ ID NO:5; FIG. 5), or PHP23236 (SEQ ID NO:6; FIG. 6), to obtain a plant expression vector for use with *Arabidopsis*, soybean, and corn, respectively.

The attP1 and attP2 sites of donor vectors pDONR™/Zeo or pDONR™ 221 are shown in FIGS. 2 and 3, respectively. The attR1 and attR2 sites of destination vectors pBC-Yellow, PHP27840, and PHP23236 are shown in FIGS. 4, 5 and 6, respectively.

Alternatively a MultiSite GATEWAY® LR recombination reaction between multiple entry clones and a suitable destination vector can be performed to create an expression vector.

Example 10

Preparation of Soybean Expression Vectors and Transformation of Soybean with Validated *Arabidopsis* Lead Genes Soybean plants can be transformed to overexpress each validated *Arabidopsis* gene or the corresponding homologs from various species in order to examine the resulting phenotype.

The same GATEWAY® entry clone described in Example 5 can be used to directionally clone each gene into the PHP27840 vector (SEQ ID NO:5; FIG. 5) such that expression of the gene is under control of the SCP1 promoter.

Soybean embryos may then be transformed with the expression vector comprising sequences encoding the instant polypeptides.

To induce somatic embryos, cotyledons, 3-5 mm in length dissected from surface sterilized, immature seeds of the soybean cultivar A2872, can be cultured in the light or dark at 26° C. on an appropriate agar medium for six to ten weeks. Somatic embryos, which produce secondary embryos, are then excised and placed into a suitable liquid medium. After repeated selection for clusters of somatic embryos which multiply as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al., *Nature* (London) 327:70-73 (1987), U.S. Pat. No. 4,945,050). A DUPONT BIOLISTIC™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al., *Nature* 313:810-812 (1985)), the hygromycin phosphotransferase gene from plasmid pJR225 (from *E. coli*; Gritz et al., *Gene* 25:179-188 (1983)) and the 3' region of the nopaline synthase gene from the T-DNA of the Ti plasmid of *Agrobacterium tumefaciens*. Another selectable marker gene which can be used to facilitate soybean transformation is an herbicide-resistant acetolactate synthase (ALS) gene from soybean or *Arabidopsis*. ALS is the first common enzyme in the biosynthesis of the branched-chain amino acids valine, leucine and isoleucine. Mutations in ALS have been identified that convey resistance to some or all of three classes of inhibitors of ALS (U.S. Pat. No. 5,013,659; the entire contents of which are herein incorporated by reference). Expression of the herbicide-resistant ALS gene can be under the control of a SAM synthetase promoter (U.S. Patent Application No. US-2003-0226166-A1; the entire contents of which are herein incorporated by reference).

To 50 μL of a 60 mg/mL 1 μm gold particle suspension is added (in order): 5 μL DNA (1 μg/μL), 20 μL spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment, with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Soybean plants transformed with validated genes can be assayed to study agronomic characteristics relative to control or reference plants. For example, yield enhancement and/or stability under low and high nitrogen conditions (e.g., nitrogen limiting conditions and nitrogen-sufficient conditions) can be assayed.

Example 11

Transformation of Maize with Validated *Arabidopsis* Lead Genes Using Particle Bombardment Maize plants can be transformed to overexpress a validated *Arabidopsis* lead gene or the corresponding homologs from various species in order to examine the resulting phenotype.

The same GATEWAY® entry clones described in Example 5 can be used to directionally clone each respective gene into a maize transformation vector. Expression of the gene in the maize transformation vector can be under control of a constitutive promoter such as the maize ubiquitin promoter (Christensen et al., *Plant Mol. Biol.* 12:619-632 (1989) and Christensen et al., *Plant Mol. Biol.* 18:675-689 (1992))

The recombinant DNA construct described above can then be introduced into maize cells by the following procedure. Immature maize embryos can be dissected from developing caryopses derived from crosses of the inbred maize lines H99 and LH132. The embryos are isolated ten to eleven days after pollination when they are 1.0 to 1.5 mm long. The embryos are then placed with the axis-side facing down and in contact with agarose-solidified N6 medium (Chu et al., *Sci. Sin. Peking* 18:659-668 (1975)). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every two to three weeks.

The plasmid, p35S/Ac (obtained from Dr. Peter Eckes, Hoechst Ag, Frankfurt, Germany) may be used in transformation experiments in order to provide for a selectable marker. This plasmid contains the pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al., *Nature* 313:810-812 (1985)) and the 3' region of the nopaline synthase gene from the T-DNA of the Ti plasmid of *Agrobacterium tumefaciens*.

The particle bombardment method (Klein et al., *Nature* 327:70-73 (1987)) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After ten minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μl of ethanol. An aliquot (5 μl) of the DNA-coated gold particles can be placed in the center of a KAPTON™ flying disc (Bio-Rad Labs). The particles are then accelerated into the maize tissue with a BIOLISTIC™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covers a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialaphos (5 mg per liter) and lacks casein or proline. The tissue continues to grow slowly on this medium. After an additional two weeks the tissue can be transferred to fresh N6 medium containing bialaphos. After six weeks, areas of about 1 cm in diameter of actively growing callus can be identified on some of the plates containing the bialaphos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., *Bio/Technology* 8:833-839 (1990)).

Transgenic TO plants can be regenerated and their phenotype determined following HTP procedures. T1 seed can be collected.

T1 plants can be grown under nitrogen limiting conditions, for example 1 mM nitrate, and analyzed for phenotypic changes. The following parameters can be quantified using image analysis: plant area, volume, growth rate and color analysis can be collected and quantified. Overexpression constructs that result in an alteration, compared to suitable control plants, in greenness (green color bin), yield, growth rate, biomass, fresh or dry weight at maturation, fruit or seed yield, total plant nitrogen content, fruit or seed nitrogen content, nitrogen content in vegetative tissue, free amino acid content in the whole plant, free amino acid content in vegetative tissue, free amino acid content in the fruit or seed, protein content in the fruit or seed, or protein content in a vegetative tissue can be considered evidence that the *Arabidopsis* lead gene functions in maize to enhance tolerance to nitrogen deprivation (increased nitrogen tolerance). Furthermore, a recombinant DNA construct containing a validated *Arabidopsis* gene can be introduced into a maize inbred line either by direct transformation or introgression from a separately transformed line.

Example 12

Electroporation of *Agrobacterium tumefaciens* LBA4404 (General Description)

Electroporation competent cells (40 μL), such as *Agrobacterium tumefaciens* LBA4404 (containing PHP10523), are thawed on ice (20-30 min). PHP10523 contains VIR genes for T-DNA transfer, an *Agrobacterium* low copy number plasmid origin of replication, a tetracycline resistance gene, and a Cos site for in vivo DNA bimolecular recombination. Meanwhile the electroporation cuvette is chilled on ice. The electroporator settings are adjusted to 2.1 kV. A DNA aliquot (0.5 μL parental DNA at a concentration of 0.2 μg-1.0 μg in low salt buffer or twice distilled $H_2O$) is mixed with the thawed *Agrobacterium tumefaciens* LBA4404 cells while still on ice. The mixture is transferred to the bottom of electroporation cuvette and kept at rest on ice for 1-2 min. The cells are electroporated (Eppendorf electroporator 2510) by pushing the "pulse" button twice (ideally achieving a 4.0 millisecond pulse). Subsequently, 0.5 mL of room temperature 2×YT medium (or SOC medium) are added to the cuvette and transferred to a 15 mL snap-cap tube (e.g., FALCON™ tube). The cells are incubated at 28-30° C., 200-250 rpm for 3 h.

Aliquots of 2504 are spread onto plates containing YM medium and 50 μg/mL spectinomycin and incubated three days at 28-30° C. To increase the number of transformants one of two optional steps can be performed:

Option 1: Overlay plates with 30 μm of 15 mg/mL rifampicin. LBA4404 has a chromosomal resistance gene for rifampicin. This additional selection eliminates some contaminating colonies observed when using poorer preparations of LBA4404 competent cells.

Option 2: Perform two replicates of the electroporation to compensate for poorer electrocompetent cells.

Identification of Transformants:

Four independent colonies are picked and streaked on plates containing AB minimal medium and 50 μg/mL spectinomycin for isolation of single colonies. The plates are incubated at 28° C. for two to three days. A single colony for each putative cointegrate is picked and inoculated with 4 mL of 10 g/L bactopeptone, 10 g/L yeast extract, 5 g/L sodium chloride, and 50 mg/L spectinomycin. The mixture is incubated for 24 h at 28° C. with shaking. Plasmid DNA from 4 mL of culture is isolated using QIAGEN Miniprep and an optional Buffer PB wash. The DNA is eluted in 30 μL. Aliquots of 2 μl are used to electroporate 20 μl of DH10b+20 μl of twice distilled $H_2O$ as per above. Optionally a 15 μl aliquot can be used to transform 75-100 μl of INVITROGEN™ Library Efficiency DH5a. The cells are spread on plates containing LB medium and 50 μg/mL spectinomycin and incubated at 37° C. overnight.

Three to four independent colonies are picked for each putative cointegrate and inoculated 4 mL of 2×YT medium (10 g/L bactopeptone, 10 g/L yeast extract, 5 g/L sodium chloride) with 50 μg/mL spectinomycin. The cells are incubated at 37° C. overnight with shaking. Next, the plasmid DNA is isolated from 4 mL of culture using QIAprep® Miniprep with optional Buffer PB wash (elute in 50 4). 8 μl used for digestion with SalI (using parental DNA and PHP10523 as controls). Three more digestions using restriction enzymes BamHI, EcoRI, and HindIII are performed for 4 plasmids that represent 2 putative cointegrates with correct SalI digestion pattern (using parental DNA and PHP10523 as controls). Electronic gels are recommended for comparison.

Alternatively, for high throughput applications, such as that described for Gaspe Flint Derived Maize Lines (Example 16), instead of evaluating the resulting cointegrate vectors by restriction analysis, three colonies can be simultaneously used for the infection step as described in Example 13 (transformation via *Agrobacterium*).

Example 13

Transformation of Maize Using *Agrobacterium*

Maize plants can be transformed to overexpress a validated *Arabidopsis* lead gene or the corresponding homologs from various species in order to examine the resulting phenotype.

*Agrobacterium*-mediated transformation of maize is performed essentially as described by Zhao et al., in *Meth. Mol. Biol.* 318:315-323 (2006) (see also Zhao et al., *Mol. Breed.* 8:323-333 (2001) and U.S. Pat. No. 5,981,840 issued Nov. 9, 1999, incorporated herein by reference). The transformation process involves bacterium inoculation, co-cultivation, resting, selection, and plant regeneration.

1. Immature Embryo Preparation:

Immature maize embryos are dissected from caryopses and placed in a 2 mL microtube containing 2 mL PHI-A medium.

2. *Agrobacterium* Infection and Co-Cultivation of Immature Embryos:

2.1 Infection Step:

PHI-A medium of (1) is removed with 1 mL micropipettor, and 1 mL of *Agrobacterium* suspension is added. The tube is gently inverted to mix. The mixture is incubated for 5 min at room temperature.

2.2 Co-culture Step:

The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for three days. L-Cysteine can be used in the co-cultivation phase. With the standard binary vector, the co-cultivation medium supplied with 100-400 mg/L L-cysteine is critical for recovering stable transgenic events.

3. Selection of Putative Transgenic Events:

To each plate of PHI-D medium in a 100×15 mm Petri dish, 10 embryos are transferred, maintaining orientation, and the dishes are sealed with parafilm. The plates are incubated in darkness at 28° C. Actively growing putative events, evinced as pale yellow embryonic tissue, are expected to be visible in six to eight weeks. Embryos that produce no events may be brown and necrotic, and little friable tissue growth is evident. Putative transgenic embryonic tissue is subcultured to fresh PHI-D plates at two-three week intervals, depending on growth rate. The events are recorded.

4. Regeneration of T0 plants:

Embryonic tissue propagated on PHI-D medium is subcultured to PHI-E medium (somatic embryo maturation medium), in 100×25 mm Petri dishes and incubated at 28° C., in darkness, until somatic embryos mature, for about ten to eighteen days. Individual, matured somatic embryos with well-defined scutellum and coleoptile are transferred to PHI-F embryo germination medium and incubated at 28° C. in the light (about 80 µE from cool white or equivalent fluorescent lamps). In seven to ten days, regenerated plants, about 10 cm tall, are potted in horticultural mix and hardened-off using standard horticultural methods.

Media for Plant Transformation:
1. PHI-A: 4 g/L CHU basal salts, 1.0 mL/L 1000× Eriksson's vitamin mix, 0.5 mg/L thiamin HCl, 1.5 mg/L 2,4-D, 0.69 g/L L-proline, 68.5 g/L sucrose, 36 g/L glucose, pH 5.2. Add 100 µM acetosyringone (filter-sterilized).
2. PHI-B: PHI-A without glucose, increase 2,4-D to 2 mg/L, reduce sucrose to 30 g/L and supplemented with 0.85 mg/L silver nitrate (filter-sterilized), 3.0 g/L GEL-RITE®, 100 µM acetosyringone (filter-sterilized), pH 5.8.
3. PHI-C: PHI-B without GELRITE® and acetosyringone, reduce 2,4-D to 1.5 mg/L and supplemented with 8.0 g/L agar, 0.5 g/L 2-[N-morpholino]ethane-sulfonic acid (MES) buffer, 100 mg/L carbenicillin (filter-sterilized).
4. PHI-D: PHI-C supplemented with 3 mg/L bialaphos (filter-sterilized).
5. PHI-E: 4.3 g/L of Murashige and Skoog (MS) salts, (GIBCO, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, Cat. No. Z-0164), 1 mg/L indole acetic acid (IAA), 26.4 µg/L abscisic acid (ABA), 60 g/L sucrose, 3 mg/L bialaphos (filter-sterilized), 100 mg/L carbenicillin (filter-sterilized), 8 g/L agar, pH 5.6.
6. PHI-F: PHI-E without zeatin, IAA, ABA; reduce sucrose to 40 g/L; replacing agar with 1.5 g/L GELRITE®; pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm et al., *Bio/Technology* 8:833-839 (1990)).

Transgenic T0 plants can be regenerated and their phenotype determined. T1 seed can be collected.

T1 plants can be grown under nitrogen limiting conditions, for example 1 mM nitrate, and analyzed for phenotypic changes. The following parameters can be quantified using image analysis: plant area, volume, growth rate and color analysis can be collected and quantified. Overexpression constructs that result in an alteration, compared to suitable control plants, in greenness (green color bin), yield, growth rate, biomass, fresh or dry weight at maturation, fruit or seed yield, total plant nitrogen content, fruit or seed nitrogen content, nitrogen content in vegetative tissue, free amino acid content in the whole plant, free amino acid content in vegetative tissue, free amino acid content in the fruit or seed, protein content in the fruit or seed, or protein content in a vegetative tissue can be considered evidence that the *Arabidopsis* lead gene functions in maize to enhance tolerance to nitrogen deprivation (increased nitrogen tolerance).

Furthermore, a recombinant DNA construct containing a validated *Arabidopsis* gene can be introduced into a maize inbred line either by direct transformation or introgression from a separately transformed line.

Example 14A

Preparation of Expression Vector for Transformation of Maize Lines with Validated Candidate *Arabidopsis* Gene (At5g50930) Using *Agrobacterium*

Using the INVITROGEN™ GATEWAY® technology, an LR Recombination Reaction was performed with the GATEWAY® entry clone containing the *Arabidopsis* Int2-2 (described in Example 5), entry clone PHP23112 (SEQ ID NO:14), entry clone PHP20234 (SEQ ID NO:9; FIG. 9) and destination vector PHP22655 (SEQ ID NO:10) to generate the precursor plasmid PHP28699. Likewise, an LR Recombination Reaction was performed with the GATEWAY® entry clone containing the *Arabidopsis* Int2-2 (described in Example 5), entry clone PHP23112 (SEQ ID NO:14), entry clone PHP20234 (SEQ ID NO:9; FIG. 9) and destination vector PHP22655 (SEQ ID NO:10) to generate the precursor plasmid PHP28700. PHP28699 and PHP28700 each contain the following expression cassettes:

1. Ubiquitin promoter::moPAT::PinII terminator cassette expressing the PAT herbicide resistance gene used for selection during the transformation process.

2. LTP2 promoter::DS-RED2::PinII terminator cassette expressing the DS-RED color marker gene used for seed sorting.

In addition, PHP28699 contains the Ubiquitin promoter:Int2-2::PinII terminator cassette overexpressing the *Arabidopsis* LNT2-2, and PHP28700 contains the Ubiquitin promoter:Int2-3::PinII terminator cassette overexpressing the *Arabidopsis* LNT2-3.

Example 14B

Transformation of Maize Lines with Validated Candidate *Arabidopsis* Gene (At5q50930) Using *Agrobacterium*

The LNT2-2 expression cassette present in vector PHP28699 (described in Example 14A) can be introduced into a maize inbred line, or a transformable maize line derived from an elite maize inbred line, using *Agrobacterium*-mediated transformation as described in Examples 12 and 13. The same procedures can also be used to introduce the LNT2-3 expression cassette present in PHP28700 into a maize inbred line, or a transformable maize line derived from an elite maize inbred line.

Expression vector PHP28699 can be electroporated into the LBA4404 *Agrobacterium* strain containing vector PHP10523 (SEQ ID NO:7, FIG. 7) to create the co-integrate vector PHP28841, which contains the Int2-2 expression cassette. The co-integrate vector is formed by recombination of the two plasmids, PHP28699 and PHP10523, through the COS recombination sites contained on each vector and contains the same three expression cassettes as above (Example 14A) in addition to other genes (TET, TET, TRFA, OR1 terminator, CTL, ORI V, VIR C1, VIR C2, VIR G, VIR B) needed for the *Agrobacterium* strain and the *Agrobacterium*-mediated transformation. Similarly, expression vector PHP28700 can be electroporated into the LBA4404 *Agrobacterium* strain containing vector PHP10523 (SEQ ID NO:7, FIG. 7) to create the co-integrate vector PHP28840, which contains the Int2-3 expression cassette. The electroporation protocol in, but not limited to, Example 12 may be used.

Example 15

Preparation of the Destination Vector PHP23236 for Transformation into Gaspe Flint derived Maize Lines Destination vector PHP23236 (FIG. 6; SEQ ID NO:6) was obtained by transformation of *Agrobacterium* strain LBA4404 containing PHP10523 (FIG. 7; SEQ ID NO:7) with vector PHP23235 (FIG. 8; SEQ ID NO:8) and isolation of the resulting co-integration product.

Destination vector PHP23236 can be used in a recombination reaction with an entry clone, as described in Example 16, to create a maize expression vector for transformation of Gaspe Flint derived maize lines.

Example 16

Preparation of Expression Constructs for Transformation into Gaspe Flint Derived Maize Lines Using the INVITROGEN™ GATEWAY® LR Recombination technology, the same entry clones described in Example 5 can be used to directionally clone the expression cassettes into the GATEWAY® destination vector PHP23236 (SEQ ID NO:6; FIG. 6) to create corresponding expression vectors. Expression vectors PHP29694 and PHP29689 contain Int2-2 (SEQ ID NO:29) and Int2-3 (SEQ ID NO:31), respectively. Each expression vector contains the cDNA of interest under control of the UBI promoter and is a T-DNA binary for *Agrobacterium*-mediated transformation into maize as described, but not limited to, the examples described herein.

Example 17A

Transformation of Gaspe Flint Derived Maize Lines with Validated Candidate *Arabidopsis* Gene (At5g50930)

Maize plants can be transformed to overexpress the *Arabidopsis* At5g50930 gene (and the corresponding homologs from other species) in order to examine the resulting phenotype. Expression constructs such as the one described in Example 16 may be used.

Recipient Plants

Recipient plant cells can be from a uniform maize line having a short life cycle ("fast cycling"), a reduced size, and high transformation potential. Typical of these plant cells for maize are plant cells from any of the publicly available Gaspe Flint (GF) line varieties. One possible candidate plant line variety is the F1 hybrid of GF×QTM (Quick Turnaround Maize, a publicly available form of Gaspe Flint selected for growth under greenhouse conditions) disclosed in Tomes et al. (U.S. application Ser. No. 10/367,416 filed Feb. 13, 2003; U.S. Patent Publication No. 2003/0221212 A1 published Nov. 27, 2003). Transgenic plants obtained from this line are of such a reduced size that they can be grown in four inch pots (¼ the space needed for a normal sized maize plant) and mature in less than 2.5 months. (Traditionally 3.5 months is required to obtain transgenic T0 seed once the transgenic plants are acclimated to the greenhouse.) Another suitable line includes but is not limited to a double haploid line of GS3 (a highly transformable line)×Gaspe Flint. Yet another suitable line is a transformable elite maize inbred line carrying a transgene which causes early flowering, reduced stature, or both.

Transformation Protocol

Any suitable method may be used to introduce the transgenes into the maize cells, including but not limited to inoculation type procedures using *Agrobacterium* based vectors (see, for example, Examples 12 and 13). Transformation may be performed on immature embryos of the recipient (target) plant.

Precision Growth and Plant Tracking

The event population of transgenic (T0) plants resulting from the transformed maize embryos is grown in a controlled greenhouse environment using a modified randomized block design to reduce or eliminate environmental error. A randomized block design is a plant layout in which the experimental plants are divided into groups (e.g., thirty plants per group), referred to as blocks, and each plant is randomly assigned a location within the block.

For a group of thirty plants, twenty-four transformed, experimental plants and six control plants (plants with a set phenotype) (collectively, a "replicate group") are placed in pots which are arranged in an array (a.k.a. a replicate group or block) on a table located inside a greenhouse. Each plant, control or experimental, is randomly assigned to a location within the block which is mapped to a unique, physical greenhouse location as well as to the replicate group. Multiple replicate groups of thirty plants each may be grown in the same greenhouse in a single experiment. The layout (arrangement) of the replicate groups should be determined to minimize space requirements as well as environmental effects within the greenhouse. Such a layout may be referred to as a compressed greenhouse layout.

An alternative to the addition of a specific control group is to identify those transgenic plants that do not express the gene of interest. A variety of techniques such as RT-PCR can be applied to quantitatively assess the expression level of the introduced gene. T0 plants that do not express the transgene can be compared to those which do.

Each plant in the event population is identified and tracked throughout the evaluation process, and the data gathered from that plant is automatically associated with that plant so that the gathered data can be associated with the transgene carried by the plant. For example, each plant container can have a machine readable label (such as a Universal Product Code (UPC) bar code) which includes information about the plant identity, which in turn is correlated to a greenhouse location so that data obtained from the plant can be automatically associated with that plant.

Alternatively any efficient, machine readable, plant identification system can be used, such as two-dimensional matrix codes or even radio frequency identification tags (RFID) in which the data is received and interpreted by a radio frequency receiver/processor. See U.S. application Ser. No.

10/324,288 filed Dec. 19, 2002 (U.S. Patent Publication No. 2004/0122592 A1 published Jun. 24, 2004), incorporated herein by reference.

Phenotypic Analysis Using Three-Dimensional Imaging

Each greenhouse plant in the T0 event population, including any control plants, is analyzed for agronomic characteristics of interest, and the agronomic data for each plant is recorded or stored in a manner so that it is associated with the identifying data (see above) for that plant. Confirmation of a phenotype (gene effect) can be accomplished in the T1 generation with a similar experimental design to that described above.

The T0 plants are analyzed at the phenotypic level using quantitative, non-destructive imaging technology throughout the plant's entire greenhouse life cycle to assess the traits of interest. In an embodiment, a digital imaging analyzer is used for automatic multi-dimensional analyzing of total plants. The imaging may be done inside the greenhouse. Two camera systems, located at the top and side, and an apparatus to rotate the plant, are used to view and image plants from all sides. Images are acquired from the top, front and side of each plant. All three images together provide sufficient information to evaluate, for example, the biomass, size, and morphology of each plant.

Due to the change in size of the plants from the time the first leaf appears from the soil to the time the plants are at the end of their development, the early stages of plant development are In an embodiment documented with a higher magnification from the top. This imaging may be accomplished by using a motorized zoom lens system that is fully controlled by the imaging software.

In a single imaging analysis operation, the following events occur: (1) the plant is conveyed inside the analyzer area, rotated 360 degrees so its machine readable label can be read, and left at rest until its leaves stop moving; (2) the side image is taken and entered into a database; (3) the plant is rotated 90 degrees and again left at rest until its leaves stop moving, and (4) the plant is transported out of the analyzer.

Plants are allowed at least six hours of darkness per twenty four hour period in order to have a normal day/night cycle.

Imaging Instrumentation

Any suitable imaging instrumentation may be used, including but not limited to light spectrum digital imaging instrumentation commercially available from LemnaTec GmbH of Wurselen, Germany. The images are taken and analyzed with a LemnaTec Scanalyzer HTS LT-0001-2 having a ½" IT Progressive Scan IEE CCD imaging device. The imaging cameras may be equipped with a motor zoom, motor aperture, and motor focus. All camera settings may be made using LemnaTec software. In an embodiment, the instrumental variance of the imaging analyzer is less than about 5% for major components and less than about 10% for minor components.

Software

The imaging analysis system comprises a LemnaTec HTS Bonit software program for color and architecture analysis and a server database for storing data from about 500,000 analyses, including the analysis dates. The original images and the analyzed images are stored together to allow the user to do as much reanalyzing as desired. The database can be connected to the imaging hardware for automatic data collection and storage. A variety of commercially available software systems (e.g., Matlab, others) can be used for quantitative interpretation of the imaging data, and any of these software systems can be applied to the image data set.

Conveyor System

A conveyor system with a plant rotating device may be used to transport the plants to the imaging area and rotate them during imaging. For example, up to four plants, each with a maximum height of 1.5 m, are loaded onto cars that travel over the circulating conveyor system and through the imaging measurement area. In this case the total footprint of the unit (imaging analyzer and conveyor loop) is about 5 m×5 m.

The conveyor system can be enlarged to accommodate more plants at a time. The plants are transported along the conveyor loop to the imaging area and are analyzed for up to 50 seconds per plant. Three views of the plant are taken. The conveyor system, as well as the imaging equipment, should be capable of being used in greenhouse environmental conditions.

Illumination

Any suitable mode of illumination may be used for the image acquisition. For example, a top light above a black background can be used. Alternatively, a combination of top- and backlight using a white background can be used. The illuminated area should be housed to ensure constant illumination conditions. The housing should be longer than the measurement area so that constant light conditions prevail without requiring the opening and closing or doors. Alternatively, the illumination can be varied to cause excitation of either transgene (e.g., green fluorescent protein (GFP), red fluorescent protein (RFP)) or endogenous (e.g. Chlorophyll) fluorophores).

Biomass Estimation Based on Three-Dimensional Imaging

For best estimation of biomass the plant images should be taken from at least three axes, In an embodiment the top and two side (sides 1 and 2) views. These images are then analyzed to separate the plant from the background, pot and pollen control bag (if applicable). The volume of the plant can be estimated by the calculation:

$$\text{Volume(voxels)} = \sqrt{\text{TopArea(pixels)}} \times \sqrt{\text{Side1Area(pixels)}} \times \sqrt{\text{Side2Area(pixels)}}$$

In the equation above the units of volume and area are "arbitrary units". Arbitrary units are entirely sufficient to detect gene effects on plant size and growth in this system because what is desired is to detect differences (both positive-larger and negative-smaller) from the experimental mean, or control mean. The arbitrary units of size (e.g. area) may be trivially converted to physical measurements by the addition of a physical reference to the imaging process. For instance, a physical reference of known area can be included in both top and side imaging processes. Based on the area of these physical references a conversion factor can be determined to allow conversion from pixels to a unit of area such as square centimeters ($cm^2$). The physical reference may or may not be an independent sample. For instance, the pot, with a known diameter and height, could serve as an adequate physical reference.

Color Classification

The imaging technology may also be used to determine plant color and to assign plant colors to various color classes. The assignment of image colors to color classes is an inherent feature of the LemnaTec software. With other image analysis software systems color classification may be determined by a variety of computational approaches.

For the determination of plant size and growth parameters, a useful classification scheme is to define a simple color scheme including two or three shades of green (In an embodiment hues 50-66, see FIG. 12) and, in addition, a color class for chlorosis, necrosis and bleaching, should these conditions occur. A background color class which includes non plant colors in the image (for example pot and soil colors) is also used and these pixels are specifically excluded from the determination of size. The plants are analyzed under controlled constant illumination so that any change within one plant over time, or between plants or different batches of plants (e.g. seasonal differences) can be quantified.

In addition to its usefulness in determining plant size growth, color classification can be used to assess other yield component traits. For these other yield component traits additional color classification schemes may be used. For instance, the trait known as "staygreen", which has been associated with improvements in yield, may be assessed by a color classification that separates shades of green from shades of yellow and brown (which are indicative of senescing tissues). By applying this color classification to images taken toward the end of the T0 or T1 plants' life cycle, plants that have increased amounts of green colors relative to yellow and brown colors (expressed, for instance, as Green/Yellow Ratio) may be identified. Plants with a significant difference in this Green/Yellow ratio can be identified as carrying transgenes which impact this important agronomic trait.

The skilled plant biologist will recognize that other plant colors arise which can indicate plant health or stress response (for instance anthocyanins), and that other color classification schemes can provide further measures of gene action in traits related to these responses.

Plant Architecture Analysis

Transgenes which modify plant architecture parameters may also be identified using the present invention, including such parameters as maximum height and width, internodal distances, angle between leaves and stem, number of leaves starting at nodes, and leaf length. The LemnaTec system software may be used to determine plant architecture as follows. The plant is reduced to its main geometric architecture in a first imaging step and then, based on this image, parameterized identification of the different architecture parameters can be performed. Transgenes that modify any of these architecture parameters either singly or in combination can be identified by applying the statistical approaches previously described.

Pollen Shed Date

Pollen shed date is an important parameter to be analyzed in a transformed plant, and may be determined by the first appearance on the plant of an active male flower. To find the male flower object, the upper end of the stem is classified by color to detect yellow or violet anthers. This color classification analysis is then used to define an active flower, which in turn can be used to calculate pollen shed date.

Alternatively, pollen shed date and other easily visually detected plant attributes (e.g., pollination date, first silk date) can be recorded by the personnel responsible for performing plant care. To maximize data integrity and process efficiency, this data is tracked by utilizing the same barcodes utilized by the LemnaTec light spectrum digital analyzing device. A computer with a barcode reader, a palm device, or a notebook PC may be used for ease of data capture recording time of observation, plant identifier, and the operator who captured the data.

Orientation of the Plants

Mature maize plants grown at densities approximating commercial planting often have a planar architecture. That is, the plant has a clearly discernable broad side, and a narrow side. The image of the plant from the broadside is determined. To each plant a well defined basic orientation is assigned to obtain the maximum difference between the broadside and edgewise images. The top image is used to determine the main axis of the plant, and an additional rotating device is used to turn the plant to the appropriate orientation prior to starting the main image acquisition.

Example 17B

Transformation of Gaspe Flint Derived Maize Lines with Maize Homolog

Using the INVITROGEN™ GATEWAY® LR Recombination technology, an entry clone may be created for the maize homolog (SEQ ID NO:17) (see Example 5 for entry clone preparation) and can be directionally cloned into the GATEWAY® destination vector PHP23236 (SEQ ID NO:6; FIG. 6) to create an expression vector PHP30115. This expression vector now contains the cDNA of interest under control of the UBI promoter and is a T-DNA binary for Agrobacterium-mediated transformation into maize as described, but not limited to, the examples described herein.

Example 18

Screening of Gaspe Flint Derived Maize Lines Under Optimal and Reduced Nitrogen Conditions Transgenic plants contain two or three doses of Gaspe Flint-3 with one dose of GS3 (GS3/(Gaspe-3)2× or GS3/(Gaspe-3)3×) and segregate 1:1 for a dominant transgene. Transgenic plants containing PHP29689 (expression cassette=Int2-3) were planted in 100% Turface in classic 200 pots. Plants were watered with 1.0 mM $KNO_3$ growth medium (see FIG. 13) until segregant determination. At 8 DAP (days after planting), seedlings were randomized and placed equally into respective treatment groups. Two treatments were applied: optimal (6.5 mMol $KNO_3$) and reduced nitrogen (1.0 mMol $KNO_3$), twice daily until 13 DAP. The daily irrigation schedule consisted of a 9:00 AM, 12:00 PM, and 3:00 PM nutrient watering for 3 minutes (156 ml) between 13 and 24 DAP. A fourth watering was added at 5:00 AM on 25 DAP, and a fifth watering was added at 5:00 PM on 31 DAP. pH was monitored at least three times weekly for each table, and days to emergence and days to shed were recorded. Imaging to assess surface area accumulation, specific growth rates (sgr), and changes in color, was performed for each plant three times per week (Monday, Wednesday, and Friday). Plants were sampled for ELISA MOPAT on 8 DAP and for expression and metabolic profiling analysis on 35 DAP. Fresh weight data was obtained from harvested tissue, obtained at 37 DAP, and the harvested tissue was then oven dried (70° C. for 120 hrs.) to obtain dry weight data.

Four events for PHP29689 were evaluated (FIG. 16). The probability of a greater Student's t test was calculated for each transgenic mean compared to the appropriate null mean (either segregant null or construct null). A minimum (P<t) of 0.1 was used as a cut off. Table 5 shows the variables for each event that were significantly increased, as compared to the segregant nulls.

TABLE 5

| PHP29689 event summary | | |
| --- | --- | --- |
| Event | Reduced nitrogen | Optimal nitrogen |
| EA2391.314.1.5 | % light green end exponential<br>% light green harvest day<br>Total area harvest day | % light green end exponential<br>Ear diameter<br>Ear dry weight |

TABLE 5-continued

PHP29689 event summary

| Event | Reduced nitrogen | Optimal nitrogen |
|---|---|---|
|  | Days to shed | Ear fresh weight |
|  | Maximum total area |  |
|  | Specific growth rate |  |
|  | Shoot fresh rate |  |
| EA2391.314.1.6 | Total area end exponential | % light green end exponential |
|  | Total area harvest day | % light green harvest day |
|  | Maximum total area | Total area end exponential |
|  | Shoot dry weight | Total area harvest day |
|  | Shoot fresh weight | Maximum total area |
|  | Shoot + ear dry weight | Specific growth rate |
|  | Shoot + ear fresh weight | Shoot dry weight |
|  | Stalk + ear diameter | Shoot fresh weight |
|  |  | Shoot + ear dry weight |
|  |  | Shoot + ear fresh weight |
| EA2391.314.1.8 | Days to shed | % light green end exponential |
|  | Specific growth rate |  |
|  | Shoot fresh weight | % light green harvest day |
|  | Shoot + ear fresh weight | Days to shed |
|  |  | Specific growth rate |
| EA2391.314.1.9 |  | % light green end exponential |
|  |  | % light green harvest day |
|  |  | Total area harvest day |
|  |  | Maximum total area |
|  |  | Specific growth rate |

When all events were considered relative to the construct null (FIG. 17), the construct, on average, evinced a significant increase over the construct null for a number of variables (data summarized in Table 6).

TABLE 6

PHP29689 construct summary

| Reduced nitrogen | Optimal nitrogen |
|---|---|
| % light green harvest day | % light green end exponential |
| Total area harvest day | % light green harvest day |
| Days to shed | Total area end exponential |
| Max total area | Total area harvest day |
| Specific growth rate | Days to shed |
| Shoot fresh weight | Max total area |
|  | Specific growth rate |
|  | Shoot dry weight |
|  | Shoot fresh weight |
|  | Shoot + ear dry weight |
|  | Shoot + ear fresh weight |

Example 19

Yield Analysis of Maize Lines with the *Arabidopsis* Lead Genes

Transgenic plants, either inbreds or topcross hybrids, can undergo more vigorous field-based experiments to study yield enhancement and/or stability under nitrogen limiting and non-limiting conditions. For example, yield analysis can be done to determine whether plants that contain a validated *Arabidopsis* Int2-2 or Int2-3 gene have an improvement in yield performance (under nitrogen limiting or non-limiting conditions), when compared to the control (or reference) plants, that are either construct null or wild-type. Nitrogen limiting conditions are provided by a combination of previous fertility practices in which nitrogen is applied at reduced levels for one or more years where corn or an alternative crop is grown and the seed crop is removed each season. Under such conditions, a low nitrogen (LN) environment consists of a less than normal amount of nitrogen fertilizer applied in early spring or summer, whereas a normal nitrogen (NN) environment consists of adding adequate nitrogen for normal yields, based on soil test standards established for specific growing areas by Federal and State Extension services.

Corn hybrid testcrosses, containing either the validated *Arabidopsis* Int2-2 or Int2-3 gene, and their controls were grown in LN and NN environments in Woodland, Calif., and in Johnston, Iowa, and yield was assessed. Yield reduction was observed in LN environments compared to that obtained in NN environments. Yields of the corn hybrid testcrosses, containing either the validated *Arabidopsis* Int2-2 or Int2-3 gene, were compared to that of the construct nulls. The results of these yield trials are shown in FIGS. 18-21.

Individual events of plants containing PHP28840 (expression cassette=Int2-3) showed significantly increased yield under LN conditions in 2007 for events E6919.105.1.11 and E6919.105.1.21 in Woodland, while the E6919.105.1.21 event tested in Johnston in 2007 was numerically higher in yield. Similar testing in 2008 revealed significantly improved yield for event E6919.105.1.21 in both Woodland and Johnston and for events E6919.105.1.2 and E6919.105.1.24, in Woodland and in Johnston, respectively. The results for PHP28840-containing plants under low nitrogen conditions are shown in FIG. 18

Under normal nitrogen (NN) treatments, event E6919.105.1.11 was similar in yield to the construct null (not statistically different) in both Woodland and Johnston in 2007, suggesting that under higher nitrogen levels, this event retains high yield potential. A similar result was obtained in 2008 at the Woodland location. In contrast, event E3919.105.1.11 in Johnston in 2008 and events E6919.105.1.21 and E6919.105.1.24 in Johnston in 2007 and 2008 had significantly lower yields. The results for PHP28840-containing plants under normal nitrogen conditions are shown in FIG. 20.

Individual events of plants containing PHP28841 (expression cassette=Int2-2) showed a statistically significant increase in yield for events E6919.106.1.17 and E6919.106.1.3 under LN conditions in Woodland in 2007. However, in Johnston in 2007 under LN conditions, event E6919.106.1.3 showed significantly lower yields, and yields were not collected for event E6919.106.1.17. The results for PHP28841-containing plants under low nitrogen (LN) conditions are shown in FIG. 19.

Under normal nitrogen (NN) treatments, E6919.106.1.17 had numerically higher yields in both Woodland and Johnston in 2007, as compared to the construct null, while event E6919.106.1.3 showed a significant increase in yield in Woodland in 2007 and a numerical increase in Johnston in 2007. Events E6919.106.1.22 and E619.106.1.8 showed significant decreases in yield in Woodland. The results for PHP28841-containing plants under normal nitrogen (NN) conditions are shown in FIG. 21.

Example 20

NUE Maize Seedling Assay

Seed of transgenic events (having construct PHP28841 or PHP28840) were separated into transgene (heterozygous) and null seed using a seed color marker. Two different random assignments of treatments were made to each block of 54 pots, which were arranged 6 rows by 9 columns using 9 replicates of all treatments. In one case, 4 null seed of 5 events of the same construct were mixed and used as a bulked control for comparisons of the 5 positive events in this block, making up 6 treatment combinations in each block. In the second case, 3 transgenic positive treatments and their corresponding nulls were randomly assigned to the 54 pots of the block, making 6 treatment combinations (3 positive and corresponding nulls) for each block, containing 9 replicates of all treatment combinations. In the first case, transgenic parameters were compared to a bulked construct null; in the second case, transgenic parameters were compared to the corresponding event null. In cases where there were 10, 15, or 20 events per construct, the events were assigned in groups of 5 events and the variances were calculated for each block of 54 pots. However, the block null means were pooled across blocks before transgenic mean comparisons were made.

For each treatment, two seeds were planted in a 4 inch square pot containing Turface, on 8 inch, staggered centers. The pots were watered four times each day with a solution containing the following nutrients: 1 mM $CaCl_2$, 2 mM $MgSO_4$, 0.5 mM $KH_2PO_4$, 83 ppm Sprint330, 3 mM KCl, 1 mM $KNO_3$, 1 μM $ZnSO_4$, 1 μM $MnCl_2$, 3 μM $H_3BO_4$, 0.1 μM $CuSO_4$, and 0.1 μM $NaMoO_4$.

After emergence, the plants were thinned to one seed per pot. Treatments were routinely planted on a Monday, and the plants emerged the following Friday.

The plants were then harvested 18 days after planting. At harvest, plants were removed from the pots, and the Turface was washed from the roots. The roots were separated from the shoot, placed in a paper bag and dried at 70° C. for 70 hr. The dried plant parts (roots and shoots) were weighed and placed in a 50 ml conical tube with approximately 20 5/32 inch steel balls and then ground by shaking in a paint shaker. Approximately, 30 mg of the ground tissue (weight recorded for later adjustment) was hydrolyzed in 2 ml of 20% $H_2O_2$ and 6M $H_2SO_4$ for 30 min at 170° C. After cooling, water was added to 20 ml, and the solution was mixed thoroughly. A 50 μl aliquot was removed and added to 950 μl 1M $Na_2CO_3$. The ammonia in this solution was used to estimate total reduced plant nitrogen by placing 100 μl of this solution into individual wells of a 96 well plate and then adding 50 μl of OPA solution. Fluorescence, excitation=360 nM/emission=530 nM, was determined and compared to $NH_4Cl$ standards dissolved in a similar solution and treated with OPA solution.

The following solutions were used in the aforementioned experiments:

OPA solution—5 μl Mercaptoethanol+1 ml OPA stock solution (make fresh, daily)

OPA stock—50 mg o-phthadialdehyde (OPA—Sigma #P0657) dissolved in 1.5 ml methanol+4.4 ml 1M Borate buffer pH9.5 (3.09 g $H_3BO_4$+1g NaOH in 50 ml water)+0.55 ml 20% SDS (made fresh weekly)

The following parameters were measured, and the means were compared to null mean parameters using a Student's t test: SPAD (greenness), stem diameter, root dry weight, shoot dry weight, total dry weight, and plant N concentration. Variance was calculated within each block using a nearest neighbor calculation as well as by Analysis of Variance (ANOVA) using a completely random design (CRD) model. An overall treatment effect for each block was calculated using an F statistic, by dividing overall block treatment mean square by the overall block error mean square. The probability of a greater Student's t test was calculated for each transgenic mean compared to the appropriate null (either construct bulked or individual event null mean) mean. A minimum (P<t) of 0.1 was used as a cut off.

The results of the NUE seedling assay for the PHP28840 (expression cassette=Int2-3) and PHP28841 (expression cassette=Int2-2) constructs are shown in FIG. 22. Event E6919.105.1.21, which contains the UBI:Int2-3 expression cassette, showed a statistically significant increase in the following: shoot dry weight, nitrogen concentration, and total N. Another event with the UBI:Int2-3 expression cassette and four out of six events with the UBI:Int2-2 expression cassette evinced a statistically significant increase in plant N concentration. In addition, two out of six events containing the UBI:Int2-2 expression cassette showed a statistically significant increase in total N.

Example 21

Transformation and Evaluation of Soybean with Soybean Homologs of Validated Lead Genes Based on homology searches, one or several candidate soybean homologs of validated *Arabidopsis* leads can be identified and also be assessed for their ability to enhance tolerance to nitrogen limiting conditions in soybean. Vector construction, plant transformation and phenotypic analysis will be similar to that in previously described Examples.

Example 22

Transformation and Evaluation of Maize with Maize Homologs of Validated Lead Genes Based on homology searches, one or several candidate maize homologs of validated *Arabidopsis* lead genes can be identified (e.g., SEQ ID NOs:18 and 20) and also be assessed for their ability to enhance tolerance to nitrogen limiting conditions in maize. Vector construction, plant transformation and phenotypic analysis can be similar to that in previously described Examples.

Example 23

Transformation of *Arabidopsis* with Maize and Soybean Homologs of Validated Lead Genes Soybean and maize homologs to validated *Arabidopsis* lead genes can be transformed into *Arabidopsis* under control of the 35S promoter and assayed for leaf area and green color bin accumulation when grown on low nitrogen medium. Vector construction and plant transformation can be as described in the examples herein. Assay conditions, data capture and data analysis can be similar to that in previously described Examples.

What is claimed is:

1. A method of increasing nitrogen stress tolerance in a plant, comprising:
    (a) introducing into a regenerable plant cell a recombinant DNA construct comprising a polynucleotide operably linked to at least one regulatory sequence, wherein the polynucleotide encodes a polypeptide having an amino acid sequence of at least 98% sequence identity, based on the Clustal V method of alignment, when compared to SEQ ID NO:32; and
    (b) regenerating a transgenic plant from the regenerable plant cell after step (a), wherein the transgenic plant comprises in its genome the recombinant DNA construct; the polynucleotide is expressed in the transgenic plant; and the transgenic plant exhibits increased nitrogen stress tolerance when compared to a control plant not comprising the recombinant DNA construct.

2. The method of claim 1, further comprising:
    (c) obtaining a progeny plant from the transgenic plant, wherein said progeny plant comprises in its genome the recombinant DNA construct; the polynucleotide is expressed in the progeny plant; and the progeny plant exhibits increased nitrogen stress tolerance when compared to a control plant not comprising the recombinant DNA construct.

* * * * *

SEQUENCE LISTING

<160> NUMBER OF SEQ ID NOS: 36

<210> SEQ ID NO 1
<211> LENGTH: 18491

<212> TYPE: DNA
<213> ORGANISM: Artificial Sequence
<220> FEATURE:
<223> OTHER INFORMATION: pHSbarEND2s activation tagging vector

<400> SEQUENCE: 1

```
catgaatcaa acaaacatac acagcgactt attcacacga gctcaaatta caacggtata      60
tatcctgccg tcgacaacca tggtctagac aggatcccg ggtaccgagc tcgaatttgc      120
aggtcgactg cgtcatccct tacgtcagtg gagatatcac atcaatccac ttgctttgaa     180
gacgtggttg gaacgtcttc ttttccacg atgctcctcg tgggtggggg tccatctttg      240
ggaccactgt cggcagaggc atcttgaacg atagccttttc ctttatcgca atgatggcat    300
ttgtaggtgc caccttcctt ttctactgtc cttttgatga agtgacagat agctgggcaa     360
tggaatccga ggaggtttcc cgatattacc ctttgttgaa aagtctcaat tgcccttgg     420
tcttctgaga ctgttgcgtc atcccttacg tcagtggaga tatcacatca atccacttgc    480
tttgaagacg tggttggaac gtcttctttt tccacgatgc tcctcgtggg tggggtcca     540
tctttgggac cactgtcggc agaggcatct tgaacgatag cctttccttt atcgcaatga    600
tggcatttgt aggtgccacc ttccttttct actgtccttt tgatgaagtg acagatagct    660
ggcaatgga atccgaggag gtttcccgat attacccttt gttgaaaagt ctcagttaac    720
ccgcgatcct gcgtcatccc ttacgtcagt ggagatatca catcaatcca cttgctttga    780
agacgtggtt ggaacgtctt cttttccac gatgctcctc gtgggtgggg gtccatcttt     840
gggaccactg tcggcagagg catcttgaac gatagccttt cctttatcgc aatgatggca    900
tttgtaggtg ccaccttcct tttctactgt ccttttgatg aagtgacaga tagctgggca    960
atggaatccg aggaggtttc ccgatattac cctttgttga aaagtctcaa ttgcccttg     1020
gtcttctgag actgttgcgt catcccttac gtcagtggag atatcacatc aatccacttg    1080
ctttgaagac gtggttggaa cgtcttcttt tccacgatg ctcctcgtgg gtggggtcc      1140
atctttggga ccactgtcgg cagaggcatc ttgaacgata gcctttcctt tatcgcaatg    1200
atggcatttg taggtgccac cttccttttc tactgtcctt tgatgaagt gacagatagc    1260
tgggcaatgg aatccgagga ggtttcccga tattacccttt gttgaaaaag tctcagttaa    1320
cccgcaattc actggccgtc gttttacaac gtcgtgactg ggaaaaccct ggcgttaccc    1380
aacttaatcg ccttgcagca catcccccctt tcgccagctg gcgtaatagc gaagaggccc    1440
gcaccgatcg cccttcccaa cagttgcgca gcctgaatgg cgaatggatc gatccgtcga    1500
tcgaccaaag cggccatcgt gcctccccac tcctgcagtt cgggggcatg gatgcgcgga    1560
tagccgctgc tggtttcctg gatgccgacg gatttgcact gccggtagaa ctccgcgagg    1620
tcgtccagcc tcaggcagca gctgaaccaa ctcgcgaggg gatcgagccc ctgctgagcc    1680
tcgacatgtt gtcgcaaaat tcgccctgga cccgcccaac gatttgtcgt cactgtcaag    1740
gtttgacctg cacttcattt ggggcccaca tacaccaaaa aaatgctgca taattctcgg    1800
ggcagcaagt cggttacccg gccgccgtgc tggaccgggt tgaatggtgc ccgtaacttt    1860
cggtagagcg gacggccaat actcaacttc aaggaatctc acccatgcgc gccggcggg     1920
aaccggagtt cccttcagtg aacgttatta gttcgccgct cggtgtgtcg tagatactag    1980
cccctggggc ttttgaaat ttgaataaga tttatgtaat cagtctttta ggtttgaccg     2040
gttctgccgc ttttttaaa attggatttg taataataaa acgcaattgt ttgttattgt     2100
ggcgctctat catgagatgt ctataaaacc tattcagcac aatatattgt tttcattta    2160
atattgtaca tataagtagt agggtacaat cagtaaattg aacggagaat attattcata    2220
```

```
aaaatacgat agtaacgggt gatatattca ttagaatgaa ccgaaaccgg cggtaaggat    2280
ctgagctaca catgctcagg ttttttacaa cgtgcacaac agaattgaaa gcaaatatca    2340
tgcgatcata ggcgtctcgc atatctcatt aaagcagggg gtgggcgaag aactccagca    2400
tgagatcccc gcgctggagg atcatccagc cggcgtcccg gaaaacgatt ccgaagccca    2460
acctttcata gaaggcggcg gtggaatcga atctcgtga tggcaggttg ggcgtcgctt    2520
ggtcggtcat ttcgaacccc agagtcccgc tcagaagaac tcgtcaagaa ggcgatagaa    2580
ggcgatgcgc tgcgaatcgg gagcggcgat accgtaaagc acgaggaagc ggtcagccca    2640
ttcgccgcca agctcttcag caatatcacg ggtagccaac gctatgtcct gatagcggtc    2700
cgccacaccc agccgccac agtcgatgaa tccagaaaag cggccatttt ccaccatgat    2760
attcggcaag caggcatcgc catgggtcac gacgagatcc tcgccgtcgg gcatgccccc    2820
caattcactg gccgtcgttt tacaacgtcg tgactgggaa aaccctggcg ttacccaact    2880
taatcgcctt gcagcacatc cccctttcgc cagctggcgt aatagcgaag aggcccgcac    2940
cgatcgccct tcccaacagt tgcgcagcct gaatggcgaa tggcgcctga tgcggtattt    3000
tctccttacg catctgtgcg gtatttcaca ccgcatatgg tgcactctca gtacaatctg    3060
ctctgatgcc gcatagttaa gccagccccg acacccgcca cacccgctg acgcgccctg    3120 acgggcttgt ctgctcccgg catccgctta cagacaagct gtgaccgtct ccgggagctg    3180
catgtgtcag aggttttcac cgtcatcacc gaaacgcgcg agacgaaagg cctcgtgat    3240 acgcctattt ttataggtta atgtcatgat aataatggtt tcttagacgt caggtggcac    3300
ttttcgggga atgtgcgcg gaacccctat ttgtttattt ttctaaatac attcaaatat    3360
gtatccgctc atgagacaat aaccctgata aatgcttcaa taatattgaa aaaggaagag    3420
tatgagtatt caacatttcc gtgtcgccct tattcccttt tttgcggcat tttgccttcc    3480 tgttttgct cacccagaaa cgctggtgaa agtaaaagat gctgaagatc agttgggtgc    3540
acgagtgggt tacatcgaac tggatctcaa cagcggtaag atccttgaga gttttcgccc    3600
cgaagaacgt tttccaatga tgagcacttt taaagttctg ctatgtggcg cggtattatc    3660
ccgtattgac gccgggcaag agcaactcgg tcgccgcata cactattctc agaatgactt    3720
ggttgagtac tcaccagtca cagaaaagca tcttacggat ggcatgacag taagagaatt    3780
atgcagtgct gccataacca tgagtgataa cactgcggcc aacttacttc tgacaacgat    3840
cggaggaccg aaggagctaa ccgcttttt gcacaacatg ggggatcatg taactcgcct    3900
tgatcgttgg gaaccggagc tgaatgaagc cataccaaac gacgagcgtg acaccacgat    3960
gcctgtagca atggcaacaa cgttgcgcaa actattaact ggcgaactac ttactctagc    4020
ttcccggcaa caattaatag actggatgga ggcggataaa gttgcaggac cacttctgcg    4080
ctcggccctt ccggctggct ggtttattgc tgataaatct ggagccggtg agcgtgggtc    4140
tcgcggtatc attgcagcac tggggccaga tggtaagccc tcccgtatcg tagttatcta    4200
cacgacgggg agtcaggcaa ctatggatga acgaaataga cagatcgctg agataggtgc    4260
ctcactgatt aagcattggt aactgtcaga ccaagtttac tcatatatac tttagattga    4320
tttaaaactt catttttaat ttaaaaggat ctaggtgaag atccttttg ataatctcat    4380 gaccaaaatc ccttaacgtg agtttcgtt ccactgagcg tcagacccg tagaaaagat    4440 caaaggatct tcttgagatc cttttttct gcgcgtaatc tgctgcttgc aaacaaaaaa    4500
accaccgcta ccagcggtgg tttgtttgcc ggatcaagag ctaccaactc ttttccgaa    4560 ggtaactggc ttcagcagag cgcagatacc aaatactgtc cttctagtgt agccgtagtt    4620
```

```
aggccaccac ttcaagaact ctgtagcacc gcctacatac ctcgctctgc taatcctgtt    4680
accagtggct gctgccagtg gcgataagtc gtgtcttacc gggttggact caagacgata    4740
gttaccggat aaggcgcagc ggtcgggctg aacgggggt tcgtgcacac agcccagctt     4800
ggagcgaacg acctacaccg aactgagata cctacagcgt gagcattgag aaagcgccac    4860
gcttcccgaa gggagaaagg cggacaggta tccggtaagc ggcagggtcg aacaggaga     4920 gcgcacgagg gagcttccag ggggaaacgc ctggtatctt tatagtcctg tcgggtttcg    4980
ccacctctga cttgagcgtc gattttttgtg atgctcgtca gggggcgga gcctatggaa    5040 aaacgccagc aacgcggcct ttttacggtt cctggccttt tgctggcctt ttgctcacat    5100
gttctttcct gcgttatccc ctgattctgt ggataaccgt attaccgcct ttgagtgagc    5160
tgataccgct cgccgcagcc gaacgaccga gcgcagcgag tcagtgagcg aggaagcgga    5220
agagcgccca atacgcaaac cgcctctccc cgcgcgttgg ccgattcatt aatgcagctg    5280
gcacgacagg tttcccgact ggaaagcggg cagtgagcgc aacgcaatta atgtgagtta    5340
gctcactcat taggcacccc aggctttaca ctttatgctt ccggctcgta tgttgtgtgg    5400
aattgtgagc ggataacaat ttcacacagg aaacagctat gaccatgatt acgccaagct    5460
ttctaggggg ggggtaccga tctgagatcg gtaacgaaaa cgaacgggta gggatgaaaa    5520
cggtcggtaa cggtcggtaa aatacctcta ccgttttcat tttcatattt aacttgcggg    5580
acggaaacga aaacgggata taccggtaac gaaaacgaac gggataaata cggtaatcga    5640
aaaccgatac gatccggtcg ggttaaagtc gaaatcggac gggaaccggt attttttgttc    5700 ggtaaaatca cacatgaaaa catatattca aaacttaaaa acaaatataa aaaattgtaa    5760
acacaagtct taatgatcac tagtggcgcg cctaggagat ctcgagtagg gataacaggg    5820
taatacatag ataaaatcca tataaatctg gagcacacat agtttaatgt agcacataag    5880
tgataagtct tgggctcttg gctaacataa gaagccatat aagtctacta gcacacatga    5940
cacaatataa agtttaaaac acatattcat aatcacttgc tcacatctgg atcacttagc    6000
atgctacagc tagtgcaata ttagacactt tccaatattt ctcaaacttt tcactcattg    6060
caacggccat tctcctaatg acaaattttt catgaacaca ccattggtca atcaaatcct    6120
ttatctcaca gaacctttg taaaataaat ttgcagtgga atattgagta ccagatagga    6180
gttcagtgag atcaaaaaac ttcttcaaac acttaaaaag agttaatgcc atcttccact    6240
cctcggcttt aggacaaatt gcatcgtacc tacaataatt gacatttgat taattgagaa    6300
tttataatga tgacatgtac aacaattgag acaaacatac ctgcgaggat cacttgtttt    6360
aagccgtgtt agtgcaggct tataatataa ggcatccctc aacatcaaat aggttgaatt    6420
ccatctagtt gagacatcat atgagatccc tttagattta tccaagtcac attcactagc    6480
acacttcatt agttcttccc actgcaaagg agaagatttt acagcaagaa caatcgcttt    6540
gattttctca attgttcctg caattacagc caagccatcc tttgcaacca agttcagtat    6600
gtgacaagca cacctcacat gaaagaaagc accatcacaa actagatttg aatcagtgtc    6660
ctgcaaatcc tcaattatat cgtgcacagc tacttcattt gcactagcat tatccaaaga    6720
caaggcaaac aatttttttct caatgttcca cttaaccatg attgcagtga aggtttgtga    6780
taacctttgg ccagtgtggc gcccttcaac atgaaaaaag ccaacaattc ttttttggag    6840
acaccaatca tcatcaatcc aatggatggt gacacacatg tatgacttat tttgacaaga    6900
tgtccacata tccatagttg tactgaagcg agactgaaca tcttttagtt ttccatacaa    6960
cttttctttt tcttccaaat acaaatccat gatatatttt ctagcagtga cacgggactt    7020
```

```
tattggaaag tgagggcgca gagacttaac aaactcaaca aagtactcat gttctacaat      7080
attgaaagga tattcatgca tgattattgc caaatgaagc ttcttagcc taaccacttc       7140 atcgtactta taaggctcaa tgagatttat gtctttgcca tgatccttt cactttttag      7200 acacaactga cctttaacta aactatgtga tgttctcaag tgatttcgaa atccgcttgt      7260
tccatgatga ccctcagccc tatacttagc cttgcaatta ggaaagttgc aatgtcccca     7320
tacctgaacg tatttctttc catcgacctc cacttcaatt tccttcttgg tgaaatgctg     7380
ccatacatcc gatgtgcact tctttgccct cttctgtggt gcttcttctt cgggttcagg     7440
ttgtggctgt ggttgtggtt ctggttgtgg ttgtggttgt ggttgtggtt catgaacaat     7500
agccatatca tcttgactcg gatctgtagc tgtaccattt gcattactac tgcttacact     7560
ctgaataaaa tgcctctcgg cctcagctgt tgatgatgat ggtgatgtgc ggccacatcc     7620
atgcccacgc gcacgtgcac gtacattctg aatccgacta aagaggctt cagcttttct      7680 tttcaaccct gttataaaca gattttcgt attattctac agtcaatatg atgcttccca      7740
atctacaacc aattagtaat gctaatgcta ttgctactgt ttttctaata tataccttga     7800
gcatatgcag agaatacgga atttgttttg cgagtagaag gcgctcttgt ggtagacatc     7860
aacttggcca atcttatggc tgagcctgag ggaggattat ttccaaccgg aggcgtcatc     7920
tgaggaatgg agtcgtagcc ggctagccga agtggagagc agagccctgg acagcaggtg    7980
ttcagcaatc agcttggtgc tgtactgctg tgacttgtga gcacctggac ggctggacag     8040
caatcagcag gtgttgcaga gcccctggac agcacacaaa tgacacaaca gcttggtgca    8100
atggtgctga cgtgctgtac tgctaagtgc tgtgagcctg tgagcagccg tggagacagg    8160
gagaccgcgg atggccggat gggcgagcgc cgagcagtgg aggtctggag accgctgac     8220 cgcagatggc ggatggcgga tgggcggacc gcggatgggc gagcagtgga gtggaggtct    8280
gggcggatgg gcggaccgcg gcgcggatgg gcgagtcgcg agcagtggag tggagggcgg    8340
accgtggatg gcggcgtctg cgtccggcgt gccgcgtcac ggccgtcacc gcgtgtggtg    8400
cctggtgcag cccagcggcc ggccggctgg gagacaggga gagtcggaga gagcaggcga    8460
gagcgagacg cgtcgccggc gtcggcgtgc ggctggcggc gtccggactc cggcgtgggc    8520
gcgtggcggc gtgtgaatgt gtgatgctgt tactcgtgtg gtgcctggcc gcctgggaga    8580
gaggcagagc agcgttcgct aggtatttct tacatgggct gggcctcagt ggttatggat    8640
gggagttgga gctggccata ttgcagtcat cccgaattag aaaatacggt aacgaaacgg    8700
gatcatcccg attaaaaacg ggatcccggt gaaacggtcg ggaaactagc tctaccgttt    8760
ccgtttccgt ttaccgtttt gtatatcccg tttccgttcc gttttcgttt tttacctcgg    8820
gttcgaaatc gatcgggata aaactaacaa aatcggttat acgataacgg tcggtacggg    8880
attttcccat cctactttca tccctgagat tattgtcgtt tctttcgcag atcggtaccc    8940 ccccctaga gtcgacatcg atctagtaac atagatgaca ccgcgcgcga taatttatcc     9000
tagtttgcgc gctatatttt gttttctatc gcgtattaaa tgtataattg cgggactcta    9060
atcataaaaa cccatctcat aaataacgtc atgcattaca tgttaattat tacatgctta    9120
acgtaattca acagaaatta tatgataatc atcgcaagac cggcaacagg attcaatctt     9180
aagaaacttt attgccaaat gtttgaacga tctgcttcga cgcactcctt ctttaggtac     9240
ggactagatc tcggtgacgg gcaggaccgg acggggcggt accggcaggc tgaagtccag     9300
ctgccagaaa cccacgtcat gccagttccc gtgcttgaag ccggccgccc gcagcatgcc     9360
gcggggggca tatccgagcg cctcgtgcat gcgcacgctc gggtcgttgg gcagcccgat     9420
```

```
gacagcgacc acgctcttga agccctgtgc ctccagggac ttcagcaggt gggtgtagag   9480
cgtggagccc agtcccgtcc gctggtggcg gggggagacg tacacggtcg actcggccgt   9540
ccagtcgtag gcgttgcgtg ccttccaggg gcccgcgtag gcgatgccgg cgacctcgcc   9600
gtccacctcg gcgacgagcc agggatagcg ctcccgcaga cggacgaggt cgtccgtcca   9660
ctcctgcggt tcctgcggct cggtacggaa gttgaccgtg cttgtctcga tgtagtggtt   9720
gacgatggtg cagaccgccg gcatgtccgc ctcggtggca cggcggatgt cggccgggcg   9780
tcgttctggg ctcatggatc tggattgaga gtgaatatga gactctaatt ggataccgag   9840
gggaatttat ggaacgtcag tggagcattt ttgacaagaa atatttgcta gctgatagtg   9900
accttaggcg acttttgaac gcgcaataat ggtttctgac gtatgtgctt agctcattaa   9960
actccagaaa cccgcggctg agtggctcct tcaatcgttg cggttctgtc agttccaaac  10020
gtaaaacggc ttgtcccgcg tcatcggcgg gggtcataac gtgactccct taattctccg  10080
ctcatgatcc ccgggtaccg agctcgaatt gcggctgagt ggctccttca atcgttgcgg  10140
ttctgtcagt tccaaacgta aaacggcttg tcccgcgtca tcggcggggg tcataacgtg  10200
actcccttaa ttctccgctc atgatcttga tcccctgcgc catcagatcc ttggcggcaa  10260
gaaagccatc cagtttactt tgcagggctt cccaaccttta ccagagggcg ccccagctgg  10320
caattccggt tcgcttgctg tatcgatatg gtggatttat cacaaatggg acccgccgcc  10380
gacagaggtg tgatgttagg ccaggacttt gaaaatttgc gcaactatcg tatagtggcc  10440
gacaaattga cgccgagttg acagactgcc tagcatttga gtgaattatg tgaggtaatg  10500
ggctacactg aattggtagc tcaaactgtc agtatttatg tatatgagtg tatattttcg  10560
cataatctca gaccaatctg aagatgaaat gggtatctgg gaatggcgaa atcaaggcat  10620
cgatcgtgaa gtttctcatc taagccccca tttggacgtg aatgtagaca cgtcgaaata  10680
aagatttccg aattagaata atttgtttat tgctttcgcc tataaatacg acggatcgta  10740
atttgtcgtt ttatcaaaat gtactttcat tttataataa cgctgcggac atctacattt  10800
ttgaattgaa aaaaaattgg taattactct ttcttttcct ccatattgac catcatactc  10860
attgctgatc catgtagatt tcccggacat gaagccattt acaattgaat atatcctgcc  10920
gccgctgccg ctttgcaccc ggtggagctt gcatgttggt ttctacgcag aactgagccg  10980
gttaggcaga taatttccat tgagaactga gccatgtgca ccttcccccc aacacggtga  11040 gcgacgggc aacggagtga tccacatggg acttttaaac atcatccgtc ggatggcgtt  11100
gcgagagaag cagtcgatcc gtgagatcag ccgacgcacc gggcaggcgc gcaacacgat  11160
cgcaaagtat ttgaacgcag gtacaatcga gccgacgttc accgtcaccc tggatgctgt  11220
aggcataggc ttggttatgc cggtactgcc gggcctcttg cgggatatcg tccattccga  11280
cagcatcgcc agtcactatg gcgtgctgct agcgctatat gcgttgatgc aatttctatg  11340
cgcacccgtt ctcggagcac tgtccgaccg ctttggccgc cgcccagtcc tgctcgcttc  11400
gctacttgga gccactatcg actacgcgat catggcgacc acacccgtcc tgtggtccaa  11460
cccctccgct gctatagtgc agtcggcttc tgacgttcag tgcagccgtc ttctgaaaac  11520
gacatgtcgc acaagtccta agttacgcga caggctgccg ccctgccctt ttcctggcgt  11580
tttcttgtcg cgtgttttag tcgcataaag tagaatactt gcgactagaa ccggagacat  11640
tacgccatga acaagagcgc cgccgctggc ctgctgggct atgcccgcgt cagcaccgac  11700
gaccaggact tgaccaacca acgggccgaa ctgcacgcgg ccggctgcac caagctgtttt  11760 tccgagaaga tcaccggcac caggcgcgac cgcccggagc tggccaggat gcttgaccac  11820
```

```
ctacgccctg gcgacgttgt gacagtgacc aggctagacc gcctggcccg cagcacccgc   11880
gacctactgg acattgccga gcgcatccag gaggccggcg cgggcctgcg tagcctggca   11940
gagccgtggg ccgacaccac cacgccggcc ggccgcatgg tgttgaccgt gttcgccggc   12000
attgccgagt tcgagcgttc cctaatcatc gaccgcaccc ggagcgggcg cgaggccgcc   12060
aaggcccgag gcgtgaagtt tggccccgc cctaccctca ccccggcaca gatcgcgcac   12120
gcccgcgagc tgatcgacca ggaaggccgc accgtgaaag aggcggctgc actgcttggc   12180
gtgcatcgct cgaccctgta ccgcgcactt gagcgcagcg aggaagtgac gcccaccgag   12240
gccaggcggc gcggtgcctt ccgtgaggac gcattgaccg aggccgacgc cctggcggcc   12300
gccgagaatg aacgccaaga ggaacaagca tgaaaccgca ccaggacggc caggacgaac   12360 cgttttcat taccgaagag atcgaggcgg agatgatcgc ggccgggtac gtgttcgagc   12420
cgcccgcgca cgtctcaacc gtgcggctgc atgaaatcct ggccggtttg tctgatgcca   12480
agctggcggc ctgccggcc agcttggccg ctgaagaaac cgagcgccgc cgtctaaaaa   12540
ggtgatgtgt atttgagtaa aacagcttgc gtcatgcggt cgctgcgtat atgatgcgat   12600
gagtaaataa acaaatacgc aagggaacgc atgaagttat cgctgtactt aaccagaaag   12660
gcgggtcagg caagacgacc atcgcaaccc atctagcccg cgccctgcaa ctcgccgggg   12720
ccgatgttct gttagtcgat tccgatcccc agggcagtgc ccgcgattgg gcggccgtgc   12780
gggaagatca accgctaacc gttgtcggca tcgaccgccc gacgattgac cgcgacgtga   12840
aggccatcgg ccggcgcgac ttcgtagtga tcgacggagc gccccaggcg gcggacttgg   12900
ctgtgtccgc gatcaaggca gccgacttcg tgctgattcc ggtgcagcca gcccttacg   12960 acatatgggc caccgccgac ctggtggagc tggttaagca gcgcattgag gtcacggatg   13020
gaaggctaca gcggcctttt gtcgtgtcgc gggcgatcaa aggcacgcgc atcggcggtg   13080
aggttgccga ggcgctggcc gggtacgagc tgcccattct tgagtcccgt atcacgcagc   13140
gcgtgagcta cccaggcact gccgccgccg gcacaaccgt tcttgaatca gaacccgagg   13200
gcgacgctgc ccgcgaggtc caggcgctgg ccgctgaaat taaatcaaaa ctcatttgag   13260
ttaatgaggt aaagagaaaa tgagcaaaag cacaaacacg ctaagtgccg gccgtccgag   13320
cgcacgcagc agcaaggctg caacgttggc cagcctggca gacacgccag ccatgaagcg   13380
ggtcaacttt cagttgccgg cggaggatca caccaagctg aagatgtacg cggtacgcca   13440
aggcaagacc attaccgagc tgctatctga atacatcgcg cagctaccag agtaaatgag   13500
caaatgaata aatgagtaga tgaattttag cggctaaagg aggcggcatg gaaaatcaag   13560
aacaaccagg caccgacgcc gtggaatgcc ccatgtgtgg aggaacgggc ggttggccag   13620
gcgtaagcgg ctgggttgtc tgccggccct gcaatggcac tggaaccccc aagcccgagg   13680
aatcggcgtg agcggtcgca aaccatccgg cccggtacaa atcggcgcgg cgctgggtga   13740
tgacctggtg gagaagttga aggccgcgca ggccgcccag cggcaacgca tcgaggcaga   13800
agcacgcccc ggtgaatcgt ggcaagcggc cgctgatcga atccgcaaag aatcccggca   13860
accgccggca gccggtgcgc cgtcgattag gaagccgccc aagggcgacg agcaaccaga   13920
ttttttcgtt ccgatgctct atgacgtggg cacccgcgat agtcgcagca tcatggacgt   13980
ggccgttttc cgtctgtcga agcgtgaccg acgagctggc gaggtgatcc gctacgagct   14040
tccagacggg cacgtagagg tttccgcagg ccggccgcgc atggccagtg tgtgggatta   14100
cgacctggta ctgatggcgg tttcccatct aaccgaatcc atgaaccgat accgggaagg   14160
gaagggagac aagcccggcc gcgtgttccg tccacacgtt gcggacgtac tcaagttctg   14220
```

```
ccggcgagcc gatggcggaa agcagaaaga cgacctggta gaaacctgca ttcggttaaa   14280
caccacgcac gttgccatgc agcgtacgaa gaaggccaag aacggccgcc tggtgacggt   14340
atccgagggt gaagccttga ttagccgcta caagatcgta aagagcgaaa ccggcggcc    14400
ggagtacatc gagatcgagc tagctgattg gatgtaccgc gagatcacag aaggcaagaa   14460
cccgacgtg  ctgacggttc acccccgatta cttttttgatc gatcccggca tcggccgttt  14520
tctctaccgc ctggcacgcc gcgccgcagg caaggcagaa gccagatggt tgttcaagac   14580
gatctacgaa cgcagtggca gcgcggaga  gttcaagaag ttctgtttca ccgtgcgcaa   14640
gctgatcggg tcaaatgacc tgccggagta cgatttgaag gaggaggcgg ggcaggctgg   14700
cccgatccta gtcatgcgct accgcaacct gatcgagggc gaagcatccg ccggttccta   14760
atgtacggag cagatgctag ggcaaattgc cctagcaggg gaaaaaggtc gaaaaggtct   14820
ctttcctgtg gatagcacgt acattgggaa cccaaagccg tacattggga accggaaccc   14880
gtacattggg aacccaaagc cgtacattgg gaaccggtca cacatgtaag tgactgatat   14940
aaaagagaaa aaaggcgatt tttccgccta aaactctta  aaacttatta aaactcttaa   15000
aacccgcctg gcctgtgcat aactgtctgg ccagcgcaca gccgaagagc tgcaaaaagc   15060
gcctacccct cggtcgctgc gctccctacg ccccgccgct tcgcgtcggc ctatcgcggc   15120
cgctggccgc tcaaaaatgg ctggcctacg gccaggcaat ctaccagggc gcggacaagc   15180
gcgccgtcg  ccactcgacc gccggcgccc acatcaaggc accctgcctc gcgcgtttcg   15240
gtgatgacgg tgaaaacctc tgacacatgc agctcccgga gacggtcaca gcttgtctgt   15300
aagcggatgc cgggagcaga caagcccgtc agggcgcgtc agcgggtgtt ggcgggtgtc   15360
ggggcgcagc catgacccag tcacgtagcg atagcggagt gtatactggc ttaactatgc   15420
ggcatcagag cagattgtac tgagagtgca ccatatgcgg tgtgaaatac cgcacagatg   15480
cgtaaggaga aaataccgca tcaggcgctc ttccgcttcc tcgctcactg actcgctgcg   15540
ctcggtcgtt cggctgcggc gagcggtatc agctcactca aaggcggtaa tacggttatc   15600
cacagaatca ggggataacg caggaaagaa catgtgagca aaaggccagc aaaaggccag   15660
gaaccgtaaa aaggccgcgt tgctggcgtt tttccatagg ctccgccccc ctgacgagca   15720
tcacaaaaat cgacgctcaa gtcagaggtg gcgaaacccg acaggactat aaagatacca   15780
ggcgtttccc cctggaagct ccctcgtgcg ctctcctgtt ccgaccctgc cgcttaccgg   15840
atacctgtcc gcctttctcc cttcgggaag cgtggcgctt tctcatagct cacgctgtag   15900
gtatctcagt tcggtgtagg tcgttcgctc caagctgggc tgtgtgcacg aacccccgt   15960
tcagcccgac cgctgcgcct tatccggtaa ctatcgtctt gagtccaacc cggtaagaca   16020
cgacttatcg ccactggcag cagccactgg taacaggatt agcagagcga ggtatgtagg   16080
cggtgctaca gagttcttga agtggtggcc taactacggc tacactagaa ggacagtatt   16140
tggtatctgc gctctgctga agccagttac cttcggaaaa agagttggta gctcttgatc   16200
cggcaaacaa accaccgctg gtagcggtgg tttttttgtt tgcaagcagc agattacgcg   16260
cagaaaaaaa ggatctcaag aagatccttt gatcttttct acggggtctg acgctcagtg   16320
gaacgaaaac tcacgttaag ggattttggt catgagatta tcaaaaagga tcttcaccta   16380
gatccttta  aattaaaaat gaagttttaa atcaatctaa agtatatatg agtaaacttg   16440
gtctgacagt taccaatgct taatcagtga ggcacctatc tcagcgatct gtctatttcg   16500
ttcatccata gttgcctgac tccccgtcgt gtagataact acgatacggg agggcttacc   16560
atctggcccc agtgctgcaa tgataccgcg agacccacgc tcaccggctc cagatttatc   16620
```

```
agcaataaac cagccagccg gaagggccga gcgcagaagt ggtcctgcaa ctttatccgc    16680
ctccatccag tctattaatt gttgccggga agctagagta agtagttcgc cagttaatag    16740
tttgcgcaac gttgttgcca ttgctacagg catcgtggtg tcacgctcgt cgtttggtat    16800
ggcttcattc agctccggtt cccaacgatc aaggcgagtt acatgatccc ccatgttgtg    16860
caaaaaagcg gttagctcct tcggtcctcc gatcgttgtc agaagtaagt tggccgcagt    16920
gttatcactc atggttatgg cagcactgca taattctctt actgtcatgc catccgtaag    16980
atgcttttct gtgactggtg agtactcaac caagtcattc tgagaatagt gtatgcggcg    17040
accgagttgc tcttgcccgg cgtcaacacg ggataatacc gcgccacata gcagaacttt    17100
aaaagtgctc atcattggaa aagacctgca ggggggggg ggaaagccac gttgtgtctc    17160
aaaatctctg atgttacatt gcacaagata aaaatatatc atcatgaaca ataaaactgt    17220
ctgcttacat aaacagtaat acaaggggtg ttatgagcca tattcaacgg gaaacgtctt    17280
gctcgaggcc gcgattaaat tccaacatgg atgctgattt atatgggtat aaatgggctc    17340
gcgataatgt cgggcaatca ggtgcgacaa tctatcgatt gtatgggaag cccgatgcgc    17400
cagagttgtt tctgaaacat ggcaaaggta gcgttgccaa tgatgttaca gatgagatgg    17460
tcagactaaa ctggctgacg gaatttatgc ctcttccgac catcaagcat tttatccgta    17520
ctcctgatga tgcatggtta ctcaccactg cgatccccgg gaaaacagca ttccaggtat    17580
tagaagaata tcctgattca ggtgaaaata ttgttgatgc gctggcagtg ttcctgcgcc    17640
ggttgcattc gattcctgtt tgtaattgtc cttttaacag cgatcgcgta tttcgtctcg    17700
ctcaggcgca atcacgaatg aataacggtt tggttgatgc gagtgatttt gatgacgagc    17760
gtaatggctg gcctgttgaa caagtctgga agaaatgca taagcttttg ccattctcac    17820
cggattcagt cgtcactcat ggtgatttct cacttgataa ccttattttt gacgagggga    17880
aattaatagg ttgtattgat gttggacgag tcggaatcgc agaccgatac caggatcttg    17940
ccatcctatg gaactgcctc ggtgagtttt ctccttcatt acagaaacgg ctttttcaaa    18000
aatatggtat tgataatcct gatatgaata aattgcagtt tcatttgatg ctcgatgagt    18060
ttttctaatc agaattggtt aattggttgt aacactggca gagcattacg ctgacttgac    18120
gggacggcgg ctttgttgaa taaatcgaac ttttgctgag ttgaaggatc agatcacgca    18180
tcttcccgac aacgcagacc gttccgtggc aaagcaaaag ttcaaaatca ccaactggtc    18240
cacctacaac aaagctctca tcaaccgtgg ctccctcact ttctggctgg atgatggggc    18300
gattcaggcc tggtatgagt cagcaacacc ttcttcacga ggcagacctc agcgcccccc    18360
cccccctgca ggtcaattcg gtcgatatgg ctattacgaa gaaggctcgt gcgcggagtc    18420
ccgtgaactt tcccacgcaa caagtgaacc gcaccgggtt tgccggaggc catttcgtta    18480
aaatgcgcag c                                                         18491
```

<210> SEQ ID NO 2
<211> LENGTH: 4291
<212> TYPE: DNA
<213> ORGANISM: Artificial Sequence
<220> FEATURE:
<223> OTHER INFORMATION: pDONRZeo construct

<400> SEQUENCE: 2

```
ctttcctgcg ttatcccctg attctgtgga taaccgtatt accgcctttg agtgagctga      60
taccgctcgc cgcagccgaa cgaccgagcg cagcgagtca gtgagcgagg aagcggaaga     120
gcgcccaata cgcaaaccgc ctctccccgc gcgttggccg attcattaat gcagctggca     180
```

```
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt cccagtcac gacgttgtaa     540 aacgacggcc agtcttaagc tcgggcccca aataatgatt ttattttgac tgatagtgac    600
ctgttcgttg caacacattg atgagcaatg cttttttata atgccaactt tgtacaaaaa    660
agctgaacga gaaacgtaaa atgatataaa tatcaatata ttaaattaga ttttgcataa    720
aaaacagact acataatact gtaaaacaca acatatccag tcactatgaa tcaactactt    780
agatggtatt agtgacctgt agtcgaccga cagccttcca aatgttcttc gggtgatgct    840
gccaacttag tcgaccgaca gccttccaaa tgttcttctc aaacggaatc gtcgtatcca    900
gcctactcgc tattgtcctc aatgccgtat taaatcataa aaagaaataa gaaaaagagg    960
tgcgagcctc ttttttgtgt gacaaaataa aaacatctac ctattcatat acgctagtgt   1020
catagtcctg aaaatcatct gcatcaagaa caatttcaca actcttatac ttttctctta   1080
caagtcgttc ggcttcatct ggattttcag cctctatact tactaaacgt gataaagttt   1140
ctgtaatttc tactgtatcg acctgcagac tggctgtgta aagggagcc tgacatttat    1200 attccccaga acatcaggtt aatggcgttt ttgatgtcat tttcgcggtg gctgagatca   1260
gccacttctt ccccgataac ggagaccggc acactggcca tatcggtggt catcatgcgc   1320 cagcttttcat ccccgatatg caccaccggg taaagttcac gggagacttt atctgacagc  1380
agacgtgcac tggccagggg gatcaccatc cgtcgcccgg gcgtgtcaat aatatcactc   1440
tgtacatcca caaacagacg ataacggctc tctcttttat aggtgtaaac cttaaactgc   1500
atttcaccag cccctgttct cgtcagcaaa agagccgttc atttcaataa accgggcgac   1560
ctcagccatc ccttcctgat tttccgcttt ccagcgttcg gcacgcagac gacgggcttc   1620
attctgcatg gttgtgctta ccagaccgga gatattgaca tcatatatgc cttgagcaac   1680
tgatagctgt cgctgtcaac tgtcactgta atacgctgct tcatagcata cctctttttg   1740
acatacttcg ggtatacata tcagtatata ttcttatacc gcaaaaatca gcgcgcaaat   1800
acgcatactg ttatctggct tttagtaagc cggatccacg cggcgtttac gccccgccct   1860
gccactcatc gcagtactgt tgtaattcat taagcattct gccgacatgg aagccatcac   1920
agacggcatg atgaacctga atcgccagcg gcatcagcac cttgtcgcct tgcgtataat   1980
atttgcccat ggtgaaaacg ggggcgaaga agttgtccat attggccacg tttaaatcaa   2040
aactggtgaa actcacccag ggattggctg agacgaaaaa catattctca ataaaccctt   2100
tagggaaata ggccaggttt tcaccgtaac acgccacatc ttgcgaatat atgtgtagaa   2160
actgccggaa atcgtcgtgg tattcactcc agagcgatga aaacgtttca gtttgctcat   2220
ggaaaacggt gtaacaaggg tgaacactat cccatatcac cagctcaccg tctttcattg   2280
ccatacggaa ttccggatga gcattcatca ggcgggcaag aatgtgaata aaggccggat   2340
aaaacttgtg cttattttc tttacggtct ttaaaaaggc cgtaatatcc agctgaacgg    2400
tctggttata ggtacattga gcaactgact gaaatgcctc aaaatgttct ttacgatgcc   2460
attgggatat atcaacggtg gtatatccag tgatttttt ctccatttta gcttccttag    2520
ctcctgaaaa tctcgataac tcaaaaaata cgcccggtag tgatcttatt tcattatggt   2580
```

```
gaaagttgga acctcttacg tgccgatcaa cgtctcattt tcgccaaaag ttggcccagg    2640
gcttcccggt atcaacaggg acaccaggat ttatttattc tgcgaagtga tcttccgtca    2700
caggtattta ttcggcgcaa agtgcgtcgg gtgatgctgc caacttagtc gactacaggt    2760
cactaatacc atctaagtag ttgattcata gtgactggat atgttgtgtt ttacagtatt    2820
atgtagtctg ttttttatgc aaaatctaat ttaatatatt gatatttata tcattttacg    2880
tttctcgttc agctttcttg tacaaagttg gcattataag aaagcattgc ttatcaattt    2940
gttgcaacga acaggtcact atcagtcaaa ataaaatcat tatttgccat ccagctgata    3000
tcccctatag tgagtcgtat tacatggtca tagctgtttc ctggcagctc tggcccgtgt    3060
ctcaaaatct ctgatgttac attgcacaag ataaaataat atcatcatga tcagtcctgc    3120
tcctcggcca cgaagtgcac gcagttgccg gccgggtcgc gcagggcgaa ctcccgcccc    3180
cacggctgct cgccgatctc ggtcatggcc ggcccggagg cgtcccggaa gttcgtggac    3240
acgacctccg accactcggc gtacagctcg tccaggccgc gcacccacac ccaggccagg    3300
gtgttgtccg gcaccacctg gtcctggacc gcgctgatga acagggtcac gtcgtcccgg    3360
accacaccgg cgaagtcgtc ctccacgaag tcccgggaga cccgagccg tcggtccag    3420 aactcgaccg ctccggcgac gtcgcgcgcg gtgagcaccg gaacggcact ggtcaacttg    3480
gccatggttt agttcctcac cttgtcgtat tatactatgc cgatatacta tgccgatgat    3540
taattgtcaa cacgtgctga tcatgaccaa aatcccttaa cgtgagttac gcgtcgttcc    3600
actgagcgtc agaccccgta gaaaagatca aaggatcttc ttgagatcct ttttttctgc    3660
gcgtaatctg ctgcttgcaa acaaaaaaac caccgctacc agcggtggtt tgtttgccgg    3720
atcaagagct accaactctt tttccgaagg taactggctt cagcagagcg cagataccaa    3780
atactgttct tctagtgtag ccgtagttag gccaccactt caagaactct gtagcaccgc    3840
ctacatacct cgctctgcta atcctgttac cagtggctgc tgccagtggc gataagtcgt    3900
gtcttaccgg gttggactca agacgatagt taccggataa ggcgcagcgg tcgggctgaa    3960
cggggggttc gtgcacacag cccagcttgg agcgaacgac ctacaccgaa ctgagatacc    4020
tacagcgtga gctatgagaa agcgccacgc ttcccgaagg gagaaaggcg gacaggtatc    4080
cggtaagcgg cagggtcgga acaggagagc gcacgaggga gcttccaggg ggaaacgcct    4140
ggtatcttta tagtcctgtc gggtttcgcc acctctgact tgagcgtcga ttttttgtgat    4200 gctcgtcagg ggggcggagc ctatggaaaa acgccagcaa cgcggccttt ttacggttcc    4260
tggccttttg ctggcctttt gctcacatgt t                                   4291
```

<210> SEQ ID NO 3
<211> LENGTH: 4762
<212> TYPE: DNA
<213> ORGANISM: Artificial Sequence
<220> FEATURE:
<223> OTHER INFORMATION: pDONR221

<400> SEQUENCE: 3

```
ctttcctgcg ttatcccctg attctgtgga taaccgtatt accgcctttg agtgagctga     60
taccgctcgc cgcagccgaa cgaccgagcg cagcgagtca gtgagcgagg aagcggaaga   120
gcgcccaata cgcaaaccgc ctctccccgc gcgttggccg attcattaat gcagctggca   180
cgacaggttt cccgactgga aagcgggcag tgagcgcaac gcaattaata cgcgtaccgc   240
tagccaggaa gagtttgtag aaacgcaaaa aggccatccg tcaggatggc cttctgctta   300
gtttgatgcc tggcagttta tggcgggcgt cctgcccgcc accctccggg ccgttgcttc   360
```

```
acaacgttca atccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcccca ataatgatt ttattttgac tgatagtgac    600
ctgttcgttg caacacattg atgagcaatg cttttttata atgccaactt tgtacaaaaa    660
agctgaacga gaaacgtaaa atgatataaa tatcaatata ttaaattaga ttttgcataa    720
aaaacagact acataatact gtaaaacaca acatatccag tcactatgaa tcaactactt    780
agatggtatt agtgacctgt agtcgaccga cagccttcca aatgttcttc gggtgatgct    840
gccaacttag tcgaccgaca gccttccaaa tgttcttctc aaacggaatc gtcgtatcca    900
gcctactcgc tattgtcctc aatgccgtat taaatcataa aaagaaataa gaaaaagagg    960
tgcgagcctc ttttttgtgt gacaaaataa aaacatctac ctattcatat acgctagtgt    1020
catagtcctg aaaatcatct gcatcaagaa caatttcaca actcttatac ttttctctta    1080
caagtcgttc ggcttcatct ggattttcag cctctatact tactaaacgt gataaagttt    1140
ctgtaatttc tactgtatcg acctgcagac tggctgtgta aagggagcc tgacatttat    1200 attccccaga acatcaggtt aatggcgttt ttgatgtcat tttcgcggtg gctgagatca    1260
gccacttctt ccccgataac ggagaccggc acactggcca tatcggtggt catcatgcgc    1320
cagctttcat ccccgatatg caccaccggg taaagttcac gggagacttt atctgacagc    1380
agacgtgcac tggccagggg gatcaccatc cgtcgcccgg gcgtgtcaat aatatcactc    1440
tgtacatcca caaacagacg ataacggctc tctctttat aggtgtaaac cttaaactgc    1500
atttcaccag cccctgttct cgtcagcaaa agagccgttc atttcaataa accgggcgac    1560
ctcagccatc ccttcctgat tttccgcttt ccagcgttcg gcacgcagac gacgggcttc    1620
attctgcatg gttgtgctta ccagaccgga gatattgaca tcatatatgc cttgagcaac    1680
tgatagctgt cgctgtcaac tgtcactgta atacgctgct tcatagcata cctcttttg    1740 acatacttcg ggtatacata tcagtatata ttcttatacc gcaaaatca gcgcgcaaat    1800 acgcatactg ttatctggct tttagtaagc cggatccacg cggcgtttac gccccgccct    1860
gccactcatc gcagtactgt tgtaattcat taagcattct gccgacatgg aagccatcac    1920
agacggcatg atgaacctga atcgccagcg gcatcagcac cttgtcgcct tgcgtataat    1980
atttgcccat ggtgaaaacg ggggcgaaga agttgtccat attggccacg tttaaatcaa    2040
aactggtgaa actcacccag ggattggctg agacgaaaaa catattctca ataaacccct    2100
tagggaaata ggccaggttt tcaccgtaac acgccacatc ttgcgaatat atgtgtagaa    2160
actgccggaa atcgtcgtgg tattcactcc agagcgatga aaacgtttca gtttgctcat    2220
ggaaaacggt gtaacaaggg tgaacactat cccatatcac cagctcaccg tctttcattg    2280
ccatacggaa ttccggatga gcattcatca ggcgggcaag aatgtgaata aaggccggat    2340
aaaacttgtg cttattttc tttacggtct taaaaaggc cgtaatatcc agctgaacgg    2400
tctggttata ggtacattga gcaactgact gaaatgcctc aaaatgttct ttacgatgcc    2460
attgggatat atcaacggtg gtatatccag tgattttttt ctccatttta gcttccttag    2520
ctcctgaaaa tctcgataac tcaaaaaata cgcccgtag tgatcttatt tcattatggt    2580
gaaagttgga acctcttacg tgccgatcaa cgtctcattt tcgccaaaag ttggcccagg    2640
gcttcccggt atcaacaggg acaccaggat ttattattc tgcgaagtga tcttccgtca    2700
caggtattta ttcggcgcaa agtgcgtcgg gtgatgctgc caacttagtc gactacaggt    2760
```

```
cactaataacc atctaagtag ttgattcata gtgactggat atgttgtgtt ttacagtatt    2820
atgtagtctg ttttttatgc aaaatctaat ttaatatatt gatatttata tcattttacg    2880
tttctcgttc agcttcttg tacaaagttg gcattataag aaagcattgc ttatcaattt    2940
gttgcaacga acaggtcact atcagtcaaa ataaaatcat tatttgccat ccagctgata    3000 tccctatag tgagtcgtat tacatggtca tagctgtttc ctggcagctc tggcccgtgt    3060
ctcaaaatct ctgatgttac attgcacaag ataaaataat atcatcatga acaataaaac    3120
tgtctgctta cataaacagt aatacaaggg gtgttatgag ccatattcaa cgggaaacgt    3180
cgaggccgcg attaaattcc aacatggatg ctgatttata tgggtataaa tgggctcgcg    3240
ataatgtcgg gcaatcaggt gcgacaatct atcgcttgta tgggaagccc gatgcgccag    3300
agttgtttct gaaacatggc aaaggtagcg ttgccaatga tgttacagat gagatggtca    3360
gactaaactg gctgacggaa tttatgcctc ttccgaccat caagcatttt atccgtactc    3420
ctgatgatgc atggttactc accactgcga tccccggaaa aacagcattc caggtattag    3480
aagaatatcc tgattcaggt gaaaatattg ttgatgcgct ggcagtgttc ctgcgccggt    3540
tgcattcgat tcctgtttgt aattgtcctt ttaacagcga tcgcgtattt cgtctcgctc    3600
aggcgcaatc acgaatgaat aacggtttgg ttgatgcgag tgattttgat gacgagcgta    3660
atggctggcc tgttgaacaa gtctggaaag aaatgcataa acttttgcca ttctcaccgg    3720
attcagtcgt cactcatggt gatttctcac ttgataacct tatttttgac gaggggaaat    3780
taataggttg tattgatgtt ggacgagtcg gaatcgcaga ccgataccag gatcttgcca    3840
tcctatggaa ctgcctcggt gagttttctc cttcattaca gaaacggctt tttcaaaaat    3900
atggtattga taatcctgat atgaataaat tgcagtttca tttgatgctc gatgagtttt    3960
tctaatcaga attggttaat tggttgtaac actggcagag cattacgctg acttgacggg    4020
acggcgcaag ctcatgacca aaatccctta acgtgagtta cgcgtcgttc cactgagcgt    4080 cagacccgt agaaaagatc aaaggatctt cttgagatcc ttttttctg cgcgtaatct    4140 gctgcttgca acaaaaaaa ccaccgctac cagcggtggt ttgtttgccg gatcaagagc    4200
taccaactct ttttccgaag gtaactggct tcagcagagc gcagatacca atactgttc    4260 ttctagtgta gccgtagtta ggccaccact tcaagaactc tgtagcaccg cctacatacc    4320
tcgctctgct aatcctgtta ccagtggctg ctgccagtgg cgataagtcg tgtcttaccg    4380
ggttggactc aagacgatag ttaccggata aggcgcagcg gtcgggctga acgggggggtt    4440 cgtgcacaca gcccagcttg gagcgaacga cctacaccga actgagatac ctacagcgtg    4500
agctatgaga aagcgccacg cttcccgaag ggagaaaggc ggacaggtat ccggtaagcg    4560
gcagggtcgg aacaggagag cgcacgaggg agcttccagg gggaaacgcc tggtatcttt    4620
atagtcctgt cgggtttcgc cacctctgac ttgagcgtcg atttttgtga tgctcgtcag    4680
ggggggggag cctatggaaa aacgccagca acgcggcctt tttacggttc ctggccttt    4740 gctggccttt tgctcacatg tt                                              4762
```

<210> SEQ ID NO 4
<211> LENGTH: 16843
<212> TYPE: DNA
<213> ORGANISM: Artificial Sequence
<220> FEATURE:
<223> OTHER INFORMATION: pBC-yellow construct

<400> SEQUENCE: 4

```
ccgggctggt tgccctcgcc gctgggctgg cggccgtcta tggccctgca aacgcgccag      60
```

-continued

```
aaacgccgtc gaagccgtgt gcgagacacc gcggccgccg gcgttgtgga tacctcgcgg    120
aaaacttggc cctcactgac agatgagggg cggacgttga cacttgaggg gccgactcac    180
ccggcgcggt gttgacagat gaggggcagg ctcgatttcg gccggcgacg tggagctggc    240
cagcctcgca aatcggcgaa aacgcctgat tttacgcgag tttcccacag atgatgtgga    300
caagcctggg gataagtgcc ctgcggtatt gacacttgag gggcgcgact actgacagat    360
gaggggcgcg atccttgaca cttgagggge agagtgctga cagatgaggg gcgcacctat    420
tgacatttga ggggctgtcc acaggcagaa aatccagcat ttgcaagggt ttccgcccgt    480
ttttcggcca ccgctaacct gtcttttaac ctgcttttaa accaatattt ataaaccttg    540
tttttaacca gggctgcgcc ctgtgcgcgt gaccgcgcac gccgaagggg ggtgcccccc    600
cttctcgaac cctcccggcc cgctaacgcg ggcctcccat cccccaggg gctgcgcccc     660 tcggccgcga acggcctcac cccaaaaatg gcagcgctgg cagtccttgc cattgccggg    720
atcggggcag taacgggatg ggcgatcagc ccgagcgcga cgcccggaag cattgacgtg    780
ccgcaggtgc tggcatcgac attcagcgac caggtgccgg gcagtgaggg cggcggcctg    840
ggtggcggcc tgcccttcac ttcggccgtc ggggcattca cggacttcat ggcggggccg    900 gcaatttta ccttgggcat tcttggcata gtggtcgcgg gtgccgtgct cgtgttcggg      960
ggtgcgataa acccagcgaa ccatttgagg tgataggtaa gattataccg aggtatgaaa    1020
acgagaattg gaccttaca gaattactct atgaagcgcc atatttaaaa agctaccaag     1080
acgaagagga tgaagaggat gaggaggcag attgccttga atatattgac aatactgata    1140
agataatata tcttttatat agaagatatc gccgtatgta aggatttcag ggggcaaggc    1200
ataggcagcg cgcttatcaa tatatctata gaatgggcaa agcataaaaa cttgcatgga    1260
ctaatgcttg aaacccagga caataacctt atagcttgta aattctatca taattgggta    1320
atgactccaa cttattgata gtgttttatg ttcagataat gcccgatgac tttgtcatgc    1380
agctccaccg attttgagaa cgacagcgac ttccgtccca gccgtgccag gtgctgcctc    1440
agattcaggt tatgccgctc aattcgctgc gtatatcgct tgctgattac gtgcagcttt    1500
cccttcaggc gggattcata cagcggccag ccatccgtca tccatatcac cacgtcaaag    1560
ggtgacagca ggctcataag acgccccagc gtcgccatag tgcgttcacc gaatacgtgc    1620
gcaacaaccg tcttccggag actgtcatac gcgtaaaaca gccagcgctg gcgcgattta    1680
gccccgacat agccccactg ttcgtccatt tccgcgcaga cgatgacgtc actgcccggc    1740
tgtatgcgcg aggttaccga ctgcggcctg agttttttaa gtgacgtaaa atcgtgttga    1800
ggccaacgcc cataatgcgg gctgttgccc ggcatccaac gccattcatg gccatatcaa    1860
tgattttctg gtgcgtaccg ggttgagaag cggtgtaagt gaactgcagt tgccatgttt    1920
tacggcagtg agagcagaga tagcgctgat gtccggcggt gcttttgccg ttacgcacca    1980
ccccgtcagt agctgaacag gagggacagc tgatagacac agaagccact ggagcacctc    2040
aaaaacacca tcatacacta aatcagtaag ttggcagcat cacccataat tgtggtttca    2100
aaatcggctc cgtcgatact atgttatacg ccaactttga aaacaacttt gaaaagctg     2160 ttttctggta tttaaggttt tagaatgcaa ggaacagtga attggagttc gtcttgttat    2220
aattagcttc ttggggtatc tttaaatact gtagaaaaga ggaaggaaat aataaatggc    2280
taaaatgaga atatcaccgg aattgaaaaa actgatcgaa aaataccgct gcgtaaaaga    2340
tacgaaggaa atgtctcctg ctaaggtata taagctggtg ggagaaaatg aaaacctata    2400
tttaaaaatg acggacagcc ggtataaagg gaccacctat gatgtggaac gggaaaagga    2460
```

```
catgatgcta tggctggaag gaaagctgcc tgttccaaag gtcctgcact ttgaacggca   2520
tgatggctgg agcaatctgc tcatgagtga ggccgatggc gtcctttgct cggaagagta   2580
tgaagatgaa caaagccctg aaaagattat cgagctgtat gcggagtgca tcaggctctt   2640
tcactccatc gacatatcgg attgtccta tacgaatagc ttagacagcc gcttagccga    2700
attggattac ttactgaata cgatctggc cgatgtggat tgcgaaaact gggaagaaga    2760
cactccattt aaagatccgc gcgagctgta tgatttttta aagacggaaa agcccgaaga   2820
ggaacttgtc ttttcccacg gcgacctggg agacagcaac atctttgtga aagatggcaa   2880
agtaagtggc tttattgatc ttgggagaag cggcagggcg acaagtggt atgacattgc    2940 cttctgcgtc cggtcgatca gggaggatat cggggaagaa cagtatgtcg agctatttt     3000 tgacttactg gggatcaagc ctgattggga gaaaataaaa tattatattt tactggatga   3060
attgttttag tacctagatg tggcgcaacg atgccggcga caagcaggag cgcaccgact   3120
tcttccgcat caagtgtttt ggctctcagg ccgaggccca cggcaagtat ttgggcaagg   3180
ggtcgctggt attcgtgcag ggcaagattc ggaataccaa gtacgagaag gacggccaga   3240
cggtctacgg gaccgacttc attgccgata aggtggatta tctggacacc aaggcaccag   3300
gcgggtcaaa tcaggaataa gggcacattg ccccggcgtg agtcggggca atcccgcaag   3360
gagggtgaat gaatcggacg tttgaccgga aggcatacag gcaagaactg atcgacgcgg   3420
ggttttccgc cgaggatgcc gaaaccatcg caagccgcac cgtcatgcgt gcgccccgcg   3480
aaaccttcca gtccgtcggc tcgatggtcc agcaagctac ggccaagatc gagcgcgaca   3540
gcgtgcaact ggctccccct gccctgcccg cgccatcggc cgccgtggag cgttcgcgtc   3600
gtctcgaaca ggaggcggca ggtttggcga agtcgatgac catcgacacg cgaggaacta   3660
tgacgaccaa gaagcgaaaa accgccggcg aggacctggc aaaacaggtc agcgaggcca   3720
agcaggccgc gttgctgaaa cacacgaagc agcagatcaa ggaaatgcag ctttccttgt   3780
tcgatattgc gccgtggccg gacacgatgc gagcgatgcc aaacgacacg gcccgctctg   3840
ccctgttcac cacgcgcaac aagaaaatcc gcgcgaggc gctgcaaaac aaggtcattt    3900
tccacgtcaa caaggacgtg aagatcacct acaccggcgt cgagctgcgg gccgacgatg   3960
acgaactggt gtggcagcag gtgttggagt acgcgaagcg caccctatc ggcgagccga    4020 tcaccttcac gttctacgag cttgccagg acctgggctg gtcgatcaat ggccggtatt     4080
acacgaaggc cgaggaatgc ctgtcgcgcc tacaggcgac ggcgatgggc ttcacgtccg   4140
accgcgttgg gcacctggaa tcggtgtcgc tgctgcaccg cttccgcgtc ctggaccgtg   4200
gcaagaaaac gtcccgttgc caggtcctga tcgacgagga atcgtcgtg ctgtttgctg     4260 gcgaccacta cacgaaattc atatgggaga agtaccgcaa gctgtcgccg acggcccgac   4320
ggatgttcga ctatttcagc tcgcaccggg agccgtaccc gctcaagctg gaaaccttcc   4380
gcctcatgtg cggatcggat ccacccgcg tgaagaagtg gcgcgagcag gtcggcgaag    4440
cctgcgaaga gttgcgaggc agcggcctgg tggaacacgc ctgggtcaat gatgacctgg   4500
tgcattgcaa acgctagggc cttgtggggt cagttccggc tgggggttca gcagccagcg   4560
ctttactggc atttcaggaa caagcgggca ctgctcgacg cacttgcttc gctcagtatc   4620
gctcgggacg cacggcgcgc tctacgaact gccgataaac agaggattaa aattgacaat   4680
tgtgattaag gctcagattc gacggcttgg agcggccgac gtgcaggatt ccgcgagat    4740 ccgattgtcg gccctgaaga aagctccaga gatgttcggg tccgtttacg agcacgagga   4800
gaaaaagccc atggaggcgt tcgctgaacg gttgcgagat gccgtggcat tcggcgccta   4860
```

```
catcgacggc gagatcattg ggctgtcggt cttcaaacag gaggacggcc ccaaggacgc   4920
tcacaaggcg catctgtccg gcgttttcgt ggagcccgaa cagcgaggcc gagggtcgc    4980 cggtatgctg ctgcgggcgt tgccggcggg tttattgctc gtgatgatcg tccgacagat   5040
tccaacggga atctggtgga tgcgcatctt catcctcggc gcacttaata tttcgctatt   5100
ctggagcttg ttgtttattt cggtctaccg cctgccgggc ggggtcgcgg cgacggtagg   5160
cgctgtgcag ccgctgatgg tcgtgttcat ctctgccgct ctgctaggta gcccgatacg   5220
attgatggcg gtcctggggg ctatttgcgg aactgcgggc gtggcgctgt tggtgttgac   5280
accaaacgca gcgctagatc ctgtcggcgt cgcagcgggc ctggcggggg cggtttccat   5340
ggcgttcgga accgtgctga cccgcaagtg gcaacctccc gtgcctctgc tcacctttac   5400
cgcctggcaa ctggcggccg gaggacttct gctcgttcca gtagctttag tgtttgatcc   5460
gccaatcccg atgcctacag gaaccaatgt tctcggcctg gcgtggctcg gcctgatcgg   5520
agcgggttta acctacttcc tttggttccg ggggatctcg cgactcgaac ctacagttgt   5580
ttccttactg ggctttctca gccccagatc tggggtcgat cagccgggga tgcatcaggc   5640
cgacagtcgg aacttcgggt ccccgacctg taccattcgg tgagcaatgg ataggggagt   5700
tgatatcgtc aacgttcact tctaaagaaa tagcgccact cagcttcctc agcggcttta   5760
tccagcgatt tcctattatg tcggcatagt tctcaagatc gacagcctgt cacgttaag    5820 cgagaaatga ataagaaggc tgataattcg gatctctgcg agggagatga tatttgatca   5880
caggcagcaa cgctctgtca tcgttacaat caacatgcta ccctccgcga gatcatccgt   5940
gtttcaaacc cggcagctta gttgccgttc ttccgaatag catcggtaac atgagcaaag   6000
tctgccgcct tacaacggct ctcccgctga cgccgtcccg gactgatggg ctgcctgtat   6060
cgagtggtga ttttgtgccg agctgccggt cggggagctg ttggctggct ggtggcagga   6120
tatattgtgg tgtaaacaaa ttgacgctta gacaacttaa taacacattg cggacgtttt   6180
taatgtactg gggtggtttt tcttttcacc agtgagacgg gcaacagctg attgcccttc   6240
accgcctggc cctgagagag ttgcagcaag cggtccacgc tggtttgccc cagcaggcga   6300
aaatcctgtt tgatggtggt tccgaaatcg gcaaaatccc ttataaatca aaagaatagc   6360
ccgagatagg gttgagtgtt gttccagttt ggaacaagag tccactatta agaacgtgg    6420 actccaacgt caaagggcga aaaccgtctt atcagggcga tgcccactta cctgtatggc   6480
cgcattcgca aaacacacct agactagatt tgttttgcta acccaattga tattaattat   6540
atatgattaa tatttatatg tatatggatt tggttaatga aatgcatctg gttcatcaaa   6600
gaattataaa gacacgtgac attcatttag gataagaaat atggatgatc tctttctctt   6660
ttattcagat aactagtaat tacacataac acacaacttt gatgcccaca ttatagtgat   6720
tagcatgtca ctatgtgtgc atcctttat ttcatacatt aattaagttg gccaatccag    6780
aagatggaca agtctaggtt aaccatgtgg tacctacgcg ttcgaatatc catgggccgc   6840
ttcaggccag ggcgctgggg aaggcgatgg cgtgctcggt cagctgccac ttctggttct   6900
tggcgtcgct ccggtcctcc cgcagcagct tgtgctggat gaagtgccac tcgggcatct   6960
tgctgggcac gctcttggcc ttgtacacgg tgtcgaactg gcaccggtac cggccgccgt   7020
ccttcagcag caggtacatg ctcacgtcgc ccttcaggat gccctgctta ggcacgggca   7080
tgatcttctc gcagctggcc tcccagttgg tggtcatctt cttcatcacg ggccgtcgg    7140 cggggaagtt cacgccgttg aagatgctct tgtggtagat gcagttctcc ttcacgctca   7200
cggtgatgtc cacgttacag atgcacacgg cgccgtcctc gaacaggaag ctccggcccc   7260
```

```
aggtgtagcc ggcggggcag ctgttcttga agtagtccac gatgtcctgg gggtactcgg    7320
tgaagatccg gtcgccgtac ttgaagccgg cgctcaggat gtcctcgctg aagggcaggg    7380
ggccgccctc gatcacgcac aggttgatgg tctgcttgcc cttgaagggg tagccgatgc    7440
cctcgccggt gatcacgaac ttgtggccgt tcacgcagcc ctccatgtgg tacttcatgg    7500
tcatctcctc cttcaggccg tgcttgctgt gggccatggt ggcgaccggt gaattcgagc    7560
tcggtacccg gggatcctga gtaaaacaga ggagggtctc actaagttta tagagagact    7620
gagagagata aagggacacg tatgaagcgt ctgttttcgt ggtgtgacgt caaagtcatt    7680
ttgctctcta cgcgtgtctg tgtcggcttg atctttttt ttgcttttg gaactcatgt    7740 cggtagtata tcttttattt atttttctt tttttccctt ttctttcaaa ctgatgtcgg    7800
tatgatattt attccatcct aaaatgtaac ttactattat tagtagtcgg tccatgtcta    7860
ttggcccatc atgtggtcat tttacgttta cgtcgtgtgg ctgtttatta taacaaacgg    7920
cacatccttc tcattcgaat tgtatttctc cttaatcgtt ctaataggta tgatctttta    7980
ttttatacgt aaaattaaaa ttgaatgatg tcaagaacga aaattaattt gtatttacaa    8040
aggagctaaa tattgtttat tcctctactg gtagaagata aagaagtag atgaaataat    8100 gatcttacta gagaatattc ctcatttaca ctagtcaaat ggaaatcttg taaacttta    8160 caataattta tcctgaaaat atgaaaaaat agaagaaaat gtttacctcc tctctcctct    8220
taattcacct acgatcggtg cgggcctctt cgctattacg ccagctggcg aaaggggat    8280 gtgctgcaag gcgattaagt tgggtaacgc cagggttttc ccagtcacga cgttgtaaaa    8340
cgacggccag tgaattcgag ctcggtaccc ggggatcctc tagagtcgac ctgcaggcat    8400
gcaagcttgt tgaaacatcc ctgaagtgtc tcattttatt ttatttattc tttgctgata    8460
aaaaaataaa ataaaagaag ctaagcacac ggtcaaccat tgctctactg ctaaaagggt    8520
tatgtgtagt gttttactgc ataaattatg cagcaaacaa gacaactcaa attaaaaaat    8580
ttcctttgct tgttttttg ttgtctctga cttgactttc ttgtggaagt tggttgtata    8640
aggattggga cacaccattg tccttcttaa tttaatttta tttctttgct gataaaaaaa    8700
aaaaatttca tatagtgtta ataataatt tgttaaataa ccaaaaagtc aaatatgttt    8760
actctcgttt aaataattga gagtcgtcca gcaaggctaa acgattgtat agatttatga    8820
caatatttac ttttttatag ataaatgtta tattataata aatttatata catatattat    8880
atgttattta ttatttatta ttattttaaa tccttcaata ttttatcaaa ccaactcata    8940 atttttttt tatctgtaag aagcaataaa attaaataga cccactttaa ggatgatcca    9000 accttatac agagtaagag agttcaaata gtaccctttc atatacatat caactaaat    9060 attagaaata tcatggatca aaccttataa agacattaaa taagtggata agtataatat    9120
ataaatgggt agtatataat atataaatgg atacaaactt ctctctttat aattgttatg    9180
tctccttaac atcctaatat aatacataag tgggtaatat ataatatata aatggagaca    9240
aacttcttcc attataattg ttatgtcttc ttaacactta tgtctcgttc acaatgctaa    9300
agttagaatt gtttagaaag tcttatagta cacatttgtt tttgtactat ttgaagcatt    9360
ccataagccg tcacgattca gatgatttat aataataaga ggaaatttat catgaacaa    9420 taaggtgcat agatagagtg ttaatatatc ataacatcct ttgtttattc atagaagaag    9480
tgagatggag ctcagttatt atactgttac atggtcggat acaatattcc atgctctcca    9540
tgagctctta cacctacatg catttttagtt catacttcat gcacgtggcc atcacagcta    9600
gctgcagcta catatttaca ttttacaaca ccaggagaac tgccctgtta gtgcataaca    9660
```

```
atcagaagat ggccgtggct actcgagtta tcgaaccact ttgtacaaga aagctgaacg   9720
agaaacgtaa aatgatataa atatcaatat attaaattag attttgcata aaaaacagac   9780
tacataatac tgtaaaacac aacatatcca gtcactatgg tcgacctgca gactggctgt   9840
gtataaggga gcctgacatt tatattcccc agaacatcag gttaatggcg ttttttgatgt  9900
cattttcgcg gtggctgaga tcagccactt cttcccgat aacggagacc ggcacactgg    9960
ccatatcggt ggtcatcatg cgccagcttt catccccgat atgcaccacc gggtaaagtt  10020
cacgggagac tttatctgac agcagacgtg cactggccag ggggatcacc atccgtcgcc  10080
cgggcgtgtc aataatatca ctctgtacat ccacaaacag acgataacgg ctctctcttt  10140
tataggtgta aaccttaaac tgcatttcac cagtccctgt tctcgtcagc aaaagagccg  10200
ttcatttcaa taaaccgggc gacctcagcc atcccttcct gattttccgc tttccagcgt  10260
tcggcacgca gacgacgggc ttcattctgc atggttgtgc ttaccagacc ggagatattg  10320
acatcatata tgccttgagc aactgatagc tgtcgctgtc aactgtcact gtaatacgct  10380
gcttcatagc acacctcttt ttgacatact tcgggtatac atatcagtat atattcttat  10440
accgcaaaaa tcagcgcgca aatacgcata ctgttatctg cttttagta agccggatcc   10500
tctagattac gccccgccct gccactcatc gcagtactgt tgtaattcat taagcattct  10560
gccgacatgg aagccatcac agacggcatg atgaacctga atcgccagcg gcatcagcac  10620
cttgtcgcct tgcgtataat atttgcccat ggtgaaaacg ggggcgaaga agttgtccat  10680
attggccacg tttaaatcaa aactggtgaa actcacccag ggattggctg agacgaaaaa  10740
catattctca ataaacccctt tagggaaata ggccaggttt tcaccgtaac acgccacatc  10800
ttgcgaatat atgtgtagaa actgccggaa atcgtcgtgg tattcactcc agagcgatga  10860
aaacgtttca gtttgctcat ggaaaacggt gtaacaaggg tgaacactat cccatatcac  10920
cagctcaccg tctttcattg ccatacgaaa ttccggatga gcattcatca ggcgggcaag  10980
aatgtgaata aaggccggat aaaacttgtg cttatttttc tttacggtct ttaaaaaggc  11040
cgtaatatcc agctgaacgg tctggttata ggtacattga gcaactgact gaaatgcctc  11100
aaaatgttct ttacgatgcc attgggatat atcaacggtg gtatatccag tgatttttt    11160
ctccatttta gcttccttag ctcctgaaaa tctcgccgga tcctaactca aaatccacac  11220
attatacgag ccggaagcat aaagtgtaaa gcctggggtg cctaatgcgg ccgccatagt  11280
gactggatat gttgtgtttt acagtattat gtagtctgtt ttttatgcaa atctaatttt   11340
aatatattga tatttatatc attttacgtt tctcgttcag cttttttgta caaacttgtt  11400
tgataaccgg tactagtgtg cacgtcgagc gtgtcctctc caaatgaaat gaacttcctt  11460
atatagagga agggtcttgc gaaggatagt gggattgtgc gtcatccctt acgtcagtgg  11520
agatgtcaca tcaatccact tgctttgaag acgtggttgg aacgtcttct ttttccacga  11580
tgctcctcgt gggtgggggt ccatctttgg gaccactgtc ggcagaggca tcttgaatga  11640
tagccttcc tttatcgcaa tgatggcatt tgtaggagcc accttccttt tctactgtcc   11700
tttcgatgaa gtgacagata gctgggcaat ggaatccgag gaggtttccc gaaattatcc  11760
tttgttgaaa agtctcaata gcccttggt cttctgagac tgtatctttg acatttttgg   11820
agtagaccag agtgtcgtgc tccaccatgt tgacgaagat tttcttcttg tcattgagtc  11880
gtaaaagact ctgtatgaac tgttcgccag tcttcacggc gagttctgtt agatcctcga  11940
tttgaatctt agactccatg catggcctta gattcagtag gaactacctt tttagagact  12000
ccaatctcta ttacttgcct tggtttatga agcaagcctt gaatcgtcca tactggaata  12060
```

```
gtacttctga tcttgagaaa tatgtctttc tctgtgttct tgatgcaatt agtcctgaat    12120
cttttgactg catctttaac cttcttggga aggtatttga tctcctggag attgttactc    12180
gggtagatcg tcttgatgag acctgctgcg taggcctctc taaccatctg tgggtcagca    12240
ttctttctga aattgaagag gctaaccttc tcattatcag tggtgaacat agtgtcgtca    12300
ccttcacctt cgaacttcct tcctagatcg taaagataga ggaaatcgtc cattgtaatc    12360
tccggggcaa aggagatctc ttttggggct ggatcactgc tgggccttt ggttcctagc    12420 gtgagccagt gggcttttg ctttggtggg cttgttaggg ccttagcaaa gctcttgggc    12480
ttgagttgag cttctccttt ggggatgaag ttcaacctgt ctgtttgctg acttgttgtg    12540
tacgcgtcag ctgctgctct tgcctctgta atagtggcaa atttcttgtg tgcaactccg    12600
ggaacgccgt ttgttgccgc ctttgtacaa ccccagtcat cgtatatacc ggcatgtgga    12660
ccgttataca caacgtagta gttgatatga gggtgttgaa tacccgattc tgctctgaga    12720
ggagcaactg tgctgttaag ctcagatttt tgtgggattg gaattggatc ctctagagca    12780
aagcttggcg taatcatggt catagctgtt cctgtgtga aattgttatc cgctcacaat    12840
tccacacaac atacgagccg gaagcataaa gtgtaaagcc tggggtgcct aatgagtgag    12900
ctaactcaca ttaattgcgt tgcgctcact gcccgctttc cagtcgggaa acctgtcgtg    12960
ccagctgcat taatgaatcg gccaacgcgc ggggagaggc ggtttgcgta ttgggccaaa    13020 gacaaaggg cgacattcaa ccgattgagg gagggaaggt aaatattgac ggaaattatt    13080
cattaaaggt gaattatcac cgtcaccgac ttgagccatt tgggaattag agccagcaaa    13140
atcaccagta gcaccattac cattagcaag gccggaaacg tcaccaatga aaccatcatc    13200
tagtaacata gatgacaccg cgcgcgataa tttatcctag tttgcgcgct atattttgtt    13260
ttctatcgcg tattaaatgt ataattgcgg gactctaatc ataaaaaccc atctcataaa    13320
taacgtcatg cattacatgt taattattac atgcttaacg taattcaaca gaaattatat    13380
gataatcatc gcaagaccgg caacaggatt caatcttaag aaactttatt gccaaatgtt    13440
tgaacgatct gcttcgacgc actccttctt taggtacgga ctagatctcg gtgacgggca    13500
ggaccggacg gggcggtacc ggcaggctga agtccagctg ccagaaaccc acgtcatgcc    13560
agttcccgtg cttgaagccg gccgcccgca gcatgccgcg gggggcatat ccgagcgcct    13620
cgtgcatgcg cacgctcggg tcgttgggca gcccgatgac agcgaccacg ctcttgaagc    13680
cctgtgcctc cagggacttc agcaggtggg tgtagagcgt ggagcccagt cccgtccgct    13740
ggtggcgggg ggagacgtac acggtcgact cggccgtcca gtcgtaggcg ttgcgtgcct    13800
tccaggggcc cgcgtaggcg atgccggcga cctcgccgtc cacctcggcg acgagccagg    13860
gatagcgctc ccgcagacgg acgaggtcgt ccgtccactc ctgcggttcc tgcggctcgg    13920
tacggaagtt gaccgtgctt gtctcgatgt agtggttgac gatggtgcag accgccggca    13980
tgtccgcctc ggtggcacgg cggatgtcgg ccgggcgtcg ttctgggctc atggatctgg    14040
attgagagtg aatatgagac tctaattgga taccgagggg aatttatgga acgtcagtgg    14100 agcattttg acaagaaata tttgctagct gatagtgacc ttaggcgact tttgaacgcg    14160
caataatggt ttctgacgta tgtgcttagc tcattaaact ccagaaaccc gcggctgagt    14220
ggctccttca acgttgcggt tctgtcagtt ccaaacgtaa aacggcttgt cccgcgtcat    14280 cggcggggt cataacgtga ctcccttaat tctccgctca tgatcagatt gtcgtttccc    14340
gccttcagtt taaactatca gtgtttgaca ggatatattg gcgggtaaac ctaagagaaa    14400
agagcgttta ttagaataat cggatattta aaagggcgtg aaaaggttta tccgttcgtc    14460
```

```
catttgtatg tgcatgccaa ccacagggtt ccccagatct ggcgccggcc agcgagacga   14520
gcaagattgg ccgccgcccg aaacgatccg acagcgcgcc cagcacaggt gcgcaggcaa   14580
attgcaccaa cgcatacagc gccagcagaa tgccatagtg ggcggtgacg tcgttcgagt   14640
gaaccagatc gcgcaggagg cccggcagca ccggcataat caggccgatg ccgacagcgt   14700
cgagcgcgac agtgctcaga attacgatca ggggtatgtt gggtttcacg tctggcctcc   14760
ggaccagcct ccgctggtcc gattgaacgc gcggattctt tatcactgat aagttggtgg   14820
acatattatg tttatcagtg ataaagtgtc aagcatgaca aagttgcagc cgaatacagt   14880
gatccgtgcc gccctggacc tgttgaacga ggtcggcgta gacggtctga cgacacgcaa   14940
actggcggaa cggttggggg ttcagcagcc ggcgctttac tggcacttca ggaacaagcg   15000
ggcgctgctc gacgcactgg ccgaagccat gctggcggag aatcatacgc attcggtgcc   15060
gagagccgac gacgactggc gctcatttct gatcggaat gcccgcagct caggcaggc    15120
gctgctcgcc taccgcgatg gcgcgcgcat ccatgccggc acgcgaccgg cgcaccgca   15180
gatggaaacg gccgacgcgc agcttcgctt cctctgcgag gcgggttttt cggccgggga   15240
cgccgtcaat gcgctgatga caatcagcta cttcactgtt ggggccgtgc ttgaggagca   15300
ggccggcgac agcgatgccg gcgagcgcgg cggcaccgtt gaacaggctc cgctctcgcc   15360
gctgttgcgg gccgcgatag acgccttcga cgaagccggt ccggacgcag cgttcgagca   15420
gggactcgcg gtgattgtcg atggattggc gaaaaggagg ctcgttgtca ggaacgttga   15480
aggaccgaga aagggtgacg attgatcagg accgctgccg gagcgcaacc cactcactac   15540
agcagagcca tgtagacaac atccctccc ctttccacc gcgtcagacg cccgtagcag    15600
cccgctacgg gctttttcat gccctgccct agcgtccaag cctcacggcc gcgctcggcc   15660
tctctggcgg ccttctggcg ctcttccgct tcctcgctca ctgactcgct gcgctcggtc   15720
gttcggctgc ggcgagcggt atcagctcac tcaaaggcgg taatacggtt atccacagaa   15780
tcagggata acgcaggaaa gaacatgtga gcaaaaggcc agcaaaaggc caggaaccgt    15840
aaaaaggccg cgttgctggc gtttttccat aggctccgcc ccctgacga gcatcacaaa    15900
aatcgacgct caagtcagag gtggcgaaac ccgacaggac tataaagata ccaggcgttt   15960
cccctggaa gctccctcgt gcgctctcct gttccgaccc tgccgcttac cggataccig   16020
tccgcctttc tcccttcggg aagcgtggcg cttttccgct gcataaccct gcttcggggt   16080
cattatagcg atttttcgg tatatccatc cttttcgca cgatatacag gattttgcca   16140
aagggttcgt gtagactttc cttggtgtat ccaacggcgt cagccgggca ggataggtga   16200
agtaggccca cccgcgagcg ggtgttcctt cttcactgtc ccttattcgc acctggcggt   16260
gctcaacggg aatcctgctc tgcgaggctg gccggctacc gccggcgtaa cagatgaggg   16320
caagcggatg gctgatgaaa ccaagccaac caggaagggc agcccaccta tcaaggtgta   16380
ctgccttcca gacgaacgaa gagcgattga ggaaaaggcg gcggcggccg gcatgagcct   16440
gtcggcctac ctgctggccg tcggccaggg ctacaaaatc acgggcgtcg tggactatga   16500
gcacgtccgc gagctggccc gcatcaatgg cgacctgggc cgcctgggcg gctgctgaa    16560
actctggctc accgacgacc cgcgcacggc gcggttcggt gatgccacga tcctcgccct   16620
gctggcgaag atcgaagaga agcaggacga gcttggcaag gtcatgatgg gcgtggtccg   16680
cccgagggca gagccatgac ttttttagcc gctaaacgg ccgggggtg cgcgtgattg    16740
ccaagcacgt ccccatgcgc tccatcaaga agagcgactt cgcggagctg gtgaagtaca   16800
tcaccgacga gcaaggcaag accgagcgcc tttgcgacgc tca                     16843
```

<210> SEQ ID NO 5
<211> LENGTH: 9142
<212> TYPE: DNA
<213> ORGANISM: Artificial Sequence
<220> FEATURE:
<223> OTHER INFORMATION: PHP27840 construct

<400> SEQUENCE: 5

| | |
|---|---|
| ctagttatct gaataaaaga gaaagagatc atccatattt cttatcctaa atgaatgtca | 60 |
| cgtgtcttta taattctttg atgaaccaga tgcatttcat taaccaaatc catatacata | 120 |
| taaatattaa tcatatataa ttaatatcaa ttgggttagc aaaacaaatc tagtctaggt | 180 |
| gtgttttgcg aattcgatat caagcttgat gggtaccggc gcgcccgatc atccggatat | 240 |
| agttcctcct ttcagcaaaa aacccctcaa gacccgttta gaggcccaa ggggttatgc | 300 |
| tagttattgc tcagcggtgg cagcagccaa ctcagcttcc tttcgggctt tgttagcagc | 360 |
| cggatcgatc caagctgtac ctcactattc ctttgccctc ggacgagtgc tggggcgtcg | 420 |
| gtttccacta tcggcgagta cttctacaca gccatcggtc cagacggccg cgcttctgcg | 480 |
| ggcgatttgt gtacgcccga cagtcccggc tccggatcgg acgattgcgt cgcatcgacc | 540 |
| ctgcgcccaa gctgcatcat cgaaattgcc gtcaaccaag ctctgataga gttggtcaag | 600 |
| accaatgcgg agcatatacg cccggagccg cggcgatcct gcaagctccg gatgcctccg | 660 |
| ctcgaagtag cgcgtctgct gctccataca agccaaccac ggcctccaga agaagatgtt | 720 |
| ggcgacctcg tattgggaat ccccgaacat cgcctcgctc cagtcaatga ccgctgttat | 780 |
| gcggccattg tccgtcagga cattgttgga gccgaaatcc gcgtgcacga ggtgccggac | 840 |
| ttcggggcag tcctcggccc aaagcatcag ctcatcgaga gcctgcgcga cggacgcact | 900 |
| gacggtgtcg tccatcacag tttgccagtg atacacatgg ggatcagcaa tcgcgcatat | 960 |
| gaaatcacgc catgtagtgt attgaccgat tccttgcggt ccgaatgggc cgaacccgct | 1020 |
| cgtctggcta agatcggccg cagcgatcgc atccatagcc tccgcgaccg gctgcagaac | 1080 |
| agcgggcagt tcggtttcag gcaggtcttg caacgtgaca ccctgtgcac ggcgggagat | 1140 |
| gcaataggtc aggctctcgc tgaattcccc aatgtcaagc acttccggaa tcgggagcgc | 1200 |
| ggccgatgca aagtgccgat aaacataacg atctttgtag aaaccatcgg cgcagctatt | 1260 |
| tacccgcagg acatatccac gccctcctac atcgaagctg aaagcacgag attcttcgcc | 1320 |
| ctccgagagc tgcatcaggt cggagacgct gtcgaacttt tcgatcagaa acttctcgac | 1380 |
| agacgtcgcg gtgagttcag gctttttcat gggtatatct ccttcttaaa gttaaacaaa | 1440 |
| attatttcta gagggaaacc gttgtggtct ccctatagtg agtcgtatta atttcgcggg | 1500 |
| atcgagatct gatcaacctg cattaatgaa tcggccaacg cgcggggaga ggcggtttgc | 1560 |
| gtattgggcg ctcttccgct tcctcgctca ctgactcgct gcgctcggtc gttcggctgc | 1620 |
| ggcgagcggt atcagctcac tcaaaggcgg taatacggtt atccacagaa tcaggggata | 1680 |
| acgcaggaaa gaacatgtga gcaaaaggcc agcaaaaggc caggaaccgt aaaaaggccg | 1740 |
| cgttgctggc gtttttccat aggctccgcc ccctgacga gcatcacaaa aatcgacgct | 1800 |
| caagtcagag gtggcgaaac ccgacaggac tataaagata ccaggcgttt ccccctggaa | 1860 |
| gctccctcgt gcgctctcct gttccgaccc tgccgcttac cggatacctg tccgcctttc | 1920 |
| tcccttcggg aagcgtggcg ctttctcaat gctcacgctg taggtatctc agttcggtgt | 1980 |
| aggtcgttcg ctccaagctg ggctgtgtgc acgaaccccc cgttcagccc gaccgctgcg | 2040 |
| ccttatccgg taactatcgt cttgagtcca acccggtaag acacgactta tcgccactgg | 2100 |

```
cagcagccac tggtaacagg attagcagag cgaggtatgt aggcggtgct acagagttct    2160
tgaagtggtg gcctaactac ggctacacta gaaggacagt atttggtatc tgcgctctgc    2220
tgaagccagt taccttcgga aaaagagttg gtagctcttg atccggcaaa caaaccaccg    2280
ctggtagcgg tggttttttt gtttgcaagc agcagattac gcgcagaaaa aaaggatctc    2340
aagaagatcc tttgatcttt tctacggggt ctgacgctca gtggaacgaa aactcacgtt    2400
aagggatttt ggtcatgaca ttaacctata aaaataggcg tatcacgagg ccctttcgtc    2460
tcgcgcgttt cggtgatgac ggtgaaaacc tctgacacat gcagctcccg gagacggtca    2520
cagcttgtct gtaagcggat gccgggagca gacaagcccg tcagggcgcg tcagcgggtg    2580
ttggcgggtg tcggggctgg cttaactatg cggcatcaga gcagattgta ctgagagtgc    2640
accatatgga catattgtcg ttagaacgcg gctacaatta atacataacc ttatgtatca    2700
tacacatacg atttaggtga cactatagaa cggcgcgcca agctgggtct agaactagaa    2760
acgtgatgcc acttgttatt gaagtcgatt acagcatcta ttctgtttta ctatttataa    2820
ctttgccatt tctgactttt gaaaactatc tctggatttc ggtatcgctt tgtgaagatc    2880
gagcaaaaga gacgttttgt ggacgcaatg gtccaaatcc gttctacatg aacaaattgg    2940
tcacaatttc cactaaaagt aaataaatgg caagttaaaa aaggaatatg cattttactg    3000
attgcctagg tgagctccaa gagaagttga atctacacgt ctaccaaccg ctaaaaaaag    3060
aaaaacattg aatatgtaac ctgattccat tagcttttga cttcttcaac agattctcta    3120
cttagatttc taacagaaat attattacta gcacatcatt ttcagtctca ctacagcaaa    3180
aaatccaacg gcacaataca gacaacagga gatatcagac tacagagata gatagatgct    3240
actgcatgta gtaagttaaa taaaaggaaa ataaaatgtc ttgctaccaa aactactaca    3300
gactatgatg ctcaccacag gccaaatcct gcaactagga cagcattatc ttatatatat    3360
tgtacaaaac aagcatcaag gaacatttgg tctaggcaat cagtacctcg ttctaccatc    3420
accctcagtt atcacatcct tgaaggatcc attactggga atcatcggca acacatgctc    3480
ctgatggggc acaatgacat caagaaggta ggggccaggg gtgtccaaca ttctctgaat    3540
tgccgctcta agctcttcct tcttcgtcac tcgcgctgcc ggtatcccac aagcatcagc    3600
aaacttgagc atgtttggga atatctcgct ctcgctagac ggatctccaa gataggtgtg    3660
agctctattg gacttgtaga acctatcctc caactgaacc accatacccc aatgctgatt    3720
gttcaacaac aatatcttaa ctgggagatt ctccactctt atagtggcca actcctgaac    3780
attcatgatg aaactaccat ccccatcaat gtcaaccaca acagcccag ggttagcaac     3840 agcagcacca atagccgcag gcaatccaaa acccatggct ccaagacccc ctgaggtcaa    3900
ccactgcctc ggtctcttgt acttgtaaaa ctgcgcagcc cacatttgat gctgcccaac    3960
cccagtacta acaatagcat ctccattagt caactcatca agaacctcga tagcatgctg    4020
cggagaaatc gcgtcctgga atgtcttgta acccaatgga aacttgtgtt tctgcacatt    4080
aatctcttct ctccaacctc caagatcaaa cttaccctcc actcctttct cctccaaaat    4140
catattaatt cccttcaagg ccaacttcaa atccgcgcaa accgacacgt gcgcctgctt    4200
gttcttccca atctcggcag aatcaatatc aatgtgaaca atcttagccc tactagcaaa    4260
agcctcaagc ttcccagtaa cacggtcatc aaaccttacc ccaaaggcaa gcaacaaatc    4320
actattgtca acagcatagt tagcataaac agtaccatgc atacccagca tctgaaggga    4380
atattcatca ccaataggaa aagttccaag acccattaaa gtgctagcaa cgggaatacc    4440
agtgagttca acaaagcgcc tcaattcagc actggaattc aaactgccac cgccgacgta    4500
```

```
gagaacgggc ttttgggcct ccatgatgag tctgacaatg tgttccaatt gggcctcggc    4560 gggggggcctg ggcagcctgg cgaggtaacc ggggaggtta acgggctcgt cccaattagg   4620
cacggcgagt tgctgctgaa cgtctttggg aatgtcgatg aggaccggac cggggcggcc    4680
ggaggtggcg acgaagaaag cctcggcgac gacgcggggg atgtcgtcga cgtcgaggat    4740
gaggtagttg tgcttcgtga tggatctgct cacctccacg atcggggttt cttggaaggc    4800
gtcggtgccg atcatccggc gggcgacctg gccggtgatg gcgacgactg ggacgctgtc    4860
cattaaagcg tcggcgaggc cgctcacgag gttggtggcg ccggggccgg aggtggcaat    4920
gcagacgccg gggaggccgg aggaacgcgc gtagccttcg gcggcgaaga cgccgccctg    4980
ctcgtggcgc gggagcacgt tgcggatggc ggcggagcgc gtgagcgcct ggtggatctc    5040
catcgacgca ccgccggggt acgcgaacac cgtcgtcacg ccctgcctct ccagcgcctc    5100
cacaaggatg tccgcgccct tgcgaggttc gccggaggcg aaccgtgaca cgaagggctc    5160
cgtggtcggc gcttccttgg tgaagggcgc cgccgtgggg ggtttggaga tggaacattt    5220
gattttgaga gcgtggttgg gtttggtgag ggtttgatga gagagaggga gggtggatct    5280
agtaatgcgt ttggggaagg tggggtgtga agaggaagaa gagaatcggg tggttctgga    5340
agcggtggcc gccattgtgt tgtgtggcat ggttatactt caaaaactgc acaacaagcc    5400
tagagttagt acctaaacag taaatttaca acagagagca aagacacatg caaaaatttc    5460
agccataaaa aaagttataa tagaatttaa agcaaaagtt tcattttta aacatatata    5520 caaacaaact ggatttgaag gaagggatta attcccctgc tcaaagtttg aattcctatt    5580
gtgacctata ctcgaataaa attgaagcct aaggaatgta tgagaaacaa gaaaacaaaa    5640
caaaactaca gacaaacaag tacaattaca aaattcgcta aaattctgta atcaccaaac    5700
cccatctcag tcagcacaag gcccaaggtt tattttgaaa taaaaaaaaa gtgattttat    5760
ttctcataag ctaaagaaa gaaaggcaat tatgaaatga tttcgactag atctgaaagt    5820
caaacgcgta ttccgcagat attaaagaaa gagtagagtt tcacatggat cctagatgga    5880
cccagttgag gaaaagcaa ggcaaagcaa accagaagtg caagatccga aattgaacca    5940
cggaatctag gatttggtag agggagaaga aaagtacctt gagaggtaga agagaagaga    6000
agagcagaga gatatatgaa cgagtgtgtc ttggtctcaa ctctgaagcg atacgagttt    6060
agaggggagc attgagttcc aatttatagg gaaaccgggt ggcaggggtg agttaatgac    6120
ggaaaagccc ctaagtaacg agattggatt gtgggttaga ttcaaccgtt tgcatccgcg    6180
gcttagattg gggaagtcag agtgaatctc aaccgttgac tgagttgaaa attgaatgta    6240
gcaaccaatt gagccaaccc cagcctttgc cctttgattt tgatttgttt gttgcatact    6300
ttttatttgt cttctggttc tgactctctt tctctcgttt caatgccagg ttgcctactc    6360
ccacaccact cacaagaaga ttctactgtt agtattaaat attttttaat gtattaaatg    6420
atgaatgctt ttgtaaacag aacaagacta tgtctaataa gtgtcttgca acatttttta    6480
agaaattaaa aaaatatat ttattatcaa aatcaaatgt atgaaaaatc atgaataata    6540 taatttttata cattttttta aaaatctttt taattctta attaatatct taaaaataat    6600
gattaatatt taacccaaaa taattagtat gattggtaag gaagatatcc atgttatgtt    6660
tggatgtgag tttgatctag agcaaagctt actagagtcg acctgcagcc cctccaccgc    6720
ggtggcggcc gctctagaga tccgtcaaca tggtggagca cgacactctc gtctactcca    6780
agaatatcaa agatacagtc tcagaagacc aaagggctat tgagactttt caacaaaggg    6840
taatatcggg aaacctcctc ggattccatt gcccagctat ctgtcacttc atcaaaagga    6900
```

```
cagtagaaaa ggaaggtggc acctacaaat gccatcattg cgataaagga aaggctatcg    6960
ttcaagatgc ctctgccgac agtggtccca aagatggacc cccacccacg aggagcatcg    7020
tggaaaaaga agacgttcca accacgtctt caaagcaagt ggattgatgt gatgatccta    7080
tgcgtatggt atgacgtgtg ttcaagatga tgacttcaaa cctacctatg acgtatggta    7140
tgacgtgtgt cgactgatga cttagatcca ctcgagcggc tataaatacg tacctacgca    7200
ccctgcgcta ccatccctag agctgcagct tattttttaca acaattacca acaacaacaa    7260
acaacaaaca acattacaat tactatttac aattacagtc gacccatcaa caagtttgta    7320
caaaaaagct gaacgagaaa cgtaaaatga tataaatatc aatatattaa attagatttt    7380
gcataaaaaa cagactacat aatactgtaa aacacaacat atccagtcat attggcggcc    7440
gcattaggca ccccaggctt tacactttat gcttccggct cgtataatgt gtggattttg    7500
agttaggatc cgtcgagatt ttcaggagct aaggaagcta aaatggagaa aaaaatcact    7560
ggatatacca ccgttgatat atcccaatgg catcgtaaag aacattttga ggcatttcag    7620
tcagttgctc aatgtaccta taaccagacc gttcagctgg atattacggc cttttttaaag    7680 accgtaaaga aaaataagca caagttttat ccggccttta ttcacattct tgcccgcctg    7740
atgaatgctc atccggaatt ccgtatggca atgaaagacg gtgagctggt gatatgggat    7800
agtgttcacc cttgttacac cgttttccat gagcaaactg aaacgttttc atcgctctgg    7860
agtgaatacc acgacgattt ccggcagttt ctacacatat attcgcaaga tgtggcgtgt    7920
tacggtgaaa acctggccta tttccctaaa gggtttattg agaatatgtt tttcgtctca    7980
gccaatccct gggtgagttt caccagtttt gatttaaacg tggccaatat ggacaacttc    8040 ttcgccccg ttttcaccat gggcaaatat tatacgcaag cgacaaggt gctgatgccg    8100 ctggcgattc aggttcatca tgccgtttgt gatggcttcc atgtcggcag aatgcttaat    8160
gaattacaac agtactgcga tgagtggcag ggcggggcgt aaagatctgg atccggctta    8220
ctaaaagcca gataacagta tgcgtatttg cgcgctgatt tttgcggtat aagaatatat    8280
actgatatgt atacccgaag tatgtcaaaa agaggtatgc tatgaagcag cgtattacag    8340
tgacagttga cagcgacagc tatcagttgc tcaaggcata tatgatgtca atatctccgg    8400
tctggtaagc acaaccatgc agaatgaagc ccgtcgtctg cgtgccgaac gctgaaaagc    8460
ggaaaatcag gaagggatgg ctgaggtcgc ccggtttatt gaaatgaacg gctcttttgc    8520
tgacgagaac aggggctggt gaaatgcagt ttaaggttta cacctataaa agagagagcc    8580
gttatcgtct gtttgtggat gtacagagtg atattattga cacgcccggg cgacggatgg    8640
tgatccccct ggccagtgca cgtctgctgt cagataaagt ctcccgtgaa ctttacccgg    8700
tggtgcatat cggggatgaa agctggcgca tgatgaccac cgatatggcc agtgtgccgg    8760
tctccgttat cggggaagaa gtggctgatc tcagccaccg cgaaaatgac atcaaaaacg    8820
ccattaacct gatgttctgg ggaatataaa tgtcaggctc ccttatacac agccagtctg    8880
caggtcgacc atagtgactg gatatgttgt gttttacagt attatgtagt ctgttttta    8940 tgcaaaatct aatttaatat attgatattt atatcatttt acgtttctcg ttcagctttc    9000
ttgtacaaag tggttgataa cctagacttg tccatcttct ggattggcca acttaattaa    9060
tgtatgaaat aaaaggatgc acacatagtg acatgctaat cactataatg tgggcatcaa    9120
agttgtgtgt tatgtgtaat ta                                             9142
```

<210> SEQ ID NO 6
<211> LENGTH: 49911

<212> TYPE: DNA
<213> ORGANISM: Artificial Sequence
<220> FEATURE:
<223> OTHER INFORMATION: PHP23236 construct

<400> SEQUENCE: 6

```
gtgcagcgtg acccggtcgt gcccctctct agagataatg agcattgcat gtctaagtta      60
taaaaaatta ccacatattt tttttgtcac acttgtttga agtgcagttt atctatcttt     120
atacatatat ttaaacttta ctctacgaat aatataatct atagtactac aataatatca     180
gtgttttaga gaatcatata aatgaacagt tagacatggt ctaaaggaca attgagtatt     240
ttgacaacag gactctacag ttttatcttt ttagtgtgca tgtgttctcc ttttttttg      300
caaatagctt cacctatata atacttcatc cattttatta gtacatccat ttagggttta     360
gggttaatgg tttttataga ctaattttt tagtacatct atttattct attttagcct       420
ctaaattaag aaaactaaaa ctctatttta gttttttat ttaataattt agatataaaa      480
tagaataaaa taaagtgact aaaaattaaa caaataccct ttaagaaatt aaaaaaacta     540
aggaaacatt tttcttgttt cgagtagata atgccagcct gttaaacgcc gtcgacgagt     600
ctaacggaca ccaaccagcg aaccagcagc gtcgcgtcgg gccaagcgaa gcagacggca     660
cggcatctct gtcgctgcct ctggaccoct ctcgagagtt ccgctccacc gttggacttg     720
ctccgctgtc ggcatccaga aattgcgtgg cggagcggca gacgtgagcc ggcacggcag     780
gcggcctcct cctcctctca cggcacggca gctacggggg attccttcc caccgctcct     840
tcgctttccc ttcctcgccc gccgtaataa atagacaccc cctccacacc ctctttcccc     900
aacctcgtgt tgttcggagc gcacacacac acaaccagat ctcccccaaa tccacccgtc     960
ggcacctccg cttcaaggta cgccgctcgt cctccccccc ccccctctc taccttctct    1020
agatcggcgt tccggtccat ggttagggcc cggtagttct acttctgttc atgtttgtgt   1080
tagatccgtg tttgtgttag atccgtgctg ctagcgttcg tacacggatg cgacctgtac   1140
gtcagacacg ttctgattgc taacttgcca gtgtttctct ttggggaatc ctgggatggc   1200
tctagccgtt ccgcagacgg gatcgatttc atgattttt ttgtttcgtt gcatagggtt    1260
tggtttgccc ttttccttta tttcaatata tgccgtgcac ttgtttgtcg ggtcatcttt   1320
tcatgctttt ttttgtcttg gttgtgatga tgtggtctgg ttgggcggtc gttctagatc   1380
ggagtagaat tctgtttcaa actacctggt ggatttatta attttggatc tgtatgtgtg   1440
tgccatacat attcatagtt acgaattgaa gatgatggat ggaaatatcg atctaggata   1500
ggtatacatg ttgatgcggg ttttactgat gcatatacag agatgctttt tgttcgcttg   1560
gttgtgatga tgtggtgtgg ttgggcggtc gttcattcgt tctagatcgg agtagaatac   1620
tgtttcaaac tacctggtgt atttattaat tttggaactg tatgtgtgtg tcatacatct   1680
tcatagttac gagtttaaga tggatggaaa tatcgatcta ggataggtat acatgttgat   1740
gtgggtttta ctgatgcata tacatgatgg catatgcagc atctattcat atgctctaac   1800
cttgagtacc tatctattat aataaacaag tatgttttat aattatttg atcttgatat    1860
acttggatga tggcatatgc agcagctata tgtggatttt tttagccctg ccttcatacg   1920
ctatttattt gcttggtact gtttcttttg tcgatgctca ccctgttgtt tggtgttact   1980
tctgcaggtc gactctagag gatccacaag tttgtacaaa aaagctgaac gagaaacgta   2040
aaatgatata aatatcaata tattaaatta gattttgcat aaaaaacaga ctacataata   2100
ctgtaaaaca caacatatcc agtcactatg gcggccgcat taggcacccc aggctttaca   2160
ctttatgctt ccggctcgta taatgtgtgg attttgagtt aggatttaaa tacgcgttga   2220
```

```
tccggcttac taaaagccag ataacagtat gcgtatttgc gcgctgattt ttgcggtata    2280
agaatatata ctgatatgta tacccgaagt atgtcaaaaa gaggtatgct atgaagcagc    2340
gtattacagt gacagttgac agcgacagct atcagttgct caaggcatat atgatgtcaa    2400
tatctccggt ctggtaagca caaccatgca gaatgaagcc cgtcgtctgc gtgccgaacg    2460
ctggaaagcg gaaaatcagg aagggatggc tgaggtcgcc cggtttattg aaatgaacgg    2520
ctcttttgct gacgagaaca ggggctggtg aaatgcagtt taaggtttac acctataaaa    2580
gagagagccg ttatcgtctg tttgtggatg tacagagtga tatcattgac acgcccggtc    2640
gacggatggt gatccccctg gccagtgcac gtctgctgtc agataaagtc tcccgtgaac    2700
tttacccggt ggtgcatatc ggggatgaaa gctggcgcat gatgaccacc gatatggcca    2760
gtgtgccggt ctccgttatc ggggaagaag tggctgatct cagccaccgc gaaaatgaca    2820
tcaaaaacgc cattaacctg atgttctggg aatataaat gtcaggctcc cttatacaca    2880
gccagtctgc aggtcgacca tagtgactgg atatgttgtg ttttacagta ttatgtagtc    2940
tgttttttat gcaaaatcta atttaatata ttgatattta tatcatttta cgtttctcgt    3000
tcagctttct tgtacaaagt ggtgttaacc tagacttgtc catcttctgg attggccaac    3060
ttaattaatg tatgaaataa aaggatgcac acatagtgac atgctaatca ctataatgtg    3120
ggcatcaaag ttgtgtgtta tgtgtaatta ctagttatct gaataaaaga gaagagatc    3180 atccatattt cttatcctaa atgaatgtca cgtgtcttta taattctttg atgaaccaga    3240
tgcatttcat taaccaaatc catatacata taaatattaa tcatatataa ttaatatcaa    3300
ttgggttagc aaaacaaatc tagtctaggt gtgttttgcg aattgcggcc gccaccgcgg    3360
tggagctcga attccggtcc gggtcacctt tgtccaccaa gatggaactg cggccgctca    3420
ttaattaagt caggcgcgcc tctagttgaa gacacgttca tgtcttcatc gtaagaagac    3480
actcagtagt cttcggccag aatggccatc tggattcagc aggcctagaa ggccatttaa    3540
atcctgagga tctggtcttc ctaaggaccc gggatatcgg accgattaaa ctttaattcg    3600
gtccgaagct tgcatgcctg cagtgcagcg tgacccggtc gtgcccctct ctagagataa    3660
tgagcattgc atgtctaagt tataaaaaat taccacatat ttttttttgtc acacttgttt    3720 gaagtgcagt ttatctatct ttatacatat atttaaactt tactctacga ataatataat    3780
ctatagtact acaataatat cagtgtttta gagaatcata taaatgaaca gttagacatg    3840
gtctaaagga caattgagta ttttgacaac aggactctac agttttatct ttttagtgtg    3900
catgtgttct ccttttttttt tgcaaatagc ttcacctata taatacttca tccattttat    3960
tagtacatcc atttagggtt tagggttaat ggttttttata gactaatttt tttagtacat    4020
ctattttatt ctattttagc ctctaaatta agaaaactaa aactctattt tagttttttt    4080
atttaataat ttagatataa aatagaataa aataaagtga ctaaaaatta aacaaatacc    4140
ctttaagaaa ttaaaaaaac taaggaaaca tttttcttgt ttcgagtaga taatgccagc    4200
ctgttaaacg ccgtcgacga gtctaacgga caccaaccag cgaaccagca gcgtcgcgtc    4260
gggccaagcg aagcagacgg cacggcatct ctgtcgctgc ctctggaccc ctctcgagag    4320
ttccgctcca ccgttggact tgctccgctg tcggcatcca gaaattgcgt ggcggagcgg    4380
cagacgtgag ccggcacggc aggcggcctc ctcctcctct cacggcaccg gcagctacgg    4440
gggattcctt tcccaccgct ccttcgcttt cccttcctcg cccgccgtaa taaatagaca    4500
ccccctccac accctctttc cccaacctcg tgttgttcgg agcgcacaca cacacaacca    4560
gatctccccc aaatccaccc gtcggcacct ccgcttcaag gtacgccgct cgtcctcccc    4620
```

```
cccccccctc tctaccttct ctagatcggc gttccggtcc atgcatggtt agggcccggt    4680
agttctactt ctgttcatgt ttgtgttaga tccgtgtttg tgttagatcc gtgctgctag    4740
cgttcgtaca cggatgcgac ctgtacgtca gacacgttct gattgctaac ttgccagtgt    4800
ttctctttgg ggaatcctgg gatggctcta gccgttccgc agacgggatc gatttcatga    4860
ttttttttgt ttcgttgcat agggtttggt ttgccctttt cctttatttc aatatatgcc    4920
gtgcacttgt ttgtcgggtc atcttttcat gcttttttt gtcttggttg tgatgatgtg     4980
gtctggttgg gcggtcgttc tagatcggag tagaattctg tttcaaacta cctggtggat    5040
ttattaattt tggatctgta tgtgtgtgcc atacatattc atagttacga attgaagatg    5100
atggatggaa atatcgatct aggataggta tacatgttga tgcgggtttt actgatgcat    5160
atacagagat gcttttttgtt cgcttggttg tgatgatgtg gtgtggttgg gcggtcgttc   5220
attcgttcta gatcggagta gaatactgtt caaactacc tggtgtattt attaattttg     5280
gaactgtatg tgtgtgtcat acatcttcat agttacgagt ttaagatgga tggaaatatc    5340
gatctaggat aggtatacat gttgatgtgg gttttactga tgcatataca tgatggcata    5400
tgcagcatct attcatatgc tctaaccttg agtacctatc tattataata aacaagtatg    5460
ttttataatt attttgatct tgatatactt ggatgatggc atatgcagca gctatatgtg    5520
gattttttta gccctgcctt catacgctat ttatttgctt ggtactgttt cttttgtcga    5580
tgctcaccct gttgtttggt gttacttctg caggtcgact ttaacttagc ctaggatcca    5640
cacgacacca tgtcccccga gcgccgcccc gtcgagatcc gccggccac cgccgccgac     5700
atggccgccg tgtgcgacat cgtgaaccac tacatcgaga cctccaccgt gaacttccgc    5760
accgagccgc agacccgca ggagtggatc gacgacctgg agcgcctcca ggaccgctac    5820
ccgtggctcg tggccgaggt ggagggcgtg gtggccggca tcgcctacgc cggcccgtgg    5880
aaggcccgca acgcctacga ctggaccgtg gagtccaccg tgtacgtgtc ccaccgccac    5940
cagcgcctcg gcctcggctc caccctctac acccacctcc tcaagagcat ggaggcccag    6000
ggcttcaagt ccgtggtggc cgtgatcggc ctcccgaacg accgtccgt gcgcctccac     6060
gaggccctcg gctacaccgc ccgcggcacc ctccgcgccg ccggctacaa gcacggcggc    6120
tggcacgacg tcggcttctg gcagcgcgac ttcgagctgc cggccccgcc gcgcccggtg    6180
cgcccggtga cgcagatctg agtcgaaacc tagacttgtc catcttctgg attggccaac    6240
ttaattaatg tatgaaataa aaggatgcac acatagtgac atgctaatca ctataatgtg    6300
ggcatcaaag ttgtgtgtta tgtgtaatta ctagttatct gaataaaaga gaaagagatc    6360
atccatattt cttatcctaa atgaatgtca cgtgtcttta taattctttg atgaaccaga    6420
tgcatttcat taaccaaatc catatacata taaatattaa tcatatataa ttaatatcaa    6480
ttgggttagc aaaacaaatc tagtctaggt gtgttttgcg aattgcggcc gccaccgcgg    6540
tggagctcga attcattccg attaatcgtg gcctcttgct cttcaggatg aagagctatg    6600
tttaaacgtg caagcgctac tagacaattc agtacattaa aaacgtccgc aatgtgttat    6660
taagttgtct aagcgtcaat ttggtttaca ccacaatata tcctgccacc agccagccaa    6720
cagctccccg accggcagct cggcacaaaa tcaccactcg atacaggcag cccatcagtc    6780
cgggacggcg tcagcgggag agccgttgta aggcggcaga ctttgctcat gttaccgatg    6840
ctattcggaa gaacggcaac taagctgccg ggtttgaaac acggatgatc tcgcggaggg    6900
tagcatgttg attgtaacga tgacagagcg ttgctgcctg tgatcaaata tcatctccct    6960
cgcagagatc cgaattatca gccttcttat tcatttctcg cttaaccgtg acaggctgtc    7020
```

```
gatcttgaga actatgccga cataatagga aatcgctgga taaagccgct gaggaagctg   7080
agtggcgcta tttctttaga agtgaacgtt gacgatcgtc gaccgtaccc cgatgaatta   7140
attcggacgt acgttctgaa cacagctgga tacttacttg ggcgattgtc atacatgaca   7200
tcaacaatgt acccgtttgt gtaaccgtct cttggaggtt cgtatgacac tagtggttcc   7260
cctcagcttg cgactagatg ttgaggccta acattttatt agagagcagg ctagttgctt   7320
agatacatga tcttcaggcc gttatctgtc agggcaagcg aaaattggcc atttatgacg   7380
accaatgccc cgcagaagct cccatctttg ccgccataga cgccgcgccc cccttttggg   7440
gtgtagaaca tcctttttgcc agatgtggaa aagaagttcg ttgtcccatt gttggcaatg   7500
acgtagtagc cggcgaaagt gcgagaccca tttgcgctat atataagcct acgatttccg   7560
ttgcgactat tgtcgtaatt ggatgaacta ttatcgtagt tgctctcaga gttgtcgtaa   7620
tttgatggac tattgtcgta attgcttatg gagttgtcgt agttgcttgg agaaatgtcg   7680
tagttggatg gggagtagtc atagggaaga cgagcttcat ccactaaaac aattggcagg   7740
tcagcaagtg cctgccccga tgccatcgca agtacgaggc ttagaaccac cttcaacaga   7800
tcgcgcatag tcttccccag ctctctaacg cttgagttaa gccgcgccgc gaagcggcgt   7860
cggcttgaac gaattgttag acattatttg ccgactacct tggtgatctc gcctttcacg   7920
tagtgaacaa attcttccaa ctgatctgcg cgcgaggcca agcgatcttc ttgtccaaga   7980
taagcctgcc tagcttcaag tatgacgggc tgatactggg ccggcaggcg ctccattgcc   8040
cagtcggcag cgacatcctt cggcgcgatt ttgccggtta ctgcgctgta ccaaatgcgg   8100
gacaacgtaa gcactacatt tcgctcatcg ccagcccagt cgggcggcga gttccatagc   8160
gttaaggttt catttagcgc ctcaaataga tcctgttcag gaaccggatc aaagagttcc   8220
tccgccgctg gacctaccaa ggcaacgcta tgttctcttg cttttgtcag caagatagcc   8280
agatcaatgt cgatcgtggc tggctcgaag atacctgcaa gaatgtcatt gcgctgccat   8340
tctccaaatt gcagttcgcg cttagctgga taacgccacg gaatgatgtc gtcgtgcaca   8400
acaatggtga cttctacagc gcggagaatc tcgctctctc caggggaagc cgaagtttcc   8460
aaaaggtcgt tgatcaaagc tcgccgcgtt gtttcatcaa gccttacagt caccgtaacc   8520
agcaaatcaa tatcactgtg tggcttcagg ccgccatcca ctgcggagcc gtacaaatgt   8580
acggccagca acgtcggttc gagatggcgc tcgatgacgc caactacctc tgatagttga   8640
gtcgatactt cggcgatcac cgcttccctc atgatgttta actcctgaat taagccgcgc   8700
cgcgaagcgg tgtcggcttg aatgaattgt taggcgtcat cctgtgctcc cgagaaccag   8760
taccagtaca tcgctgtttc gttcgagact tgaggtctag ttttatacgt gaacaggtca   8820
atgccgccga gagtaaagcc acattttgcg tacaaattgc aggcaggtac attgttcgtt   8880
tgtgtctcta atcgtatgcc aaggagctgt ctgcttagtg cccactttttt cgcaaattcg   8940
atgagactgt gcgcgactcc tttgcctcgg tgcgtgtgcg acacaacaat gtgttcgata   9000
gaggctagat cgttccatgt tgagttgagt tcaatcttcc cgacaagctc ttggtcgatg   9060
aatgcgccat agcaagcaga gtcttcatca gagtcatcat ccgagatgta atccttccgg   9120
taggggctca cacttctggt agatagttca aagccttggt cggataggtg cacatcgaac   9180
acttcacgaa caatgaaatg gttctcagca tccaatgttt ccgccacctg ctcagggatc   9240
accgaaatct tcatatgacg cctaacgcct ggcacagcgg atcgcaaacc tggcgcggct   9300
tttggcacaa aaggcgtgac aggtttgcga atccgttgct gccacttgtt aacccttttg   9360
ccagatttgg taactataat ttatgttaga ggcgaagtct tgggtaaaaa ctggcctaaa   9420
```

```
attgctgggg atttcaggaa agtaaacatc accttccggc tcgatgtcta ttgtagatat    9480
atgtagtgta tctacttgat cgggggatct gctgcctcgc gcgtttcggt gatgacggtg    9540
aaaacctctg acacatgcag ctcccggaga cggtcacagc ttgtctgtaa gcggatgccg    9600
ggagcagaca agcccgtcag ggcgcgtcag cgggtgttgg cgggtgtcgg ggcgcagcca    9660
tgacccagtc acgtagcgat agcggagtgt atactggctt aactatgcgg catcagagca    9720
gattgtactg agagtgcacc atatgcggtg tgaaataccg cacagatgcg taaggagaaa    9780
ataccgcatc aggcgctctt ccgcttcctc gctcactgac tcgctgcgct cggtcgttcg    9840
gctgcggcga gcggtatcag ctcactcaaa ggcggtaata cggttatcca cagaatcagg    9900
ggataacgca ggaaagaaca tgtgagcaaa aggccagcaa aaggccagga accgtaaaaa    9960
ggccgcgttg ctggcgtttt tccataggct ccgcccccct gacgagcatc acaaaaatcg   10020
acgctcaagt cagaggtggc gaaacccgac aggactataa agataccagg cgtttccccc   10080
tggaagctcc ctcgtgcgct ctcctgttcc gaccctgccg cttaccggat acctgtccgc   10140
ctttctccct tcgggaagcg tggcgctttc tcatagctca cgctgtaggt atctcagttc   10200
ggtgtaggtc gttcgctcca agctgggctg tgtgcacgaa ccccccgttc agcccgaccg   10260
ctgcgcctta tccggtaact atcgtcttga gtccaacccg gtaagacacg acttatcgcc   10320
actggcagca gccactggta acaggattag cagagcgagg tatgtaggcg gtgctacaga   10380
gttcttgaag tggtggccta actacggcta cactagaagg acagtatttg gtatctgcgc   10440
tctgctgaag ccagttacct tcggaaaaag agttggtagc tcttgatccg gcaaacaaac   10500
caccgctggt agcggtggtt tttttgtttg caagcagcag attacgcgca gaaaaaaagg   10560
atctcaagaa gatcctttga tcttttctac ggggtctgac gctcagtgga acgaaaactc   10620
acgttaaggg attttggtca tgagattatc aaaaaggatc ttcacctaga tccttttaaa   10680
ttaaaaatga agttttaaat caatctaaag tatatatgag taaacttggt ctgacagtta   10740
ccaatgctta atcagtgagg cacctatctc agcgatctgt ctatttcgtt catccatagt   10800
tgcctgactc cccgtcgtgt agataactac gatacgggag ggcttaccat ctggccccag   10860
tgctgcaatg ataccgcgag acccacgctc accggctcca gatttatcag caataaacca   10920
gccagccgga agggccgagc gcagaagtgg tcctgcaact ttatccgcct ccatccagtc   10980
tattaattgt tgccgggaag ctagagtaag tagttcgcca gttaatagtt tgcgcaacgt   11040
tgttgccatt gctgcagggg ggggggggggg ggggacttc cattgttcat tccacggaca   11100
aaaacagaga aaggaaacga cagaggccaa aaagcctcgc tttcagcacc tgtcgtttcc   11160
tttcttttca gagggtattt taaataaaaa cattaagtta tgacgaagaa gaacggaaac   11220
gccttaaacc ggaaaatttt cataaatagc gaaaacccgc gaggtcgccg ccccgtaacc   11280
tacctgtcgg atcaccggaa aggacccgta aagtgataat gattatcatc tacatatcac   11340
aacgtgcgtg gaggccatca aaccacgtca ataatcaat tatgacgcag gtatcgtatt   11400
aattgatctg catcaactta acgtaaaaac aacttcagac aatacaaatc agcgacactg   11460
aatacggggc aacctcatgt ccccccccccc ccccccctg caggcatcgt ggtgtcacgc   11520
tcgtcgtttg gtatggcttc attcagctcc ggttcccaac gatcaaggcg agttacatga   11580
tcccccatgt tgtgcaaaaa agcggttagc tccttcggtc ctccgatcgt tgtcagaagt   11640
aagttggccg cagtgttatc actcatggtt atggcagcac tgcataattc tcttactgtc   11700
atgccatccg taagatgctt ttctgtgact ggtgagtact caaccaagtc attctgagaa   11760
tagtgtatgc ggcgaccgag ttgctcttgc ccggcgtcaa cacgggataa taccgcgcca   11820
```

```
catagcagaa ctttaaaagt gctcatcatt ggaaaacgtt cttcggggcg aaaactctca   11880
aggatcttac cgctgttgag atccagttcg atgtaaccca ctcgtgcacc caactgatct   11940
tcagcatctt ttactttcac cagcgtttct gggtgagcaa aaacaggaag gcaaaatgcc   12000
gcaaaaaagg gaataagggc gacacggaaa tgttgaatac tcatactctt ccttttcaa    12060 tattattgaa gcatttatca gggttattgt ctcatgagcg gatacatatt tgaatgtatt   12120
tagaaaaata aacaaatagg ggttccgcgc acatttcccc gaaaagtgcc acctgacgtc   12180
taagaaacca ttattatcat gacattaacc tataaaaata ggcgtatcac gaggcccttt   12240
cgtcttcaag aattcggagc ttttgccatt ctcaccggat tcagtcgtca ctcatggtga   12300
tttctcactt gataaccta tttttgacga ggggaaatta ataggttgta ttgatgttgg    12360
acgagtcgga atcgcagacc gataccagga tcttgccatc ctatggaact gcctcggtga   12420
gttttctcct tcattacaga aacggctttt tcaaaaatat ggtattgata atcctgatat   12480
gaataaattg cagtttcatt tgatgctcga tgagtttttc taatcagaat tggttaattg   12540
gttgtaacac tggcagagca ttacgctgac ttgacgggac ggcggctttg ttgaataaat   12600
cgaacttttg ctgagttgaa ggatcagatc acgcatcttc ccgacaacgc agaccgttcc   12660
gtggcaaagc aaaagttcaa aatcaccaac tggtccacct acaacaaagc tctcatcaac   12720
cgtggctccc tcactttctg gctggatgat ggggcgattc aggcctggta tgagtcagca   12780
acaccttctt cacgaggcag acctcagcgc cagaaggccg ccagagaggc cgagcgcggc   12840
cgtgaggctt ggacgctagg gcagggcatg aaaaagcccg tagcgggctg ctacgggcgt   12900
ctgacgcggt ggaaagggg aggggatgtt gtctacatgg ctctgctgta gtgagtgggt    12960
tgcgctccgg cagcggtcct gatcaatcgt caccctttct cggtccttca acgttcctga   13020
caacgagcct ccttttcgcc aatccatcga caatcaccgc gagtccctgc tcgaacgctg   13080
cgtccggacc ggcttcgtcg aaggcgtcta tcgcggcccg caacagcggc gagagcggag   13140
cctgttcaac ggtgccgccg cgctcgccgg catcgctgtc gccggcctgc tcctcaagca   13200
cggccccaac agtgaagtag ctgattgtca tcagcgcatt gacggcgtcc ccggccgaaa   13260
aacccgcctc gcagaggaag cgaagctgcg cgtcggccgt ttccatctgc ggtgcgcccg   13320
gtcgcgtgcc ggcatggatg cgcgcgccat cgcggtaggc gagcagcgcc tgcctgaagc   13380
tgcgggcatt cccgatcaga aatgagcgcc agtcgtcgtc ggctctcggc accgaatgcg   13440
tatgattctc cgccagcatg gcttcggcca gtgcgtcgag cagcgcccgc ttgttcctga   13500
agtgccagta aagcgccggc tgctgaaccc ccaaccgttc cgccagtttg cgtgtcgtca   13560
gaccgtctac gccgacctcg ttcaacaggt ccagggcggc acggatcact gtattcggct   13620
gcaactttgt catgcttgac actttatcac tgataaacat aatatgtcca ccaacttatc   13680
agtgataaag aatccgcgcg ttcaatcgga ccagcgagg ctggtccgga ggccagacgt     13740
gaaacccaac ataccctga tcgtaattct gagcactgtc gcgctcgacg ctgtcggcat     13800
cggcctgatt atgccggtgc tgccgggcct cctgcgcgat ctggttcact cgaacgacgt   13860
caccgcccac tatggcattc tgctggcgct gtatgcgttg gtgcaatttg cctgcgcacc   13920
tgtgctgggc gcgctgtcgg atcgtttcgg gcggcggcca atcttgctcg tctcgctggc   13980
cggcgccact gtcgactacg ccatcatggc gacagcgcct ttcctttggg ttctctatat   14040
cgggcggatc gtggccggca tcaccggggc gactggggcg gtagccggcg cttatattgc   14100
cgatatcact gatggcgatg agcgcgcgcg gcacttcggc ttcatgagcg cctgtttcgg   14160
gttcgggatg gtcgcgggac ctgtgctcgg tgggctgatg ggcggttct cccccacgc    14220
```

```
tccgttcttc gccgcggcag ccttgaacgg cctcaatttc ctgacgggct gtttccttt    14280
gccggagtcg cacaaaggcg aacgccggcc gttacgccgg gaggctctca acccgctcgc   14340
ttcgttccgg tgggcccggg gcatgaccgt cgtcgccgcc ctgatggcgg tcttcttcat   14400
catgcaactt gtcggacagg tgccggccgc gctttgggtc attttcggcg aggatcgctt   14460
tcactgggac gcgaccacga tcggcatttc gcttgccgca tttggcattc tgcattcact   14520
cgcccaggca atgatcaccg gccctgtagc cgcccggctc ggcgaaaggc gggcactcat   14580
gctcggaatg attgccgacg gcacaggcta catcctgctt gccttcgcga cacggggatg   14640
gatggcgttc ccgatcatgg tcctgcttgc ttcgggtggc atcggaatgc cggcgctgca   14700
agcaatgttg tccaggcagg tggatgagga acgtcagggg cagctgcaag gctcactggc   14760
ggcgctcacc agcctgacct cgatcgtcgg accccctcctc ttcacggcga tctatgcggc   14820
ttctataaca acgtgaacg ggtgggcatg gattgcaggc gctgccctct acttgctctg    14880
cctgccggcg ctgcgtcgcg ggcttttggag cggcgcaggg caacgagccg atcgctgatc   14940
gtggaaacga taggcctatg ccatgcgggt caaggcgact tccggcaagc tatacgcgcc   15000
ctaggagtgc ggttggaacg ttgggcccagc cagatactcc cgatcacgag caggacgccg   15060
atgatttgaa gcgcactcag cgtctgatcc aagaacaacc atcctagcaa cacggcggtc   15120
cccgggctga gaaagcccag taaggaaaca actgtaggtt cgagtcgcga gatccccgg    15180
aaccaaagga agtaggttaa acccgctccg atcaggccga gccacgccag gccgagaaca   15240
ttggttcctg taggcatcgg gattggcgga tcaaacacta aagctactgg aacgagcaga   15300
agtcctccgg ccgccagttg ccaggcggta aggtgagca gaggcacggg aggttgccac     15360
ttgcgggtca gcacggttcc gaacgccatg gaaaccgccc ccgccaggcc cgctgcgacg   15420
ccgacaggat ctagcgctgc gtttggtgtc aacaccaaca gcgccacgcc cgcagttccg   15480
caaatagccc ccaggaccgc catcaatcgt atcgggctac ctagcagagc ggcagagatg   15540
aacacgacca tcagcggctg cacagcgcct accgtcgccg cgaccccgcc cggcaggcgg   15600
tagaccgaaa taacaacaa gctccagaat agcgaaatat taagtgcgcc gaggatgaag   15660
atgcgcatcc accagattcc cgttggaatc tgtcggacga tcatcacgag caataaaccc   15720
gccggcaacg cccgcagcag catccggcg acccctcggc ctcgctgttc gggctccacg    15780
aaaacgccgg acagatgcgc cttgtgagcg tccttgggc cgtcctcctg tttgaagacc    15840
gacagcccaa tgatctcgcc gtcgatgtag gcgccgaatg ccacggcatc tcgcaaccgt   15900
tcagcgaacg cctccatggg cttttctcc tcgtgctcgt aaacggaccc gaacatctct    15960
ggagctttct tcagggccga caatcggatc tcgcggaaat cctgcacgtc ggccgctcca    16020
agccgtcgaa tctgagcctt aatcacaatt gtcaatttta atcctctgtt tatcggcagt    16080
tcgtagagcg cgccgtgcgt cccgagcgat actgagcgaa gcaagtgcgt cgagcagtgc    16140
ccgcttgttc ctgaaatgcc agtaaagcgc tggctgctga accccagcc ggaactgacc     16200
ccacaaggcc ctagcgtttg caatgcacca ggtcatcatt gacccaggcg tgttccacca   16260
ggccgctgcc tcgcaactct tcgcaggctt cgccgacctg ctcgcgccac ttcttcacgc   16320
gggtggaatc cgatccgcac atgaggcgga aggtttccag cttgagcggg tacggctccc   16380
ggtgcgagct gaaatagtcg aacatccgtc gggccgtcgg cgacagcttg cggtactct    16440
cccatatgaa tttcgtgtag tggtcgccag caaacagcac gacgatttcc tcgtcgatca   16500
ggacctggca acgggacgtt ttcttgccac ggtccaggac gcggaagcgg tgcagcagcg   16560
acaccgattc caggtgccca acgcggtcgg acgtgaagcc catcgccgtc gcctgtaggc   16620
```

```
gcgacaggca ttcctcggcc ttcgtgtaat accggccatt gatcgaccag cccaggtcct    16680
ggcaaagctc gtagaacgtg aaggtgatcg gctcgccgat aggggtgcgc ttcgcgtact    16740
ccaacacctg ctgccacacc agttcgtcat cgtcggcccg cagctcgacg ccggtgtagg    16800
tgatcttcac gtccttgttg acgtggaaaa tgaccttgtt ttgcagcgcc tcgcgcggga    16860
ttttcttgtt gcgcgtggtg aacagggcag agcgggccgt gtcgtttggc atcgctcgca    16920
tcgtgtccgg ccacggcgca atatcgaaca aggaaagctg catttccttg atctgctgct    16980
tcgtgtgttt cagcaacgcg gcctgcttgg cctcgctgac ctgttttgcc aggtcctcgc    17040
cggcggtttt tcgcttcttg gtcgtcatag ttcctcgcgt gtcgatggtc atcgacttcg    17100
ccaaacctgc cgcctcctgt tcgagacgac gcgaacgctc cacggcgcc gatggcgcgg    17160 gcagggcagg gggagccagt tgcacgctgt cgcgctcgat cttggccgta gcttgctgga    17220
ccatcgagcc gacggactgg aaggtttcgc ggggcgcacg catgacgtg cggcttgcga    17280 tggtttcggc atcctcggcg gaaaaccccg cgtcgatcag ttcttgcctg tatgccttcc    17340
ggtcaaacgt ccgattcatt caccctcctt gcgggattgc cccgactcac gccggggcaa    17400
tgtgccctta ttcctgattt gacccgcctg gtgccttggt gtccagataa tccaccttat    17460
cggcaatgaa gtcggtcccg tagaccgtct ggccgtcctt tcgtacttg gtattccgaa    17520 tcttgccctg cacgaatacc agcgacccct tgcccaaata cttgccgtgg gcctcggcct    17580
gagagccaaa acacttgatg cggaagaagt cggtgcgctc ctgcttgtcg ccggcatcgt    17640
tgcgccactc ttcattaacc gctatatcga aaattgcttg cggcttgtta gaattgccat    17700
gacgtacctc ggtgtcacgg gtaagattac cgataaactg gaactgatta tggctcatat    17760
cgaaagtctc cttgagaaag gagactctag tttagctaaa cattggttcc gctgtcaaga    17820
actttagcgg ctaaaattt gcgggccgcg accaaaggtg cgaggggcgg cttccgctgt    17880
gtacaaccag atattttca ccaacatcct tcgtctgctc gatgagcggg gcatgacgaa    17940
acatgagctg tcggagaggg caggggtttc aatttcgttt ttatcagact taaccaacgg    18000
taaggccaac ccctcgttga aggtgatgga ggcattgcc gacgccctgg aaactcccct    18060
acctcttctc ctggagtcca ccgaccttga ccgcgaggca ctcgcggaga ttgcgggtca    18120
tcctttcaag agcagcgtgc cgcccggata cgaacgcatc agtgtggttt tgccgtcaca    18180
taaggcgttt atcgtaaaga aatggggcga cgacaccccga aaaagctgc gtggaaggct    18240 ctgacgccaa gggttagggc ttgcacttcc ttctttagcc gctaaaacgg ccccttctct    18300
gcgggccgtc ggctcgcgca tcatatcgac atcctcaacg gaagccgtgc cgcgaatggc    18360
atcgggcggg tgcgctttga cagttgtttt ctatcagaac ccctacgtcg tgcggttcga    18420
ttagctgttt gtcttgcagg ctaaacactt tcggtatatc gtttgcctgt gcgataatgt    18480
tgctaatgat ttgttgcgta ggggttactg aaaagtgagc gggaagaag agtttcagac    18540 catcaaggag cgggccaagc gcaagctgga acgcgacatg ggtgcggacc tgttggccgc    18600
gctcaacgac ccgaaaaccg ttgaagtcat gctcaacgcg gacggcaagg tgtggcacga    18660
acgccttggc gagccgatgc ggtacatctg cgacatgcgg cccagccagt cgcaggcgat    18720
tatagaaacg gtggccggat tccacggcaa agaggtcacg cggcattcgc ccatcctgga    18780
aggcgagttc cccttggatg gcagccgctt tgccggccaa ttgccgccgg tcgtggccgc    18840
gccaaccttt gcgatccgca agcgcgcggt cgccatcttc acgctggaac agtacgtcga    18900
ggcgggcatc atgacccgcg agcaatacga ggtcattaaa agcgccgtcg cggcgcatcg    18960
aaacatcctc gtcattggcg gtactggctc gggcaagacc acgctcgtca acgcgatcat    19020
```

```
caatgaaatg gtcgccttca acccgtctga gcgcgtcgtc atcatcgagg acaccggcga   19080
aatccagtgc gccgcagaga acgccgtcca ataccacacc agcatcgacg tctcgatgac   19140
gctgctgctc aagacaacgc tgcgtatgcg ccccgaccgc atcctggtcg gtgaggtacg   19200
tggccccgaa gcccttgatc tgttgatggc ctggaacacc gggcatgaag gaggtgccgc   19260
caccctgcac gcaaacaacc ccaaagcggg cctgagccgg ctcgccatgc ttatcagcat   19320
gcacccggat tcaccgaaac ccattgagcc gctgattggc gaggcggttc atgtggtcgt   19380
ccatatcgcc aggacccta gcggccgtcg agtgcaagaa attctcgaag ttcttggtta   19440
cgagaacggc cagtacatca ccaaaaccct gtaaggagta tttccaatga caacggctgt   19500
tccgttccgt ctgaccatga atcgcggcat tttgttctac cttgccgtgt tcttcgttct   19560
cgctctcgcg ttatccgcgc atccggcgat ggcctcggaa ggcaccggcg gcagcttgcc   19620
atatgagagc tggctgacga acctgcgcaa ctccgtaacc ggcccggtgg ccttcgcgct   19680
gtccatcatc ggcatcgtcg tcgccggcgg cgtgctgatc ttcggcggcg aactcaacgc   19740
cttcttccga accctgatct tcctggttct ggtgatggcg ctgctggtcg gcgcgcagaa   19800
cgtgatgagc accttcttcg gtcgtggtgc cgaaatcgcg ccctcggca acggggcgct   19860 gcaccaggtg caagtcgcgg cggcggatgc cgtgcgtgcg gtagcggctg acggctcgc   19920 ctaatcatgg ctctgcgcac gatccccatc cgtcgcgcag gcaaccgaga aaacctgttc   19980
atgggtggtg atcgtgaact ggtgatgttc tcgggcctga tggcgtttgc gctgatttc   20040 agcgcccaag agctgcgggc caccgtggtc ggtctgatcc tgtggttcgg ggcgctctat   20100
gcgttccgaa tcatggcgaa ggccgatccg aagatgcggt tcgtgtacct gcgtcaccgc   20160
cggtacaagc cgtattaccc ggcccgctcg accccgttcc gcgagaacac caatagccaa   20220
gggaagcaat accgatgatc caagcaattg cgattgcaat cgcgggcctc ggcgcgcttc   20280
tgttgttcat cctcttttgcc cgcatccgcg cggtcgatgc cgaactgaaa ctgaaaaagc   20340
atcgttccaa ggacgccggc ctggccgatc tgctcaacta cgccgctgtc gtcgatgacg   20400
gcgtaatcgt gggcaagaac ggcagcttta tggctgcctg gctgtacaag ggcgatgaca   20460
acgcaagcag caccgaccag cagcgcgaag tagtgtccgc ccgcatcaac caggccctcg   20520
cgggcctggg aagtgggtgg atgatccatg tggacgccgt gcggcgtcct gctccgaact   20580
acgcggagcg gggcctgtcg gcgttccctg accgtctgac ggcagcgatt gaagaagagc   20640
gctcggtctt gccttgctcg tcggtgatgt acttcaccag ctccgcgaag tcgctcttct   20700
tgatggagcg catggggacg tgcttggcaa tcacgcgcac cccccggccg ttttagcggc   20760 taaaaagtc atggctctgc cctcgggcgg accacgccca tcatgacctt gccaagctcg   20820
tcctgcttct cttcgatctt cgccagcagg gcgaggatcg tggcatcacc gaaccgcgcc   20880
gtgcgcgggt cgtcggtgag ccagagtttc agcaggccgc ccaggcggcc caggtcgcca   20940
ttgatgcggg ccagctcgcg gacgtgctca tagtccacga cgcccgtgat tttgtagccc   21000
tggccgacgg ccagcaggta ggccgacagg ctcatgccgg ccgccgccgc cttttcctca   21060
atcgctcttc gttcgtctgg aaggcagtac accttgatag gtgggctgcc cttcctggtt   21120
ggcttggttt catcagccat ccgcttgccc tcatctgtta cgccggcggt agccggccag   21180
cctcgcagag caggattccc gttgagcacc gccaggtgca ataagggac agtgaagaag   21240 gaacacccgc tcgcgggtgg gcctacttca cctatcctgc ccggctgacg ccgttggata   21300
caccaaggaa agtctacacg aacccttttgg caaaatcctg tatatcgtgc gaaaaggat   21360 ggatataccg aaaaaatcgc tataatgacc ccgaagcagg gttatgcagc ggaaaagcgc   21420
```

```
tgcttccctg ctgttttgtg gaatatctac cgactggaaa caggcaaatg caggaaatta   21480
ctgaactgag gggacaggcg agagacgatg ccaaagagct acaccgacga gctggccgag   21540
tgggttgaat cccgcgcggc caagaagcgc cggcgtgatg aggctgcggt tgcgttcctg   21600
gcggtgaggg cggatgtcga ggcggcgtta gcgtccggct atgcgctcgt caccatttgg   21660
gagcacatgc gggaaacggg gaaggtcaag ttctcctacg agacgttccg ctcgcacgcc   21720
aggcggcaca tcaaggccaa gcccgccgat gtgcccgcac cgcaggccaa ggctgcggaa   21780
cccgcgccgg cacccaagac gccggagcca cggcggccga agcagggggg caaggctgaa   21840
aagccggccc ccgctgcggc cccgaccggc ttcaccttca acccaacacc ggacaaaaag   21900
gatctactgt aatggcgaaa attcacatgg ttttgcaggg caaggcggg gtcggcaagt    21960 cggccatcgc cgcgatcatt gcgcagtaca agatggacaa ggggcagaca cccttgtgca   22020
tcgacaccga cccggtgaac gcgacgttcg agggctacaa ggccctgaac gtccgccggc   22080
tgaacatcat ggccggcgac gaaattaact cgcgcaactt cgacaccctg gtcgagctga   22140
ttgcgccgac caaggatgac gtggtgatcg acaacggtgc cagctcgttc gtgcctctgt   22200
cgcattacct catcagcaac caggtgccgg ctctgctgca agaaatgggg catgagctgg   22260
tcatccatac cgtcgtcacc ggcggccagg ctctcctgga cacggtgagc ggcttcgccc   22320
agctcgccag ccagttcccg gccgaagcgc ttttcgtggt ctggctgaac ccgtattggg   22380
ggcctatcga gcatgagggc aagagctttg agcagatgaa ggcgtacacg gccaacaagg   22440
cccgcgtgtc gtccatcatc cagattccgg ccctcaagga agaaacctac ggccgcgatt   22500
tcagcgacat gctgcaagag cggctgacgt tcgaccaggc gctggccgat gaatcgctca   22560
cgatcatgac gcggcaacgc ctcaagatcg tgcggcgcgg cctgtttgaa cagctcgacg   22620
cggcggccgt gctatgagcg accagattga agagctgatc cgggagattg cggccaagca   22680
cggcatcgcc gtcggccgcg acgacccggt gctgatcctg cataccatca acgcccggct   22740
catggccgac agtgcggcca agcaagagga aatccttgcc gcgttcaagg aagagctgga   22800
agggatcgcc catcgttggg gcgaggacgc caaggccaaa gcggagcgga tgctgaacgc   22860
ggccctggcg gccagcaagg acgcaatggc gaaggtaatg aaggacagcg ccgcgcaggc   22920
ggccgaagcg atccgcaggg aaatcgacga cggccttggc cgccagctcg cggccaaggt   22980
cgcggacgcg cggcgcgtgg cgatgatgaa catgatcgcc ggcggcatgg tgttgttcgc   23040
ggccgccctg gtggtgtggg cctcgttatg aatcgcagag gcgcagatga aaaagcccgg   23100
cgttgccggg cttttgttttt gcgttagctg ggcttgtttg acaggcccaa gctctgactg   23160
cgcccgcgct cgcgctcctg ggcctgtttc ttctcctgct cctgcttgcg catcagggcc   23220
tggtgccgtc gggctgcttc acgcatcgaa tcccagtcgc cggccagctc gggatgctcc   23280
gcgcgcatct tgcgcgtcgc cagttcctcg atcttgggcg cgtgaatgcc catgccttcc   23340
ttgatttcgc gcaccatgtc cagccgcgtg tgcagggtct gcaagcgggc ttgctgttgg   23400
gcctgctgct gctgccaggc ggcctttgta cgcggcaggg acagcaagcc gggggcattg   23460
gactgtagct gctgcaaacg cgcctgctga cggtctacga gctgttctag gcggtcctcg   23520
atgcgctcca cctggtcatg ctttgcctgc acgtagagcg caagggtctg ctggtaggtc   23580
tgctcgatgg gcgcggattc taagagggcc tgctgttccg tctcggcctc ctgggccgcc   23640
tgtagcaaat cctcgccgct gttgccgctg gactgcttta ctgccgggga ctgctgttgc   23700
cctgctcgcg ccgtcgtcgc agttcggctt gcccccactc gattgactgc ttcatttcga   23760
gccgcagcga tgcgatctcg gattgcgtca acggacgggg cagcgcggag gtgtccggct   23820
```

```
tctccttggg tgagtcggtc gatgccatag ccaaaggttt ccttccaaaa tgcgtccatt   23880
gctggaccgt gtttctcatt gatgcccgca agcatcttcg gcttgaccgc caggtcaagc   23940
gcgccttcat gggcggtcat gacggacgcc gccatgacct tgccgccgtt gttctcgatg   24000
tagccgcgta atgaggcaat ggtgccgccc atcgtcagcg tgtcatcgac aacgatgtac   24060
ttctggccgg ggatcacctc cccctcgaaa gtcgggttga acgccaggcg atgatctgaa   24120
ccggctccgg ttcgggcgac cttctcccgc tgcacaatgt ccgtttcgac ctcaaggcca   24180
aggcggtcgg ccagaacgac cgccatcatg gccggaatct tgttgttccc cgccgcctcg   24240
acggcgagga ctgaacgat gcggggcttg tcgtcgccga tcagcgtctt gagctgggca   24300
acagtgtcgt ccgaaatcag gcgctcgacc aaattaagcg ccgcttccgc gtcgccctgc   24360
ttcgcagcct ggtattcagg ctcgttggtc aaagaaccaa ggtcgccgtt gcgaaccacc   24420
ttcgggaagt ctccccacgg tgcgcgctcg gctctgctgt agctgctcaa gacgcctccc   24480
tttttagccg ctaaaactct aacgagtgcg cccgcgactc aacttgacgc tttcggcact   24540
tacctgtgcc ttgccacttg cgtcataggt gatgcttttc gcactcccga tttcaggtac   24600
tttatcgaaa tctgaccggg cgtgcattac aaagttcttc cccacctgtt ggtaaatgct   24660
gccgctatct gcgtggacga tgctgccgtc gtggcgctgc gacttatcgg ccttttgggc   24720
catatagatg ttgtaaatgc caggtttcag ggccccggct ttatctacct tctgttcgt   24780 ccatgcgcct tggttctcgg tctggacaat tctttgccca ttcatgacca ggaggcggtg   24840
tttcattggg tgactcctga cggttgcctc tggtgttaaa cgtgtcctgg tcgcttgccg   24900
gctaaaaaaa agccgacctc ggcagttcga ggccggcttt ccctagagcc gggcgcgtca   24960
aggttgttcc atctatttta gtgaactgcg ttcgatttat cagttacttt cctcccgctt   25020
tgtgtttcct cccactcgtt tccgcgtcta gccgacccct caacatagcg gcctcttctt   25080
gggctgcctt tgcctcttgc cgcgcttcgt cacgctcggc ttgcaccgtc gtaaagcgct   25140
cggcctgcct ggccgcctct tgcgccgcca acttcctttg ctcctggtgg gcctcggcgt   25200
cggcctgcgc cttcgctttc accgctgcca actccgtgcg caaactctcc gcttcgcgcc   25260
tggtggcgtc gcgctcgccg cgaagcgcct gcatttcctg gttggccgcg tccagggtct   25320
tgcggctctc ttctttgaat gcgcgggcgt cctggtgagc gtagtccagc tcggcgcgca   25380
gctcctgcgc tcgacgctcc acctcgtcgg cccgctgcgt cgccagcgcg gcccgctgct   25440
cggctcctgc cagggcggtg cgtgcttcgg ccagggcttg ccgctggcgt gcggccagct   25500
cggccgcctc ggcggcctgc tgctctagca atgtaacgcg cgcctgggct tcttccagct   25560
cgcgggcctg cgcctcgaag gcgtcggcca gctccccgcg cacggcttcc aactcgttgc   25620
gctcacgatc ccagccggct tgcgctgcct gcaacgattc attggcaagg gcctgggcgg   25680
cttgccagag ggcggccacg gcctggttgc cggcctgctg caccgcgtcc ggcacctgga   25740
ctgccagcgg ggcggcctgc gccgtgcgct ggcgtcgcca ttcgcgcatg ccggcgctgg   25800
cgtcgttcat gttgacgcgg gcggccttac gcactgcatc cacggtcggg aagttctccc   25860
ggtcgccttg ctcgaacagc tcgtccgcag ccgcaaaaat gcggtcgcgc gtctctttgt   25920
tcagttccat gttggctccg gtaattggta agaataataa tactcttacc taccttatca   25980
gcgcaagagt ttagctgaac agttctcgac ttaacgcag gttttttagc ggctgaaggg   26040
caggcaaaaa aagccccgca cggtcggcgg gggcaaaggg tcagcgggaa ggggattagc   26100
gggcgtcggg cttcttcatg cgtcgggcc gcgcttcttg gatggagca cgacgaagcg   26160 cgcacgcgca tcgtcctcgg ccctatcggc ccgcgtcgcg gtcaggaact tgtcgcgcgc   26220
```

```
taggtcctcc ctggtgggca ccaggggcat gaactcggcc tgctcgatgt aggtccactc    26280
catgaccgca tcgcagtcga ggccgcgttc cttcaccgtc tcttgcaggt cgcggtacgc    26340
ccgctcgttg agcggctggt aacgggccaa ttggtcgtaa atggctgtcg gccatgagcg    26400
gcctttcctg ttgagccagc agccgacgac gaagccggca atgcaggccc ctggcacaac    26460
caggccgacg ccggggggcag gggatggcag cagctcgcca accaggaacc ccgccgcgat    26520
gatgccgatg ccggtcaacc agcccttgaa actatccggc cccgaaacac ccctgcgcat    26580
tgcctggatg ctgcgccgga tagcttgcaa catcaggagc cgtttctttt gttcgtcagt    26640
catggtccgc cctcaccagt tgttcgtatc ggtgtcggac gaactgaaat cgcaagagct    26700
gccggtatcg gtccagccgc tgtccgtgtc gctgctgccg aagcacggcg agggtccgc     26760 gaacgccgca gacggcgtat ccggccgcag cgcatcgccc agcatggccc cggtcagcga    26820
gccgccggcc aggtagccca gcatggtgct gttggtcgcc ccggccacca gggccgacgt    26880
gacgaaatcg ccgtcattcc ctctggattg ttcgctgctc ggcggggcag tgcgccgcgc    26940
cggcggcgtc gtggatggct cgggttggct ggcctgcgac ggccggcgaa aggtgcgcag    27000
cagctcgtta tcgaccggct gcggcgtcgg ggccgccgcc ttgcgctgcg gtcggtgttc    27060
cttcttcggc tcgcgcagct tgaacagcat gatcgcggaa accagcagca acgccgcgcc    27120
tacgcctccc gcgatgtaga acagcatcgg attcattctt cggtcctcct tgtagcggaa    27180
ccgttgtctg tgcggcgcgg gtggcccgcg ccgctgtctt tggggatcag ccctcgatga    27240
gcgcgaccag tttcacgtcg gcaaggttcg cctcgaactc ctggccgtcg tcctcgtact    27300
tcaaccaggc atagccttcc gccggcggcc gacggttgag gataaggcgg gcagggcgct    27360
cgtcgtgctc gacctggacg atggccttt tcagcttgtc cgggtccggc tccttcgcgc     27420
ccttttcctt ggcgtcctta ccgtcctggt cgccgtcctc gccgtcctgg ccgtcgccgg    27480
cctccgcgtc acgctcggca tcagtctggc cgttgaaggc atcgacggtg ttgggatcgc    27540
ggcccttctc gtccaggaac tcgcgcagca gcttgaccgt gccgcgcgtg atttcctggg    27600
tgtcgtcgtc aagccacgcc tcgacttcct ccggggcgctt cttgaaggcc gtcaccagct    27660
cgttcaccac ggtcacgtcg cgcacgcggc cggtgttgaa cgcatcggcg atcttctccg    27720
gcaggtccag cagcgtgacg tgctgggtga tgaacgccgg cgacttgccg atttccttgg    27780
cgatatcgcc tttcttcttg cccttcgcca gctcgcggcc aatgaagtcg gcaatttcgc    27840
gcggggtcag ctcgttgcgt tgcaggttct cgataacctg gtcggcttcg ttgtagtcgt    27900
tgtcgatgaa cgccgggatg gacttcttgc cggcccactt cgagccacgg tagcggcggg    27960
cgccgtgatt gatgatatag cggcccggct gctcctggtt ctcgcgcacc gaaatgggtg    28020
acttcacccc gcgctctttg atcgtggcac cgatttccgc gatgctctcc ggggaaaagc    28080
cggggttgtc ggccgtccgc ggctgatgcg gatcttcgtc gatcaggtcc aggtccagct    28140 cgataggggcc ggaaccgccc tgagacgccg caggagcgtc caggaggctc gacaggtcgc    28200
cgatgctatc caaccccagg ccggacggct gcgccgcgcc tgcggcttcc tgagcggccg    28260
cagcggtgtt tttcttggtg gtcttggctt gagccgcagt cattgggaaa tctccatctt    28320
cgtgaacacg taatcagcca gggcgcgaac ctctttcgat gccttgcgcg cggccgtttt    28380
cttgatcttc cagaccggca caccggatgc gagggcatcg gcgatgctgc tgcgcaggcc    28440
aacggtggcc ggaatcatca tcttggggta cgcggccagc agctcggctt ggtggcgcgc    28500
gtggcgcgga ttccgcgcat cgaccttgct gggcaccatg ccaaggaatt gcagcttggc    28560
gttcttctgg cgcacgttcg caatggtcgt gaccatcttc ttgatgccct ggatgctgta    28620
```

```
cgcctcaagc tcgatggggg acagcacata gtcggccgcg aagagggcgg ccgccaggcc   28680
gacgccaagg gtcggggccg tgtcgatcag gcacacgtcg aagccttggt tcgccagggc   28740
cttgatgttc gccccgaaca gctcgcgggc gtcgtccagc gacagccgtt cggcgttcgc   28800
cagtaccggg ttggactcga tgagggcgag gcgcgcggcc tggccgtcgc cggctgcggg   28860
tgcggtttcg gtccagccgc cggcagggac agcgccgaac agcttgcttg catgcaggcc   28920
ggtagcaaag tccttgagcg tgtaggacgc attgccctgg gggtccaggt cgatcacggc   28980
aacccgcaag ccgcgctcga aaagtcgaa ggcaagatgc acaagggtcg aagtcttgcc   29040
gacgccgcct ttctggttgg ccgtgaccaa agttttcatc gtttggtttc ctgtttttc   29100 ttggcgtccg cttcccactt ccggacgatg tacgcctgat gttccggcag aaccgccgtt   29160
acccgcgcgt acccctcggg caagttcttg tcctcgaacg cggcccacac gcgatgcacc   29220
gcttgcgaca ctgcgcccct ggtcagtccc agcgacgttg cgaacgtcgc ctgtggcttc   29280
ccatcgacta agacgcccg cgctatctcg atggtctgct gccccacttc cagccctgg   29340 atcgcctcct ggaactggct ttcggtaagc cgtttcttca tggataacac ccataattg   29400 ctccgcgcct tggttgaaca tagcggtgac agccgccagc acatgagaga gtttagcta   29460 aacatttctc gcacgtcaac acctttagcc gctaaaactc gtccttggcg taacaaaaca   29520
aaagcccgga aacggggctt tcgtctcttg ccgcttatgg ctctgcaccc ggctccatca   29580
ccaacaggtc gcgcacgcgc ttcactcggt tgcggatcga cactgccagc ccaacaaagc   29640
cggttgccgc cgccgccagg atcgcgccga tgatgccggc cacaccggcc atcgcccacc   29700
aggtcgccgc cttccggttc cattcctgct ggtactgctt cgcaatgctg gacctcggct   29760
caccataggc tgaccgctcg atggcgtatg ccgcttctcc ccttggcgta aaacccagcg   29820
ccgcaggcgg cattgccatg ctgcccgccg cttccccgac cacgacgcgc gcaccaggct   29880
tgcggtccag accttcggcc acggcgagct gcgcaaggac ataatcagcc gccgacttgg   29940
ctccacgcgc ctcgatcagc tcttgcactc gcgcgaaatc cttggcctcc acggccgcca   30000
tgaatcgcgc acgcggcgaa ggctccgcag ggccggcgtc gtgatcgccg ccgagaatgc   30060
ccttcaccaa gttcgacgac acgaaaatca tgctgacggc tatcaccatc atgcagacgg   30120
atcgcacgaa cccgctgaat tgaacacgag cacggcaccc gcgaccacta tgccaagaat   30180
gcccaaggta aaaattgccg gccccgccat gaagtccgtg aatgccccga cggccgaagt   30240
gaagggcagg ccgccaccca ggccgccgcc ctcactgccc ggcacctggt cgctgaatgt   30300
cgatgccagc acctgcggca cgtcaatgct tccgggcgtc gcgctcgggc tgatcgccca   30360
tcccgttact gccccgatcc cggcaatggc aaggactgcc agcgctgcca ttttgggt   30420 gaggccgttc gcggccgagg ggcgcagccc ctgggggat gggaggcccg cgttagcggg   30480
ccgggagggt tcgagaaggg ggggcacccc ccttcggcgt gcgcggtcac gcgcacaggg   30540
cgcagccctg gttaaaaaca aggtttataa atattggttt aaaagcaggt taaaagacag   30600
gttagcggtg gccgaaaaac gggcggaaac ccttgcaaat gctggatttt ctgcctgtgg   30660
acagcccctc aaatgtcaat aggtgcgccc ctcatctgtc agcactctgc ccctcaagtg   30720
tcaaggatcg cgcccctcat ctgtcagtag tcgcgcccct caagtgtcaa taccgcaggg   30780
cacttatccc caggcttgtc cacatcatct gtgggaaact cgcgtaaaat caggcgtttt   30840
cgccgatttg cgaggctggc cagctccacg tcgccggccg aaatcgagcc tgccctcat   30900 ctgtcaacgc cgcgccgggt gagtcggccc ctcaagtgtc aacgtccgcc cctcatctgt   30960
cagtgagggc caagtttccc gcgaggtatc cacaacgccg gcggccgcgg tgtctcgcac   31020
```

```
acggcttcga cggcgtttct ggcgcgtttg cagggccata gacggccgcc agcccagcgg   31080
cgagggcaac cagcccggtg agcgtcggaa aggcgctgga agccccgtag cgacgcggag   31140
aggggcgaga caagccaagg gcgcaggctc gatgcgcagc acgacatagc cggttctcgc   31200
aaggacgaga atttccctgc ggtgcccctc aagtgtcaat gaaagtttcc aacgcgagcc   31260
attcgcgaga gccttgagtc cacgctagat gagagctttg ttgtaggtgg accagttggt   31320
gattttgaac ttttgctttg ccacggaacg gtctgcgttg tcgggaagat gcgtgatctg   31380
atccttcaac tcagcaaaag ttcgatttat tcaacaaagc cacgttgtgt ctcaaaatct   31440
ctgatgttac attgcacaag ataaaaatat atcatcatga acaataaaac tgtctgctta   31500
cataaacagt aatacaaggg gtgttatgag ccatattcaa cgggaaacgt cttgctcgac   31560
tctagagctc gttcctcgag gaacggtacc tgcggggaag cttacaataa tgtgtgttgt   31620
taagtcttgt tgcctgtcat cgtctgactg actttcgtca taaatcccgg cctccgtaac   31680
ccagctttgg gcaagctcac ggatttgatc cggcggaacg ggaatatcga gatgccgggc   31740
tgaacgctgc agttccagct ttcccttccg ggacaggtac tccagctgat tgattatctg   31800
ctgaagggtc ttggttccac ctcctggcac aatgcgaatg attacttgag cgcgatcggg   31860
catccaattt tctcccgtca ggtgcgtggt caagtgctac aaggcacctt tcagtaacga   31920
gcgaccgtcg atccgtcgcc gggatacgga caaaatggag cgcagtagtc catcgagggc   31980
ggcgaaagcc tcgccaaaag caatacgttc atctcgcaca gcctccagat ccgatcgagg   32040
gtcttcggcg taggcagata gaagcatgga tacattgctt gagagtattc cgatggactg   32100
aagtatggct tccatctttt ctcgtgtgtc tgcatctatt tcgagaaagc ccccgatgcg   32160
gcgcaccgca acgcgaattg ccatactatc cgaaagtccc agcaggcgcg cttgatagga   32220
aaaggtttca tactcggccg atcgcagacg ggcactcacg accttgaacc cttcaacttt   32280
cagggatcga tgctggttga tggtagtctc actcgacgtg gctctggtgt gttttgacat   32340
agcttcctcc aaagaaagcg gaaggtctgg atactccagc acgaaatgtg cccgggtaga   32400
cggatggaag tctagccctg ctcaatatga aatcaacagt acatttacag tcaatactga   32460
atatacttgc tacatttgca attgtcttat aacgaatgtg aaataaaaat agtgtaacaa   32520
cgcttttact catcgataat cacaaaaaca tttatacgaa caaaaataca aatgcactcc   32580
ggtttcacag gataggcggg atcagaatat gcaacttttg acgttttgtt cttttcaaagg   32640 gggtgctggc aaaaccaccg cactcatggg cctttgcgct gctttggcaa atgacggtaa   32700
acgagtggcc ctctttgatg ccgacgaaaa ccggcctctg acgcgatgga gagaaaacgc   32760
cttacaaagc agtactggga tcctcgctgt gaagtctatt ccgccgacga atgccccttt   32820
cttgaagcag cctatgaaaa tgccgagctc gaaggatttg attatgcgtt ggccgatacg   32880
cgtggcggct cgagcgagct caacaacaca atcatcgcta gctcaaacct gcttctgatc   32940
cccaccatgc taacgccgct cgacatcgat gaggcactat ctacctaccg ctacgtcatc   33000
gagctgctgt tgagtgaaaa tttggcaatt cctacagctg ttttgcgcca acgcgtcccg   33060
gtcggccgat tgacaacatc gcaacgcagg atgtcagaga cgctagagag ccttccagtt   33120
gtaccgtctc ccatgcatga aagagatgca tttgccgcga tgaaagaacg cggcatgttg   33180
catcttacat tactaaacac gggaactgat ccgacgatgc gcctcataga gaggaatctt   33240
cggattgcga tggaggaagt cgtggtcatt tcgaaactga tcagcaaaat cttggaggct   33300
tgaagatggc aattcgcaag cccgcattgt cggtcggcga agcacggcgg cttgctggtg   33360
ctcgacccga gatccaccat cccaacccga cacttgttcc ccagaagctg gacctccagc   33420
```

```
acttgcctga aaaagccgac gagaaagacc agcaacgtga gcctctcgtc gccgatcaca   33480
tttacagtcc cgatcgacaa cttaagctaa ctgtggatgc ccttagtcca cctccgtccc   33540
cgaaaaagct ccaggttttt ctttcagcgc gaccgcccgc gcctcaagtg tcgaaaacat   33600
atgacaacct cgttcggcaa tacagtccct cgaagtcgct acaaatgatt ttaaggcgcg   33660
cgttggacga tttcgaaagc atgctggcag atggatcatt tcgcgtggcc ccgaaaagtt   33720
atccgatccc ttcaactaca gaaaaatccg ttctcgttca gacctcacgc atgttcccgg   33780
ttgcgttgct cgaggtcgct cgaagtcatt ttgatccgtt ggggttggag accgctcgag   33840
cttccggcca caagctggct accgccgcgc tcgcgtcatt cttttgctgga gagaagccat   33900 cgagcaattg gtgaagaggg acctatcgga accctcacc aaatattgag tgtaggtttg   33960
aggccgctgg ccgcgtcctc agtcacctt tgagccagat aattaagagc caaatgcaat   34020
tggctcaggc tgccatcgtc ccccgtgcg aaacctgcac gtccgcgtca aagaaataac   34080
cggcacctct tgctgttttt atcagttgag ggcttgacgg atccgcctca agtttgcggc   34140
gcagccgcaa aatgagaaca tctatactcc tgtcgtaaac ctcctcgtcg cgtactcgac   34200
tggcaatgag aagttgctcg cgcgatagaa cgtcgcgggg tttctctaaa aacgcgagga   34260
gaagattgaa ctcacctgcc gtaagtttca cctcaccgcc agcttcggac atcaagcgac   34320
gttgcctgag attaagtgtc cagtcagtaa aacaaaaaga ccgtcggtct ttggagcgga   34380
caacgttggg gcgcacgcgc aaggcaaccc gaatgcgtgc aagaaactct ctcgtactaa   34440
acggcttagc gataaaatca cttgctccta gctcgagtgc aacaacttta tccgtctcct   34500
caaggcggtc gccactgata attatgattg gaatatcaga cttttgccgcc agatttcgaa   34560 cgatctcaag cccatcttca cgacctaaat ttagatcaac aaccacgaca tcgaccgtcg   34620
cggaagagag tactctagtg aactgggtgc tgtcggctac cgcggtcact ttgaaggcgt   34680
ggatcgtaag gtattcgata ataagatgcc gcatagcgac atcgtcatcg ataagaagaa   34740
cgtgtttcaa cggctcacct ttcaatctaa aatctgaacc cttgttcaca gcgcttgaga   34800
aattttcacg tgaaggatgt acaatcatct ccagctaaat gggcagttcg tcagaattgc   34860
ggctgaccgc ggatgacgaa aatgcgaacc aagtatttca atttatgac aaaagttctc   34920 aatcgttgtt acaagtgaaa cgcttcgagg ttacagctac tattgattaa ggagatcgcc   34980
tatggtctcg ccccggcgtc gtgcgtccgc cgcgagccag atctcgccta cttcataaac   35040
gtcctcatag gcacggaatg gaatgatgac atcgatcgcc gtagagagca tgtcaatcag   35100
tgtgcgatct tccaagctag caccttgggc gctacttttg acaagggaaa acagtttctt   35160
gaatccttgg attggattcg cgccgtgtat tgttgaaatc gatcccggat gtcccgagac   35220
gacttcactc agataagccc atgctgcatc gtcgcgcatc tcgccaagca atatccggtc   35280
cggccgcata cgcagacttg cttggagcaa gtgctcggcg ctcacagcac ccagcccagc   35340
accgttcttg gagtagagta gtctaacatg attatcgtgt ggaatgacga gttcgagcgt   35400
atcttctatg gtgattagcc tttcctgggg ggggatggcg ctgatcaagg tcttgctcat   35460
tgttgtcttg ccgcttccgg tagggccaca tagcaacatc gtcagtcggc tgacgacgca   35520
tgcgtgcaga aacgcttcca aatccccgtt gtcaaaatgc tgaaggatag cttcatcatc   35580
ctgattttgg cgtttccttc gtgtctgcca ctggttccac ctcgaagcat cataacggga   35640
ggagacttct ttaagaccag aaacacgcga gcttggccgt cgaatggtca agctgacggt   35700
gcccgaggga acgtcggcg gcagacagat ttgtagtcgt tcaccaccag gaagttcagt   35760
ggcgcagagg gggttacgtg gtccgacatc ctgctttctc agcgcgcccg ctaaaatagc   35820
```

```
gatatcttca agatcatcat aagagacggg caaaggcatc ttggtaaaaa tgccggcttg    35880
gcgcacaaat gcctctccag gtcgattgat cgcaatttct tcagtcttcg ggtcatcgag    35940
ccattccaaa atcggcttca gaagaaagcg tagttgcgga tccacttcca tttacaatgt    36000
atcctatctc taagcggaaa tttgaattca ttaagagcgg cggttcctcc cccgcgtggc    36060
gccgccagtc aggcggagct ggtaaacacc aaagaaatcg aggtcccgtg ctacgaaaat    36120
ggaaacggtg tcaccctgat tcttcttcag ggttggcggt atgttgatgg ttgccttaag    36180
ggctgtctca gttgtctgct caccgttatt ttgaaagctg ttgaagctca tcccgccacc    36240
cgagctgccg gcgtaggtgc tagctgcctg gaaggcgcct gaacaacac tcaagagcat     36300 agctccgcta aaacgctgcc agaagtggct gtcgaccgag cccggcaatc ctgagcgacc    36360
gagttcgtcc gcgcttggcg atgttaacga gatcatcgca tggtcaggtg tctcggcgcg    36420
atcccacaac acaaaaacgc gcccatctcc ctgttgcaag ccacgctgta tttcgccaac    36480
aacggtggtg ccacgatcaa gaagcacgat attgttcgtt gttccacgaa atcctgagg    36540 caagacacac tttacatagc ctgccaaatt tgtgtcgatt gcggtttgca agatgcacgg    36600
aattattgtc ccttgcgtta ccataaaatc ggggtgcggc aagagcgtgg cgctgctggg    36660
ctgcagctcg gtgggtttca tacgtatcga caaatcgttc tcgccggaca cttcgccatt    36720
cggcaaggag ttgtcgtcac gcttgccttc ttgtcttcgg cccgtgtcgc cctgaatggc    36780
gcgtttgctg acccctgat cgccgctgct atatgcaaaa atcggtgttt cttccggccg    36840
tggctcatgc cgctccggtt cgcccctcgg cggtagagga gcagcaggct gaacagcctc    36900
ttgaaccgct ggaggatccg gcggcacctc aatcggagct ggatgaaatg gcttggtgtt    36960
tgttgcgatc aaagttgacg gcgatgcgtt ctcattcacc ttcttttggc gcccacctag    37020
ccaaatgagg cttaatgata acgcgagaac gacacctccg acgatcaatt tctgagaccc    37080
cgaaagacgc cggcgatgtt tgtcggagac cagggatcca gatgcatcaa cctcatgtgc    37140
cgcttgctga ctatcgttat tcatcccttc gccccttca ggacgcgttt cacatcgggc      37200
ctcaccgtgc ccgtttgcgg cctttggcca acgggatcgt aagcggtgtt ccagatacat    37260
agtactgtgt ggccatccct cagacgccaa cctcgggaaa ccgaagaaat ctcgacatcg    37320
ctccctttaa ctgaatagtt ggcaacagct tccttgccat caggattgat ggtgtagatg    37380
gagggtatgc gtacattgcc cggaaagtgg aataccgtcg taaatccatt gtcgaagact    37440
tcgagtggca acagcgaacg atcgccttgg gcgacgtagt gccaattact gtccgccgca    37500
ccaagggctg tgacaggctg atccaataaa ttctcagctt tccgttgata ttgtgcttcc    37560
gcgtgtagtc tgtccacaac agccttctgt tgtgcctccc ttcgccgagc cgccgcatcg    37620
tcggcggggt aggcgaattg gacgctgtaa tagagatcgg gctgctcttt atcgaggtgg    37680
gacagagtct tggaacttat actgaaaaca taacggcgca tcccgagtc gcttgcggtt     37740 agcacgatta ctggctgagg cgtgaggacc tggcttgcct tgaaaaatag ataatttccc    37800
cgcggtaggg ctgctagatc tttgctattt gaaacggcaa ccgctgtcac cgtttcgttc    37860
gtggcgaatg ttacgaccaa agtagctcca accgccgtcg agaggcgcac cacttgatcg    37920
ggattgtaag ccaaataacg catgcgcgga tctagcttgc ccgccattgg agtgtcttca    37980
gcctccgcac cagtcgcagc ggcaaataaa catgctaaaa tgaaagtgc ttttctgatc     38040 atggttcgct gtggcctacg tttgaaacgg tatcttccga tgtctgatag gaggtgacaa    38100
ccagacctgc cgggttggtt agtctcaatc tgccgggcaa gctggtcacc ttttcgtagc    38160
gaactgtcgc ggtccacgta ctcaccacag gcattttgcc gtcaacgacg agggtccttt    38220
```

```
tatagcgaat tgctgcgtg cttggagtta catcatttga agcgatgtgc tcgacctcca    38280
ccctgccgcg tttgccaaga atgacttgag gcgaactggg attgggatag ttgaagaatt   38340
gctggtaatc ctggcgcact gttggggcac tgaagttcga taccaggtcg taggcgtact   38400
gagcggtgtc ggcatcataa ctctcgcgca ggcgaacgta ctcccacaat gaggcgttaa   38460
cgacggcctc ctcttgagtt gcaggcaatc gcgagacaga cacctcgctg tcaacggtgc   38520
cgtccggccg tatccataga tatacgggca caagcctgct caacggcacc attgtggcta   38580
tagcgaacgc ttgagcaaca tttcccaaaa tcgcgatagc tgcgacagct gcaatgagtt   38640
tggagagacg tcgcgccgat ttcgctcgcg cggtttgaaa ggcttctact tccttatagt   38700
gctcggcaag gctttcgcgc gccactagca tggcatattc aggccccgtc atagcgtcca   38760
cccgaattgc cgagctgaag atctgacgga gtaggctgcc atcgcccac attcagcggg    38820 aagatcgggc cttttgcagct cgctaatgtg tcgtttgtct ggcagccgct caaagcgaca   38880
actaggcaca gcaggcaata cttcatagaa ttctccattg aggcgaattt ttgcgcgacc   38940
tagcctcgct caacctgagc gaagcgacgg tacaagctgc tggcagattg ggttgcgccg   39000
ctccagtaac tgcctccaat gttgccgcg atcgccggca aagcgacaat gagcgcatcc    39060
cctgtcagaa aaacatatc gagttcgtaa agaccaatga tcttggccgc ggtcgtaccg    39120
gcgaaggtga ttacaccaag cataagggtg agcgcagtcg cttcggttag gatgacgatc   39180
gttgccacga ggtttaagag gagaagcaag agaccgtagg tgataagttg cccgatccac   39240
ttagctgcga tgtcccgcgt gcgatcaaaa atatatccga cgaggatcag aggcccgatc   39300
gcgagaagca ctttcgtgag aattccaacg gcgtcgtaaa ctccgaaggc agaccagagc   39360
gtgccgtaaa ggacccactg tgcccccttgg aaagcaagga tgtcctggtc gttcatcgga   39420
ccgatttcgg atgcgatttt ctgaaaaacg gcctgggtca cggcgaacat tgtatccaac   39480
tgtgccggaa cagtctgcag aggcaagccg gttacactaa actgctgaac aaagtttggg   39540
accgtctttt cgaagatgga aaccacatag tcttggtagt tagcctgccc aacaattaga   39600
gcaacaacga tggtgaccgt gatcacccga gtgataccgc tacgggtatc gacttcgccg   39660
cgtatgacta aaatacccctg aacaataatc caaagagtga cacaggcgat caatggcgca   39720
ctcaccgcct cctggatagt ctcaagcatc gagtccaagc ctgtcgtgaa ggctacatcg   39780
aagatcgtat gaatggccgt aaacggcgcc ggaatcgtga aattcatcga ttggacctga   39840
acttgactgg tttgtcgcat aatgttggat aaaatgagct cgcattcggc gaggatgcgg   39900
gcggatgaac aaaatcgccca gccttagggg agggcaccaa agatgacagc ggtctttga   39960 tgctcctgc gttgagcggc cgcctcttcc gcctcgtgaa ggccggcctg cgcggtagtc    40020
atcgttaata ggcttgtcgc ctgtacattt tgaatcattg cgtcatggat ctgcttgaga   40080
agcaaaccat tggtcacggt tgcctgcatg atattgcgag atcgggaaag ctgagcagac    40140
gtatcagcat tcgccgtcaa gcgtttgtcc atcgtttcca gattgtcagc cgcaatgcca   40200
gcgctgtttg cggaaccggt gatctgcgat cgcaacaggt ccgcttcagc atcactaccc   40260
acgactgcac gatctgtatc gctggtgatc gcacgtgccg tggtcgacat tggcattcgc    40320
ggcgaaaaca tttcattgtc taggtccttc gtcgaaggat actgattttt ctggttgagc    40380
gaagtcagta gtccagtaac gccgtaggcc gacgtcaaca tcgtaaccat cgctatagtc    40440
tgagtgagat tctccgcagt cgcgagcgca gtcgcgagcg tctcagcctc cgttgccggg   40500
tcgctaacaa caaactgcgc ccgcgcgggc tgaatatata gaaagctgca ggtcaaaact   40560
gttgcaataa gttgcgtcgt cttcatcgtt tcctaccttta tcaatcttct gcctcgtggt   40620
```

```
gacgggccat gaattcgctg agccagccag atgagttgcc ttcttgtgcc tcgcgtagtc   40680
gagttgcaaa gcgcaccgtg ttggcacgcc ccgaaagcac ggcgacatat tcacgcatat   40740
cccgcagatc aaattcgcag atgacgcttc cactttctcg tttaagaaga aacttacggc   40800
tgccgaccgt catgtcttca cggatcgcct gaaattcctt ttcggtacat ttcagtccat   40860
cgacataagc cgatcgatct gcggttggtg atggatagaa aatcttcgtc atacattgcg   40920
caaccaagct ggctcctagc ggcgattcca gaacatgctc tggttgctgc gttgccagta   40980
ttagcatccc gttgtttttt cgaacggtca ggaggaattt gtcgacgaca gtcgaaaatt   41040
tagggtttaa caaataggcg cgaaactcat cgcagctcat cacaaaacgg cggccgtcga   41100
tcatggctcc aatccgatgc aggagatatg ctgcagcggg agcgcatact tcctcgtatt   41160
cgagaagatg cgtcatgtcg aagccggtaa tcgacggatc taactttact tcgtcaactt   41220
cgccgtcaaa tgcccagcca agcgcatggc cccggcacca gcgttggagc cgcgctcctg   41280
cgccttcggc gggcccatgc aacaaaaatt cacgtaaccc cgcgattgaa cgcatttgtg   41340
gatcaaacga gagctgacga tggataccac ggaccagacg gcggttctct tccggagaaa   41400
tcccaccccg accatcactc tcgatgagag ccacgatcca ttcgcgcaga aaatcgtgtg   41460
aggctgctgt gttttctagg ccacgcaacg gcgccaaccc gctgggtgtg cctctgtgaa   41520
gtgccaaata tgttcctcct gtggcgcgaa ccagcaattc gccacccggg tccttgtcaa   41580
agaacacgac cgtacctgca cggtcgacca tgctctgttc gagcatggct agaacaaaca   41640
tcatgagcgt cgtcttaccc ctcccgatag gcccgaatat tgccgtcatg ccaacatcgt   41700
gctcatgcgg gatatagtcg aaaggcgttc cgccattggt acgaaatcgg gcaatcgcgt   41760
tgccccagtg gcctgagctg gcgccctctg gaaagttttc gaaagagaca acccctgcga   41820
aattgcgtga agtgattgcg ccagggcgtg tgcgccactt aaaattcccc ggcaattggg   41880
accaataggc cgcttccata ccaataccttt cttggacaac cacggcacct gcatccgcca   41940
ttcgtgtccg agcccgcgcg cccctgtccc caagactatt gagatcgtct gcatagacgc   42000
aaaggctcaa atgatgtgag cccataacga attcgttgct cgcaagtgcg tcctcagcct   42060
cggataattt gccgatttga gtcacggctt tatcgccgga actcagcatc tggctcgatt   42120
tgaggctaag tttcgcgtgc gcttgcgggc gagtcaggaa cgaaaaactc tgcgtgagaa   42180
caagtggaaa atcgagggat agcagcgcgt tgagcatgcc cggccgtgtt tttgcagggt   42240
attcgcgaaa cgaatagatg gatccaacgt aactgtcttt tggcgttctg atctcgagtc   42300
ctcgcttgcc gcaaatgact ctgtcggtat aaatcgaagc gccgagtgag ccgctgacga   42360
ccggaaccgg tgtgaaccga ccagtcatga tcaaccgtag cgcttcgcca atttcggtga   42420
agagcacacc ctgcttctcg cggatgccaa gacgatgcag gccatacgct ttaagagagc   42480
cagcgacaac atgccaaaga tcttccatgt tcctgatctg gcccgtgaga tcgtttttccc   42540 tttttccgct tagcttggtg aacctcctct ttaccttccc taaagccgcc tgtgggtaga   42600
caatcaacgt aaggaagtgt tcattgcgga ggagttggcc ggagagcacg cgctgttcaa   42660
aagcttcgtt caggctagcg gcgaaaacac tacggaagtg tcgcggcgcc gatgatggca   42720
cgtcggcatg acgtacgagg tgagcatata ttgacacatg atcatcagcg atattgcgca   42780
acagcgtgtt gaacgcacga caacgcgcat tgcgcatttc agtttcctca agctcgaatg   42840
caacgccatc aattctcgca atggtcatga tcgatccgtc ttcaagaagg acgatatggt   42900
cgctgaggtg gccaatataa gggagataga tctcaccgga tctttcggtc gttccactcg   42960
cgccgagcat cacaccattc ctctccctcg tgggggaacc ctaattggat ttgggctaac   43020
```

```
agtagcgccc ccccaaactg cactatcaat gcttcttccc gcggtccgca aaaatagcag   43080
gacgacgctc gccgcattgt agtctcgctc cacgatgagc cgggctgcaa accataacgg   43140
cacgagaacg acttcgtaga gcgggttctg aacgataacg atgacaaagc cggcgaacat   43200
catgaataac cctgccaatg tcagtggcac cccaagaaac aatgcgggcc gtgtggctgc   43260
gaggtaaagg gtcgattctt ccaaacgatc agccatcaac taccgccagt gagcgtttgg   43320
ccgaggaagc tcgccccaaa catgataaca atgccgccga cgacgccggc aaccagccca   43380
agcgaagccc gcccgaacat ccaggagatc ccgatagcga caatgccgag aacagcgagt   43440
gactggccga acggaccaag gataaacgtg catatattgt taaccattgt ggcggggtca   43500
gtgccgccac ccgcagattg cgctgcggcg ggtccggatg aggaaatgct ccatgcaatt   43560
gcaccgcaca agcttggggc gcagctcgat atcacgcgca tcatcgcatt cgagagcgag   43620
aggcgattta gatgtaaacg gtatctctca aagcatcgca tcaatgcgca cctccttagt   43680
ataagtcgaa taagacttga ttgtcgtctg cggatttgcc gttgtcctgg tgtggcggtg   43740
gcggagcgat taaccgcca gcgccatcct cctgcgagcg gcgctgatat gaccccaaa     43800
catcccacgt ctcttcggat tttagcgcct cgtgatcgtc ttttggaggc tcgattaacg   43860
cgggcaccag cgattgagca gctgtttcaa cttttcgcac gtagccgttt gcaaaaccgc   43920
cgatgaaatt accggtgttg taagcggaga tcgcccgacg aagcgcaaat tgcttctcgt   43980
caatcgtttc gccgcctgca taacgacttt tcagcatgtt tgcagcggca gataatgatg   44040
tgcacgcctg gagcgcaccg tcaggtgtca gaccgagcat agaaaaattt cgagagttta   44100
tttgcatgag gccaacatcc agcgaatgcc gtgcatcgag acggtgcctg acgacttggg   44160
ttgcttggct gtgatcttgc cagtgaagcg tttcgccggt cgtgttgtca tgaatcgcta   44220
aaggatcaaa gcgactctcc accttagcta tcgccgcaag cgtagatgtc gcaactgatg   44280
gggcacactt gcgagcaaca tggtcaaact cagcagatga gagtggcgtg gcaaggctcg   44340
acgaacagaa ggagaccatc aaggcaagag aaagcgaccc cgatctctta agcatacctt   44400
atctccttag ctcgcaacta acaccgcctc tcccgttgga agaagtgcgt tgttttatgt   44460
tgaagattat cgggagggtc ggttactcga aaattttcaa ttgcttcttt atgatttcaa   44520
ttgaagcgag aaacctcgcc cggcgtcttg gaacgcaaca tggaccgaga accgcgcatc   44580
catgactaag caaccggatc gacctattca ggccgcagtt ggtcaggtca ggctcagaac   44640
gaaaatgctc ggcgaggtta cgctgtctgt aaacccattc gatgaacggg aagcttcctt   44700
ccgattgctc ttggcaggaa tattggccca tgcctgcttg cgcttt gcaa atgctcttat   44760
cgcgttggta tcatatgcct tgtccgccag cagaaacgca ctctaagcga ttatttgtaa   44820
aaatgtttcg gtcatgcggc ggtcatgggc ttgacccgct gtcagcgcaa gacggatcgg   44880
tcaaccgtcg gcatcgacaa cagcgtgaat cttggtggtc aaaccgccac gggaacgtcc   44940
catacagcca tcgtcttgat cccgcтgтттт cccgtcgccg catgttggtg gacgcggaca   45000
caggaactgt caatcatgac gacaтттстат cgaaagcctt ggaaatcaca ctcagaatat   45060
gatcccagac gtctgcctca cgccatcgta caaagcgatt gtagcaggtt gtacaggaac   45120
cgtatcgatc aggaacgtct gcccagggcg ggcccgtccg gaagcgccac aagatgacat   45180
tgatcacccg cgtcaacgcg cggcacgcga cgcggcttat tgggaacaa aggactgaac   45240
aacagtccat tcgaaatcgg tgacatcaaa gcggggacgg tttatcagtg gcctccaagt   45300
caagcctcaa tgaatcaaaa tcagaccgat ttgcaaacct gaттттaтgag tgtgcggcct   45360
aaatgatgaa atcgtccttc tagatcgcct ccgtggtgta gcaacacctc gcagtatcgc   45420
```

```
cgtgctgacc ttggccaggg aattgactgg caagggtgct ttcacatgac cgctcttttg   45480
gccgcgatag atgatttcgt tgctgctttg ggcacgtaga aggagagaag tcatatcgga   45540
gaaattcctc ctggcgcgag agcctgctct atcgcgacgg catcccactg tcgggaacag   45600
accggatcat tcacgaggcg aaagtcgtca acacatgcgt tataggcatc ttcccttgaa   45660
ggatgatctt gttgctgcca atctggaggt gcggcagccg caggcagatg cgatctcagc   45720
gcaacttgcg gcaaaacatc tcactcacct gaaaaccact agcgagtctc gcgatcagac   45780
gaaggccttt tacttaacga cacaatatcc gatgtctgca tcacaggcgt cgctatccca   45840
gtcaatacta aagcggtgca ggaactaaag attactgatg acttaggcgt gccacgaggc   45900
ctgagacgac gcgcgtagac agttttttga aatcattatc aaagtgatgg cctccgctga   45960
agcctatcac ctctgcgccg gtctgtcgga gagatgggca agcattatta cggtcttcgc   46020
gcccgtacat gcattggacg attgcagggt caatggatct gagatcatcc agaggattgc   46080
cgcccttacc ttccgtttcg agttggagcc agcccctaaa tgagacgaca tagtcgactt   46140
gatgtgacaa tgccaagaga gagatttgct taacccgatt ttttgctca agcgtaagcc   46200 tattgaagct tgccggcatg acgtccgcgc cgaaagaata tcctacaagt aaaacattct   46260
gcacaccgaa atgcttggtg tagacatcga ttatgtgacc aagatcctta gcagtttcgc   46320
ttggggaccg ctccgaccag aaataccgaa gtgaactgac gccaatgaca ggaatccctt   46380
ccgtctgcag ataggtacca tcgatagatc tgctgcctcg cgcgtttcgg tgatgacggt   46440
gaaaacctct gacacatgca gctcccggag acggtcacag cttgtctgta agcggatgcc   46500
gggagcagac aagcccgtca gggcgcgtca gcgggtgttg gcgggtgtcg gggcgcagcc   46560
atgacccagt cacgtagcga tagcggagtg tatactggct taactatgcg gcatcagagc   46620
agattgtact gagagtgcac catatgcggt gtgaaatacc gcacagatgc gtaaggagaa   46680
aataccgcat caggcgctct tccgcttcct cgctcactga ctcgctgcgc tcggtcgttc   46740
ggctgcggcg agcggtatca gctcactcaa aggcggtaat acggttatcc acagaatcag   46800
gggataacgc aggaaagaac atgtgagcaa aaggccagca aaaggccagg aaccgtaaaa   46860
aggccgcgtt gctggcgttt ttccataggc tccgcccccc tgacgagcat cacaaaaatc   46920
gacgctcaag tcagaggtgg cgaaacccga caggactata aagataccag gcgtttcccc   46980
ctggaagctc cctcgtgcgc tctcctgttc cgaccctgcc gcttaccgga tacctgtccg   47040
cctttctccc ttcgggaagc gtggcgcttt ctcatagctc acgctgtagg tatctcagtt   47100
cggtgtaggt cgttcgctcc aagctgggct gtgtgcacga accccccgtt cagcccgacc   47160
gctgcgcctt atccggtaac tatcgtcttg agtccaaccc ggtaagacac gacttatcgc   47220
cactggcagc agccactggt aacaggatta gcagagcgag gtatgtaggc ggtgctacag   47280
agttcttgaa gtggtggcct aactacggct acactagaag gacagtattt ggtatctgcg   47340
ctctgctgaa gccagttacc ttcggaaaaa gagttggtag ctcttgatcc ggcaaacaaa   47400
ccaccgctgg tagcggtggt ttttttgttt gcaagcagca gattacgcgc agaaaaaaag   47460
gatctcaaga agatcctttg atcttttcta cggggtctga cgctcagtgg aacgaaaact   47520
cacgttaagg gattttggtc atgagattat caaaaaggat cttcacctag atccttttaa   47580
attaaaaatg aagttttaaa tcaatctaaa gtatatatga gtaaacttgg tctgacagtt   47640
accaatgctt aatcagtgag gcacctatct cagcgatctg tctatttcgt tcatccatag   47700
ttgcctgact ccccgtcgtg tagataacta cgatacggga gggcttacca tctgccccca   47760
gtgctgcaat gataccgcga gacccacgct caccggctcc agatttatca gcaataaacc   47820
```

-continued

```
agccagccgg aagggccgag cgcagaagtg gtcctgcaac tttatccgcc tccatccagt    47880
ctattaattg ttgccgggaa gctagagtaa gtagttcgcc agttaatagt ttgcgcaacg    47940
ttgttgccat tgctgcaggg gggggggggg gggggacttc ccattgttca ttccacggac    48000
aaaaacagag aaaggaaacg acagaggcca aaaagcctcg ctttcagcac ctgtcgtttc    48060
ctttcttttc agagggtatt ttaaataaaa acattaagtt atgacgaaga gaacgaaa      48120
cgccttaaac cggaaaattt tcataaatag cgaaaacccg cgaggtcgcc gccccgtagt    48180
cggatcaccg gaaaggaccc gtaaagtgat aatgattatc atctacatat cacaacgtgc    48240
gtggaggcca tcaaaccacg tcaaataatc aattatgacg caggtatcgt attaattgat    48300
ctgcatcaac ttaacgtaaa aacaacttca gacaatacaa atcagcgaca ctgaatacgg    48360
ggcaacctca tgtccccccc cccccccccc ctgcaggcat cgtggtgtca cgctcgtcgt    48420
ttggtatggc ttcattcagc tccggttccc aacgatcaag gcgagttaca tgatccccca    48480
tgttgtgcaa aaaagcggtt agctccttcg gtcctccgat cgttgtcaga agtaagttgg    48540
ccgcagtgtt atcactcatg gttatggcag cactgcataa ttctcttact gtcatgccat    48600
ccgtaagatg cttttctgtg actggtgagt actcaaccaa gtcattctga aatagtgta     48660
tgcggcgacc gagttgctct tgcccggcgt caacacggga taataccgcg ccacatagca    48720
gaactttaaa agtgctcatc attggaaaac gttcttcggg gcgaaaactc tcaaggatct    48780
taccgctgtt gagatccagt tcgatgtaac ccactcgtgc acccaactga tcttcagcat    48840
cttttacttt caccagcgtt tctgggtgag caaaaacagg aaggcaaaat gccgcaaaaa    48900
agggaataag ggcgacacgg aaatgttgaa tactcatact cttcctttt caatattatt     48960
gaagcattta tcagggttat tgtctcatga gcggatacat atttgaatgt atttagaaaa    49020
ataaacaaat aggggttccg cgcacatttc cccgaaaagt gccacctgac gtctaagaaa    49080
ccattattat catgacatta acctataaaa ataggcgtat cacgaggccc tttcgtcttc    49140
aagaattggt cgacgatctt gctgcgttcg gatattttcg tggagttccc gccacagacc    49200
cggattgaag gcgagatcca gcaactcgcg ccagatcatc ctgtgacgga actttggcgc    49260
gtgatgactg gccaggacgt cggccgaaag agcgacaagc agatcacgct tttcgacagc    49320
gtcggatttg cgatcgagga ttttttcggcg ctgcgctacg tccgcgaccg cgttgaggga    49380
tcaagccaca gcagcccact cgaccttcta gccgacccag acgagccaag ggatcttttt    49440
ggaatgctgc tccgtcgtca ggcttttccga cgtttgggtg gttgaacaga agtcattatc    49500
gtacggaatg ccaagcactc ccgaggggaa ccctgtggtt ggcatgcaca tacaaatgga    49560
cgaacggata aacctttca cgccctttta aatatccgtt attctaataa acgctctttt    49620
ctcttaggtt tacccgccaa tatatcctgt caaacactga tagtttaaac tgaaggcggg    49680
aaacgacaat ctgatcatga gcggagaatt aagggagtca cgttatgacc cccgccgatg    49740
acgcgggaca agccgtttta cgtttggaac tgacagaacc gcaacgttga aggagccact    49800
cagcaagctg gtacgattgt aatacgactc actatagggc gaattgagcg ctgtttaaac    49860
gctcttcaac tggaagagcg gttacccgga ccgaagcttg catgcctgca g              49911
```

<210> SEQ ID NO 7
<211> LENGTH: 36909
<212> TYPE: DNA
<213> ORGANISM: Artificial Sequence
<220> FEATURE:
<223> OTHER INFORMATION: PHP10523 construct

<400> SEQUENCE: 7

```
tctagagctc gttcctcgag gcctcgaggc ctcgaggaac ggtacctgcg gggaagctta      60
caataatgtg tgttgttaag tcttgttgcc tgtcatcgtc tgactgactt tcgtcataaa     120
tcccggcctc cgtaacccag ctttgggcaa gctcacggat ttgatccggc ggaacgggaa     180
tatcgagatg ccgggctgaa cgctgcagtt ccagctttcc ctttcgggac aggtactcca     240
gctgattgat tatctgctga agggtcttgg ttccacctcc tggcacaatg cgaatgatta     300
cttgagcgcg atcgggcatc caattttctc ccgtcaggtg cgtggtcaag tgctacaagg     360
caccttcag taacgagcga ccgtcgatcc gtcgccggga tacggacaaa atggagcgca     420
gtagtccatc gagggcggcg aaagcctcgc caaaagcaat acgttcatct cgcacagcct     480
ccagatccga tcgagggtct tcggcgtagg cagatagaag catggataca ttgcttgaga     540
gtattccgat ggactgaagt atggcttcca tcttttctcg tgtgtctgca tctatttcga     600
gaaagccccc gatgcggcgc accgcaacgc gaattgccat actatccgaa agtcccagca     660
ggcgcgcttg ataggaaaag gtttcatact cggccgatcg cagacgggca ctcacgacct     720
tgaacccttc aactttcagg gatcgatgct ggttgatggt agtctcactc gacgtggctc     780
tggtgtgttt tgacatagct tcctccaaag aaagcggaag gtctggatac tccagcacga     840
aatgtgcccg ggtagacgga tggaagtcta gccctgctca atatgaaatc aacagtacat     900
ttacagtcaa tactgaatat acttgctaca tttgcaattg tcttataacg aatgtgaaat     960
aaaaatagtg taacaacgct tttactcatc gataatcaca aaaacattta tacgaacaaa    1020
aatacaaatg cactccggtt tcacaggata ggcgggatca gaatatgcaa cttttgacgt    1080
tttgttcttt caaggggggt gctggcaaaa ccaccgcact catgggcctt tgcgctgctt    1140
tggcaaatga cggtaaacga gtggccctct ttgatgccga cgaaaaccgg cctctgacgc    1200
gatggagaga aaacgcccta caaagcagta ctgggatcct cgctgtgaag tctattccgc    1260
cgacgaaatg cccccttctt gaagcagcct atgaaaatgcc gagctcgaag gatttgatta    1320
tgcgttggcc gatacgcgtg gcggctcgag cgagctcaac aacacaatca tcgctagctc    1380
aaacctgctt ctgatcccca ccatgctaac gccgctcgac atcgatgagg cactatctac    1440
ctaccgctac gtcatcgagc tgctgttgag tgaaaatttg gcaattccta cagctgtttt    1500
gcgccaacgc gtcccggtcg gccgattgac aacatcgcaa cgcaggatgt cagagacgct    1560
agagagcctt ccagttgtac cgtctcccat gcatgaaaga gatgcatttg ccgcgatgaa    1620
agaacgcggc atgttgcatc ttacattact aaacacggga actgatccga cgatgcgcct    1680
catagagagg aatcttcgga ttgcgatgga ggaagtcgtg gtcatttcga aactgatcag    1740
caaaatcttg gaggcttgaa gatggcaatt cgcaagcccg cattgtcggt cggcgaagca    1800
cggcggcttg ctggtgctcg acccgagatc caccatccca acccgacact tgttccccag    1860
aagctggacc tccagcactt gcctgaaaaa gccgacgaga aagaccagca acgtgagcct    1920
ctcgtcgccg atcacattta cagtcccgat cgacaactta agctaactgt ggatgccctt    1980
agtccacctc cgtccccgaa aaagctccag gtttttcttt cagcgcgacc gcccgcgcct    2040
caagtgtcga aaacatatga caacctcgtt cggcaataca gtccctcgaa gtcgctacaa    2100
atgatttta a ggcgcgcgtt ggacgatttc gaaagcatgc tggcagatgg atcatttcgc    2160
gtggcccga aaagttatcc gatcccttca actacagaaa aatccgttct cgttcagacc    2220
tcacgcatgt tcccggttgc gttgctcgag gtcgctcgaa gtcattttga tccgttgggg    2280
ttggagaccg ctcgagcttt cggccacaag ctggctaccg ccgcgctcgc gtcattcttt    2340
gctggagaga agccatcgag caattggtga agagggacct atcggaaccc ctcaccaaat    2400
```

```
attgagtgta ggtttgaggc cgctggccgc gtcctcagtc accttttgag ccagataatt    2460
aagagccaaa tgcaattggc tcaggctgcc atcgtcccccc cgtgcgaaac ctgcacgtcc    2520
gcgtcaaaga aataaccggc acctcttgct gtttttatca gttgagggct tgacggatcc    2580
gcctcaagtt tgcggcgcag ccgcaaaatg agaacatcta tactcctgtc gtaaacctcc    2640
tcgtcgcgta ctcgactggc aatgagaagt tgctcgcgcg atagaacgtc gcggggtttc    2700
tctaaaaacg cgaggagaag attgaactca cctgccgtaa gtttcacctc accgccagct    2760
tcggacatca agcgacgttg cctgagatta agtgtccagt cagtaaaaca aaaagaccgt    2820
cggtctttgg agcggacaac gttggggcgc acgcgcaagg caacccgaat gcgtgcaaga    2880
aactctctcg tactaaacgg cttagcgata aaatcacttg ctcctagctc gagtgcaaca    2940
actttatccg tctcctcaag gcggtcgcca ctgataatta tgattggaat atcagacttt    3000
gccgccagat ttcgaacgat ctcaagccca tcttcacgac ctaaatttag atcaacaacc    3060
acgacatcga ccgtcgcgga agagagtact ctagtgaact gggtgctgtc ggctaccgcg    3120
gtcactttga aggcgtggat cgtaaggtat tcgataataa gatgccgcat agcgacatcg    3180
tcatcgataa aagaacgtg tttcaacggc tcaccttttca atctaaaatc tgaacccttg    3240
ttcacagcgc ttgagaaatt ttcacgtgaa ggatgtacaa tcatctccag ctaaatgggc    3300
agttcgtcag aattgcggct gaccgcggat gacgaaaatg cgaaccaagt atttcaattt    3360
tatgacaaaa gttctcaatc gttgttacaa gtgaaacgct tcgaggttac agctactatt    3420
gattaaggag atcgcctatg gtctcgcccc ggcgtcgtgc gtccgccgcg agccagatct    3480
cgcctacttc ataaacgtcc tcataggcac ggaatggaat gatgacatcg atcgccgtag    3540
agagcatgtc aatcagtgtg cgatcttcca agctagcacc ttgggcgcta cttttgacaa    3600
gggaaaacag tttcttgaat ccttggattg gattcgcgcc gtgtattgtt gaaatcgatc    3660
ccggatgtcc cgagacgact tcactcagat aagcccatgc tgcatcgtcg cgcatctcgc    3720
caagcaatat ccggtccggc cgcatacgca gacttgcttg gagcaagtgc tcggcgctca    3780
cagcacccag cccagcaccg ttcttggagt agagtagtct aacatgatta tcgtgtggaa    3840
tgacgagttc gagcgtatct tctatggtga ttagccttc ctggggggg atggcgctga    3900 tcaaggtctt gctcattgtt gtcttgccgc ttccggtagg gccacatagc aacatcgtca    3960
gtcggctgac gacgcatgcg tgcagaaacg cttccaaatc cccgttgtca aaatgctgaa    4020
ggatagcttc atcatcctga ttttggcgtt tccttcgtgt ctgccactgg ttccacctcg    4080
aagcatcata acgggaggag acttcttaa gaccagaaac acgcgagctt ggccgtcgaa    4140
tggtcaagct gacggtgccc gagggaacgg tcggcggcag acagatttgt agtcgttcac    4200
caccaggaag ttcagtggcg cagaggggggt tacgtggtcc gacatcctgc tttctcagcg    4260
cgcccgctaa aatagcgata tcttcaagat catcataaga gacgggcaaa ggcatcttgg    4320
taaaaatgcc ggcttggcgc acaaatgcct ctccaggtcg attgatcgca atttcttcag    4380
tcttcgggtc atcgagccat tccaaaatcg gcttcagaag aaagcgtagt tgcggatcca    4440 cttccatta caatgtatcc tatctctaag cggaaatttg aattcattaa gagcggcggt    4500
tcctcccccg cgtggcgccg ccagtcaggc ggagctggta acaccaaaag aaatcgaggt    4560
cccgtgctac gaaaatggaa acggtgtcac cctgattctt cttcagggtt ggcggtatgt    4620
tgatggttgc cttaagggct gtctcagttg tctgctcacc gttatttttga aagctgttga    4680 agctcatccc gccacccgag ctgccggcgt aggtgctagc tgcctggaag cgccttgaa    4740 caacactcaa gagcatagct ccgctaaaac gctgccagaa gtggctgtcg accgagcccg    4800
```

```
gcaatcctga gcgaccgagt tcgtccgcgc ttggcgatgt taacgagatc atcgcatggt    4860
caggtgtctc ggcgcgatcc cacaacacaa aaacgcgccc atctccctgt tgcaagccac    4920
gctgtatttc gccaacaacg gtggtgccac gatcaagaag cacgatattg ttcgttgttc    4980
cacgaatatc ctgaggcaag acacacttta catagcctgc caaatttgtg tcgattgcgg    5040
tttgcaagat gcacggaatt attgtccctt gcgttaccat aaaatcgggg tgcggcaaga    5100
gcgtggcgct gctgggctgc agctcggtgg gtttcatacg tatcgacaaa tcgttctcgc    5160
cggacacttc gccattcggc aaggagttgt cgtcacgctt gccttcttgt cttcggcccg    5220
tgtcgccctg aatggcgcgt ttgctgaccc cttgatcgcc gctgctatat gcaaaaatcg    5280
gtgtttcttc cggccgtggc tcatgccgct ccggttcgcc cctcggcggt agaggagcag    5340
caggctgaac agcctcttga accgctggag gatccggcgg cacctcaatc ggagctggat    5400
gaaatggctt ggtgtttgtt gcgatcaaag ttgacggcga tgcgttctca ttcaccttct    5460
tttggcgccc acctagccaa atgaggctta atgataacgc gagaacgaca cctccgacga    5520
tcaatttctg agaccccgaa agacgccggc gatgtttgtc ggagaccagg gatccagatg    5580
catcaaccta atgtgccgct tgctgactat cgttattcat cccttcgccc ccttcaggac    5640
gcgtttcaca tcgggcctca ccgtgcccgt ttgcggcctt tggccaacgg gatcgtaagc    5700
ggtgttccag atacatagta ctgtgtggcc atccctcaga cgccaacctc gggaaaccga    5760
agaaatctcg acatcgctcc ctttaactga atagttggca acagcttcct tgccatcagg    5820
attgatggtg tagatggagg gtatgcgtac attgcccgga aagtggaata ccgtcgtaaa    5880
tccattgtcg aagacttcga gtggcaacag cgaacgatcg ccttgggcga cgtagtgcca    5940
attactgtcc gccgcaccaa gggctgtgac aggctgatcc aataaattct cagcttttccg    6000 ttgatattgt gcttccgcgt gtagtctgtc cacaacagcc ttctgttgtg cctccctcg    6060 ccgagccgcc gcatcgtcgg cggggtaggc gaattggacg ctgtaataga gatcgggctg    6120
ctctttatcg aggtgggaca gagtcttgga acttatactg aaaacataac ggcgcatccc    6180
ggagtcgctt gcggttagca cgattactgg ctgaggcgtg aggacctggc ttgccttgaa    6240
aaatagataa tttccccgcg gtagggctgc tagatctttg ctatttgaaa cggcaaccgc    6300
tgtcaccgtt tcgttcgtgg cgaatgttac gaccaaagta gctccaaccg ccgtcgagag    6360
gcgcaccact tgatcgggat tgtaagccaa ataacgcatg cgcggatcta gcttgcccgc    6420
cattggagtg tcttcagcct ccgcaccagt cgcagcggca aataaacatg ctaaaatgaa    6480
aagtgctttt ctgatcatgg ttcgctgtgg cctacgtttg aaacggtatc ttccgatgtc    6540
tgataggagg tgacaaccag acctgccggg ttggttagtc tcaatctgcc gggcaagctg    6600 gtcaccttt cgtagcgaac tgtcgcggtc cacgtactca ccacaggcat tttgccgtca    6660
acgacgaggg tccttttata gcgaatttgc tgcgtgcttg gagttacatc atttgaagcg    6720
atgtgctcga cctccaccct gccgcgtttg ccaagaatga cttgaggcga actgggattg    6780
ggatagttga agaattgctg gtaatcctgg cgcactgttg gggcactgaa gttcgatacc    6840
aggtcgtagg cgtactgagc ggtgtcggca tcataactct cgcgcaggcg aacgtactcc    6900
cacaatgagg cgttaacgac ggcctcctct tgagttgcag gcaatcgcga gacagacacc    6960
tcgctgtcaa cggtgccgtc cggccgtatc catagatata cgggcacaag cctgctcaac    7020
ggcaccattg tggctatagc gaacgcttga gcaacatttc ccaaaatcgc gatagctgcg    7080
acagctgcaa tgagtttgga gagacgtcgc gccgatttcg ctcgcgcggt ttgaaaggct    7140
tctacttcct tatagtgctc ggcaaggctt tcgcgcgcca ctagcatggc atattcaggc    7200
```

```
cccgtcatag cgtccacccg aattgccgag ctgaagatct gacggagtag gctgccatcg    7260
ccccacattc agcgggaaga tcgggccttt gcagctcgct aatgtgtcgt ttgtctggca    7320
gccgctcaaa gcgacaacta ggcacagcag gcaatacttc atagaattct ccattgaggc    7380
gaatttttgc gcgacctagc ctcgctcaac ctgagcgaag cgacggtaca agctgctggc    7440
agattgggtt gcgccgctcc agtaactgcc tccaatgttg ccggcgatcg ccggcaaagc    7500
gacaatgagc gcatcccctg tcagaaaaaa catatcgagt tcgtaaagac caatgatctt    7560
ggccgcggtc gtaccggcga aggtgattac accaagcata agggtgagcg cagtcgcttc    7620
ggttaggatg acgatcgttg ccacgaggtt taagaggaga agcaagagac cgtaggtgat    7680
aagttgcccg atccacttag ctgcgatgtc ccgcgtgcga tcaaaatat atccgacgag     7740
gatcagaggc ccgatcgcga aagcacttt cgtgagaatt ccaacggcgt cgtaaactcc     7800
gaaggcagac cagagcgtgc cgtaaaggac ccactgtgcc ccttggaaag caaggatgtc    7860
ctggtcgttc atcggaccga tttcggatgc gattttctga aaaacggcct gggtcacggc    7920
gaacattgta tccaactgtg ccggaacagt ctgcagaggc aagccggtta cactaaactg    7980
ctgaacaaag tttgggaccg tcttttcgaa gatggaaacc acatagtctt ggtagttagc    8040
ctgcccaaca attagagcaa caacgatggt gaccgtgatc acccgagtga taccgctacg    8100
ggtatcgact tcgccgcgta tgactaaaat accctgaaca ataatccaaa gagtgacaca    8160
ggcgatcaat ggcgcactca ccgcctcctg gatagtctca agcatcgagt ccaagcctgt    8220
cgtgaaggct acatcgaaga tcgtatgaat ggccgtaaac ggcgccggaa tcgtgaaatt    8280
catcgattgg acctgaactt gactggtttg tcgcataatg ttggataaaa tgagctcgca    8340
ttcggcgagg atgcgggcgg atgaacaaat cgcccagcct taggggaggg caccaaagat    8400
gacagcggtc ttttgatgct ccttgcgttg agcggccgcc tcttccgcct cgtgaaggcc    8460
ggcctgcgcg gtagtcatcg ttaataggct tgtcgcctgt acattttgaa tcattgcgtc    8520
atggatctgc ttgagaagca aaccattggt cacggttgcc tgcatgatat tgcgagatcg    8580
ggaaagctga gcagacgtat cagcattcgc cgtcaagcgt ttgtccatcg tttccagatt    8640
gtcagccgca atgccagcgc tgtttgcgga accggtgatc tgcgatcgca acaggtccgc    8700
ttcagcatca ctacccacga ctgcacgatc tgtatcgctg gtgatcgcac gtgccgtggt    8760
cgacattggc attcgcggcg aaaacatttc attgtctagg tccttcgtcg aaggatactg    8820
attttctggt tgagcgaagt cagtagtcc agtaacgccg taggccgacg tcaacatcgt    8880
aaccatcgct atagtctgag tgagattctc cgcagtcgcg agcgcagtcg cgagcgtctc    8940
agcctccgtt gccgggtcgc taacaacaaa ctgcgcccgc gcgggctgaa tatatagaaa    9000
gctgcaggtc aaaactgttg caataagttg cgtcgtcttc atcgtttcct accttatcaa    9060
tcttctgcct cgtggtgacg ggccatgaat tcgctgagcc agccagatga gttgccttct    9120
tgtgcctcgc gtagtcgagt tgcaaagcgc accgtgttgg cacgcccga aagcacggcg     9180
acatattcac gcatatcccg cagatcaaat tcgcagatga cgcttccact ttctcgttta    9240
agaagaaact tacggctgcc gaccgtcatg tcttcacgga tcgcctgaaa ttccttttcg    9300
gtacatttca gtccatcgac ataagccgat cgatctgcgg ttggtgatgg atagaaaatc    9360
ttcgtcatac attgcgcaac caagctggct cctagcggcg attccagaac atgctctggt    9420
tgctgcgttg ccagtattag catcccgttg ttttttcgaa cggtcaggag gaatttgtcg    9480
acgacagtcg aaaatttagg gtttaacaaa taggcgcgaa actcatcgca gctcatcaca    9540
aaacggcggc cgtcgatcat ggctccaatc cgatgcagga gatatgctgc agcggagcg    9600
```

```
catacttcct cgtattcgag aagatgcgtc atgtcgaagc cggtaatcga cggatctaac    9660
tttacttcgt caacttcgcc gtcaaatgcc cagccaagcg catggcccg gcaccagcgt     9720
tggagccgcg ctcctgcgcc ttcggcgggc ccatgcaaca aaaattcacg taaccccgcg    9780
attgaacgca tttgtggatc aaacgagagc tgacgatgga taccacggac cagacggcgg   9840
ttctcttccg gagaaatccc accccgacca tcactctcga tgagagccac gatccattcg    9900
cgcagaaaat cgtgtgaggc tgctgtgttt tctaggccac gcaacggcgc caacccgctg    9960
ggtgtgcctc tgtgaagtgc caaatatgtt cctcctgtgg cgcgaaccag caattcgcca   10020
ccccggtcct tgtcaaagaa cacgaccgta cctgcacggt cgaccatgct ctgttcgagc   10080
atggctagaa caaacatcat gagcgtcgtc ttaccctcc cgataggccc gaatattgcc     10140
gtcatgccaa catcgtgctc atgcgggata tagtcgaaag gcgttccgcc attggtacga   10200
aatcgggcaa tcgcgttgcc ccagtggcct gagctggcgc cctctggaaa gttttcgaaa   10260
gagacaaacc ctgcgaaatt gcgtgaagtg attgcgccag gcgtgtgcg ccacttaaaa     10320
ttccccggca attgggacca ataggccgct tccataccaa taccttcttg gacaaccacg   10380
gcacctgcat ccgccattcg tgtccgagcc gcgcgcccc tgtccccaag actattgaga      10440
tcgtctgcat agacgcaaag gctcaaatga tgtgagccca taacgaattc gttgctcgca   10500
agtgcgtcct cagcctcgga taatttgccg atttgagtca cggctttatc gccgaactc     10560
agcatctggc tcgatttgag gctaagtttc gcgtgcgctt gcgggcgagt caggaacgaa   10620
aaactctgcg tgagaacaag tggaaaatcg agggatagca gcgcgttgag catgcccggc   10680
cgtgtttttg cagggtattc gcgaaacgaa tagatggatc caacgtaact gtcttttggc    10740
gttctgatct cgagtcctcg cttgccgcaa atgactctgt cggtataaat cgaagcgccg   10800
agtgagccgc tgacgaccgg aaccggtgtg aaccgaccag tcatgatcaa ccgtagcgct    10860
tcgccaattt cggtgaagag cacccctgc ttctcgcgga tgccaagacg atgcaggcca     10920
tacgctttaa gagagccagc gacaacatgc caaagatctt ccatgttcct gatctggccc   10980
gtgagatcgt tttcccttt tccgcttagc ttggtgaacc tcctctttac cttccctaaa     11040
gccgcctgtg ggtagacaat caacgtaagg aagtgttcat tgcggaggag ttggccggag   11100
agcacgcgct gttcaaaagc ttcgttcagg ctagcggcga aaacactacg gaagtgtcgc   11160
ggcgccgatg atggcacgtc ggcatgacgt acgaggtgag catatattga cacatgatca   11220
tcagcgatat tgcgcaacag cgtgttgaac gcacgacaac gcgcattgcg catttcagtt   11280
tcctcaagct cgaatgcaac gccatcaatt ctcgcaatgg tcatgatcga tccgtcttca   11340
agaaggacga tatggtcgct gaggtggcca atataaggga gatagatctc accggatctt   11400
tcggtcgttc cactcgcgcc gagcatcaca ccattcctct ccctcgtggg ggaaccctaa    11460
ttggatttgg gctaacagta gcgccccccc aaactgcact atcaatgctt cttcccgcgg   11520
tccgcaaaaa tagcaggacg acgctcgccg cattgtagtc tcgctccacg atgagccggg   11580
ctgcaaacca taacggcacg agaacgactt cgtagagcgg ttctgaacg ataacgatga     11640
caaagccggc gaacatcatg ataaccctg ccaatgtcag tggcacccca agaaacaatg     11700
cgggccgtgt ggctgcgagg taaagggtcg attcttccaa acgatcagcc atcaactacc   11760
gccagtgagc gtttggccga ggaagctcgc cccaaacatg ataacaatgc cgccgacgac   11820
gccggcaacc agcccaagcg aagcccgccc gaacatccag gagatcccga tagcgacaat   11880
gccgagaaca gcgagtgact ggccgaacgg accaaggata aacgtgcata tattgttaac    11940
cattgtggcg gggtcagtgc cgccacccgc agattgcgct gcggcgggtc cggatgagga   12000
```

```
aatgctccat gcaattgcac cgcacaagct tggggcgcag ctcgatatca cgcgcatcat   12060
cgcattcgag agcgagaggc gatttagatg taaacggtat ctctcaaagc atcgcatcaa   12120
tgcgcacctc cttagtataa gtcgaataag acttgattgt cgtctgcgga tttgccgttg   12180
tcctggtgtg gcggtggcgg agcgattaaa ccgccagcgc catcctcctg cgagcggcgc   12240
tgatatgacc cccaaacatc ccacgtctct tcggatttta gcgcctcgtg atcgtctttt   12300
ggaggctcga ttaacgcggg caccagcgat tgagcagctg tttcaacttt tcgcacgtag   12360
ccgtttgcaa aaccgccgat gaaattaccg gtgttgtaag cggagatcgc ccgacgaagc   12420
gcaaattgct tctcgtcaat cgtttcgccg cctgcataac gacttttcag catgtttgca   12480
gcggcagata atgatgtgca cgcctggagc gcaccgtcag gtgtcagacc gagcatagaa   12540
aaatttcgag agtttatttg catgaggcca acatccagcg aatgccgtgc atcgagacgg   12600
tgcctgacga cttgggttgc ttggctgtga tcttgccagt gaagcgtttc gccggtcgtg   12660
ttgtcatgaa tcgctaaagg atcaaagcga ctctccacct tagctatcgc cgcaagcgta   12720
gatgtcgcaa ctgatggggc acacttgcga gcaacatggt caaactcagc agatgagagt   12780
ggcgtggcaa ggctcgacga acagaaggag accatcaagg caagagaaag cgaccccgat   12840
ctcttaagca taccttatct ccttagctcg caactaacac cgcctctccc gttggaagaa   12900
gtgcgttgtt ttatgttgaa gattatcggg agggtcggtt actcgaaaat tttcaattgc   12960
ttctttatga tttcaattga agcgagaaac ctcgcccggc gtcttggaac gcaacatgga   13020
ccgagaaccg cgcatccatg actaagcaac cggatcgacc tattcaggcc gcagttggtc   13080
aggtcaggct cagaacgaaa atgctcggcg aggttacgct gtctgtaaac ccattcgatg   13140
aacgggaagc ttccttccga ttgctcttgg caggaatatt ggcccatgcc tgcttgcgct   13200
ttgcaaatgc tcttatcgcg ttggtatcat atgccttgtc cgccagcaga aacgcactct   13260
aagcgattat ttgtaaaaat gtttcggtca tgcggcggtc atgggcttga cccgctgtca   13320
gcgcaagacg gatcggtcaa ccgtcggcat cgacaacagc gtgaatcttg gtggtcaaac   13380
cgccacggga acgtcccata cagccatcgt cttgatcccg ctgtttcccg tcgccgcatg   13440
ttggtggacg cggacacagg aactgtcaat catgacgaca ttctatcgaa agccttggaa   13500
atcacactca gaatatgatc ccagacgtct gcctcacgcc atcgtacaaa gcgattgtag   13560
caggttgtac aggaaccgta tcgatcagga acgtctgccc agggcgggcc cgtccggaag   13620
cgccacaaga tgacattgat cacccgcgtc aacgcgcggc acgcgacgcg gcttatttgg   13680
gaacaaagga ctgaacaaca gtccattcga aatcggtgac atcaaagcgg ggacgggtta   13740
tcagtggcct ccaagtcaag cctcaatgaa tcaaaatcag accgatttgc aaacctgatt   13800
tatgagtgtg cggcctaaat gatgaaatcg tccttctaga tcgcctccgt ggtgtagcaa   13860
cacctcgcag tatcgccgtg ctgaccttgg ccagggaatt gactggcaag ggtgctttca   13920
catgaccgct cttttggccg cgatagatga tttcgttgct gctttgggca cgtagaagga   13980
gagaagtcat atcggagaaa ttcctcctgg cgcgagagcc tgctctatcg cgacggcatc   14040
ccactgtcgg gaacagaccg gatcattcac gaggcgaaag tcgtcaacac atgcgttata   14100
ggcatcttcc cttgaaggat gatcttgttg ctgccaatct ggaggtgcgg cagccgcagg   14160
cagatgcgat ctcagcgcaa cttgcggcaa aacatctcac tcacctgaaa accactagcg   14220
agtctcgcga tcagacgaag gccttttact taacgacaca atatccgatg tctgcatcac   14280
aggcgtcgct atcccagtca atactaaagc ggtgcaggaa ctaaagatta ctgatgactt   14340
aggcgtgcca cgaggcctga gacgacgcgc gtagacagtt ttttgaaatc attatcaaag   14400
```

```
tgatggcctc cgctgaagcc tatcacctct gcgccggtct gtcggagaga tgggcaagca    14460
ttattacggt cttcgcgccc gtacatgcat tggacgattg cagggtcaat ggatctgaga    14520
tcatccagag gattgccgcc cttaccttcc gtttcgagtt ggagccagcc cctaaatgag    14580
acgacatagt cgacttgatg tgacaatgcc aagagagaga tttgcttaac ccgatttttt    14640
tgctcaagcg taagcctatt gaagcttgcc ggcatgacgt ccgcgccgaa agaatatcct    14700
acaagtaaaa cattctgcac accgaaatgc ttggtgtaga catcgattat gtgaccaaga    14760
tccttagcag tttcgcttgg ggaccgctcc gaccagaaat accgaagtga actgacgcca    14820
atgacaggaa tcccttccgt ctgcagatag gtaccatcga tagatctgct gcctcgcgcg    14880
tttcggtgat gacggtgaaa acctctgaca catgcagctc ccggagacgg tcacagcttg    14940
tctgtaagcg gatgccggga gcagacaagc ccgtcagggc gcgtcagcgg gtgttggcgg    15000
gtgtcggggc gcagccatga cccagtcacg tagcgatagc ggagtgtata ctggcttaac    15060
tatgcggcat cagagcagat tgtactgaga gtgcaccata tgcggtgtga ataccgcac    15120 agatgcgtaa ggagaaaata ccgcatcagg cgctcttccg cttcctcgct cactgactcg    15180
ctgcgctcgg tcgttcggct gcggcgagcg gtatcagctc actcaaaggc ggtaatacgg    15240
ttatccacag aatcagggga taacgcagga agaacatgt gagcaaaagg ccagcaaaag    15300
gccaggaacc gtaaaaaggc cgcgttgctg gcgttttcc ataggctccg ccccctgac    15360 gagcatcaca aaaatcgacg ctcaagtcag aggtggcgaa acccgacagg actataaaga    15420
taccaggcgt ttccccctgg aagctccctc gtgcgctctc ctgttccgac cctgccgctt    15480
accggatacc tgtccgcctt tctcccttcg ggaagcgtgg cgctttctca tagctcacgc    15540
tgtaggtatc tcagttcggt gtaggtcgtt cgctccaagc tgggctgtgt gcacgaaccc    15600
cccgttcagc ccgaccgctg cgccttatcc ggtaactatc gtcttgagtc aacccggta    15660 agacacgact tatcgccact ggcagcagcc actggtaaca ggattagcag agcgaggtat    15720
gtaggcggtg ctacagagtt cttgaagtgg tggcctaact acggctacac tagaaggaca    15780
gtatttggta tctgcgctct gctgaagcca gttaccttcg gaaaaagagt tggtagctct    15840
tgatccggca aacaaaccac cgctggtagc ggtggttttt ttgtttgcaa gcagcagatt    15900
acgcgcagaa aaaaggatc tcaagaagat ccttttgatct tttctacggg gtctgacgct    15960
cagtggaacg aaaactcacg ttaagggatt ttggtcatga gattatcaaa aaggatcttc    16020
acctagatcc tttttaaatta aaaatgaagt tttaaatcaa tctaaagtat atatgagtaa    16080
acttggtctg acagttacca atgcttaatc agtgaggcac ctatctcagc gatctgtcta    16140
tttcgttcat ccatagttgc ctgactcccc gtcgtgtaga taactacgat acgggagggc    16200
ttaccatctg gccccagtgc tgcaatgata ccgcgagacc cacgctcacc ggctccagat    16260
ttatcagcaa taaaccagcc agccggaagg gccgagcgca gaagtggtcc tgcaacttta    16320
tccgcctcca tccagtctat taattgttgc cgggaagcta gagtaagtag ttcgccagtt    16380
aatagtttgc gcaacgttgt tgccattgct gcaggggggg gggggggggg gttccattgt    16440
tcattccacg gacaaaaaca gagaaaggaa acgacagagg ccaaaaagct cgctttcagc    16500
acctgtcgtt tcctttcttt tcagagggta ttttaaataa aaacattaag ttatgacgaa    16560
gaagaacgga aacgccttaa accggaaaat tttcataaat agcgaaaacc cgcgaggtcg    16620
ccgccccgta acctgtcgga tcaccggaaa ggacccgtaa agtgataatg attatcatct    16680
acatatcaca acgtgcgtgg aggccatcaa accacgtcaa ataatcaatt atgacgcagg    16740
tatcgtatta attgatctgc atcaacttaa cgtaaaaaca acttcagaca atacaaatca    16800
```

```
gcgacactga atacggggca acctcatgtc cccccccccc cccccccctgc aggcatcgtg   16860 gtgtcacgct cgtcgtttgg tatggcttca ttcagctccg gttcccaacg atcaaggcga   16920
gttacatgat cccccatgtt gtgcaaaaaa gcggttagct ccttcggtcc tccgatcgtt   16980
gtcagaagta agttggccgc agtgttatca ctcatggtta tggcagcact gcataattct   17040
cttactgtca tgccatccgt aagatgcttt tctgtgactg gtgagtactc aaccaagtca   17100
ttctgagaat agtgtatgcg gcgaccgagt tgctcttgcc cggcgtcaac acgggataat   17160
accgcgccac atagcagaac tttaaaagtg ctcatcattg gaaaacgttc ttcggggcga   17220
aaactctcaa ggatcttacc gctgttgaga tccagttcga tgtaacccac tcgtgcaccc   17280
aactgatctt cagcatcttt tactttcacc agcgtttctg ggtgagcaaa acaggaagg    17340 caaaatgccg caaaaaaggg aataagggcg acacggaaat gttgaatact catactcttc   17400
ctttttcaat attattgaag catttatcag ggttattgtc tcatgagcgg atacatattt   17460
gaatgtattt agaaaaataa acaaataggg gttccgcgca catttccccg aaaagtgcca   17520
cctgacgtct aagaaaccat tattatcatg acattaacct ataaaaatag gcgtatcacg   17580
aggccctttc gtcttcaaga attcggagct tttgccattc tcaccggatt cagtcgtcac   17640
tcatggtgat ttctcacttg ataaccttat ttttgacgag gggaaattaa taggttgtat   17700
tgatgttgga cgagtcggaa tcgcagaccg ataccaggat cttgccatcc tatggaactg   17760
cctcggtgag ttttctcctt cattacagaa acggcttttt caaaaatatg gtattgataa   17820
tcctgatatg aataaattgc agtttcattt gatgctcgat gagttttttct aatcagaatt   17880 ggttaattgg ttgtaacact ggcagagcat tacgctgact tgacgggacg gcggctttgt   17940
tgaataaatc gaacttttgc tgagttgaag gatcagatca cgcatcttcc cgacaacgca   18000
gaccgttccg tggcaaagca aaagttcaaa atcaccaact ggtccaccta caacaaagct   18060
ctcatcaacc gtggctccct cacttttctgg ctggatgatg gggcgattca ggcctggtat   18120
gagtcagcaa caccttcttc acgaggcaga cctcagcgcc agaaggccgc cagagaggcc   18180
gagcgcggcc gtgaggcttg gacgctaggg cagggcatga aaagcccgt agcgggctgc    18240 tacgggcgtc tgacgcggtg gaaaggggga ggggatgttg tctacatggc tctgctgtag   18300
tgagtgggtt gcgctccggc agcggtcctg atcaatcgtc accctttctc ggtccttcaa   18360
cgttcctgac aacgagcctc cttttcgcca atccatcgac aatcaccgcg agtccctgct   18420
cgaacgctgc gtccggaccg gcttcgtcga aggcgtctat cgcggcccgc aacagcggcg   18480
agagcggagc ctgttcaacg gtgccgccgc gctcgccggc atcgctgtcg ccggcctgct   18540
cctcaagcac ggccccaaca gtgaagtagc tgattgtcat cagcgcattg acggcgtccc   18600
cggccgaaaa acccgcctcg cagaggaagc gaagctgcgc gtcggccgtt tccatctgcg   18660
gtgcgcccgg tcgcgtgccg gcatggatgc gcgcgccatc gcggtaggcg agcagcgcct   18720
gcctgaagct gcgggcattc ccgatcagaa atgagcgcca gtcgtcgtcg gctctcggca   18780
ccgaatgcgt atgattctcc gccagcatgg cttcggccag tgcgtcgagc agcgcccgct   18840
tgttcctgaa gtgccagtaa agcgccggct gctgaacccc caaccgttcc gccagtttgc   18900
gtgtcgtcag accgtctacg ccgacctcgt tcaacaggtc cagggcggca cggatcactg   18960
tattcggctg caactttgtc atgcttgaca ctttatcact gataaacata atatgtccac   19020
caacttatca gtgataaaga atccgcgcgt tcaatcggac cagcggaggc tggtccggag   19080
gccagacgtg aaacccaaca taccctgat cgtaattctg agcactgtcg cgctcgacgc    19140
tgtcggcatc ggcctgatta tgccggtgct gccgggcctc ctgcgcgatc tggttcactc   19200
```

```
gaacgacgtc accgcccact atggcattct gctggcgctg tatgcgttgg tgcaatttgc    19260
ctgcgcacct gtgctgggcg cgctgtcgga tcgtttcggg cggcggccaa tcttgctcgt    19320
ctcgctggcc ggcgccactg tcgactacgc catcatggcg acagcgcctt tcctttgggt    19380
tctctatatc gggcggatcg tggccggcat caccggggcg actggggcgg tagccggcgc    19440
ttatattgcc gatatcactg atggcgatga gcgcgcgcgg cacttcggct tcatgagcgc    19500
ctgtttcggg ttcgggatgg tcgcgggacc tgtgctcggt gggctgatgg gcggtttctc    19560
cccccacgct ccgttcttcg ccgcggcagc cttgaacggc ctcaatttcc tgacgggctg    19620
tttccttttg ccggagtcgc acaaaggcga acgccggccg ttacgccggg aggctctcaa    19680
cccgctcgct tcgttccggt gggcccgggg catgaccgtc gtcgccgccc tgatggcggt    19740
cttcttcatc atgcaacttg tcggacaggt gccggccgcg ctttgggtca ttttcggcga    19800
ggatcgcttt cactgggacg cgaccacgat cggcatttcg cttgccgcat ttggcattct    19860
gcattcactc gcccaggcaa tgatcaccgg ccctgtagcc gcccggctcg gcgaaaggcg    19920
ggcactcatg ctcggaatga ttgccgacgg cacaggctac atcctgcttg ccttcgcgac    19980
acggggatgg atggcgttcc cgatcatggt cctgcttgct tcgggtggca tcggaatgcc    20040
ggcgctgcaa gcaatgttgt ccaggcaggt ggatgaggaa cgtcaggggc agctgcaagg    20100
ctcactggcg gcgctcacca gcctgacctc gatcgtcgga cccctcctct tcacggcgat    20160
ctatgcggct tctataacaa cgtggaacgg gtgggcatgg attgcaggcg ctgccctcta    20220
cttgctctgc ctgccggcgc tgcgtcgcgg gctttggagc ggcgcagggc aacgagccga    20280
tcgctgatcg tggaaacgat aggcctatgc catgcgggtc aaggcgactt ccggcaagct    20340
atacgcgccc taggagtgcg gttgaacgt tggcccagcc agatactccc gatcacgagc    20400
aggacgccga tgatttgaag cgcactcagc gtctgatcca agaacaacca tcctagcaac    20460
acggcggtcc ccgggctgag aaagcccagt aaggaaacaa ctgtaggttc gagtcgcgag    20520
atcccccgga accaaaggaa gtaggttaaa cccgctccga tcaggccgag ccacgccagg    20580
ccgagaacat tggttcctgt aggcatcggg attggcggat caaacactaa agctactgga    20640
acgagcagaa gtcctccggc cgccagttgc caggcggtaa aggtgagcag aggcacggga    20700
ggttgccact tgcgggtcag cacggttccg aacgccatgg aaaccgcccc cgccaggccc    20760
gctgcgacgc cgacaggatc tagcgctgcg tttggtgtca acaccaacag cgccacgccc    20820
gcagttccgc aaatagcccc caggaccgcc atcaatcgta tcgggctacc tagcagagcg    20880
gcagagatga acacgaccat cagcggctgc acagcgccta ccgtcgccgc gaccccgccc    20940
ggcaggcggt agaccgaaat aaacaacaag ctccagaata gcgaaatatt aagtgcgccg    21000
aggatgaaga tgcgcatcca ccagattccc gttggaatct gtcggacgat catcacgagc    21060
aataaacccg ccggcaacgc ccgcagcagc ataccggcga cccctcggcc tcgctgttcg    21120
ggctccacga aaacgccgga cagatgcgcc ttgtgagcgt ccttggggcc gtcctcctgt    21180
ttgaagaccg acagcccaat gatctcgccg tcgatgtagg cgccgaatgc cacggcatct    21240
cgcaaccgtt cagcgaacgc ctccatgggc ttttctcct cgtgctcgta aacggacccg    21300
aacatctctg gagctttctt cagggccgac aatcggatct cgcggaaatc ctgcacgtcg    21360
gccgctccaa gccgtcgaat ctgagcctta atcacaattg tcaattttaa tcctctgttt    21420
atcggcagtt cgtagagcgc gccgtgcgtc ccgagcgata ctgagcgaag caagtgcgtc    21480
gagcagtgcc cgcttgttcc tgaaatgcca gtaaagcgct ggctgctgaa cccccagccg    21540
gaactgaccc cacaaggccc tagcgtttgc aatgcaccag gtcatcattg acccaggcgt    21600
```

```
gttccaccag gccgctgcct cgcaactctt cgcaggcttc gccgacctgc tcgcgccact  21660
tcttcacgcg ggtggaatcc gatccgcaca tgaggcggaa ggtttccagc ttgagcgggt  21720
acggctcccg gtgcgagctg aaatagtcga acatccgtcg ggccgtcggc gacagcttgc  21780
ggtacttctc ccatatgaat tcgtgtagt ggtcgccagc aaacagcacg acgatttcct  21840
cgtcgatcag gacctggcaa cgggacgttt tcttgccacg gtccaggacg cggaagcggt  21900
gcagcagcga caccgattcc aggtgcccaa cgcggtcgga cgtgaagccc atcgccgtcg  21960
cctgtaggcg cgacaggcat tcctcggcct tcgtgtaata ccggccattg atcgaccagc  22020
ccaggtcctg gcaaagctcg tagaacgtga aggtgatcgg ctcgccgata ggggtgcgct  22080
tcgcgtactc caaacctgc tgccacacca gttcgtcatc gtcggcccgc agctcgacgc  22140
cggtgtaggt gatcttcacg tccttgttga cgtggaaaat gaccttgttt tgcagcgcct  22200
cgcgcgggat tttcttgttg cgcgtggtga acagggcaga gcgggccgtg tcgtttggca  22260
tcgctcgcat cgtgtccggc cacggcgcaa tatcgaacaa ggaaagctgc atttccttga  22320
tctgctgctt cgtgtgtttc agcaacgcgg cctgcttggc ctcgctgacc tgttttgcca  22380
ggtcctcgcc ggcggttttt cgcttcttgg tcgtcatagt tcctcgcgtg tcgatggtca  22440
tcgacttcgc caaacctgcc gcctcctgtt cgagacgacg cgaacgctcc acggcggccg  22500
atggcgcggg cagggcaggg ggagccagtt gcacgctgtc gcgctcgatc ttggccgtag  22560
cttgctggac catcgagccg acggactgga aggtttcgcg gggcgcacgc atgacggtgc  22620
ggcttgcgat ggtttcggca tcctcggcgg aaaaccccgc gtcgatcagt tcttgcctgt  22680
atgccttccg gtcaaacgtc cgattcattc accctccttg cgggattgcc ccgactcacg  22740
ccggggcaat gtgcccttat tcctgatttg acccgcctgg tgccttggtg tccagataat  22800
ccaccttatc ggcaatgaag tcggtcccgt agaccgtctg gccgtccttc tcgtacttgg  22860
tattccgaat cttgccctgc acgaatacca gcgaccccctt gcccaaatac ttgccgtggg  22920
cctcggcctg agagccaaaa cacttgatgc ggaagaagtc ggtgcgctcc tgcttgtcgc  22980
cggcatcgtt gcgccactct tcattaaccg ctatatcgaa aattgcttgc ggcttgttag  23040
aattgccatg acgtacctcg gtgtcacggg taagattacc gataaactgg aactgattat  23100
ggctcatatc gaaagtctcc ttgagaaagg agactctagt ttagctaaac attggttccg  23160
ctgtcaagaa ctttagcggc taaaattttg cgggccgcga ccaaaggtgc gaggggcggc  23220
ttccgctgtg tacaaccaga tatttttcac caacatcctt cgtctgctcg atgagcgggg  23280
catgacgaaa catgagctgt cggagagggc aggggtttca atttcgtttt tatcagactt  23340
aaccaacggt aaggccaacc cctcgttgaa ggtgatggag gccattgccg acgccctgga  23400
aactccccta cctcttctcc tggagtccac cgaccttgac cgcgaggcac tcgcggagat  23460
tgcgggtcat cctttcaaga gcagcgtgcc gcccggatac gaacgcatca gtgtggtttt  23520
gccgtcacat aaggcgttta tcgtaaagaa atggggcgac gacacccgaa aaaagctgcg  23580
tggaaggctc tgacgccaag ggttagggct tgcacttcct tctttagccg ctaaaacggc  23640
cccttctctg cgggccgtcg gctcgcgcat catatcgaca tcctcaacgg aagccgtgcc  23700
gcgaatggca tcgggcgggt gcgctttgac agttgttttc tatcagaacc cctacgtcgt  23760
gcggttcgat tagctgtttg tcttgcaggc taaacacttt cggtatatcg tttgcctgtg  23820
cgataatgtt gctaatgatt tgttgcgtag gggttactga aaagtgagcg ggaaagaaga  23880
gtttcagacc atcaaggagc gggccaagcg caagctggaa cgcgacatgg gtgcggacct  23940
gttggccgcg ctcaacgacc cgaaaaccgt tgaagtcatg ctcaacgcgg acggcaaggt  24000
```

```
gtggcacgaa cgccttggcg agccgatgcg gtacatctgc gacatgcggc ccagccagtc   24060
gcaggcgatt atagaaacgg tggccggatt ccacggcaaa gaggtcacgc ggcattcgcc   24120
catcctggaa ggcgagttcc ccttggatgg cagccgcttt gccggccaat tgccgccggt   24180
cgtggccgcg ccaacctttg cgatccgcaa gcgcgcggtc gccatcttca cgctggaaca   24240
gtacgtcgag gcgggcatca tgacccgcga gcaatacgag gtcattaaaa gcgccgtcgc   24300
ggcgcatcga aacatcctcg tcattggcgg tactggctcg ggcaagacca cgctcgtcaa   24360
cgcgatcatc aatgaaatgg tcgccttcaa cccgtctgag cgcgtcgtca tcatcgagga   24420
caccggcgaa atccagtgcg ccgcagagaa cgccgtccaa taccacacca gcatcgacgt   24480
ctcgatgacg ctgctgctca agacaacgct gcgtatgcgc cccgaccgca tcctggtcgg   24540
tgaggtacgt ggccccgaag cccttgatct gttgatggcc tggaacaccg gcatgaagg   24600 aggtgccgcc accctgcacg caaacaaccc caaagcgggc ctgagccggc tcgccatgct   24660
tatcagcatg cacccggatt caccgaaacc cattgagccg ctgattggcg aggcggttca   24720
tgtggtcgtc catatcgcca ggaccctag cggccgtcga gtgcaagaaa ttctcgaagt   24780
tcttggttac gagaacggcc agtacatcac caaaaccctg taaggagtat ttccaatgac   24840
aacggctgtt ccgttccgtc tgaccatgaa tcgcggcatt ttgttctacc ttgccgtgtt   24900
cttcgttctc gctctcgcgt tatccgcgca tccggcgatg gcctcggaag gcaccggcgg   24960
cagcttgcca tatgagagct ggctgacgaa cctgcgcaac tccgtaaccg gcccggtggc   25020
cttcgcgctg tccatcatcg gcatcgtcgt cgccggcggc gtgctgatct tcggcggcga   25080
actcaacgcc ttcttccgaa ccctgatctt cctggttctg gtgatggcgc tgctggtcgg   25140
cgcgcagaac gtgatgagca ccttcttcgg tcgtggtgcc gaaatcgcgg ccctcggcaa   25200
cggggcgctg caccaggtgc aagtcgcggc ggcggatgcc gtgcgtgcgg tagcggctgg   25260
acggctcgcc taatcatggc tctgcgcacg atccccatcc gtcgcgcagg caaccgagaa   25320
aacctgttca tgggtggtga tcgtgaactg gtgatgttct cgggcctgat ggcgtttgcg   25380
ctgattttca gcgcccaaga gctgcgggcc accgtggtcg gtctgatcct gtggttcggg   25440
gcgctctatg cgttccgaat catggcgaag gccgatccga agatgcggtt cgtgtacctg   25500
cgtcaccgcc ggtacaagcc gtattacccg gcccgctcga ccccgttccg cgagaacacc   25560
aatagccaag ggaagcaata ccgatgatcc aagcaattgc gattgcaatc gcgggcctcg   25620
gcgcgcttct gttgttcatc ctctttgccc gcatccgcgc ggtcgatgcc gaactgaaac   25680
tgaaaaagca tcgttccaag gacgccggcc tggccgatct gctcaactac gccgctgtcg   25740
tcgatgacgg cgtaatcgtg ggcaagaacg gcagctttat ggctgcctgg ctgtacaagg   25800
gcgatgacaa cgcaagcagc accgaccagc agcgcgaagt agtgtccgcc cgcatcaacc   25860
aggccctcgc gggcctggga agtgggtgga tgatccatgt ggacgccgtg cggcgtcctg   25920
ctccgaacta cgcggagcgg ggcctgtcgg cgttccctga ccgtctgacg gcagcgattg   25980
aagaagagcg ctcggtcttg ccttgctcgt cggtgatgta cttcaccagc tccgcgaagt   26040
cgctcttctt gatggagcgc atgggacgt gcttggcaat cacgcgcacc cccggccgt   26100 tttagcggct aaaaaagtca tggctctgcc ctcgggcgga ccacgccat catgaccttg   26160 ccaagctcgt cctgcttctc ttcgatcttc gccagcaggg cgaggatcgt ggcatcaccg   26220
aaccgcgccg tgcgcgggtc gtcggtgagc cagagtttca gcaggccgcc caggcggccc   26280
aggtcgccat tgatgcgggc cagctcgcgg acgtgctcat agtccacgac gcccgtgatt   26340
ttgtagccct ggccgacggc cagcaggtag gccgacaggc tcatgccggc cgccgccgcc   26400
```

```
ttttcctcaa tcgctcttcg ttcgtctgga aggcagtaca ccttgatagg tgggctgccc   26460
ttcctggttg gcttggtttc atcagccatc cgcttgccct catctgttac gccggcggta   26520
gccggccagc ctcgcagagc aggattcccg ttgagcaccg ccaggtgcga ataagggaca   26580
gtgaagaagg aacacccgct cgcgggtggg cctacttcac ctatcctgcc cggctgacgc   26640
cgttggatac accaaggaaa gtctacacga acccttggc aaaatcctgt atatcgtgcg   26700
aaaaggatg atataccga aaaaatcgct ataatgaccc cgaagcaggg ttatgcagcg   26760
gaaaagcgct gcttccctgc tgttttgtgg aatatctacc gactggaaac aggcaaatgc   26820
aggaaattac tgaactgagg ggacaggcga gagacgatgc caaagagcta caccgacgag   26880
ctggccgagt gggttgaatc ccgcgcggcc aagaagcgcc ggcgtgatga ggctgcggtt   26940
gcgttcctgg cggtgagggc ggatgtcgag gcggcgttag cgtccggcta tgcgctcgtc   27000
accatttggg agcacatgcg ggaaacgggg aaggtcaagt tctcctacga gacgttccgc   27060
tcgcacgcca ggcggcacat caaggccaag cccgccgatg tgcccgcacc gcaggccaag   27120
gctgcggaac ccgcgccggc acccaagacg ccggagccac ggcggccgaa gcagggggc   27180
aaggctgaaa agccggcccc cgctgcgcc ccgaccggct tcaccttcaa cccaacaccg   27240
gacaaaaagg atctactgta atggcgaaaa ttcacatggt tttgcagggc aagggcgggg   27300
tcggcaagtc ggccatcgcc gcgatcattg cgcagtacaa gatggacaag gggcagacac   27360
ccttgtgcat cgacaccgac ccggtgaacg cgacgttcga gggctacaag gccctgaacg   27420
tccgccggct gaacatcatg gccggcgacg aaattaactc gcgcaacttc gacaccctgg   27480
tcgagctgat tgcgccgacc aaggatgacg tggtgatcga caacggtgcc agctcgttcg   27540
tgcctctgtc gcattacctc atcagcaacc aggtgccggc tctgctgcaa gaaatggggc   27600
atgagctggt catccatacc gtcgtcaccg gcggccaggc tctcctggac acggtgagcg   27660
gcttcgccca gctcgccagc cagttcccgg ccgaagcgct tttcgtggtc tggctgaacc   27720
cgtattgggg gcctatcgag catgagggca agagctttga gcagatgaag gcgtacacgg   27780
ccaacaaggc ccgcgtgtcg tccatcatcc agattccggc cctcaaggaa gaaacctacg   27840
gccgcgattt cagcgacatg ctgcaagagc ggctgacgtt cgaccaggcg ctggccgatg   27900
aatcgctcac gatcatgacg cggcaacgcc tcaagatcgt gcggcgcggc ctgtttgaac   27960
agctcgacgc ggcggccgtg ctatgagcga ccagattgaa gagctgatcc gggagattgc   28020
ggccaagcac ggcatcgccg tcggccgcga cgacccggtg ctgatcctgc ataccatcaa   28080
cgcccggctc atggccgaca gtgcggccaa gcaagaggaa atccttgccg cgttcaagga   28140
agagctggaa gggatcgccc atcgttgggg cgaggacgcc aaggccaaag cggagcggat   28200
gctgaacgcg gccctggcgg ccagcaagga cgcaatggcg aaggtaatga aggacagcgc   28260
cgcgcaggcg gccgaagcga tccgcaggga aatcgacgac ggccttggcc gccagctcgc   28320
ggccaaggtc gcggacgcgc ggcgcgtggc gatgatgaac atgatcgccg gcggcatggt   28380
gttgttcgcg gccgccctgg tggtgtgggc ctcgttatga atcgcagagg cgcagatgaa   28440
aaagcccggc gttgccgggc tttgttttg cgttagctgg gcttgtttga caggcccaag   28500
ctctgactgc gcccgcgctc gcgctcctgg gcctgtttct tctcctgctc ctgcttgcgc   28560
atcagggcct ggtgccgtcg ggctgcttca cgcatcgaat cccagtcgcc ggccagctcg   28620
ggatgctccg cgcgcatctt gcgcgtcgcc agttcctcga tcttgggcgc gtgaatgccc   28680
atgccttcct tgatttcgcg caccatgtcc agccgcgtgt gcagggtctg caagcgggct   28740
tgctgttggg cctgctgctg ctgccaggcg gccttgtac gcggcaggga cagcaagccg   28800
```

```
ggggcattgg actgtagctg ctgcaaacgc gcctgctgac ggtctacgag ctgttctagg   28860
cggtcctcga tgcgctccac ctggtcatgc tttgcctgca cgtagagcgc aagggtctgc   28920
tggtaggtct gctcgatggg cgcggattct aagagggcct gctgttccgt ctcggcctcc   28980
tgggccgcct gtagcaaatc ctcgccgctg ttgccgctgg actgctttac tgccggggac   29040
tgctgttgcc ctgctcgcgc cgtcgtcgca gttcggcttg ccccactcg attgactgct    29100
tcatttcgag ccgcagcgat gcgatctcgg attgcgtcaa cggacggggc agcgcggagg   29160
tgtccggctt ctccttgggt gagtcggtcg atgccatagc caaaggtttc cttccaaaat   29220
gcgtccattg ctggaccgtg tttctcattg atgcccgcaa gcatcttcgg cttgaccgcc   29280
aggtcaagcg cgccttcatg ggcggtcatg acggacgccg ccatgacctt gccgccgttg   29340
ttctcgatgt agccgcgtaa tgaggcaatg gtgccgccca tcgtcagcgt gtcatcgaca   29400
acgatgtact tctggccggg gatcacctcc ccctcgaaag tcgggttgaa cgccaggcga   29460
tgatctgaac cggctccggt tcgggcgacc ttctcccgct gcacaatgtc cgtttcgacc   29520
tcaaggccaa ggcggtcggc cagaacgacc gccatcatgg ccggaatctt gttgttcccc   29580
gccgcctcga cggcgaggac tggaacgatg cggggcttgt cgtcgccgat cagcgtcttg   29640
agctgggcaa cagtgtcgtc cgaaatcagg cgctcgacca aattaagcgc cgcttccgcg   29700
tcgccctgct tcgcagcctg gtattcaggc tcgttggtca aagaaccaag gtcgccgttg   29760
cgaaccacct tcgggaagtc tccccacggt gcgcgctcgg ctctgctgta gctgctcaag   29820
acgcctccct ttttagccgc taaaactcta acgagtgcgc ccgcgactca acttgacgct   29880
ttcggcactt acctgtgcct tgccacttgc gtcataggtg atgcttttcg cactcccgat   29940
ttcaggtact ttatcgaaat ctgaccgggc gtgcattaca aagttcttcc ccacctgttg   30000
gtaaatgctg ccgctatctg cgtggacgat gctgccgtcg tggcgctgcg acttatcggc   30060
cttttgggcc atatagatgt tgtaaatgcc aggtttcagg gccccggctt tatctacctt   30120
ctggttcgtc catgcgcctt ggttctcggt ctggacaatt ctttgcccat tcatgaccag   30180
gaggcggtgt tcattgggt gactcctgac ggttgcctct ggtgttaaac gtgtcctggt    30240
cgcttgccgg ctaaaaaaaa gccgacctcg gcagttcgag gccggctttc cctagagccg   30300
ggcgcgtcaa ggttgttcca tctattttag tgaactgcgt tcgatttatc agttactttc   30360
ctcccgcttt gtgtttcctc ccactcgttt ccgcgtctag ccgaccctc aacatagcgg    30420
cctcttcttg ggctgccttt gcctcttgcc gcgcttcgtc acgctcggct tgcaccgtcg   30480
taaagcgctc ggcctgcctg gccgcctctt gcgccgccaa cttcctttgc tcctggtggg   30540
cctcggcgtc ggcctgcgcc ttcgctttca ccgctgccaa ctccgtgcgc aaactctccg   30600
cttcgcgcct ggtggcgtcg cgctcgccgc gaagcgcctg catttcctgg ttggccgcgt   30660
ccagggtctt gcggctctct tctttgaatg cgcgggcgtc ctggtgagcg tagtccagct   30720
cggcgcgcag ctcctgcgct cgacgctcca cctcgtcggc ccgctgcgtc gccagcgcgg   30780
cccgctgctc ggctcctgcc agggcggtgc gtgcttcggc cagggcttgc cgctggcgtg   30840
cggccagctc ggccgcctcg gcggcctgct gctctagcaa tgtaacgcgc gcctgggctt   30900
cttccagctc gcgggcctgc gcctcgaagg cgtcggccag ctccccgcgc acggcttcca   30960
actcgttgcg ctcacgatcc cagccggctt gcgctgcctg caacgattca ttggcaaggg   31020
cctgggcggc ttgccagagg gcggccacgg cctggttgcc ggcctgctgc accgcgtccg   31080
gcacctggac tgccagcggg gcggcctgcg ccgtgcgctg gcgtcgccat tcgcgcatgc   31140
cggcgctggc gtcgttcatg ttgacgcggg cggccttacg cactgcatcc acggtcggga   31200
```

```
agttctcccg gtcgccttgc tcgaacagct cgtccgcagc cgcaaaaatg cggtcgcgcg   31260
tctctttgtt cagttccatg ttggctccgg taattggtaa gaataataat actcttacct   31320
accttatcag cgcaagagtt tagctgaaca gttctcgact taacggcagg tttttttagcg   31380 gctgaagggc aggcaaaaaa agccccgcac ggtcggcggg ggcaaagggt cagcgggaag   31440
gggattagcg ggcgtcgggc ttcttcatgc gtcggggccg cgcttcttgg gatggagcac   31500
gacgaagcgc gcacgcgcat cgtcctcggc cctatcggcc cgcgtcgcgg tcaggaactt   31560
gtcgcgcgct aggtcctccc tggtgggcac caggggcatg aactcggcct gctcgatgta   31620
ggtccactcc atgaccgcat cgcagtcgag gccgcgttcc ttcaccgtct cttgcaggtc   31680
gcggtacgcc cgctcgttga gcggctggta acgggccaat tggtcgtaaa tggctgtcgg   31740
ccatgagcgg cctttcctgt tgagccagca gccgacgacg aagccggcaa tgcaggcccc   31800
tggcacaacc aggccgacgc cggggcagg ggatggcagc agctcgccaa ccaggaaccc   31860
cgccgcgatg atgccgatgc cggtcaacca gcccttgaaa ctatccggcc ccgaaacacc   31920
cctgcgcatt gcctggatgc tgcgccggat agcttgcaac atcaggagcc gtttcttttg   31980
ttcgtcagtc atggtccgcc ctcaccagtt gttcgtatcg gtgtcggacg aactgaaatc   32040
gcaagagctg ccggtatcgg tccagccgct gtccgtgtcg ctgctgccga agcacggcga   32100
ggggtccgcg aacgccgcag acggcgtatc cggccgcagc gcatcgccca gcatggcccc   32160
ggtcagcgag ccgccggcca ggtagcccag catggtgctg ttggtcgccc cggccaccag   32220
ggccgacgta cgaaatcgc cgtcattccc tctggattgt tcgctgctcg gcggggcagt   32280
gcgccgcgcc ggcggcgtcg tggatggctc gggttggctg gcctgcgacg gccggcgaaa   32340
ggtgcgcagc agctcgttat cgaccggctg cggcgtcggg gccgccgcct tgcgctgcgg   32400
tcggtgttcc ttcttcggct cgcgcagctt gaacagcatg atcgcggaaa ccagcagcaa   32460
cgccgcgcct acgcctcccg cgatgtagaa cagcatcgga ttcattcttc ggtcctcctt   32520
gtagcggaac cgttgtctgt gcggcgcggg tggcccgcgc cgctgtcttt ggggatcagc   32580
cctcgatgag cgcgaccagt ttcacgtcgg caaggttcgc ctcgaactcc tggccgtcgt   32640
cctcgtactt caaccaggca tagccttccg ccggcggccg acggttgagg ataaggcggg   32700
cagggcgctc gtcgtgctcg acctggacga tggcctttt cagcttgtcc gggtccggct   32760
ccttcgcgcc cttttccttg gcgtccttac cgtcctggtc gccgtcctcg ccgtcctggc   32820
cgtcgccggc ctccgcgtca cgctcggcat cagtctggcc gttgaaggca tcgacggtgt   32880
tgggatcgcg gcccttctcg tccaggaact cgcgcagcag cttgaccgtg ccgcgcgtga   32940
tttcctgggt gtcgtcgtca agccacgcct cgacttcctc cgggcgcttc ttgaaggccg   33000
tcaccagctc gttcaccacg gtcacgtcgc gcacgcggcc ggtgttgaac gcatcggcga   33060
tcttctccgg caggtccagc agcgtgacgt gctgggtgat gaacgccggc gacttgccga   33120
tttccttggc gatatcgcct ttcttcttgc ccttcgccag ctcgcggcca atgaagtcgg   33180
caatttcgcg cggggtcagc tcgttgcgtt gcaggttctc gataacctgg tcggcttcgt   33240
tgtagtcgtt gtcgatgaac gccgggatgg acttcttgcc ggcccacttc gagccacggt   33300
agcggcgggc gccgtgattg atgatatagc ggcccggctg ctcctggttc tcgcgcaccg   33360
aaatgggtga cttcaccccg cgctctttga tcgtggcacc gatttccgcg atgctctccg   33420
gggaaaagcc ggggttgtcg gccgtccgcg gctgatgcgg atcttcgtcg atcaggtcca   33480
ggtccagctc gatagggccg gaaccgcct gagacgccgc aggagcgtcc aggaggctcg   33540
acaggtcgcc gatgctatcc aaccccaggc cggacggctg cgccgcgcct gcggcttcct   33600
```

```
gagcggccgc agcggtgttt ttcttggtgg tcttggcttg agccgcagtc attgggaaat   33660
ctccatcttc gtgaacacgt aatcagccag ggcgcgaacc tctttcgatg ccttgcgcgc   33720
ggccgttttc ttgatcttcc agaccggcac accggatgcg agggcatcgg cgatgctgct   33780
gcgcaggcca acggtggccg gaatcatcat cttggggtac gcggccagca gctcggcttg   33840
gtggcgcgcg tggcgcggat tccgcgcatc gaccttgctg gcaccatgc caaggaattg    33900 cagcttggcg ttcttctggc gcacgttcgc aatggtcgtg accatcttct tgatgccctg   33960
gatgctgtac gcctcaagct cgatggggga cagcacatag tcggccgcga agagggcggc   34020
cgccaggccg acgccaaggg tcggggccgt gtcgatcagg cacacgtcga agccttggtt   34080
cgccagggcc ttgatgttcg ccccgaacag ctcgcgggcg tcgtccagcg acagccgttc   34140
ggcgttcgcc agtaccgggt tggactcgat gagggcgagg cgcgcggcct ggccgtcgcc   34200
ggctgcgggt gcggtttcgg tccagccgcc ggcaggaca gcgccgaaca gcttgcttgc    34260
atgcaggccg gtagcaaagt ccttgagcgt gtaggacgca ttgccctggg ggtccaggtc   34320
gatcacggca acccgcaagc cgcgctcgaa aaagtcgaag gcaagatgca caagggtcga   34380
agtcttgccg acgccgcctt tctggttggc cgtgaccaaa gttttcatcg tttggtttcc   34440
tgttttttct tggcgtccgc ttcccacttc cggacgatgt acgcctgatg ttccggcaga   34500
accgccgtta ccccgcgcgta cccctcgggc aagttcttgt cctcgaacgc ggcccacacg   34560
cgatgcaccg cttgcgacac tgcgcccctg gtcagtccca gcgacgttgc gaacgtcgcc   34620
tgtggcttcc catcgactaa gacgcccgc gctatctcga tggtctgctg ccccacttcc    34680
agcccctgga tcgcctcctg gaactggctt tcggtaagcc gtttcttcat ggataacacc   34740
cataatttgc tccgcgcctt ggttgaacat agcggtgaca gccgccagca catgagagaa   34800
gtttagctaa acatttctcg cacgtcaaca cctttagccg ctaaaactcg tccttggcgt   34860
aacaaaacaa aagcccggaa accgggcttt cgtctcttgc cgcttatggc tctgcacccg   34920
gctccatcac caacaggtcg cgcacgcgct tcactcggtt gcggatcgac actgccagcc   34980
caacaaagcc ggttgccgcc gccgccagga tcgcgccgat gatgccggcc acaccggcca   35040
tcgcccacca ggtcgccgcc ttccggttcc attcctgctg gtactgcttc gcaatgctgg   35100
acctcggctc accataggct gaccgctcga tggcgtatgc cgcttctccc cttggcgtaa   35160
aacccagcgc cgcaggcggc attgccatgc tgcccgccgc tttcccgacc acgacgcgcg   35220
caccaggctt gcggtccaga ccttcggcca cggcgagctg cgcaaggaca taatcagccg   35280
ccgacttggc tccacgcgcc tcgatcagct cttgcactcg cgcgaaatcc ttggcctcca   35340
cggccgccat gaatcgcgca cgcggcgaag gctccgcagg gccggcgtcg tgatcgccgc   35400
cgagaatgcc cttcaccaag ttcgacgaca cgaaaatcat gctgacggct atcaccatca   35460
tgcagacgga tcgcacgaac ccgctgaatt gaacacgagc acggcacccg cgaccactat   35520
gccaagaatg cccaaggtaa aaattgccgg ccccgccatg aagtccgtga atgccccgac   35580
ggccgaagtg aagggcaggc cgccacccag gccgccgccc tcactgcccg gcacctggtc   35640
gctgaatgtc gatgccagca cctgcggcac gtcaatgctt ccgggcgtcg cgctcgggct   35700
gatcgcccat cccgttactg ccccgatccc ggcaatggca aggactgcca gcgctgccat   35760
ttttggggtg aggccgttcg cggccgaggg gcgcagcccc tgggggatg ggaggccgc     35820 gttagcgggc cggagggtt cgagaagggg gggcacccccc cttcggcgtg cgcggtcacg   35880
cgcacagggc gcagccctgg ttaaaaacaa ggttttataaa tattggttta aaagcaggtt   35940
aaaagacagg ttagcggtgg ccgaaaaacg ggcggaaacc cttgcaaatg ctggattttc   36000
```

```
tgcctgtgga cagcccctca aatgtcaata ggtgcgcccc tcatctgtca gcactctgcc   36060
cctcaagtgt caaggatcgc gcccctcatc tgtcagtagt cgcgcccctc aagtgtcaat   36120
accgcagggc acttatcccc aggcttgtcc acatcatctg tgggaaactc gcgtaaaatc   36180
aggcgttttc gccgatttgc gaggctggcc agctccacgt cgccggccga atcgagcct    36240 gccoctcatc tgtcaacgcc gcgccggtg agtcggcccc tcaagtgtca acgtccgccc    36300
ctcatctgtc agtgagggcc aagttttccg cgaggtatcc acaacgccgg cggccgcggt   36360
gtctcgcaca cggcttcgac ggcgtttctg gcgcgtttgc agggccatag acggccgcca   36420
gcccagcggc gagggcaacc agcccggtga gcgtcggaaa ggcgctggaa gccccgtagc   36480
gacgcggaga ggggcgagac aagccaaggg cgcaggctcg atgcgcagca cgacatagcc   36540
ggttctcgca aggacgagaa tttccctgcg gtgcccctca agtgtcaatg aaagtttcca   36600
acgcgagcca ttcgcgagag ccttgagtcc acgctagatg agagctttgt tgtaggtgga   36660
ccagttggtg atttttgaact tttgcttttgc cacggaacgg tctgcgttgt cgggaagatg   36720
cgtgatctga tccttcaact cagcaaaagt tcgatttatt caacaaagcc acgttgtgtc    36780
tcaaaatctc tgatgttaca ttgcacaaga taaaaatata tcatcatgaa caataaaact    36840
gtctgcttac ataaacagta atacaagggg tgttatgagc catattcaac gggaaacgtc   36900
ttgctcgac                                                          36909

<210> SEQ ID NO 8
<211> LENGTH: 13019
<212> TYPE: DNA
<213> ORGANISM: Artificial Sequence
<220> FEATURE:
<223> OTHER INFORMATION: PHP23235 construct

<400> SEQUENCE: 8
gttacccgga ccgaagctta gcccgggcat gcctgcagtg cagcgtgacc cggtcgtgcc      60
cctctctaga gataatgagc attgcatgtc taagttataa aaaattacca catattttt     120 ttgtcacact tgtttgaagt gcagtttatc tatctttata catatattta aactttactc    180
tacgaataat ataatctata gtactacaat aatatcagtg ttttagagaa tcatataaat    240
gaacagttag acatggtcta aaggacaatt gagtattttg acaacaggac tctacagttt    300
tatcttttta gtgtgcatgt gttctccttt tttttgcaa atagcttcac ctatataata     360
cttcatccat tttattagta catccattta gggtttaggg ttaatggttt ttatagacta    420
atttttttag tacatctatt ttattctatt ttagcctcta aattaagaaa actaaaactc    480
tattttagtt tttttattta ataatttaga tataaaatag aataaaataa agtgactaaa    540
aattaaacaa ataccctta agaaattaaa aaaactaagg aaacatttt cttgtttcga      600 gtagataatg ccagcctgtt aaacgccgtc gacgagtcta acggacacca accagcgaac    660
cagcagcgtc gcgtcgggcc aagcgaagca gacggcacgg catctctgtc gctgcctctg    720 gaccctctc gagagttccg ctccaccgtt ggacttgctc cgctgtcggc atccagaaat     780
tgcgtggcgg agcggcagac gtgagccggc acggcaggcg gcctcctcct cctctcacgg    840
cacggcagct acggggatt cctttcccac cgctccttcg cttttccctt ctcgcccgcc     900
gtaataaata gacacccct ccacaccctc tttcccaac ctcgtgttgt tcggagcgca      960
cacacacaca accagatctc ccccaaatcc acccgtcggc acctccgctt caaggtacgc   1020 cgtcgtcct ccccccccc ccctctctac ctttctagac tcggcgttcc ggtccatggt     1080
tagggcccgg tagttctact tctgttcatg tttgtgttag atccgtgttt gtgttagatc   1140
```

```
cgtgctgcta gcgttcgtac acggatgcga cctgtacgtc agacacgttc tgattgctaa    1200
cttgccagtg tttctctttg gggaatcctg ggatggctct agccgttccg cagacgggat    1260
cgatttcatg attttttttg tttcgttgca tagggtttgg tttgcccttt tcctttattt    1320
caatatatgc cgtgcacttg tttgtcgggt catcttttca tgctttttt tgtcttggtt     1380
gtgatgatgt ggtctggttg ggcggtcgtt ctagatcgga gtagaattct gtttcaaact    1440
acctggtgga tttattaatt ttggatctgt atgtgtgtgc catacatatt catagttacg    1500
aattgaagat gatggatgga aatatcgatc taggataggt atacatgttg atgcgggttt    1560
tactgatgca tatacagaga tgcttttgt tcgcttggtt gtgatgatgt ggtgtggttg      1620
ggcggtcgtt cattcgttct agatcggagt agaatactgt ttcaaactac ctggtgtatt    1680
tattaatttt ggaactgtat gtgtgtgtca tacatcttca tagttacgag tttaagatgg    1740
atggaaatat cgatctagga taggtataca tgttgatgtg ggttttactg atgcatatac    1800
atgatggcat atgcagcatc tattcatatg ctctaacctt gagtacctat ctattataat    1860
aaacaagtat gttttataat tattttgatc ttgatatact tggatgatgg catatgcagc    1920
agctatatgt ggatttttt agccctgcct tcatacgcta tttatttgct tggtactgtt     1980
tcttttgtcg atgctcaccc tgttgtttgg tgttacttct gcaggtcgac tctagaggat    2040
ccacaagttt gtacaaaaaa gctgaacgag aaacgtaaaa tgatataaat atcaatatat    2100
taaattagat tttgcataaa aacagacta cataatactg taaaacacaa catatccagt     2160
cactatggcg gccgcattag gcaccccagg ctttacactt tatgcttccg gctcgtataa    2220
tgtgtggatt ttgagttagg atttaaatac gcgttgatcc ggcttactaa agccagata     2280
acagtatgcg tatttgcgcg ctgatttttg cggtataaga atatatactg atatgtatac    2340
ccgaagtatg tcaaaaagag gtatgctatg aagcagcgta ttacagtgac agttgacagc    2400
gacagctatc agttgctcaa ggcatatatg atgtcaatat ctccggtctg gtaagcacaa    2460
ccatgcagaa tgaagcccgt cgtctgcgtg ccgaacgctg gaaagcggaa aatcaggaag    2520
ggatggctga ggtcgcccgg tttattgaaa tgaacggctc ttttgctgac gagaacaggg    2580
gctggtgaaa tgcagtttaa ggtttacacc tataaaagag agagccgtta tcgtctgttt    2640
gtggatgtac agagtgatat cattgacacg cccggtcgac ggatggtgat cccctggcc     2700
agtgcacgtc tgctgtcaga taaagtctcc cgtgaacttt acccggtggt gcatatcggg    2760
gatgaaagct ggcgcatgat gaccaccgat atggccagtg tgccggtctc cgttatcggg    2820
gaagaagtgg ctgatctcag ccaccgcgaa aatgacatca aaaacgccat taacctgatg    2880
ttctggggaa tataaatgtc aggctcccct atacacagcc agtctgcagg tcgaccatag    2940
tgactggata tgttgtgttt tacagtatta tgtagtctgt ttttttatgca aaatctaatt   3000
taatatattg atatttatat cattttacgt ttctcgttca gctttcttgt acaaagtggt    3060
gttaacctag acttgtccat cttctggatt ggccaactta attaatgtat gaaataaaag    3120
gatgcacaca tagtgacatg ctaatcacta taatgtgggc atcaaagttg tgtgttatgt    3180
gtaattacta gttatctgaa taaaagagaa agagatcatc catatttctt atcctaaatg    3240
aatgtcacgt gtcttttataa ttctttgatg aaccagatgc atttcattaa ccaaatccat    3300
atacatataa atattaatca tatataatta atatcaattg ggttagcaaa acaaatctag    3360
tctaggtgtg ttttgcgaat tgcggccgcc accgcggtgg agctcgaatt ccggtccggg    3420
tcacctttgt ccaccaagat ggaactgcgg ccgctcatta attaagtcag gcgcgcctct    3480
agttgaagac acgttcatgt cttcatcgta agaagacact cagtagtctt cggccagaat    3540
```

```
ggccatctgg attcagcagg cctagaaggc catttaaatc ctgaggatct ggtcttccta    3600
aggacccggg atatcggacc gattaaactt taattcggtc cgaagcttgc atgcctgcag    3660
tgcagcgtga cccggtcgtg cccctctcta gagataatga gcattgcatg tctaagttat    3720
aaaaaattac cacatatttt ttttgtcaca cttgtttgaa gtgcagttta tctatcttta    3780
tacatatatt taaactttac tctacgaata atataatcta tagtactaca ataatatcag    3840
tgttttagag aatcatataa atgaacagtt agacatggtc taaaggacaa ttgagtattt    3900
tgacaacagg actctacagt tttatctttt tagtgtgcat gtgttctcct ttttttttgc    3960
aaatagcttc acctatataa tacttcatcc attttattag tacatccatt tagggtttag    4020
ggttaatggt ttttatagac taattttttt agtacatcta ttttattcta ttttagcctc    4080
taaattaaga aaactaaaac tctattttag tttttttatt taataattta gatataaaat    4140
agaataaaat aaagtgacta aaaattaaac aaatacccct taagaaatta aaaaaactaa    4200
ggaaacattt ttcttgtttc gagtagataa tgccagcctg ttaaacgccg tcgacgagtc    4260
taacggacac caaccagcga accagcagcg tcgcgtcggg ccaagcgaag cagacggcac    4320
ggcatctctg tcgctgcctc tggaccccctc tcgagagttc cgctccaccg ttggacttgc    4380
tccgctgtcg gcatccagaa attgcgtggc ggagcggcag acgtgagccg gcacggcagg    4440
cggcctcctc ctcctctcac ggcaccggca gctacggggg attcctttcc caccgctcct    4500
tcgctttccc ttcctcgccc gccgtaataa atagacaccc cctccacacc ctctttcccc    4560
aacctcgtgt tgttcggagc gcacacacac acaaccagat ctcccccaaa tccacccgtc    4620
ggcacctccg cttcaaggta cgccgctcgt cctccccccc ccccctctct accttctcta    4680
gatcggcgtt ccgtccatg catggttagg gcccggtagt tctacttctg ttcatgtttg    4740
tgttagatcc gtgtttgtgt tagatccgtg ctgctagcgt tcgtacacgg atgcgacctg    4800
tacgtcagac acgttctgat tgctaacttg ccagtgtttc tctttgggga atcctgggat    4860
ggctctagcc gttccgcaga cgggatcgat ttcatgattt ttttttgtttc gttgcatagg    4920 gtttggtttg ccctttttcct ttatttcaat atatgccgtg cacttgtttg tcgggtcatc    4980
ttttcatgct tttttttgtc ttggttgtga tgatgtggtc tggttgggcg gtcgttctag    5040
atcggagtag aattctgttt caaactacct ggtggattta ttaattttgg atctgtatgt    5100
gtgtgccata catattcata gttacgaatt gaagatgatg gatggaaata tcgatctagg    5160
ataggtatac atgttgatgc gggttttact gatgcatata cagagatgct ttttgttcgc    5220
ttggttgtga tgatgtggtg tggttgggcg gtcgttcatt cgttctagat cggagtagaa    5280
tactgtttca aactacctgg tgtatttatt aattttggaa ctgtatgtgt gtgtcataca    5340
tcttcatagt tacgagttta agatggatgg aaatatcgat ctaggatagg tatacatgtt    5400
gatgtgggtt ttactgatgc atatacatga tggcatatgc agcatctatt catatgctct    5460
aaccttgagt acctatctat tataataaac aagtatgttt tataattatt ttgatcttga    5520
tatacttgga tgatggcata tgcagcagct atatgtggat ttttttagcc ctgccttcat    5580
acgctattta tttgcttggt actgtttctt ttgtcgatgc tcaccctgtt gtttggtgtt    5640
acttctgcag gtcgactttta acttagccta ggatccacac gacaccatgt ccccgagcg    5700 ccgccccgtc gagatccgcc cggccaccgc cgccgacatg gccgccgtgt gcgacatcgt    5760
gaaccactac atcgagacct ccaccgtgaa cttccgcacc gagccgcaga ccccgcagga    5820
gtggatcgac gacctggagc gcctccagga ccgctacccg tggctcgtgg ccgaggtgga    5880
gggcgtggtg gccggcatcg cctacgccgg cccgtggaag gcccgcaacg cctacgactg    5940
```

```
gaccgtggag tccaccgtgt acgtgtccca ccgccaccag cgcctcggcc tcggctccac    6000
cctctacacc cacctcctca agagcatgga ggcccagggc ttcaagtccg tggtggccgt    6060
gatcggcctc ccgaacgacc cgtccgtgcg cctccacgag gccctcggct acaccgcccg    6120
cggcaccctc cgcgccgccg gctacaagca cggcggctgg cacgacgtcg gcttctggca    6180
gcgcgacttc gagctgccgg ccccgccgcg cccggtgcgc ccggtgacgc agatctgagt    6240
cgaaacctag acttgtccat cttctggatt ggccaactta attaatgtat gaaataaaag    6300
gatgcacaca tagtgacatg ctaatcacta taatgtgggc atcaaagttg tgtgttatgt    6360
gtaattacta gttatctgaa taaaagagaa agagatcatc catatttctt atcctaaatg    6420
aatgtcacgt gtctttataa ttctttgatg aaccagatgc atttcattaa ccaaatccat    6480
atacatataa atattaatca tatataatta atatcaattg ggttagcaaa acaaatctag    6540
tctaggtgtg ttttgcgaat tgcggccgcc accgcggtgg agctcgaatt cattccgatt    6600
aatcgtggcc tcttgctctt caggatgaag agctatgttt aaacgtgcaa gcgctactag    6660
acaattcagt acattaaaaa cgtccgcaat gtgttattaa gttgtctaag cgtcaatttg    6720
tttacaccac aatatatcct gccaccagcc agccaacagc tccccgaccg gcagctcggc    6780
acaaaatcac cactcgatac aggcagccca tcagtccggg acggcgtcag cgggagagcc    6840
gttgtaaggc ggcagacttt gctcatgtta ccgatgctat tcggaagaac ggcaactaag    6900
ctgccgggtt tgaaacacgg atgatctcgc ggagggtagc atgttgattg taacgatgac    6960
agagcgttgc tgcctgtgat caaatatcat ctccctcgca gagatccgaa ttatcagcct    7020
tcttattcat ttctcgctta accgtgacag gctgtcgatc ttgagaacta tgccgacata    7080
ataggaaatc gctggataaa gccgctgagg aagctgagtg gcgctatttc tttagaagtg    7140
aacgttgacg atcgtcgacc gtaccccgat gaattaattc ggacgtacgt tctgaacaca    7200
gctggatact tacttgggcg attgtcatac atgacatcaa caatgtaccc gtttgtgtaa    7260
ccgtctcttg gaggttcgta tgacactagt ggttcccctc agcttgcgac tagatgttga    7320
ggcctaacat tttattagag agcaggctag ttgcttagat acatgatctt caggccgtta    7380
tctgtcaggg caagcgaaaa ttggccattt atgacgacca atgccccgca gaagctccca    7440
tctttgccgc catagacgcc gcgccccct tttggggtgt agaacatcct tttgccagat    7500
gtggaaaaga agttcgttgt cccattgttg gcaatgacgt agtagccggc gaaagtgcga    7560
gacccatttg cgctatatat aagcctacga tttccgttgc gactattgtc gtaattggat    7620
gaactattat cgtagttgct ctcagagttg tcgtaatttg atggactatt gtcgtaattg    7680
cttatggagt tgtcgtagtt gcttggagaa atgtcgtagt tggatgggga gtagtcatag    7740
ggaagacgag cttcatccac taaaacaatt ggcaggtcag caagtgcctg ccccgatgcc    7800
atcgcaagta cgaggcttag aaccaccttc aacagatcgc gcatagtctt ccccagctct    7860
ctaacgcttg agttaagccg cgccgcgaag cggcgtcggc ttgaacgaat tgttagacat    7920
tatttgccga ctaccttggt gatctcgcct ttcacgtagt gaacaaattc ttccaactga    7980
tctgcgcgcg aggccaagcg atcttcttgt ccaagataag cctgcctagc ttcaagtatg    8040
acgggctgat actgggccgg caggcgctcc attgcccagt cggcagcgac atccttcggc    8100
gcgattttgc cggttactgc gctgtaccaa atgcgggaca acgtaagcac tacatttcgc    8160
tcatcgccag cccagtcggg cggcgagttc atagcgtta aggtttcatt tagcgcctca    8220
aatagatcct gttcaggaac cggatcaaag agttcctccg ccgctggacc taccaaggca    8280
acgctatgtt ctcttgcttt tgtcagcaag atagccagat caatgtcgat cgtggctggc    8340
```

```
tcgaagatac ctgcaagaat gtcattgcgc tgccattctc caaattgcag ttcgcgctta   8400
gctggataac gccacggaat gatgtcgtcg tgcacaacaa tggtgacttc tacagcgcgg   8460
agaatctcgc tctctccagg ggaagccgaa gtttccaaaa ggtcgttgat caaagctcgc   8520
cgcgttgttt catcaagcct tacagtcacc gtaaccagca atcaatatc  actgtgtggc   8580
ttcaggccgc catccactgc ggagccgtac aaatgtacgg ccagcaacgt cggttcgaga   8640
tggcgctcga tgacgccaac tacctctgat agttgagtcg atacttcggc gatcaccgct   8700
tccctcatga tgtttaactc ctgaattaag ccgcgccgcg aagcggtgtc ggcttgaatg   8760
aattgttagg cgtcatcctg tgctcccgag aaccagtacc agtacatcgc tgtttcgttc   8820
gagacttgag gtctagtttt atacgtgaac aggtcaatgc cgccgagagt aaagccacat   8880
tttgcgtaca aattgcaggc aggtacattg ttcgtttgtg tctctaatcg tatgccaagg   8940
agctgtctgc ttagtgccca cttttttcgca aattcgatga gactgtgcgc gactcctttg   9000
cctcggtgcg tgtgcgacac aacaatgtgt tcgatagagg ctagatcgtt ccatgttgag   9060
ttgagttcaa tcttcccgac aagctcttgg tcgatgaatg cgccatagca agcagagtct   9120
tcatcagagt catcatccga gatgtaatcc ttccggtagg ggctcacact tctggtagat   9180
agttcaaagc cttggtcgga taggtgcaca tcgaacactt cacgaacaat gaaatggttc   9240
tcagcatcca atgtttccgc cacctgctca gggatcaccg aaatcttcat atgacgccta   9300
acgcctggca cagcggatcg caaacctggc gcggcttttg gcacaaaagg cgtgacaggt   9360
ttgcgaatcc gttgctgcca cttgttaacc cttttgccag atttggtaac tataattttat  9420
gttagaggcg aagtcttggg taaaaactgg cctaaaattg ctggggattt caggaaagta   9480
aacatcacct tccggctcga tgtctattgt agatatatgt agtgtatcta cttgatcggg   9540
ggatctgctg cctcgcgcgt ttcggtgatg acggtgaaaa cctctgacac atgcagctcc   9600
cggagacggt cacagcttgt ctgtaagcgg atgccgggag cagacaagcc cgtcagggcg   9660
cgtcagcggg tgttggcggg tgtcggggcg cagccatgac ccagtcacgt agcgatagcg   9720
gagtgtatac tggcttaact atgcggcatc agagcagatt gtactgagag tgcaccatat   9780
gcggtgtgaa ataccgcaca gatgcgtaag gagaaaatac cgcatcaggc gctcttccgc   9840
ttcctcgctc actgactcgc tgcgctcggt cgttcggctg cggcgagcgg tatcagctca   9900
ctcaaaggcg gtaatacggt tatccacaga atcaggggat aacgcaggaa agaacatgtg   9960
agcaaaaggc cagcaaaagg ccaggaaccg taaaaaggcc gcgttgctgg cgttttttcca  10020
taggctccgc cccctgacg  agcatcacaa aaatcgacgc tcaagtcaga ggtggcgaaa  10080
cccgacagga ctataaagat accaggcgtt tccccctgga agctccctcg tgcgctctcc  10140
tgttccgacc ctgccgctta ccggatacct gtccgccttt ctcccttcgg gaagcgtggc  10200
gctttctcat agctcacgct gtaggtatct cagttcggtg taggtcgttc gctccaagct  10260
gggctgtgtg cacgaacccc ccgttcagcc cgaccgctgc gccttatccg gtaactatcg  10320
tcttgagtcc aacccggtaa gacacgactt atcgccactg gcagcagcca ctggtaacag  10380
gattagcaga gcgaggtatg taggcggtgc tacagagttc ttgaagtggt ggcctaacta  10440
cggctacact agaaggacag tatttggtat ctgcgctctg ctgaagccag ttaccttcgg  10500
aaaaagagtt ggtagctctt gatccggcaa acaaaccacc gctggtagcg gtggtttttt  10560
tgtttgcaag cagcagatta cgcgcagaaa aaaaggatct caagaagatc ctttgatctt  10620
ttctacgggg tctgacgctc agtggaacga aaactcacgt taagggattt tggtcatgag  10680
attatcaaaa aggatcttca cctagatcct tttaaattaa aaatgaagtt ttaaatcaat  10740
```

```
ctaaagtata tatgagtaaa cttggtctga cagttaccaa tgcttaatca gtgaggcacc   10800
tatctcagcg atctgtctat ttcgttcatc catagttgcc tgactcccg  tcgtgtagat   10860 aactacgata cgggagggct taccatctgg ccccagtgct gcaatgatac cgcgagaccc   10920
acgctcaccg gctccagatt tatcagcaat aaaccagcca gccggaaggg ccgagcgcag   10980
aagtggtcct gcaactttat ccgcctccat ccagtctatt aattgttgcc gggaagctag   11040
agtaagtagt tcgccagtta atagtttgcg caacgttgtt gccattgctg caggggggg    11100 gggggggggg gacttccatt gttcattcca cggacaaaaa cagagaaagg aaacgacaga   11160
ggccaaaaag cctcgctttc agcacctgtc gtttcctttc ttttcagagg gtattttaaa   11220
taaaaacatt aagttatgac gaagaagaac ggaaacgcct taaaccggaa aattttcata   11280
aatagcgaaa acccgcgagg tcgccgcccc gtaacctgtc ggatcaccgg aaaggacccg   11340
taaagtgata atgattatca tctacatatc acaacgtgcg tggaggccat caaaccacgt   11400
caaataatca attatgacgc aggtatcgta ttaattgatc tgcatcaact taacgtaaaa   11460
acaacttcag acaatacaaa tcagcgacac tgaatacggg gcaacctcat gtccccccc    11520 cccccccccc tgcaggcatc gtggtgtcac gctcgtcgtt tggtatggct tcattcagct   11580
ccggttccca acgatcaagg cgagttacat gatccccat  gttgtgcaaa aaagcggtta   11640
gctccttcgg tcctccgatc gttgtcagaa gtaagttggc cgcagtgtta tcactcatgg   11700
ttatggcagc actgcataat tctcttactg tcatgccatc cgtaagatgc ttttctgtga   11760
ctggtgagta ctcaaccaag tcattctgag aatagtgtat gcggcgaccg agttgctctt   11820
gcccggcgtc aacacgggat aataccgcgc cacatagcag aactttaaaa gtgctcatca   11880
ttggaaaacg ttcttcgggg cgaaaactct caaggatctt accgctgttg agatccagtt   11940
cgatgtaacc cactcgtgca cccaactgat cttcagcatc ttttactttc accagcgttt   12000
ctgggtgagc aaaaacagga aggcaaaatg ccgcaaaaaa gggaataagg gcgacacgga   12060
aatgttgaat actcatactc ttcctttttc aatattattg aagcatttat cagggttatt   12120
gtctcatgag cggatacata tttgaatgta tttagaaaaa taaacaaata ggggttccgc   12180
gcacatttcc ccgaaaagtg ccacctgacg tctaagaaac cattattatc atgacattaa   12240
cctataaaaa taggcgtatc acgaggccct ttcgtcttca agaattggtc gacgatcttg   12300
ctgcgttcgg atattttcgt ggagttcccg ccacagaccc ggattgaagg cgagatccag   12360
caactcgcgc cagatcatcc tgtgacggaa cttggcgcg  tgatgactgg ccaggacgtc   12420
ggccgaaaga gcgacaagca gatcacgctt ttcgacagcg tcggatttgc gatcgaggat   12480
ttttcggcgc tgcgctacgt ccgcgaccgc gttgagggat caagccacag cagcccactc   12540
gaccttctag ccgacccaga cgagccaagg gatctttttg gaatgctgct ccgtcgtcag   12600
gctttccgac gtttgggtgg ttgaacagaa gtcattatcg tacggaatgc caagcactcc   12660 cgagggaac  cctgtggttg gcatgcacat acaaatggac gaacggataa accttttcac   12720 gccctttttaa atatccgtta ttctaataaa cgctctttc  tcttaggttt acccgccaat   12780
atatcctgtc aaacactgat agtttaaact gaaggcggga aacgacaatc tgatcatgag   12840
cggagaatta agggagtcac gttatgaccc ccgccgatga cgcgggacaa gccgttttac   12900
gtttggaact gacagaaccg caacgttgaa ggagccactg agcaagctgg tacgattgta   12960
atacgactca ctatagggcg aattgagcgc tgtttaaacg ctcttcaact ggaagagcg    13019
```

<210> SEQ ID NO 9
<211> LENGTH: 2991

<212> TYPE: DNA
<213> ORGANISM: Artificial Sequence
<220> FEATURE:
<223> OTHER INFORMATION: PHP20234 construct

<400> SEQUENCE: 9

| | | | | |
|---|---|---|---|---|
| ctttcctgcg ttatccctg attctgtgga taaccgtatt accgcctttg agtgagctga | 60 |
| taccgctcgc cgcagccgaa cgaccgagcg cagcgagtca gtgagcgagg aagcggaaga | 120 |
| gcgcccaata cgcaaaccgc ctctccccgc gcgttggccg attcattaat gcagctggca | 180 |
| cgacaggttt cccgactgga aagcgggcag tgagcgcaac gcaattaata cgcgtaccgc | 240 |
| tagccaggaa gagtttgtag aaacgcaaaa aggccatccg tcaggatggc cttctgctta | 300 |
| gtttgatgcc tggcagttta tggcgggcgt cctgcccgcc accctccggg ccgttgcttc | 360 |
| acaacgttca atccgctcc cggcggattt gtcctactca ggagagcgtt caccgacaaa | 420 |
| caacagataa aacgaaaggc ccagtcttcc gactgagcct ttcgttttat ttgatgcctg | 480 |
| gcagttccct actctcgcgt taacgctagc atggatgttt cccagtcac gacgttgtaa | 540 |
| aacgacggcc agtcttaagc tcgggccctg cagctctaga gctcgaattc tacaggtcac | 600 |
| taataccatc taagtagttg gttcatagtg actgcatatg ttgtgtttta cagtattatg | 660 |
| tagtctgttt tttatgcaaa atctaattta atatattgat attatatca ttttacgttt | 720 |
| ctcgttcaac tttcttgtac aaagtggccg ttaacggatc cagacttgtc catcttctgg | 780 |
| attggccaac ttaattaatg tatgaaataa aaggatgcac acatagtgac atgctaatca | 840 |
| ctataatgtg gcatcaaag ttgtgtgtta tgtgtaatta ctagttatct gaataaaaga | 900 |
| gaaagagatc atccatattt cttatcctaa atgaatgtca cgtgtcttta taattctttg | 960 |
| atgaaccaga tgcatttcat taaccaaatc catatacata taaatattaa tcatatataa | 1020 |
| ttaatatcaa ttgggttagc aaaacaaatc tagtctaggt gtgttttgcg aattgcggca | 1080 |
| agcttgcggc cgccccgggc aactttatta tacaaagttg gcattataaa aaagcattgc | 1140 |
| ttatcaattt gttgcaacga acaggtcact atcagtcaaa ataaaatcat tatttggagc | 1200 |
| tccatggtag cgttaacgcg gccgcgatat cccctatagt gagtcgtatt acatggtcat | 1260 |
| agctgtttcc tggcagctct ggcccgtgtc tcaaaatctc tgatgttaca ttgcacaaga | 1320 |
| taaaaatata tcatcatgaa caataaaact gtctgcttac ataaacagta atacaagggg | 1380 |
| tgttatgagc catattcaac gggaaacgtc gaggccgcga ttaaattcca acatggatgc | 1440 |
| tgatttatat gggtataaat gggctcgcga taatgtcggg caatcaggtg cgacaatcta | 1500 |
| tcgcttgtat gggaagcccg atgcgccaga gttgtttctg aaacatggca aaggtagcgt | 1560 |
| tgccaatgat gttacagatg agatggtcag actaaactgg ctgacggaat ttatgcctct | 1620 |
| tccgaccatc aagcatttta tccgtactcc tgatgatgca tggttactca ccactgcgat | 1680 |
| ccccggaaaa acagcattcc aggtattaga agaatatcct gattcaggtg aaaatattgt | 1740 |
| tgatgcgctg gcagtgttcc tgcgccggtt gcattcgatt cctgtttgta attgtccttt | 1800 |
| taacagcgat cgcgtatttc gtctcgctca ggcgcaatca cgaatgaata acggtttggt | 1860 |
| tgatgcgagt gattttgatg acgagcgtaa tggctggcct gttgaacaag tctggaaaga | 1920 |
| aatgcataaa cttttgccat tctcaccgga ttcagtcgtc actcatggtg atttctcact | 1980 |
| tgataacctt atttttgacg aggggaaatt aataggttgt attgatgttg gacgagtcgg | 2040 |
| aatcgcagac cgataccagg atcttgccat cctatggaac tgcctcggtg agttttctcc | 2100 |
| ttcattacag aaacggcttt ttcaaaaata tggtattgat aatcctgata tgaataaatt | 2160 |
| gcagtttcat ttgatgctcg atgagttttt ctaatcagaa ttggttaatt ggttgtaaca | 2220 |

```
ctggcagagc attacgctga cttgacggga cggcgcaagc tcatgaccaa aatcccttaa    2280
cgtgagttac gcgtcgttcc actgagcgtc agaccccgta gaaaagatca aaggatcttc    2340
ttgagatcct ttttttctgc gcgtaatctg ctgcttgcaa acaaaaaaac caccgctacc    2400
agcggtggtt tgtttgccgg atcaagagct accaactctt tttccgaagg taactggctt    2460
cagcagagcg cagataccaa atactgtcct tctagtgtag ccgtagttag gccaccactt    2520
caagaactct gtagcaccgc ctacatacct cgctctgcta atcctgttac cagtggctgc    2580
tgccagtggc gataagtcgt gtcttaccgg gttggactca agacgatagt taccggataa    2640
ggcgcagcgg tcgggctgaa cggggggttc gtgcacacag cccagcttgg agcgaacgac    2700
ctacaccgaa ctgagatacc tacagcgtga gcattgagaa agcgccacgc ttcccgaagg    2760
gagaaaggcg gacaggtatc cggtaagcgg cagggtcgga acaggagagc gcacgaggga    2820
gcttccaggg ggaaacgcct ggtatcttta tagtcctgtc gggtttcgcc acctctgact    2880
tgagcgtcga ttttttgtgat gctcgtcagg ggggcggagc ctatggaaaa acgccagcaa    2940
cgcggccttt ttacggttcc tggccttttg ctggcctttt gctcacatgt t              2991
```

<210> SEQ ID NO 10
<211> LENGTH: 13278
<212> TYPE: DNA
<213> ORGANISM: Artificial Sequence
<220> FEATURE:
<223> OTHER INFORMATION: PHP22655 construct (destination vector)

<400> SEQUENCE: 10

```
aagctggtac gattgtaata cgactcacta tagggcgaat tgagcgctgt ttaaacgctc      60
ttcaactgga agagcggtta ccagagctgg tcacctttgt ccaccaagat ggaactgcgg     120
ccgctcatta attaagtcag gcgcgcctct agttgaagac acgttcatgt cttcatcgta     180
agaagacact cagtagtctt cggccagaat ggcccggacc gaagctggcc gctctagaac     240
tagtggatct cgatgtgtag tctacgagaa gggttaaccg tctcttcgtg agaataaccg     300
tggcctaaaa ataagccgat gaggataaat aaaatgtggt ggtacagtac ttcaagaggt     360
ttactcatca agaggatgct tttccgatga gctctagtag tacatcggac ctcacatacc     420
tccattgtgg tgaaatattt tgtgctcatt tagtgatggg taaattttgt ttatgtcact     480
ctaggttttg acatttcagt tttgccactc ttaggttttg acaaataatt tccattccgc     540
ggcaaaagca aaacaatttt attttacttt taccactctt agctttcaca atgtatcaca     600
aatgccactc tagaaattct gtttatgcca cagaatgtga aaaaaaacac tcacttattt     660
gaagccaagg tgttcatggc atggaaatgt gacataaagt aacgttcgtg tataagaaaa     720
aattgtactc ctcgtaacaa gagacggaaa catcatgaga caatcgcgtt tggaaggctt     780
tgcatcacct ttggatgatg cgcatgaatg gagtcgtctg cttgctagcc ttcgcctacc     840
gcccactgag tccgggcggc aactaccatc ggcgaacgac ccagctgacc tctaccgacc     900
ggacttgaat gcgctacctt cgtcagcgac gatggccgcg tacgctggcg acgtgccccc     960
gcatgcatgg cggcacatgg cgagctcaga ccgtgcgtgg ctggctacaa atacgtaccc    1020
cgtgagtgcc ctagctagaa acttacacct gcaactgcga gagcgagcgt gtgagtgtag    1080
ccgagtagat cccccggtcg ccaccatggc ctcctccgaa aacgtcatca ccgagttcat    1140
gcgcttcaag gtgcgcatgg agggcaccgt gaacggccac gagttcgaga tcgagggcga    1200
gggcgagggc cgccctacg agggccacaa caccgtgaag ctgaaggtga ccaagggcgg    1260 cccccctgccc ttcgcctggg acatcctgtc cccccagttc cagtacggct ccaaggtgta    1320
```

```
cgtgaagcac cccgccgaca tccccgacta caagaagctg tccttcccccg agggcttcaa    1380 gtgggagcgc gtgatgaact tcgaggacgg cggcgtggcg accgtgaccc aggactcctc    1440
cctgcaggac ggctgcttca tctacaaggt gaagttcatc ggcgtgaact tcccctccga    1500
cggccccgtg atgcagaaga agaccatggg ctgggaggcc tccaccgagc gcctgtaccc    1560
ccgcgacggc gtgctgaagg gcgagaccca caaggccctg aagctgaagg acggcggcca    1620
ctacctggtg gagttcaagt ccatctacat ggccaagaag cccgtgcagc tgcccggcta    1680
ctactacgtg gacgccaagc tggacatcac ctcccacaac gaggactaca ccatcgtgga    1740
gcagtacgag cgcaccgagg ccgccacca cctgttcctg tagcggccca tggatattcg    1800
aacgcgtagg taccacatgg ttaacctaga cttgtccatc ttctggattg gccaacttaa    1860
ttaatgtatg aaataaaagg atgcacacat agtgacatgc taatcactat aatgtgggca    1920
tcaaagttgt gtgttatgtg taattactag ttatctgaat aaaagagaaa gagatcatcc    1980
atatttctta tcctaaatga atgtcacgtg tcttttataat tctttgatga accagatgca    2040
tttcattaac caaatccata tacatataaaa tattaatcat atataattaa tatcaattgg    2100
gttagcaaaa caaatctagt ctaggtgtgt tttgcgaatg cggccgccac cgcggtggag    2160
ctcgaattcc ggtccgggcc tagaaggcca tttaaatcct gaggatctgg tcttcctaag    2220
gacccgggat atcgctatca actttgtata gaaaagttga acgagaaacg taaaatgata    2280
taaatatcaa tatattaaat tagattttgc ataaaaaaca gactacataa tactgtaaaa    2340
cacaacatat ccagtcacta tggtcgacct gcagactggc tgtgtataag ggagcctgac    2400
atttatattc cccagaacat caggttaatg gcgttttga tgtcattttc gcggtggctg    2460
agatcagcca cttcttcccc gataacggag accggcacac tggccatatc ggtggtcatc    2520
atgcgccagc tttcatcccc gatatgcacc accgggtaaa gttcacgggg gactttatct    2580
gacagcagac gtgcactggc caggggggatc ccatccgtc gcccgggcgt gtcaataata    2640
tcactctgta catccacaaa cagacgataa cggctctctc ttttataggt gtaaaccttaa   2700 aactgcattt caccagccccc tgttctcgtc ggcaaaagag ccgttcattt caataaaccg    2760
ggcgacctca gccatcccctt cctgatttttc cgctttccag cgttcggcac gcagacgacg    2820
ggcttcattc tgcatggttg tgcttaccga accggagata ttgacatcat atatgccttg    2880
agcaactgat agctgtcgct gtcaactgtc actgtaatac gctgcttcat agcataccctc    2940 tttttgacat acttcgggta tacatatcag tatatattct tataccgcaa aaatcagcgc    3000
gcaaatacgc atactgttat ctggctttta gtaagccgga tcctctagat tacgccccgc    3060
ctgccactca tcgcagtact gttgtaattc attaagcatt ctgccgacat ggaagccatc    3120
acaaacggca tgatgaacct gaatcgccag cggcatcagc accttgtcgc cttgcgtata    3180
atatttgccc atggtgaaaa cggggcgaa gaagttgtcc atattggcca cgtttaaatc    3240
aaaactggtg aaactcaccc agggattggc tgagacgaaa aacatattct caataaaccc    3300
tttagggaaa taggccaggt tttcaccgta acacgccaca tcttgcgaat atatgtgtag    3360
aaactgccgg aaatcgtcgt ggtattcact ccagagcgat gaaaacgttt cagtttgctc    3420
atggaaaacg gtgtaacaag ggtgaacact atcccatatc accagctcac cgtctttcat    3480
tgccatacgg aattccggat gagcattcat caggcgggca agaatgtgaa taaaggccgg    3540
ataaaacttg tgcttatttt tctttacggt ctttaaaaag gccgtaatat ccagctgaac    3600
ggtctggtta taggtacatt gagcaactga ctgaaatgcc tcaaaatgtt ctttacgatg    3660
ccattgggat atatcaacgg tggtatatcc agtgatttttt ttctccattt tagcttcctt    3720
```

```
agctcctgaa aatctcgacg gatcctaact caaaatccac acattatacg agccggaagc   3780
ataaagtgta aagcctgggg tgccctaatg cggccgccat agtgactgga tatgttgtgt   3840
tttacagtat tatgtagtct gttttttatg caaaatctaa tttaatatat tgatattttat  3900
atcattttac gtttctcgtt caactttatt atacaaagtt gatagatatc ggaccgatta   3960
aactttaatt cggtccgaag cttgcatgcc tgcagtgcag cgtgacccgg tcgtgcccct   4020
ctctagagat aatgagcatt gcatgtctaa gttataaaaa attaccacat attttttttg   4080
tcacacttgt ttgaagtgca gtttatctat ctttatacat atatttaaac tttactctac   4140
gaataatata atctatagta ctacaataat atcagtgttt tagagaatca tataaatgaa   4200
cagttagaca tggtctaaag gacaattgag tattttgaca acaggactct acagttttat   4260
cttttagtg tgcatgtgtt ctccttttt tttgcaaata gcttcaccta tataatactt     4320
catccatttt attagtacat ccatttaggg tttagggtta atggtttta tagactaatt    4380
tttttagtac atctatttta ttctatttta gcctctaaat taagaaaact aaaactctat   4440
tttagttttt ttatttaata atttagatat aaaatagaat aaaataaagt gactaaaaat   4500
taaacaaata ccctttaaga aattaaaaaa actaaggaaa catttttctt gtttcgagta   4560
gataatgcca gcctgttaaa cgccgtcgac gagtctaacg acaccaacc agcgaaccag    4620
cagcgtcgcg tcgggccaag cgaagcagac ggcacggcat ctctgtcgct gcctctggac   4680
ccctctcgag agttccgctc caccgttgga cttgctccgc tgtcggcatc cagaaattgc   4740
gtggcggagc ggcagacgtg agccggcacg gcaggcggcc tcctcctcct ctcacggcac   4800
cggcagctac gggggattcc tttcccaccg ctccttcgct ttcccttcct cgcccgccgt   4860
aataaataga caccccctcc acaccctctt tccccaacct cgtgttgttc ggagcgcaca   4920
cacacacaac cagatctccc ccaaatccac ccgtcggcac ctccgcttca aggtacgccg   4980
ctcgtcctcc cccccccccc tctctacctt ctctagatcg gcgttccggt ccatgcatgg   5040
ttagggcccg gtagttctac ttctgttcat gtttgtgtta gatccgtgtt tgtgttagat   5100
ccgtgctgct agcgttcgta cacggatgcg acctgtacgt cagacacgtt ctgattgcta   5160
acttgccagt gtttctcttt ggggaatcct gggatggctc tagccgttcc gcagacggga   5220
tcgatttcat gatttttttt gtttcgttgc atagggtttg gtttgcccct ttcctttatt   5280
tcaatatatg ccgtgcactt gtttgtcggg tcatcttttc atgcttttttt ttgtcttggt   5340
tgtgatgatg tggtctggtt gggcggtcgt tctagatcgg agtagaattc tgtttcaaac   5400
tacctggtgg atttattaat tttggatctg tatgtgtgtg ccatacatat tcatagttac   5460
gaattgaaga tgatggatgg aaatatcgat ctaggatagg tatacatgtt gatgcgggtt   5520
ttactgatgc atatacagag atgcttttg ttcgcttggt tgtgatgatg tggtgtggtt    5580
gggcggtcgt tcattcgttc tagatcggag tagaatactg tttcaaacta cctggtgtat   5640
ttattaattt tggaactgta tgtgtgtgtc atacatcttc atagttacga gtttaagatg   5700
gatgaaaata tcgatctagg ataggtatac atgttgatgt gggttttact gatgcatata   5760
catgatggca tatgcagcat ctattcatat gctctaacct tgagtaccta tctattataa   5820
taaacaagta tgttttataa ttattttgat cttgatatac ttggatgatg gcatatgcag   5880
cagctatatg tggatttttt tagccctgcc ttcatacgct atttatttgc ttggtactgt   5940
ttcttttgtc gatgctcacc ctgttgtttg gtgttacttc tgcaggtcga ctttaactta   6000
gcctaggatc cacacgacac catgtccccc gagcgccgcc ccgtcgagat ccgcccggcc   6060
accgccgccg acatggccgc cgtgtgcgac atcgtgaacc actacatcga gacctccacc   6120
```

```
gtgaacttcc gcaccgagcc gcagacccccg caggagtgga tcgacgacct ggagcgcctc   6180
caggaccgct acccgtggct cgtggccgag gtggagggcg tggtggccgg catcgcctac   6240
gccggcccgt ggaaggcccg caacgcctac gactggaccg tggagtccac cgtgtacgtg   6300
tcccaccgcc accagcgcct cggcctcggc tccaccctct acacccacct cctcaagagc   6360
atggaggccc agggcttcaa gtccgtggtg gccgtgatcg gcctcccgaa cgacccgtcc   6420
gtgcgcctcc acgaggccct cggctacacc gcccgcggca ccctccgcgc cgccggctac   6480
aagcacggcg gctggcacga cgtcggcttc tggcagcgcg acttcgagct gccgccccg    6540 ccgcgcccgg tgcgcccggt gacgcagatc tgagtcgaaa cctagacttg tccatcttct   6600
ggattggcca acttaattaa tgtatgaaat aaaaggatgc acacatagtg acatgctaat   6660
cactataatg tgggcatcaa agttgtgtgt tatgtgtaat tactagttat ctgaataaaa   6720
gagaaagaga tcatccatat ttcttatcct aaatgaatgt cacgtgtctt tataattctt   6780
tgatgaacca gatgcatttc attaaccaaa tccatataca tataaatatt aatcatatat   6840
aattaatatc aattgggtta gcaaaacaaa tctagtctag gtgtgttttg cgaattgcgg   6900
ccgccaccgc ggtggagctc gaattcattc cgattaatcg tggcctcttg ctcttcagga   6960
tgaagagcta tgtttaaacg tgcaagcgct actagacaat tcagtacatt aaaaacgtcc   7020
gcaatgtgtt attaagttgt ctaagcgtca atttgtttac accacaatat atcctgccac   7080
cagccagcca acagctcccc gaccggcagc tcggcacaaa atcaccactc gatacaggca   7140
gcccatcagt ccgggacggc gtcagcggga gagccgttgt aaggcggcag actttgctca   7200
tgttaccgat gctattcgga agaacggcaa ctaagctgcc gggtttgaaa cacggatgat   7260
ctcgcggagg gtagcatgtt gattgtaacg atgacagagc gttgctgcct gtgatcaaat   7320
atcatctccc tcgcagagat ccgaattatc agccttctta ttcatttctc gcttaaccgt   7380
gacaggctgt cgatcttgag aactatgccg acataatagg aaatcgctgg ataaagccgc   7440
tgaggaagct gagtggcgct atttctttag aagtgaacgt tgacgatcgt cgaccgtacc   7500
ccgatgaatt aattcggacg tacgttctga acacagctgg atacttactt gggcgattgt   7560
catacatgac atcaacaatg tacccgtttg tgtaaccgtc tcttggaggt tcgtatgaca   7620
ctagtggttc ccctcagctt gcgactagat gttgaggcct aacatttat tagagagcag    7680 gctagttgct tagatacatg atcttcaggc cgttatctgt cagggcaagc gaaaattggc   7740
catttatgac gaccaatgcc ccgcagaagc tcccatcttt gccgccatag acgccgcgcc   7800
ccccttttgg ggtgtagaac atccttttgc cagatgtgga aaagaagttc gttgtcccat   7860
tgttggcaat gacgtagtag ccggcgaaag tgcgagaccc atttgcgcta tatataagcc   7920
tacgatttcc gttgcgacta ttgtcgtaat tggatgaact attatcgtag ttgctctcag   7980
agttgtcgta atttgatgga ctattgtcgt aattgcttat ggagttgtcg tagttgcttg   8040
gagaaatgtc gtagttggat ggggagtagt cataggggag acgagcttca tccactaaaa   8100
caattggcag gtcagcaagt gcctgccccg atgccatcgc aagtacgagg cttagaacca   8160
ccttcaacag atcgcgcata gtcttcccca gctctctaac gcttgagtta agccgcgcccg   8220 cgaagcggcg tcggcttgaa cgaattgtta gacattattt gccgactacc ttggtgatct   8280 cgccttttcac gtagtgaaca aattcttcca actgatctgc gcgcgaggcc aagcgatctt   8340
cttgtccaag ataagcctgc ctagcttcaa gtatgacggg ctgatactgg gccggcaggc   8400
gctccattgc ccagtcggca gcgacatcct tcggcgcgat tttgccggtt actgcgctgt   8460
accaaatgcg ggacaacgta agcactacat ttcgctcatc gccagcccag tcgggcggcg   8520
```

```
agttccatag cgttaaggtt tcatttagcg cctcaaatag atcctgttca ggaaccggat    8580
caaagagttc ctccgccgct ggacctacca aggcaacgct atgttctctt gcttttgtca    8640
gcaagatagc cagatcaatg tcgatcgtgg ctggctcgaa gatacctgca agaatgtcat    8700
tgcgctgcca ttctccaaat tgcagttcgc gcttagctgg ataacgccac ggaatgatgt    8760
cgtcgtgcac aacaatggtg acttctacag cgcggagaat ctcgctctct ccaggggaag    8820
ccgaagtttc caaaaggtcg ttgatcaaag ctcgccgcgt tgtttcatca agccttacag    8880
tcaccgtaac cagcaaatca atatcactgt gtggcttcag gccgccatcc actgcggagc    8940
cgtacaaatg tacggccagc aacgtcggtt cgagatggcg ctcgatgacg ccaactacct    9000
ctgatagttg agtcgatact tcggcgatca ccgcttccct catgatgttt aactcctgaa    9060
ttaagccgcg ccgcgaagcg gtgtcggctt gaatgaattg ttaggcgtca tcctgtgctc    9120
ccgagaacca gtaccagtac atcgctgttt cgttcgagac ttgaggtcta gttttatacg    9180
tgaacaggtc aatgccgccg agagtaaagc cacattttgc gtacaaattg caggcaggta    9240
cattgttcgt ttgtgtctct aatcgtatgc caaggagctg tctgcttagt gcccactttt    9300
tcgcaaattc gatgagactg tgcgcgactc ctttgcctcg gtgcgtgtgc gacacaacaa    9360
tgtgttcgat agaggctaga tcgttccatg ttgagttgag ttcaatcttc ccgacaagct    9420
cttggtcgat gaatgcgcca tagcaagcag agtcttcatc agagtcatca tccgagatgt    9480
aatccttccg gtaggggctc acacttctgg tagatagttc aaagccttgg tcggataggt    9540
gcacatcgaa cacttcacga acaatgaaat ggttctcagc atccaatgtt tccgccacct    9600
gctcagggat caccgaaatc ttcatatgac gcctaacgcc tggcacagcg gatcgcaaac    9660
ctggcgcggt ttttggcaca aaaggcgtga caggtttgcg aatccgttgc tgccacttgt    9720
taaccctttt gccagatttg gtaactataa tttatgttag aggcgaagtc ttgggtaaaa    9780
actggcctaa aattgctggg gatttcagga aagtaaacat caccttccgg ctcgatgtct    9840
attgtagata tatgtagtgt atctacttga tcggggatc tgctgcctcg cgcgtttcgg    9900
tgatgacggt gaaaacctct gacacatgca gctcccggag acggtcacag cttgtctgta    9960
agcggatgcc gggagcagac aagcccgtca gggcgcgtca gcgggtgttg gcgggtgtcg    10020
gggcgcagcc atgacccagt cacgtagcga tagcggagtg tatactggct taactatgcg    10080
gcatcagagc agattgtact gagagtgcac catatgcggt gtgaaatacc gcacagatgc    10140
gtaaggagaa ataccgcat caggcgctct tccgcttcct cgctcactga ctcgctgcgc    10200
tcggtcgttc ggctgcggcg agcggtatca gctcactcaa aggcggtaat acggttatcc    10260
acagaatcag gggataacgc aggaaagaac atgtgagcaa aaggccagca aaaggccagg    10320
aaccgtaaaa aggccgcgtt gctggcgttt ttccataggc tccgcccccc tgacgagcat    10380
cacaaaaatc gacgctcaag tcagaggtgg cgaaacccga caggactata agataccagg    10440
gcgtttcccc ctggaagctc cctcgtgcgc tctcctgttc cgaccctgcc gcttaccgga    10500
tacctgtccg cctttctccc ttcgggaagc gtggcgcttt ctcatagctc acgctgtagg    10560
tatctcagtt cggtgtaggt cgttcgctcc aagctgggct gtgtgcacga accccccgtt    10620
cagcccgacc gctgcgcctt atccggtaac tatcgtcttg agtccaaccc ggtaagacac    10680
gacttatcgc cactggcagc agccactggt aacaggatta gcagagcgag gtatgtaggc    10740
ggtgctacag agttcttgaa gtggtggcct aactacggct acactagaag gacagtattt    10800
ggtatctgcg ctctgctgaa gccagttacc ttcggaaaaa gagttggtag ctcttgatcc    10860
ggcaaacaaa ccaccgctgg tagcggtggt ttttttgttt gcaagcagca gattacgcgc    10920
```

```
agaaaaaaag gatctcaaga agatcctttg atcttttcta cggggtctga cgctcagtgg    10980
aacgaaaact cacgttaagg gattttggtc atgagattat caaaaaggat cttcacctag    11040
atccttttaa attaaaaatg aagttttaaa tcaatctaaa gtatatatga gtaaacttgg    11100
tctgacagtt accaatgctt aatcagtgag gcacctatct cagcgatctg tctatttcgt    11160
tcatccatag ttgcctgact ccccgtcgtg tagataacta cgatacggga gggcttacca    11220
tctggcccca gtgctgcaat gataccgcga gacccacgct caccggctcc agatttatca    11280
gcaataaacc agccagccgg aagggccgag cgcagaagtg gtcctgcaac tttatccgcc    11340
tccatccagt ctattaattg ttgccgggaa gctagagtaa gtagttcgcc agttaatagt    11400
ttgcgcaacg ttgttgccat tgctgcaggg ggggggggg ggggggactt ccattgttca    11460
ttccacggac aaaacagag aaaggaaacg acagaggcca aaaagcctcg ctttcagcac    11520
ctgtcgtttc ctttcttttc agagggtatt ttaaataaaa acattaagtt atgacgaaga    11580
agaacggaaa cgccttaaac cggaaaattt tcataaatag cgaaacccg cgaggtcgcc    11640
gccccgtaac ctgtcggatc accggaaagg acccgtaaag tgataatgat tatcatctac    11700
atatcacaac gtgcgtggag gccatcaaac cacgtcaaat aatcaattat gacgcaggta    11760
tcgtattaat tgatctgcat caacttaacg taaaaacaac ttcagacaat acaaatcagc    11820
gacactgaat acgggcaac ctcatgtccc cccccccccc ccccctgcag gcatcgtggt    11880
gtcacgctcg tcgtttggta tggcttcatt cagctccggt tcccaacgat caaggcgagt    11940
tacatgatcc cccatgttgt gcaaaaaagc ggttagctcc ttcggtcctc cgatcgttgt    12000
cagaagtaag ttggccgcag tgttatcact catggttatg gcagcactgc ataattctct    12060
tactgtcatg ccatccgtaa gatgcttttc tgtgactggt gagtactcaa ccaagtcatt    12120
ctgagaatag tgtatgcggc gaccgagttg ctcttgcccg gcgtcaacac gggataatac    12180
cgcgccacat agcagaactt taaaagtgct catcattgga aaacgttctt cggggcgaaa    12240
actctcaagg atcttaccgc tgttgagatc cagttcgatg taacccactc gtgcacccaa    12300
ctgatcttca gcatctttta cttttcaccag cgtttctggg tgagcaaaaa caggaaggca    12360
aaatgccgca aaaaagggaa taagggcgac acggaaatgt tgaatactca tactcttcct    12420
ttttcaatat tattgaagca tttatcaggg ttattgtctc atgagcggat acatatttga    12480
atgtatttag aaaaataaac aaatagggggt tccgcgcaca tttccccgaa aagtgccacc    12540
tgacgtctaa gaaaccatta ttatcatgac attaacctat aaaaataggc gtatcacgag    12600
gcccttttcgt cttcaagaat tggtcgacga tcttgctgcg ttcggatatt ttcgtggagt    12660
tcccgccaca gacccggatt gaaggcgaga tccagcaact cgcgccagat catcctgtga    12720
cggaactttg gcgcgtgatg actggccagg acgtcggccg aaagagcgac aagcagatca    12780
cgcttttcga cagcgtcgga tttgcgatcg aggatttttc ggcgctgcgc tacgtccgcg    12840
accgcgttga gggatcaagc cacagcagcc cactcgacct tctagccgac ccagacgagc    12900
caagggatct ttttggaatg ctgctccgtc gtcaggcttt ccgacgtttg ggtggttgaa    12960
cagaagtcat tatcgtacgg aatgccaagc actcccgagg ggaaccctgt ggttggcatg    13020
cacatacaaa tggacgaacg gataaacctt ttcacgccct tttaaatatc cgttattcta    13080
ataaacgctc ttttctctta ggtttacccg ccaatatatc ctgtcaaaca ctgatagttt    13140
aaactgaagg cgggaaacga caatctgatc atgagcggag aattaaggga gtcacgttat    13200
gacccccgcc gatgacgcgg gacaagccgt tttacgtttg gaactgacag aaccgcaacg    13260
ttgaaggagc cactcagc                                                   13278
```

<210> SEQ ID NO 11
<211> LENGTH: 50
<212> TYPE: DNA
<213> ORGANISM: Artificial Sequence
<220> FEATURE:
<223> OTHER INFORMATION: poly-linker

<400> SEQUENCE: 11
gatcactagt ggcgcgccta ggagatctcg agtagggata acagggtaat         50

<210> SEQ ID NO 12
<211> LENGTH: 25
<212> TYPE: DNA
<213> ORGANISM: Artificial Sequence
<220> FEATURE:
<223> OTHER INFORMATION: attB1 seqeunce

<400> SEQUENCE: 12
acaagtttgt acaaaaaagc aggct                                    25

<210> SEQ ID NO 13
<211> LENGTH: 25
<212> TYPE: DNA
<213> ORGANISM: Artificial Sequence
<220> FEATURE:
<223> OTHER INFORMATION: attB2 sequence

<400> SEQUENCE: 13
accactttgt acaagaaagc tgggt                                    25

<210> SEQ ID NO 14
<211> LENGTH: 4778
<212> TYPE: DNA
<213> ORGANISM: Artificial Sequence
<220> FEATURE:
<223> OTHER INFORMATION: PHP23112 construct

<400> SEQUENCE: 14
gaaaggccca gtcttccgac tgagcctttc gttttatttg atgcctggca gttccctact    60
ctcgcgttaa cgctagcatg gatgttttcc cagtcacgac gttgtaaaac gacggccagt   120
cttaagctcg ggcccgcgtt aacgctacca tggagctcca ataatgatt ttattttgac    180 tgatagtgac ctgttcgttg caacaaattg ataagcaatg cttttttata atgccaactt   240
tgtatagaaa agttgggccg aattcgagct cggtacggcc agaatggccc ggaccgggtt   300
accgaattcg agctcggtac cctgggatca gcttgcatgc ctgcagtgca gcgtgacccg   360
gtcgtgcccc tctctagaga taatgagcat tgcatgtcta agttataaaa aattaccaca   420 tattttttt gtcacacttg tttgaagtgc agtttatcta tctttataca tatatttaaa   480
ctttactcta cgaataatat aatctatagt actacaataa tatcagtgtt ttagagaatc   540
atataaatga acagttagac atggtctaaa ggacaattga gtattttgac aacaggactc   600
tacagtttta tctttttagt gtgcatgtgt tctccttttt ttttgcaaat agcttcacct   660
atataatact tcatccattt tattagtaca tccatttagg gtttagggtt aatggttttt   720
atagactaat tttttagta catctatttt attctatttt agcctctaaa ttaagaaaac   780
taaaactcta tttagttttt tttatttaat aatttagata taaatagaa taaataaag    840 tgactaaaaa ttaaacaaat acccttaag aaattaaaaa aactaaggaa acatttttct   900
tgtttcgagt agataatgcc agcctgttaa acgccgtcga cgagtctaac ggacaccaac   960
cagcgaacca gcagcgtcgc gtcgggccaa gcgaagcaga cggcacggca tctctgtcgc  1020

```
tgcctctgga cccctctcga gagttccgct ccaccgttgg acttgctccg ctgtcggcat      1080
ccagaaattg cgtggcggag cggcagacgt gagccggcac ggcaggcggc ctcctcctcc      1140
tctcacggca ccggcagcta cgggggattc ctttcccacc gctccttcgc tttcccttcc      1200
tcgcccgccg taataaatag acacccctc cacaccctct ttccccaacc tcgtgttgtt       1260
cggagcgcac acacacacaa ccagatctcc cccaaatcca cccgtcggca cctccgcttc      1320
aaggtacgcc gctcgtcctc ccccccccc ctctctacct tctctagatc ggcgttccgg       1380
tccatgcatg gttagggccc ggtagttcta cttctgttca tgtttgtgtt agatccgtgt      1440
ttgtgttaga tccgtgctgc tagcgttcgt acacggatgc gacctgtacg tcagacacgt      1500
tctgattgct aacttgccag tgtttctctt tggggaatcc tgggatggct ctagccgttc      1560
cgcagacggg atcgatttca tgattttttt tgtttcgttg catagggttt ggtttgccct      1620
tttcctttat ttcaatatat gccgtgcact tgtttgtcgg gtcatctttt catgcttttt      1680
tttgtcttgg ttgtgatgat gtggtctggt tgggcggtcg ttctagatcg gagtagaatt      1740
ctgtttcaaa ctacctggtg gatttattaa ttttggatct gtatgtgtgt gccatacata      1800
ttcatagtta cgaattgaag atgatggatg gaaatatcga tctaggatag gtatacatgt      1860
tgatgcgggt tttactgatg catatacaga gatgcttttt gttcgcttgg ttgtgatgat      1920
gtggtgtggt tgggcggtcg ttcattcgtt ctagatcgga gtagaatact gtttcaaact      1980
acctggtgta tttattaatt ttggaactgt atgtgtgtgt catacatctt catagttacg      2040
agtttaagat ggatggaaat atcgatctag gataggtata catgttgatg tgggttttac      2100
tgatgcatat acatgatggc atatgcagca tctattcata tgctctaacc ttgagtacct      2160
atctattata ataaacaagt atgttttata attattttga tcttgatata cttggatgat      2220
ggcatatgca gcagctatat gtggattttt ttagccctgc cttcatacgc tatttatttg      2280
cttggtactg tttcttttgt cgatgctcac cctgttgttt ggtgttactt ctgcaggtcg      2340
actctagagg atcagcttgg tcacccggtc cgggcctaga aggccagctt caagtttgta      2400
caaaaaagtt gaacgagaaa cgtaaaatga tataaatatc aatatattaa attagatttt      2460
gcataaaaaa cagactacat aatactgtaa aacacaacat atgcagtcac tatgaatcaa      2520
ctacttagat ggtattagtg acctgtagaa ttcgagctct agagctgcag gcggccgcg      2580 atatccccta tagtgagtcg tattacatgg tcatagctgt ttcctggcag ctctggcccg      2640
tgtctcaaaa tctctgatgt tacattgcac aagataaaaa tatatcatca tgaacaataa      2700
aactgtctgc ttacataaac agtaatacaa ggggtgttat gagccatatt caacgggaaa      2760
cgtcgaggcc gcgattaaat tccaacatgg atgctgattt atatgggtat aaatgggctc      2820
gcgataatgt cgggcaatca ggtgcgacaa tctatcgctt gtatgggaag cccgatgcgc      2880
cagagttgtt tctgaaacat ggcaaaggta gcgttgccaa tgatgttaca gatgagatgg      2940
tcagactaaa ctggctgacg gaatttatgc ctcttccgac catcaagcat tttatccgta      3000
ctcctgatga tgcatggtta ctcaccactg cgatccccgg aaaaacagca ttccaggtat      3060
tagaagaata tcctgattca ggtgaaaata ttgttgatgc gctggcagtg ttcctgcgcc      3120
ggttgcattc gattcctgtt tgtaattgtc cttttaacag cgatcgcgta tttcgtctcg      3180
ctcaggcgca atcacgaatg aataacggtt tggttgatgc gagtgatttt gatgacgagc      3240
gtaatggctg gcctgttgaa caagtctgga agaaaatgca taaacttttg ccattctcac      3300
cggattcagt cgtcactcat ggtgatttct cacttgataa ccttattttt gacgagggga      3360
aattaatagg ttgtattgat gttggacgag tcggaatcgc agaccgatac caggatcttg      3420
```

```
ccatcctatg gaactgcctc ggtgagtttt ctccttcatt acagaaacgg ctttttcaaa    3480
aatatggtat tgataatcct gatatgaata aattgcagtt tcatttgatg ctcgatgagt    3540
ttttctaatc agaattggtt aattggttgt aacactggca gagcattacg ctgacttgac    3600
gggacggcgc aagctcatga ccaaaatccc ttaacgtgag ttacgcgtcg ttccactgag    3660
cgtcagaccc cgtagaaaag atcaaaggat cttcttgaga tccttttttt ctgcgcgtaa    3720
tctgctgctt gcaaacaaaa aaaccaccgc taccagcggt ggtttgtttg ccggatcaag    3780
agctaccaac tctttttccg aaggtaactg gcttcagcag agcgcagata ccaaatactg    3840
tccttctagt gtagccgtag ttaggccacc acttcaagaa ctctgtagca ccgcctacat    3900
acctcgctct gctaatcctg ttaccagtgg ctgctgccag tggcgataag tcgtgtctta    3960
ccgggttgga ctcaagacga tagttaccgg ataaggcgca gcggtcgggc tgaacggggg    4020
gttcgtgcac acagcccagc ttggagcgaa cgacctacac cgaactgaga tacctacagc    4080
gtgagcattg agaaagcgcc acgcttcccg aagggagaaa ggcggacagg tatccggtaa    4140
gcggcagggt cggaacagga gagcgcacga gggagcttcc agggggaaac gcctggtatc    4200
tttatagtcc tgtcgggttt cgccacctct gacttgagcg tcgatttttg tgatgctcgt    4260
caggggggcg gagcctatgg aaaaacgcca gcaacgcggc ctttttacgg ttcctggcct    4320
tttgctggcc ttttgctcac atgttctttc ctgcgttatc ccctgattct gtggataacc    4380
gtattaccgc ctttgagtga gctgataccg ctcgccgcag ccgaacgacc gagcgcagcg    4440
agtcagtgag cgaggaagcg gaagagcgcc caatacgcaa accgcctctc cccgcgcgtt    4500
ggccgattca ttaatgcagc tggcacgaca ggtttcccga ctggaaagcg ggcagtgagc    4560
gcaacgcaat taatacgcgt accgctagcc aggaagagtt tgtagaaacg caaaaaggcc    4620
atccgtcagg atggccttct gcttagtttg atgcctggca gtttatggcg ggcgtcctgc    4680
ccgccaccct ccgggccgtt gcttcacaac gttcaaatcc gctcccggcg gatttgtcct    4740
actcaggaga gcgttcaccg acaaacaaca gataaaac                           4778
```

<210> SEQ ID NO 15
<211> LENGTH: 54
<212> TYPE: DNA
<213> ORGANISM: Artificial Sequence
<220> FEATURE:
<223> OTHER INFORMATION: forward primer VC062

<400> SEQUENCE: 15

```
ttaaacaagt ttgtacaaaa aagcaggctg caattaaccc tcactaaagg gaac          54
```

<210> SEQ ID NO 16
<211> LENGTH: 53
<212> TYPE: DNA
<213> ORGANISM: Artificial Sequence
<220> FEATURE:
<223> OTHER INFORMATION: reverse primer VC063

<400> SEQUENCE: 16

```
ttaaaccact ttgtacaaga aagctgggtg cgtaatacga ctcactatag ggc           53
```

<210> SEQ ID NO 17
<211> LENGTH: 788
<212> TYPE: DNA
<213> ORGANISM: Zea mays

<400> SEQUENCE: 17

```
gcaaacaccg ctccagccgc cttcgctgct gctcgtgtgt ctcgtggaag ctccgcggct    60
```

```
ggaccatgga cccggacctg gacctcgacc tagacatgga tatggagacg ctcgccggcg      120
acagcggcgg cgaggccgag cgcaacgaag ccgccgaggc cgaggctgag gtggagcggt      180
acgaggccgc cgaagccgag gccgacatcc tccgcgaccg attccgcctc gccgtcatca      240
gcatcgccac cgccgaagga agaaggccgg gaatgacggt cgccgacccc gttgtttcct      300
gcatcgccga cttggcgttc aagagcgcag agcagctagc aaaggatgca gagttgtttg      360
cacagcatgc cggtcgcaaa tccgtcagga tggatgatgt catactcaca gctcacagga      420
acgagcatct tatgggcctg ctgcggacct tctctcagga gctgaaggga aaggagcctg      480
ccagtgagag gaagagaaag aaatcgtcca agaaggatga gacggtgatc gaggtctgat      540
ttcagatctg tcctcttttt ttttagagag gaaggcatgc atttttatct cgcgaggtcc      600
tcccggcttg tacagcttcc ttgtgtcgat actatcttcc atgtcatttc gcagaacttt      660
tcttctacga acccttcat cctagtcagt ttttctagtc agttattgat ggtacttgag      720
ttgagcttgc tttctcaact gcacatagca ttagtactga gtccaaaaaa aaaaaaaaaa      780
aaaaaaaa                                                               788
```

<210> SEQ ID NO 18
<211> LENGTH: 157
<212> TYPE: PRT
<213> ORGANISM: Zea mays

<400> SEQUENCE: 18

```
Met Asp Pro Asp Leu Asp Leu Asp Met Asp Met Glu Thr Leu
1               5                   10                  15

Ala Gly Asp Ser Gly Gly Glu Ala Glu Arg Asn Glu Ala Ala Glu Ala
            20                  25                  30

Glu Ala Glu Val Glu Arg Tyr Glu Ala Ala Glu Ala Glu Ala Asp Ile
        35                  40                  45

Leu Arg Asp Arg Phe Arg Leu Ala Val Ile Ser Ile Ala Thr Ala Glu
    50                  55                  60

Gly Lys Lys Ala Gly Met Thr Val Ala Asp Pro Val Val Ser Cys Ile
65                  70                  75                  80

Ala Asp Leu Ala Phe Lys Ser Ala Glu Gln Leu Ala Lys Asp Ala Glu
                85                  90                  95

Leu Phe Ala Gln His Ala Gly Arg Lys Ser Val Arg Met Asp Asp Val
            100                 105                 110

Ile Leu Thr Ala His Arg Asn Glu His Leu Met Gly Leu Leu Arg Thr
        115                 120                 125

Phe Ser Gln Glu Leu Lys Gly Lys Glu Pro Ala Ser Glu Arg Lys Arg
    130                 135                 140

Lys Lys Ser Ser Lys Lys Asp Glu Thr Val Ile Glu Val
145                 150                 155
```

<210> SEQ ID NO 19
<211> LENGTH: 676
<212> TYPE: DNA
<213> ORGANISM: Oryza sativa

<400> SEQUENCE: 19

```
aaatcccatc tcagtccgcc atggacgcgg agatggacct cctcgccgac gacgacggcg      60
gcgaggccga gaggctggag gccgcggagg cgcaggccga cctcctccgc gatcgcctcc      120
gcctcgccgt catcagcatc gccacctccg aaggaaagaa ggcggggatg gaggtctccg      180
accccgtcgt cgcctgcatc gccgatctgg cctacaagac cgtagagcag ctggctaagg      240
```

```
atgttgagtt gtttgcacag catgctggtc gtaaatccat caagatggaa gatgttatac    300
tcacagcaca tagaaatgag catctgatgg gcctcctgcg acatttttct caagaactga    360
agggtaagga gccttccagc gagaggaaga gaaagaaatc ttcgaagaag acgacaacg     420 tgatgcaaat ctgatttaag tcatgagata aatcttcttc ccatagaaca aagtggtagg    480
ttcaagcagg aaactctgca agtaactcag gctacccact gatcctgtat ttcacacatt    540
tagatgtggt atgacacaat gttgtctgtg gaaagtggag atccttcaca cctgtaaatt    600
cactgaggct gttgtgtcaa gtagtaaatg gcaaaattca gagtttggtt cttaaaaaaa    660
aaaaaaaaaa aaaaaa                                                    676
```

<210> SEQ ID NO 20
<211> LENGTH: 137
<212> TYPE: PRT
<213> ORGANISM: Oryza sativa

<400> SEQUENCE: 20

```
Met Asp Ala Glu Met Asp Leu Leu Ala Asp Asp Gly Gly Glu Ala
1               5                   10                  15

Glu Arg Leu Glu Ala Ala Glu Ala Ala Gln Ala Asp Leu Leu Arg Asp Arg
            20                  25                  30

Leu Arg Leu Ala Val Ile Ser Ile Ala Thr Ser Glu Gly Lys Lys Ala
        35                  40                  45

Gly Met Glu Val Ser Asp Pro Val Val Ala Cys Ile Ala Asp Leu Ala
    50                  55                  60

Tyr Lys Thr Val Glu Gln Leu Ala Lys Asp Val Glu Leu Phe Ala Gln
65                  70                  75                  80

His Ala Gly Arg Lys Ser Ile Lys Met Glu Asp Val Ile Leu Thr Ala
                85                  90                  95

His Arg Asn Glu His Leu Met Gly Leu Leu Arg Thr Phe Ser Gln Glu
            100                 105                 110

Leu Lys Gly Lys Glu Pro Ser Ser Glu Arg Lys Arg Lys Lys Ser Ser
        115                 120                 125

Lys Lys Asp Asp Asn Val Met Gln Ile
    130                 135
```

<210> SEQ ID NO 21
<211> LENGTH: 513
<212> TYPE: DNA
<213> ORGANISM: Glycine max
<220> FEATURE:
<221> NAME/KEY: misc_feature
<222> LOCATION: (356)..(356)
<223> OTHER INFORMATION: n is a, c, g, t or u
<220> FEATURE:
<221> NAME/KEY: misc_feature
<222> LOCATION: (364)..(364)
<223> OTHER INFORMATION: n is a, c, g, t or u
<220> FEATURE:
<221> NAME/KEY: misc_feature
<222> LOCATION: (367)..(367)
<223> OTHER INFORMATION: n is a, c, g, t or u
<220> FEATURE:
<221> NAME/KEY: misc_feature
<222> LOCATION: (413)..(413)
<223> OTHER INFORMATION: n is a, c, g, t or u
<220> FEATURE:
<221> NAME/KEY: misc_feature
<222> LOCATION: (437)..(437)
<223> OTHER INFORMATION: n is a, c, g, t or u
<220> FEATURE:
<221> NAME/KEY: misc_feature
<222> LOCATION: (474)..(474)

```
<223> OTHER INFORMATION: n is a, c, g, t or u
<220> FEATURE:
<221> NAME/KEY: misc_feature
<222> LOCATION: (493)..(494)
<223> OTHER INFORMATION: n is a, c, g, t or u

<400> SEQUENCE: 21
cgcgaacagc gaagtcgaaa acgacgcgga aatgaagctc ttgagagata aattcaggct    60
ctccgcaatc tccatcatcg aatctcaagc aaaacaaaac ggcatggaag tatcaaaagt   120
cgtagtcact tgcgttgcgg atttggcctt caagtatacg gagcgcctgg ctagggatct   180
tcatctattt gcgcagcatg cgaatcgtaa atctgtaaat atggaagatg tgatactttg   240
tggacatagg aatgaacatg tatctggcat gttgaggagc ttctccaatg atttaaaagc   300
caaggatcct caatctgaaa ggaagcgaaa gaaagaaccc aaaagaacg acaaangaac    360 cgcntancgc atatgcctga tgcatatata tgggcctaag aacatatttt ggnacgggta   420
ggtaatttta tgtatantttt tcccccccctt aaaatgtttt tgggtttggg aagntagtgc   480
tgggatccat tannccaact taatcaattt atg                                513

<210> SEQ ID NO 22
<211> LENGTH: 428
<212> TYPE: DNA
<213> ORGANISM: Glycine max
<220> FEATURE:
<221> NAME/KEY: misc_feature
<222> LOCATION: (415)..(415)
<223> OTHER INFORMATION: n is a, c, g, t or u

<400> SEQUENCE: 22
aaaatcgtag tcacttgcat tgcggatttg gccttcaaat atacagagtg cgtggctagg    60
gatcttcatc tatttgcgca gcatgcgaat cgtaaatctg taaatatgga agatgtgata   120 cttttgtggac ataggaatga acatgtatct ggcatgttga ggagcttctc caatgtttta   180
aaagccaacg atcctcaatc tgaaaggaag cgaaagaaag aaaccaaaaa gaacgacaaa   240
ggaaccgctt agaacatatt ttggtatgat taagtaaaat cttatatata tattatttcc   300
ttacttttat tggacttgtt agctattgct ggaatctatt agtccatctt aatcatttat   360
gggtgccttt aaacttaata cctatgatgt gtgtaattga atcaatttaa tttangagca   420
ttttctat                                                             428

<210> SEQ ID NO 23
<211> LENGTH: 612
<212> TYPE: DNA
<213> ORGANISM: Glycine max

<400> SEQUENCE: 23
aaactcgacg atggaaagcg tggacgcgaa cagcgaagtc gaaaacgacg cggaaatgaa    60
gctcttgaga gataaattca ggctctccgc aatctccatc atcgaatctc aagcaaaaca   120
aaacggcatg gaagtatcaa aagtcgtagt cacttgcgtt gcggatttgg ccttcaagta   180
tacggagcgc ctggctaggg atcttcatct atttgcgcag catgcgaatc gtaaatctgt   240
aaatatggaa gatgtgatac tttgtggaca taggaatgaa catgtatctg gcatgttgag   300
gagcttctcc aatgatttaa aagccaagga tcctcaatct gaaaggaagc gaaagaaaga   360
acccaaaaag aacgacaaag gaaccgctta gcgcatatgc ctgatgcata tatatggtcc   420
taggaacata ttttggtacg gttagttaat tttatgtata tttttctctc ctttatatgt   480
ttttggattt ggtagctagt gctggaatct attagtccat cttaatcatt tatgcatgcc   540
```

```
tttaaactta attccagtaa ggcagtaact atgagtgcgt gattgaagta attaatttag    600
aagcattttt tt                                                        612
```

<210> SEQ ID NO 24
<211> LENGTH: 126
<212> TYPE: PRT
<213> ORGANISM: Glycine max

<400> SEQUENCE: 24

```
Met Glu Ser Val Asp Ala Asn Ser Glu Val Glu Asn Asp Ala Glu Met
1               5                   10                  15

Lys Leu Leu Arg Asp Lys Phe Arg Leu Ser Ala Ile Ser Ile Ile Glu
            20                  25                  30

Ser Gln Ala Lys Gln Asn Gly Met Glu Val Ser Lys Val Val Thr
        35                  40                  45

Cys Val Ala Asp Leu Ala Phe Lys Tyr Thr Glu Arg Leu Ala Arg Asp
    50                  55                  60

Leu His Leu Phe Ala Gln His Ala Asn Arg Lys Ser Val Asn Met Glu
65                  70                  75                  80

Asp Val Ile Leu Cys Gly His Arg Asn Glu His Val Ser Gly Met Leu
                85                  90                  95

Arg Ser Phe Ser Asn Asp Leu Lys Ala Lys Asp Pro Gln Ser Glu Arg
            100                 105                 110

Lys Arg Lys Lys Glu Pro Lys Lys Asn Asp Lys Gly Thr Ala
        115                 120                 125
```

<210> SEQ ID NO 25
<211> LENGTH: 578
<212> TYPE: DNA
<213> ORGANISM: Glycine max

<400> SEQUENCE: 25

```
gttgctgtcg aaaaatctcg acgatggaaa acgcggacgc gaacagcgaa gtcgaaaacg    60
acgcggaaat gaagctcttg agagataaat tcaggctctc cgcaatctcc ataatcgaat   120
ctcaagcaaa acaaaatggc atggaagtag caaaaatcgt agtcacttgc attgcggatt   180
tggccttcaa atatacagag tgcgtggcta gggatcttca tctatttgcg cagcatgcga   240
atcgtaaatc tgtaaatatg gaagatgtga tactttgtgg acataggaat gaacatgtat   300
ctggcatgtt gaggagcttc tccaatgttt taaaagccaa cgatcctcaa tctgaaagga   360
agcgaaagaa agaaaccaaa aagaacgaca aggaaccgc ttagaacata ttttggtatg   420
attagtaaaa tcttatatat atattatttc cttactttta ttggacttgt tagctattgc   480
tggaatctat tagtccatct taatcattta tgggtgcctt taaacttaat accactcact   540
gtatgatgtg tgtaattgaa tcattttaat ttaggagc                            578
```

<210> SEQ ID NO 26
<211> LENGTH: 126
<212> TYPE: PRT
<213> ORGANISM: Glycine max

<400> SEQUENCE: 26

```
Met Glu Asn Ala Asp Ala Asn Ser Glu Val Glu Asn Asp Ala Glu Met
1               5                   10                  15

Lys Leu Leu Arg Asp Lys Phe Arg Leu Ser Ala Ile Ser Ile Ile Glu
            20                  25                  30

Ser Gln Ala Lys Gln Asn Gly Met Glu Val Ala Lys Ile Val Val Thr
        35                  40                  45
```

Cys Ile Ala Asp Leu Ala Phe Lys Tyr Thr Glu Cys Val Ala Arg Asp
            50                  55                  60

Leu His Leu Phe Ala Gln His Ala Asn Arg Lys Ser Val Asn Met Glu
 65                  70                  75                  80

Asp Val Ile Leu Cys Gly His Arg Asn Glu His Val Ser Gly Met Leu
                85                  90                  95

Arg Ser Phe Ser Asn Val Leu Lys Ala Asn Asp Pro Gln Ser Glu Arg
            100                 105                 110

Lys Arg Lys Lys Glu Thr Lys Lys Asn Asp Lys Gly Thr Ala
            115                 120                 125

<210> SEQ ID NO 27
<211> LENGTH: 847
<212> TYPE: DNA
<213> ORGANISM: Arabidopsis thaliana

<400> SEQUENCE: 27
atgtttaaca tttcttacgc caaacgaaac gctaaatatt tatttaaatt gctagcctgg      60
tgtatgatga tcgaggaagc tggacctaac atcggtaaca agcaaaaagt agttctccaa     120
cttagcaaaa tgctaataat gtatatcatt ctccatataa acgctgcgtt ttggacatgg     180
aggggatact aaaacgctg cgttttacac tttgttttcc cgcgtatatt tctccctta      240 ttatcggata gcccaacaat cacacaggcg aagaaaccta gctattgctt cgccatggac     300
gtcggaggag aagacataag cgatctccag gtagaccaaa tcgttgaaga atattctatg     360
gacgatctca ttagagaccg attcagactc tccgcgatct ctatcgccga agccgaggcg     420
aagaaaaatg gaatggaaat aggtggacct gttgtggcat gtgtggcaga tttagccttc     480
aaatatgcag aaaacgttgc aaaggatctt gaactattcg ctcatcatgc tggacgcaaa     540
gttgtgaaca tggacgatgt tgttctctcc gcgcatagaa acgataactt agcagcatct     600
ttgaggtcac tatgcaatga gctaaaggca aaggagccac aatctgagag gaaacgcaag     660
aaaggatcag ccaagaaaga agacaaagcc agtagtagca atgccgttcg catcacgacc     720
gatctgtaac tcttcaagca gagtgtaaat acacgcactc ctctatatat atatataaac     780
attaactttg atggagaagc tgttattaaa ttttgtgga aattttata tagaagactt      840 ttgcatt                                                              847

<210> SEQ ID NO 28
<211> LENGTH: 242
<212> TYPE: PRT
<213> ORGANISM: Arabidopsis thaliana

<400> SEQUENCE: 28

Met Phe Asn Ile Ser Tyr Ala Lys Arg Asn Ala Lys Tyr Leu Phe Lys
  1               5                  10                  15

Leu Leu Ala Trp Cys Met Met Ile Glu Glu Ala Gly Pro Asn Ile Gly
             20                  25                  30

Asn Lys Gln Lys Val Val Leu Gln Leu Ser Lys Met Leu Ile Met Tyr
             35                  40                  45

Ile Ile Leu His Ile Asn Ala Ala Phe Trp Thr Trp Arg Gly Tyr Leu
            50                  55                  60

Lys Arg Cys Val Leu His Phe Val Phe Pro Arg Ile Phe Leu Pro Leu
 65                  70                  75                  80

Leu Ser Asp Ser Pro Thr Ile Thr Gln Ala Lys Lys Pro Ser Tyr Cys
                85                  90                  95

```
Phe Ala Met Asp Val Gly Gly Glu Asp Ile Ser Asp Leu Gln Val Asp
                100                 105                 110
Gln Ile Val Glu Glu Tyr Ser Met Asp Asp Leu Ile Arg Asp Arg Phe
            115                 120                 125
Arg Leu Ser Ala Ile Ser Ile Ala Glu Ala Ala Lys Lys Asn Gly
    130                 135                 140
Met Glu Ile Gly Gly Pro Val Val Ala Cys Val Ala Asp Leu Ala Phe
145                 150                 155                 160
Lys Tyr Ala Glu Asn Val Ala Lys Asp Leu Glu Leu Phe Ala His His
                165                 170                 175
Ala Gly Arg Lys Val Val Asn Met Asp Asp Val Val Leu Ser Ala His
            180                 185                 190
Arg Asn Asp Asn Leu Ala Ala Ser Leu Arg Ser Leu Cys Asn Glu Leu
        195                 200                 205
Lys Ala Lys Glu Pro Gln Ser Glu Arg Lys Arg Lys Gly Ser Ala
    210                 215                 220
Lys Lys Glu Asp Lys Ala Ser Ser Ser Asn Ala Val Arg Ile Thr Thr
225                 230                 235                 240

Asp Leu

<210> SEQ ID NO 29
<211> LENGTH: 665
<212> TYPE: DNA
<213> ORGANISM: Arabidopsis thaliana

<400> SEQUENCE: 29
atgtttaaca tttcttacgc caaacgaaac gctaaatatt tatttaaatt gctagcctgg      60
taggcgcgta atagagagtg ctatgtttcc ttaaatcaaa gcaaaacata gatgttgttg     120
ccggcaacga ggatggtaat cgataaagcc acaggtgtat gatgatcgag aagctggac     180 ctaacatcgg taacaagcaa aaagcgaaga aacctagcta ttgcttcgcc atggacgtcg     240
gaggagaaga cataagcgat ctccaggtag accaaatcgt tgaagaatat tctatggacg     300
atctcattag agaccgattc agactctccg cgatctctat cgccgaagcc gaggcgaaga     360
aaaatggaat ggaaataggt ggacctgttg tggcatgtgt ggcagattta gccttcaaat     420
atgcagaaaa cgttgcaaag gatcttgaac tattcgctca tcatgctgga cgcaaagttg     480
tgaacatgga cgatgttgtt ctctccgcgc atagaaacga taacttagca gcatctttga     540
ggtcactatg caatgagcta aaggcaaagg agccacaatc tgagaggaaa cgcaagaaag     600
gatcagccaa gaaagaagac aaagccagta gtagcaatgc cgttcgcatc acgaccgatc     660
tgtaa                                                                 665

<210> SEQ ID NO 30
<211> LENGTH: 168
<212> TYPE: PRT
<213> ORGANISM: Arabidopsis thaliana

<400> SEQUENCE: 30

Met Met Ile Glu Glu Ala Gly Pro Asn Ile Gly Asn Lys Gln Lys Ala
1               5                   10                  15

Lys Lys Pro Ser Tyr Cys Phe Ala Met Asp Val Gly Gly Glu Asp Ile
            20                  25                  30

Ser Asp Leu Gln Val Asp Gln Ile Val Glu Glu Tyr Ser Met Asp Asp
        35                  40                  45

Leu Ile Arg Asp Arg Phe Arg Leu Ser Ala Ile Ser Ile Ala Glu Ala
    50                  55                  60
```

Glu Ala Lys Lys Asn Gly Met Glu Ile Gly Gly Pro Val Val Ala Cys
65                  70                  75                  80

Val Ala Asp Leu Ala Phe Lys Tyr Ala Glu Asn Val Ala Lys Asp Leu
                85                  90                  95

Glu Leu Phe Ala His His Ala Gly Arg Lys Val Val Asn Met Asp Asp
            100                 105                 110

Val Val Leu Ser Ala His Arg Asn Asp Asn Leu Ala Ala Ser Leu Arg
        115                 120                 125

Ser Leu Cys Asn Glu Leu Lys Ala Lys Glu Pro Gln Ser Glu Arg Lys
    130                 135                 140

Arg Lys Lys Gly Ser Ala Lys Lys Glu Asp Lys Ala Ser Ser Ser Asn
145                 150                 155                 160

Ala Val Arg Ile Thr Thr Asp Leu
                165

<210> SEQ ID NO 31
<211> LENGTH: 669
<212> TYPE: DNA
<213> ORGANISM: Arabidopsis thaliana

<400> SEQUENCE: 31
atgtttaaca tttcttacgc caaacgaaac gctaaatatt tatttaaatt gctagcctgg      60
taggcgcgta atagagagtg ctatgttttcc ttaaatcaaa gcaaaacata gatgttgttg     120
ccggcaacga ggatggtaat cgataaagcc acaggtgtat gatgatcgag gaagctggac     180
ctaacatcgg taacaagcaa aaagtaggcg aagaaaccta gctattgctt cgccatggac     240
gtcggaggag aagacataag cgatctccag gtagaccaaa tcgttgaaga atattctatg     300
gacgatctca ttagagaccg attcagactc tccgcgatct ctatcgccga agccgaggcg     360
aagaaaaatg gaatggaaat aggtggacct gttgtggcat gtgtggcaga tttagccttc     420
aaatatgcag aaaacgttgc aaaggatctt gaactattcg ctcatcatgc tggacgcaaa     480
gttgtgaaca tggacgatgt tgttctctcc gcgcatagaa acgataactt agcagcatct     540
ttgaggtcac tatgcaatga gctaaaggca aaggagccac aatctgagag gaaacgcaag     600
aaaggatcag ccaagaaaga agacaaagcc agtagtagca atgccgttcg catcacgacc     660
gatctgtaa                                                            669

<210> SEQ ID NO 32
<211> LENGTH: 144
<212> TYPE: PRT
<213> ORGANISM: Arabidopsis thaliana

<400> SEQUENCE: 32

Met Asp Val Gly Gly Glu Asp Ile Ser Asp Leu Gln Val Asp Gln Ile
1               5                   10                  15

Val Glu Glu Tyr Ser Met Asp Asp Leu Ile Arg Asp Arg Phe Arg Leu
                20                  25                  30

Ser Ala Ile Ser Ile Ala Glu Ala Glu Ala Lys Lys Asn Gly Met Glu
            35                  40                  45

Ile Gly Gly Pro Val Val Ala Cys Val Ala Asp Leu Ala Phe Lys Tyr
        50                  55                  60

Ala Glu Asn Val Ala Lys Asp Leu Glu Leu Phe Ala His His Ala Gly
65                  70                  75                  80

Arg Lys Val Val Asn Met Asp Asp Val Val Leu Ser Ala His Arg Asn
                85                  90                  95

Asp Asn Leu Ala Ala Ser Leu Arg Ser Leu Cys Asn Glu Leu Lys Ala
            100                 105                 110

Lys Glu Pro Gln Ser Glu Arg Lys Arg Lys Gly Ser Ala Lys Lys
        115                 120                 125

Glu Asp Lys Ala Ser Ser Asn Ala Val Arg Ile Thr Thr Asp Leu
130                 135                 140

<210> SEQ ID NO 33
<211> LENGTH: 137
<212> TYPE: PRT
<213> ORGANISM: Oryza sativa

<400> SEQUENCE: 33

Met Asp Ala Glu Met Asp Leu Leu Ala Asp Asp Gly Gly Glu Ala
1               5                   10                  15

Glu Arg Leu Glu Ala Ala Glu Ala Gln Ala Asp Leu Leu Arg Asp Arg
            20                  25                  30

Leu Arg Leu Ala Val Ile Ser Ile Ala Thr Ser Glu Gly Lys Lys Ala
            35                  40                  45

Gly Met Glu Val Ser Asp Pro Val Val Ala Cys Ile Ala Asp Leu Ala
50                  55                  60

Tyr Lys Thr Val Glu Gln Leu Ala Lys Asp Val Glu Leu Phe Ala Gln
65                  70                  75                  80

His Ala Gly Arg Lys Ser Ile Lys Met Glu Asp Val Ile Leu Thr Ala
                85                  90                  95

His Arg Asn Glu His Leu Met Gly Leu Leu Arg Thr Phe Ser Gln Glu
            100                 105                 110

Leu Lys Gly Lys Glu Pro Ser Ser Glu Arg Lys Arg Lys Lys Ser Ser
            115                 120                 125

Lys Lys Asp Asp Asn Val Met Gln Ile
        130                 135

<210> SEQ ID NO 34
<211> LENGTH: 135
<212> TYPE: PRT
<213> ORGANISM: Vitis vinifera

<400> SEQUENCE: 34

Met Glu Glu Ala Arg Ser Glu Leu Glu Arg Glu Asp Glu Glu Ala
1               5                   10                  15

Thr Glu Leu Leu Arg Asp Arg Phe Arg Leu Ser Thr Ile Ser Ile Val
            20                  25                  30

Glu Ala Gln Ala Lys Lys Ser Asp Met Glu Ile Ser Glu Pro Ile Val
            35                  40                  45

Ala Cys Ile Ser Asp Leu Ala Phe Lys Tyr Thr Glu Gln Leu Ala Lys
        50                  55                  60

Asp Leu Glu Leu Phe Ser Gln His Ala Gly Arg Lys Thr Val Asn Met
65                  70                  75                  80

Glu Asp Val Ile Leu Ser Ala His Arg Asn Lys His Leu Ala Ser Ser
                85                  90                  95

Leu Arg Ser Phe Cys Asn Asp Leu Lys Ala Lys Glu Ile Pro Ser Glu
            100                 105                 110

Arg Lys Arg Lys Lys Ala Ser Arg Lys Glu Asp Lys Ala Ser Thr Ser
        115                 120                 125

Val Val His Ile Pro Asp Leu
        130                 135

-continued

```
<210> SEQ ID NO 35
<211> LENGTH: 55
<212> TYPE: DNA
<213> ORGANISM: Artificial
<220> FEATURE:
<223> OTHER INFORMATION: nucleotide sequence of the At5g50930-5' attB
      forward primer

<400> SEQUENCE: 35
ttaaacaagt ttgtacaaaa aagcaggctc aacaatgttt aacatttctt acgcc          55

<210> SEQ ID NO 36
<211> LENGTH: 50
<212> TYPE: DNA
<213> ORGANISM: Artificial
<220> FEATURE:
<223> OTHER INFORMATION: nucleotide sequence of the At5g50930-3' attB
      reverse primer

<400> SEQUENCE: 36
ttaaaccact ttgtacaaga aagctgggtt tacagatcgg tcgtgatgcg               50
```